(12) United States Patent
Sinclair et al.

(10) Patent No.: US 7,977,049 B2
(45) Date of Patent: Jul. 12, 2011

(54) METHODS AND COMPOSITIONS FOR EXTENDING THE LIFE SPAN AND INCREASING THE STRESS RESISTANCE OF CELLS AND ORGANISMS

(75) Inventors: David A. Sinclair, West Roxbury, MA (US); Kevin J. Bitterman, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 270 days.

(21) Appl. No.: 11/053,185

(22) Filed: Feb. 8, 2005

(65) Prior Publication Data

US 2005/0267023 A1 Dec. 1, 2005

Related U.S. Application Data

(63) Continuation-in-part of application No. PCT/US03/25016, filed on Aug. 8, 2003.

(60) Provisional application No. 60/402,254, filed on Aug. 9, 2002, provisional application No. 60/428,614, filed on Nov. 22, 2002.

(51) Int. Cl.
  *C12Q 1/68* (2006.01)
  *C12Q 1/00* (2006.01)
  *C12N 9/78* (2006.01)
  *C12N 15/63* (2006.01)
  *C12N 5/00* (2006.01)
  *C12N 15/00* (2006.01)
  *C12N 1/20* (2006.01)
  *A01N 63/00* (2006.01)
  *A61K 48/00* (2006.01)
  *C07H 21/04* (2006.01)

(52) U.S. Cl. ............ 435/6; 435/227; 435/455; 435/325; 435/252.3; 435/320.1; 435/4; 435/440; 424/93.1; 514/44 R; 536/23.2

(58) Field of Classification Search .................. None
See application file for complete search history.

(56) References Cited

U.S. PATENT DOCUMENTS

| | | | |
|---|---|---|---|
| 4,591,600 A | 5/1986 | Creuzet et al. |
| 5,500,367 A | 3/1996 | Hain et al. |
| 5,689,046 A | 11/1997 | Schroder et al. |
| 5,689,047 A | 11/1997 | Hain et al. |
| 5,747,536 A | 5/1998 | Cavazza |
| 5,827,898 A | 10/1998 | Khandwala et al. |
| 5,874,399 A | 2/1999 | Samal |
| 5,874,444 A | 2/1999 | West |
| 5,985,647 A | 11/1999 | Schroder et al. |
| 6,008,260 A | 12/1999 | Pezzuto et al. |
| 6,020,129 A | 2/2000 | Schroder et al. |
| 6,022,901 A | 2/2000 | Goodman |
| 6,048,903 A | 4/2000 | Toppo |
| 6,063,820 A | 5/2000 | Cavazza |
| 6,063,988 A | 5/2000 | Hain et al. |
| 6,080,701 A | 6/2000 | Jeandet et al. |
| 6,124,125 A | 9/2000 | Kemper et al. |
| 6,132,740 A | 10/2000 | Hu |
| 6,184,248 B1 | 2/2001 | Lee et al. |
| 6,190,716 B1 | 2/2001 | Galbreath, Jr. |
| 6,197,834 B1 | 3/2001 | Docherty |
| 6,211,247 B1 | 4/2001 | Goodman |
| 6,245,814 B1 | 6/2001 | Nag et al. |
| 6,264,995 B1 | 7/2001 | Newmark et al. |
| 6,270,780 B1 | 8/2001 | Carson et al. |
| 6,300,377 B1 | 10/2001 | Chopra |
| 6,319,523 B1 | 11/2001 | Zhou |
| 6,331,633 B1 | 12/2001 | Neogi et al. |
| 6,333,441 B1 | 12/2001 | Sato et al. |
| 6,355,692 B2 | 3/2002 | Docherty |
| 6,358,517 B1 | 3/2002 | Pillai et al. |
| 6,361,815 B1 | 3/2002 | Zheng et al. |
| 6,368,617 B1 | 4/2002 | Hastings et al. |
| 6,387,416 B1 | 5/2002 | Newmark et al. |
| 6,410,596 B1 | 6/2002 | Hopp et al. |
| 6,414,037 B1 | 7/2002 | Pezzuto et al. |
| 6,416,806 B1 | 7/2002 | Zhou |
| 6,423,747 B1 | 7/2002 | Lanzendorfer et al. |
| 6,426,061 B1 | 7/2002 | Li et al. |
| 6,440,433 B1 | 8/2002 | Breton et al. |
| 6,448,450 B1 | 9/2002 | Nag et al. |
| 6,469,055 B2 | 10/2002 | Lee et al. |
| 6,475,530 B1 | 11/2002 | Kuhrts |
| 6,479,466 B1 | 11/2002 | Redfield et al. |

(Continued)

FOREIGN PATENT DOCUMENTS

DE 102 30 961 2/2004

(Continued)

OTHER PUBLICATIONS

Branden et al. Introduction to Protein Structure, Garland Publishing Inc., New York, p. 247, 1991.*
Dulyaninova et al. Salvage pathway for NAD biosynthesis in Brevibacterium ammoniagenes: regulatory properties of triphosphate-dependent nicotinate phosphoribosyltransferase. Biochim Biophys Acta. May 23, 2000;1478(2):211-20.*
Ghislain et al. "Identification and functional analysis of the *Saccharomyces cerevisiae* nicotinamidase gene, PNC1." Yeast 19:215-224(2002).*
Brenda—Nicotinamidase—3.5.1.19. Printed from the internet on 1011.2009.*

(Continued)

*Primary Examiner* — Yong D Pak
(74) *Attorney, Agent, or Firm* — Wolf, Greenfield & Sacks, P.C.

(57) ABSTRACT

The invention provides methods and compositions for modulating the life span of eukaryotic and prokaryotic cells and for protecting cells against certain stresses, e.g., heatshock. One method comprises modulating the flux of the NAD+ salvage pathway in the cell, e.g., by modulating the level or activity of one or more proteins selected from the group consisting of NPT1, PNC1, NMA1 and NMA2. Another method comprises modulating the level of nicotinamide in the cell.

71 Claims, 26 Drawing Sheets

U.S. PATENT DOCUMENTS

| | | |
|---|---|---|
| 6,486,203 B1 | 11/2002 | Dannenberg |
| 6,500,451 B2 | 12/2002 | Adams |
| 6,515,020 B1 | 2/2003 | Cavazza |
| 6,537,969 B1 | 3/2003 | Blass |
| 6,541,522 B2 | 4/2003 | Inman et al. |
| 6,544,564 B1 | 4/2003 | Farley |
| 6,552,085 B2 | 4/2003 | Inman et al. |
| 6,552,213 B1 | 4/2003 | Deshpande et al. |
| 6,572,882 B1 | 6/2003 | Vercauteren et al. |
| 6,573,299 B1 | 6/2003 | Petrus |
| 6,605,296 B1 | 8/2003 | Stuckler |
| 6,615,843 B2 | 9/2003 | Pera |
| 6,624,197 B1 | 9/2003 | Nag et al. |
| 6,638,545 B1 | 10/2003 | Rombi |
| 6,656,925 B2 | 12/2003 | Petrus |
| 6,844,163 B1 | 1/2005 | Matsuzawa et al. |
| 2001/0020043 A1 | 9/2001 | Docherty |
| 2001/0039296 A1 | 11/2001 | Bagchi et al. |
| 2001/0056071 A1 | 12/2001 | Pelliccia et al. |
| 2002/0002200 A1 | 1/2002 | Nag et al. |
| 2002/0009482 A1 | 1/2002 | Adams |
| 2002/0028852 A1 | 3/2002 | Ghai et al. |
| 2002/0051799 A1 | 5/2002 | Pruche et al. |
| 2002/0052407 A1 | 5/2002 | Lee et al. |
| 2002/0058701 A1 | 5/2002 | Inman et al. |
| 2002/0058707 A1 | 5/2002 | Hopp et al. |
| 2002/0091087 A1 | 7/2002 | Zhang et al. |
| 2002/0110604 A1 | 8/2002 | Babish et al. |
| 2002/0111383 A1 | 8/2002 | Hassen |
| 2002/0119952 A1 | 8/2002 | Petrus |
| 2002/0120008 A1 | 8/2002 | Benzer et al. |
| 2002/0142017 A1 | 10/2002 | Simonnet |
| 2002/0146424 A1 | 10/2002 | Benza et al. |
| 2002/0146472 A1 | 10/2002 | Chen et al. |
| 2002/0148478 A1 | 10/2002 | Pera |
| 2002/0155075 A1 | 10/2002 | Collington |
| 2002/0164385 A1 | 11/2002 | Dannenberg et al. |
| 2002/0173472 A1 | 11/2002 | Pezzuto et al. |
| 2002/0173549 A1 | 11/2002 | Wurtman et al. |
| 2002/0182196 A1 | 12/2002 | McCleary |
| 2002/0192310 A1 | 12/2002 | Bland et al. |
| 2003/0004142 A1 | 1/2003 | Prior et al. |
| 2003/0004143 A1 | 1/2003 | Prior et al. |
| 2003/0031693 A1 | 2/2003 | Breton et al. |
| 2003/0044474 A1 | 3/2003 | C. Tao et al. |
| 2003/0044946 A1 | 3/2003 | Longo |
| 2003/0054053 A1 | 3/2003 | Young et al. |
| 2003/0054357 A1 | 3/2003 | Young et al. |
| 2003/0055108 A1 | 3/2003 | Young |
| 2003/0055114 A1 | 3/2003 | Young |
| 2003/0064913 A1 | 4/2003 | Sonis |
| 2003/0078212 A1 | 4/2003 | Li et al. |
| 2003/0082116 A1 | 5/2003 | Badejo et al. |
| 2003/0082203 A1 | 5/2003 | Farley |
| 2003/0082597 A1 | 5/2003 | Cannon et al. |
| 2003/0082647 A1 | 5/2003 | Reenan et al. |
| 2003/0084912 A1 | 5/2003 | Pera |
| 2003/0086986 A1 | 5/2003 | Bruijn et al. |
| 2003/0118536 A1 | 6/2003 | Rosenbloom |
| 2003/0118617 A1 | 6/2003 | Soby et al. |
| 2003/0124101 A1 | 7/2003 | Gu et al. |
| 2003/0124161 A1 | 7/2003 | Biatry et al. |
| 2003/0129247 A1 | 7/2003 | Ju et al. |
| 2003/0133992 A1 | 7/2003 | Bagchi et al. |
| 2003/0145354 A1 | 7/2003 | Milkowski et al. |
| 2003/0149261 A1 | 8/2003 | Schramm et al. |
| 2003/0152617 A1 | 8/2003 | Yatvin |
| 2003/0161830 A1 | 8/2003 | Jackson et al. |
| 2003/0161902 A1 | 8/2003 | Duncan |
| 2003/0165854 A1 | 9/2003 | Cunningham et al. |
| 2003/0180719 A1 | 9/2003 | Herget et al. |
| 2003/0182302 A1 | 9/2003 | Li |
| 2003/0185912 A1 | 10/2003 | Rosenbloom |
| 2003/0186898 A1 | 10/2003 | Maurya et al. |
| 2003/0190381 A1 | 10/2003 | Bland et al. |
| 2003/0191064 A1 | 10/2003 | Kopke |
| 2003/0199581 A1 | 10/2003 | Seligson et al. |
| 2003/0203973 A1 | 10/2003 | Cooper et al. |
| 2003/0207325 A1 | 11/2003 | Guarente et al. |
| 2003/0224077 A1 | 12/2003 | Mahe et al. |
| 2003/0228269 A1 | 12/2003 | DeRosa et al. |
| 2003/0232782 A1 | 12/2003 | Escalante-Semerena et al. |
| 2004/0002499 A1 | 1/2004 | Aggarwal |
| 2004/0005574 A1 | 1/2004 | Guarente et al. |
| 2004/0009197 A1 | 1/2004 | DeRosa et al. |
| 2004/0014682 A1 | 1/2004 | Ravagnan et al. |
| 2004/0014721 A1 | 1/2004 | Hensley et al. |
| 2004/0015020 A1 | 1/2004 | Deshpande et al. |
| 2004/0018987 A1 | 1/2004 | Hoffman et al. |
| 2004/0067894 A1 | 4/2004 | Carola et al. |
| 2004/0249938 A1 | 12/2004 | Bunch |
| 2004/0259938 A1 | 12/2004 | Nag et al. |
| 2005/0020511 A1 | 1/2005 | Li et al. |
| 2005/0038125 A1 | 2/2005 | Smit et al. |
| 2005/0049208 A1 | 3/2005 | Kaufmann et al. |
| 2005/0070470 A1 | 3/2005 | Coy et al. |
| 2005/0096256 A1 | 5/2005 | Sinclair |
| 2005/0136429 A1 | 6/2005 | Guarente et al. |
| 2005/0136537 A1 | 6/2005 | Sinclair et al. |
| 2005/0171027 A1 | 8/2005 | Sinclair et al. |
| 2006/0229265 A1 | 10/2006 | Milburn et al. |
| 2007/0300322 A1 | 12/2007 | De Block et al. |

FOREIGN PATENT DOCUMENTS

| | | |
|---|---|---|
| EP | 1 064 931 | 1/2001 |
| WO | 97/07790 | 3/1997 |
| WO | 98/41113 | 9/1998 |
| WO | 98/57928 | 12/1998 |
| WO | 00/21526 | 4/2000 |
| WO | 00/59522 | 10/2000 |
| WO | 00/69430 | 11/2000 |
| WO | 02/49575 | 6/2002 |
| WO | 02/49994 | 6/2002 |
| WO | 03/031404 | 4/2003 |
| WO | 03/039535 | 5/2003 |
| WO | 2004/016726 | 2/2004 |
| WO | 2004/041758 | 5/2004 |
| WO | 2004/105517 | 12/2004 |
| WO | 2005/002527 | 1/2005 |
| WO | 2005/002555 | 1/2005 |
| WO | 2005/002672 | 1/2005 |
| WO | 2005/026112 | 3/2005 |
| WO | 2005/053609 | 6/2005 |
| WO | 2005/065667 | 7/2005 |
| WO | WO 2007/107326 A1 | 9/2007 |

OTHER PUBLICATIONS

UniProt Database—P53184. Printed from the internet on 1011.2009.*

Blander, G. et al., "The SIR2 Family of Protein Deacetylases," Annu. Rev. Biochem. 73:417-435 (2004).

Aguilaniu et al., "Asymmetric Inheritance of Oxidatively Damaged Proteins During Cytokinesis", Science 2003 299:1751-1753.

Benguría et al., "Sir2p suppresses recombination of replication forks stalled at the replication fork barrier of ribosomal DNA in *Saccharomyces cerevisiae*", Nucleic Acids Research 2003 31(3):893-898.

Brachmann et al., "The *SIR2* gene family, conserved from bacteria to humans, functions in silencing, cell cycle progression, and chromosome stability", Genes & Development 1995 9:2888-2902.

Bryk et al., "Transcriptional silencing of Ty1 elements in the *RDN1* locus of yeast", Genes & Development 1997 11:255-269.

Coronado et al., "Alfalfa Root Flavonoid Production Is Nitrogen Regulated", Plant Physiol. 1995 108:533-542.

Defossez et al., "Elimination of Replication Block Protein Fob1 Extends the Life Span of Yeast Mother Cells", Molecular Cell 1999 3:447-455.

Denu, M., "Linking chromatin function with metabolic networks-:Sir2 family of $NAD^+$-dependent deacetylases", Trends in Biochemical Sciences 2003 28(1):41-48.

Dong, Z., "Molecular mechanism of the chemopreventive effect of resveratrol", Mutation Research 2003 523-524:145-150.

Ferguson, R., "Role of plant polyphenols in genomic stability", Mutation Research 2002 475:89-111.

Frye, R.A., "Phylogenetic Classification of Prokaryotic and Eukaryotic Sir2-like Proteins", Biochemical and Biophysical Research Communications 2000 273:793-798.

Glossmann et al., "Quercetin Inhibits Tyrosine Phosphorylation by the Cyclic Nucleotide-Independent, Transforming Protein Kinase, pp. $60^{src}$", Naunyn-Schmiedeberg's Arch Pharmacol 1981 317:100-102.

Gottlieb et al., "A New Role for a Yeast Transcriptional Silencer Gene, SIR2, in Regulation of Recombination in Ribosomal DNA", Cell 1989 56:771-776.

Guarente et al., "Genetic pathways that regulate ageing in model organisms", Nature 2000 408:255-262.

Hekimi et al., "Genetics and the Specificity of the Aging Process", Science 2003 299:1351-1354.

Herzenberg et al., "The History and Future of the Fluorescence Activated Cell Sorter and Flow Cytometry:A View from Stanford", Clinical Chemistry 2002 48:10 1819-1827.

Holla et al., "New bis-aminomercaptotriazoles and bis-triazolothiadiazoles as possible anticancer agents", Eur. J. Med. Chem. 2002 37:511-517.

Holzenberger et al., "IGF-1 receptor regulates lifespan and resistance to oxidative stress in mice", Nature 2003 421:182-187.

Imai et al., "Transcriptional silencing and longevity protein Sir2 is an NAD-dependent histone deacetylase", Nature 2000 403:795-800.

Jang et al., "Cancer Chemopreventive Activity of Resveratrol, a Natural Product Derived from Grapes", Science 1997 275:218-220.

Jazwinski, S. M., "Metabolic Control and Gene Dysregulation in Yeast Aging", Annals New York Academy of Sciences 2000 908:21-30.

Kaeberlein et al., "The *SIR2/3/4* complex and *SIR2* alone promote longevity in *Saccharomyces cerevisiae* by two different mechanisms", Genes & Development 1999 13:2570-2580.

Kenyon, C., "A Conserved Regulatory System for Aging", Cell 2001 105:165-168.

Landry et al., "The silencing protein SIR2 and its homologs are NAD-dependent protein deacetylases", Proc. Natl. Acad. Sci. USA 2000 97(11):5807-5811.

Langley et al., "Human SIR2 deacetylates p53 and antagonizes PML/p53-induced cellular senescence", The EMBO Journal 2002 21(10):2383-2396.

Laurenson et al., "Silencers, Silencing, and Heritable Transcriptional States", Microbiological Reviews 1992 56(4):543-560.

Longo et al., "Evolutionary Medicine:From Dwarf Model Systems to Healthy Centenarians", Science 2003 299:1342-1346.

Middleton et al., "The Effects of Plant Flavonoids on Mammalian Cells:Implications for Inflammation, Heart Disease, and Cancer", Pharmacol Rev 2000 52:673-751.

Monod et al., "On the Nature of Allosteric Transitions:A Plausible Model", J. Mol. Biol. 1965 12:88-118.

Nicolini et al., "Anti-apoptotic effect of *trans*-resveratrol on paclitaxel-induced apoptosis in the human neuroblastoma SH-SY5Y cell line", Neuroscience Letters 2001 302:41-44.

Oliver et al., "Inhibition of Mast Cell Fc R1-mediated Signaling and Effector Function by the Syk-selective Inhibitor, Piceatannol", J. Biol. Chem. 1994 269(47):29697-29703.

Pandey et al., "Analysis of histone acetyltransferase and histone deacetylase families of *Arabidopsis thaliana* suggests functional diversification of chromatin modification among multicellular eukaryotes", Nucleic Acids Research 2002 30(23):5036-5055.

Park et al., "Effects of Mutations in DNA Repair Genes on Formation of Ribosomal DNA Circles and Life Span in *Saccharomyces cerevisiae*", Molecular and Cellular Biology 1999 19(5):3848-3856.

Pont et al., "Relation Between the Chemical Structure and the Biological Activity of Hydroxystilbenes Against *Booytis cinerea*", J. Phytopathology 1990 130:1-8.

Shimokawa et al., "Life span extension by reduction of the growth hormone-insulin-like growth factor-1 axis:relation to caloric restriction", FASEB 2003 17:1108-1109.

Sinclair, D.A., "Paradigms and pitfalls of yeast longevity research", Mechanisms of Ageing and Development 2002 123:857-867.

Sinclair et al., "Extrachromosomal rDNA Circles-A Cause of Aging in Yeast", Cell 1997 91:1033-1042.

Smith et al., "An unusual form of transcriptional silencing in yeast ribosomal DNA", Genes & Development 1997 11:241-254.

Soleas et al., "Resveratrol:A Molecule Whose Time Has Come? And Gone?", Clinical Biochemistry 1997 30(2):91-113.

Stojanovi et al., "Efficiency and Mechanism of the Antioxidant Action of *trans*-Resveratrol and Its Analogues in the Radical Liposome Oxidation", Archives of Biochemistry and Biophysics 2001 391(1):79-89.

Tanner et al., "Silent information regulator 2 family of NAD-dependent histone/protein deacetylases generates a unique product, 1-0-acetyl-ADP-ribose", Proc. Natl. Acad. Sci. USA 2000 97(26):14178-14182.

Tanny et al., "Coupling of histone deacetylation to NAD breakdown by the yeast silencing protein Sir2:Evidence for acetyl transfer from substrate to an NAD breakdown product", Proc. Natl. Acad. Sci. USA 2001 98(2):415-420.

Tanny et al., "An Enzymatic Activity in the Yeast Sir2 Protein that Is Essential for Gene Silencing", Cell 1999 99:735-745.

Tatar et al., "The Endocrine Regulation of Aging by Insulin-like Signals", Science 2003 299:1346-1351.

Tissenbaum et al., "Increased dosage of a sir-2 gene extends lifespan in *Caenorhabditis elegans*", Nature 2001 410:227-230.

Vergnes et al., "Cytoplasmic SIR2 homologue overexpression promotes survival of Leishmania parasites by preventing programmed cell death", Gene 2002 296:139-150.

Borra, MT et al., Mechanism of human SIRT1 activation by resveratrol, J Biol Chem. Apr. 29, 2005; 280(17): 17187-95. Epub Mar. 4, 2005.

Lacey, J., Paul F. Glenn launches labs for aging research, Harvard Medical School Communications, Harvard University Gazette, Mar. 17, 2005.

GenBank Accession No. NP_877591. Oct. 27, 2004. pre-B-Cell colony enhancing factor 1 isoform b.

GenBank Accession No. NP_005737. Oct. 28, 2004. pre-B-cell colony enhancing factor 1 isoform a.

Wu, Z. et al., *Ginkgo biloba* extract EGb 761 increases stress resistance and extends life span of *Caenorhabditis elegans*, Cell Mol Biol (Noisy-le-grand). 2002; 48(6):725-31.

Sun, Ay et al., The "French Paradox" and beyond: neuroprotective effects of polyphenols, Free Radic Biol Med. 2002; 15;32(4):314-8.

GenBank Accession No. BC020691. Jun. 29, 2004. *Homo sapiens* pre-B-cell colony enhancing factor 1.

Sinclair, D., Sirtuins for healthy neurons, Nat Genet. Apr. 2005; 37(4):339-40.

Lamming, D.W. et al., Small molecules that regulate lifespan: evidence for xenohormesis, Mol Microbiol. 2004; 33(4):1003-9.

Wood, J.G. et al., Sirtuin activators mimic caloric restriction and delay ageing in metazoans, Nature. Aug. 5, 2004;430(7000):686-9. Epub Jul. 14, 2004.

Anderson R.M. et al., Nicotinamide and PNC1 govern lifespan extension by caloric restriction in *Saccharomyces cerevisiae*, Nature. May 8, 2003;423(6936):181-5.

Anderson, R.M. et al., Manipulation of a nuclear NAD+ salvage pathway delays aging without altering steady-state NAD+ levels, J Biol Chem. May 24, 2002;277(21):18881-90. Epub Mar. 7, 2002.

Sawada, M. et al., Cytoprotective membrane-permeable peptides designed from the Bax-binding domain of Ku70, Nat Cell Biol. Apr. 2003;5(4):352-7.

Anderson, R.M. et al., Yeast life-span extension by calorie restriction is independent of NAD fluctuation, Science. Dec. 19, 2003;302(5653):2124-6. Epub Nov. 6, 2003.

Bitterman, K.J. et al., Longevity regulation in *Saccharomyces cerevisia*: linking metabolism, genome stability, and heterochromatin, Microbiol Mol Biol Rev. Sep. 2003;6793):376-99.

Bitterman, K.J. et al., Inhibition of silencing and accelerated aging by nicotinamide, a putative negative regulator of yeast sir2 and human SIRT1, J Biol Chem. Nov. 22, 2002;277(47):45099-107. Epub Sep. 23, 2002.

Luo, J. et al., Negative control of p53 by Sir2alpha promotes cell survival under stress, Cell. Oct. 19, 2001;107(2):137-48.

Sawada, M. et al., Ku70 suppresses the apoptotic translocation of Bax to mitochondria, Nat Cell Biol. Apr. 2003;5(4):320-9 (Abstract only).

Bieganowski, P. et al., Discoveries of Nicotinamide Riboside as a Nutrient and Conserved NRK Genes Establish a Preiss-Handler Independent Route to NAD+ in Fungi and Humans, Cell, May 4, 2004;117:495-502.

Brunet, A. et al., Stress-dependent regulation of FOXO transcription factors by the SIRT1 deacetylase, Science. Mar. 26, 2004;303(5666):2011-5. Epub Feb. 19, 2004.

Cohen, H.Y. et al., Acetylation of the C Terminus of Ku70 by CBP and PCAF Controls Bax-Mediated Apoptosis, Mol Cell. Mar. 12, 2004;13:627-638.

Marcotte, P.A. et al., Fluorescence Assay of SIRT protein deacetylases using an acetylated peptide substrate and a secondary trypsin reaction, Analytical Biochemistry 332(2004):90-99.

Bedalov, A. et al., NAD to the Rescue, Science Aug. 13, 2004;305:954-955.

Araki, T. et al., Increased Nuclear NAD Biosynthesis and SIRT1 Activation Prevent Axonal Degeneration, Science, Aug. 13, 2004;305:1010-1013.

Grozinger, C.M. et al., Identification of a Class of Small Molecule Inhibitors of the Sirtuin Family of NAD-dependent Deacetylases by Phenotypic Screening, J Biol. Chem. Oct. 19, 2001;276(42):38837-38843.

Bedalov, A. et al., Identification of a small molecule inhibitor of Sir2p, PNAS, Dec. 18, 2001;98:15113-15118.

Hirao, M. et al., Identification of Selective Inhibitors of $NAD^+$-dependent Deacetylases Using Phenotypic Screens in Yeast, J Biol. Chem. Dec. 26, 2003;278(52):52773-58782.

Zhao, K. et al., Structural basis for nicotinamide cleavage and ADP-ribose transfer by $NAD^+$-dependant Sir2 histone/protein deacetylases, PNAS, Jun. 8, 2004;101(23):8563-8. Epub May 18, 2004.

Rogina, B. et al., Longevity Regulation by Drosophila Rpd3 Deacetylase and Caloric Restriction, Science, Nov. 29, 2002;298:1745.

Aging Research's Family Feud, Science, Feb. 27, 2004;303:1276-1279.

Kimura, Y. et al., Pharmacological Studies on Resveratrol, Methods Find Exp Clin Pharmacol, 2003;25(4):297-310.

De Cabo, R. et al., An in vitro model of caloric restriction, Experimental Gerontology, 2003;38:631-639.

Nemoto, S. et al., Nutrient Availability Regulates SIRT1 Through a Forkhead-Dependent Pathway, Science, Dec. 17, 2004;306:2105-2108.

Porcu, M. et al., The emerging therapeutic potential of sirtuin-interacting drugs: from cell death to lifespan extension, Trends in Pharmacological Sciences, Feb. 2005;26(2): 94-103.

Ignatowicz, E. et al., Resveratrol, A Natural Chemopreventive Agent Against Degenerative Diseases, Pol J Pharmacol, 2001;53:557-569.

Motta C.M. et al., Mammalian SIRT-1 Represses Forkhead Transcription Factors, Cell, Feb. 20, 2004;116(4):551-63. Epub Feb. 5, 2004.

Campisi, J., Aging, Chromatin, and Food Restriction-Connecting the Dots, Science, Sep. 22, 2000;289:2062-2063.

Lin, Su-Ju et al., Requirement of NAD and SIR2 for Life-Span Extension by Calorie Restriction in Saccharomyces cerevisiae, Science, Sep. 22, 2000;289:2126-2128.

Pugh, T.D. et al., Controlling caloric consumption: protocols for rodents and rhesus monkeys, Neurobiology of Aging, Apr. 20, 1999;157-165.

Subramanian, C. et al., Ku70 acetylation mediates neuroblastoma cell death induced by histone deacetylase inhbitors, PNAS Mar. 29, 2005;102(13):4842-4847.

Cohen, H.Y. et al., Calorie Restriction Promotes Mammalian Cell Survival by Inducing the SIRT1 Deacetylase, Science, Jul. 16, 2004;305:390-392.

Mai, A. et al., Histone Deacetylation in Eipgenetics: An Attractive Target for Anticancer Therapy, Medicinal Research Reviews, 2005;25:261-309.

Johnstone, R.W. et al., Histone deacetylase inhibitors in cancer therapy: Is transcription the primary target? Cancer Cell, Jul. 2003;4:13-18.

Yoshida, M. et al., Histone deacetylase as a new target for cancer chemotherapy, Cancer Chemother Pharmacol, 2001;48(1):520-526.

Kaeberlein, M. et al., The SIR2/3/4 complex and SIR2 alone promote longevity in Saccharomyces cerevisiae by two different mechanisms, Genes & Development, 1999; 13L2570-2580.

Aiston, S. et al., Glucose 6-phosphate causes translocation of phosphorylase in hepatocytes and inactivates the enzyme synergistically with glucose, Biochem J., 2004;377:195-204.

Bergeron, R. et al., Effect of 5-Aminoimidazole-4-Carboxamide-1-β-D-Ribofuranoside Infusion on In Vivo Glucose and Lipid Metabolism in Lean and Obese Zucker Rats, Diabetes, May 2001;50:1076-1082.

Zhou, G. et al., Role of AMP-activated protein kinase in machanism of metformin action, The Journal of Clinical Investigation, Oct. 2001;108(8):1167-1174.

Zern, T. et al., Grape Polyphenols Decrease Plasma Triglycerides and Cholesteral Accumulation in the Aorta of Ovariectomized Guinea Pigs[1], J. Nutr., 2003;133:2268-2272.

Howitz, K. et al., Small molecule activators of sirtuins extend Sacdharomyces cerevisiae lifespan, Nature, Sep. 11, 2003;425:191-196.

Picard, F. et al., Sirt1 promotes fat mobilization in white adipocytes by repressing PPAR-, Jun. 17, 2004;429(6993):771-6. Epub Jun. 2, 2004.

Guarente Describes Investigation into Longevity Gene at Dean's Distinguished Lecture Series, Harvard Public Health Now, Feb. 20, 2004:1-3.

Brehm, D., The skinny of fat: MIT researchers establish first link between eating and aging, Massachusetts Institute of Technology, Jun. 2, 2004.

Glam, F., PA Scientists may be on to antiaging compound, Philadelphia Inquirer; Sep. 10, 2003.

Sampson, M.T., Compound Identified in Grapes May Fight Cancer and Diabetes, htt://prohealth.com; May 27, 2002.

Michael, L., Compound in Blueberries May Prevent Heart Disease and Type 2 Diabetes, Healthy Living NYC; 2005.

American Federation for Aging Research, The Latest Research on Caloric Restriction and Animal and Human Longevity; Jul. 8, 2003.

Harvard Medical School, Molecules Discovered That Extend Life in Yeast, Human Cells, Science Blog, Aug. 2003.

Nicholas Wade, Study Spurs Hope of Finding Way to Increase Human Life, The New York Times, Aug. 25, 2003.

Study Sheds Light on Wine's Benefits, Reuters, Aug. 25, 2003.

Stephen Smith, In Lab, seeking secret of youth, Chemical abundant in red wine appears to slow aging in study, The Boston Globe, Aug. 25, 2003.

Michael LaSalandra,Wine, less dine: Age study eyes low-calorie diet . . . and a glass of red, Boston Herald, Aug. 25, 2003.

Rick Weiss, Enzymes Found to Delay Aging process, The Washington Post, Aug. 25, 2003.

To Red Wine, Long Life, Newsday.com, Aug. 26, 2003.

Lydia Polgreen, Selling Red Wine as Good (and Good for You), The New York Times, Aug. 26, 2003.

Grape Expections, The Boston Globe Editorial, Aug. 29, 2003.

Rowland, Nethaway, Do life spans of biblical proportions await us?, The Atlanta Journal Constitution, Sep. 2, 2003.

Lidia Wasowicz, Red wine ingredient may extend life, United Press International, Aug. 28, 2003.

Hildebrandt, H., Pschyrembel Klinisches Woerterbuch, 1998, XP002141063:47-49.

Parfiit et al., Antineoplastics and Immunosuppressants, Pharmaceutical Press, London, 1995, XP002329271, Martindale $32^{nd}$ ed.

Bagchi et al., Phytoestrogen, Resveratrol and Women's Health, Research Communications in Pharmacology and Toxicology, vol. 5., Nos. 1&2, 2000 XP-001018765.

Berkow R. et al., Merck Manual of Diagnosis and Therapy, 1987, Merck Manual of Diagnosis and Therapy, Rahway, Merck & Co., US, XP002141064:pp. 2392.

Sandmeier, J. et al., Telomeric and rNDA Silencing in Saccharomyces cerevisiae Are Dependent on a Nuclear NAD+ Salvage Pathway, Genetics, Mar. 2002;160:877-889.

Smith, J. et al., A phylogenetically conserved NAD+-dependent protein deacetylase activity in the Sir2 protein family, Proc. Natl. Acad. Sci. USA, Jun. 6, 2000;97(12):6658-6663.

Zhang, H. et al., Crystal Structures of *E. coli* Nicotinate Mononucleotide Adenylyltransferase and Its Complex with Deamido-NAD, Structure, Jan. 2002;10:69-79.

Raffaelli, N. et al., Identification of a novel human nicotinamide mononucleotide adenylyltransferease, Biochem Biophys Res Commun Oct. 4, 2002;297 (Abstract only).

Vaziri, H. et al., hSIR2SIRT1 Functions as an NAD-Dependent p53 Deacetylase, Cell, Oct. 2001;107:149-159.

Mills, K. et al., *MEC1*-Dependent Redistribution of the Sir3 Silencing Protein from Telomeres to DNA Double-Strand Breaks, Cell. May 28, 1999;97:609-620.

Khanna, S. et al., Dermal Would Healing Properties of Redox-Active Grape Seed Proanthocyanidins, Free Radical Biology & Medicine, 2002;33(8):1089-1096.

Regev-Shoshani, G. et al., Glycosylation of resveratrol protects it from enzymatic oxidation, Biochemical Journal Aug. 15, 2003;374:157. e-pub Apr. 16, 2003.

Brandolini, V. et al., Capillary Electrophoresis Determination, Synthesis, and Stability of Resveratrol and Related 3-*O-B-D*-Glucopyranosides, Journal of Agricultural and Food Chemistry, 2002;50:7407-7411.

South, James, Resveratrol & Quercetin—pro Heart & anti-Cancer, Offshore Pharmacy, Jun. 26, 2003 or earlier.

Perez, J. et al., Synthesis and characterization of complexes of *p*-isopropyl benzaldehyde and methyl 2-pyridyl ketone thiosemicarbazones with Zn(II) and Cd(II) metallic centers. Cytotoxic activity and induction of apoptosis in Pam-*ras* cells, J. of Inorganic Biochemistry, 1999;75:255-261.

Koubova, J. et al, How does calorie restriction work? Genes & Development, 2003;17:313-321.

Kaeberlein, M. et al., High Osmolarity Extends Life Span in *Saccharomyces cerevisiae* by a Mechanism Related to Calorie Restriction, Molecular and Cellular Biology, Nov. 2002;22(22):8056-8066.

Bastianetto, S. et al Reversatrol and Red Wine Constituents: Evaluation of Their Neuroprotective Properties, Pharmaceutical Nerws 2001 : 8(5):33-38.

Fukuhara, A. et al., Vistatin: A Protein Secreted by Visceral Fat that Mimics the Effects of Insulin, Sciencexpress/www.sciencexpress.org/Dec. 16, 2004:1/10.1126.

Jai, S. H. et al, Pre-B cell colony-enhancing factor inhibits neutrophil apoptosis in experimental inflammation and clinical sepsis, J. Clin. Invest., 2004;113:1318-1327.

Revollo, J. et al, The NAD Biosynthesis Pathway Mediated by Nicotinamide Phosphoribosyltransferase Regulates Sir2 Activity in Mammalian Cells*, The Journal of Biological Chemistry, Dec. 3, 2004;279(49):50754-50763.

Samal, B. et al., Cloning and Characterization of the cDNA Encoding a novel Human Pre-B-Cell Colony-Enhancing Factor, Molecular and Cellular Biology, Feb. 1994;14(2):1431-1437.

Ognjanovic, S. et al., Genomic organization of the gene coding for human pre-B-cell colony enhancing factor and expression in human fetal membranes, Journal of Molecular Endocrinology, 2001;16:107-117.

Hendrickson, Dyke, A dietary magic bullet? Harvard team says pill will fight effects of high-fat eating, The Journal of New England Technology, Mass. High Tech, Dec. 8-14, 2003.

Dajas, F. et al., Cell culture protection and in vivo neuroprotective capacity of flavonoids, Neurotox Res. 2003;5(6):425-32. (Abstract only).

Lui, M. et al., Antimalarial Alkoxylated and Hydroxylated Chalones: Structure—Activity Relationship Analysis, J. Med. Chem. 2004;(4):4443-4452.

Kris-Etherton P. et al., Bioactive Compounds in Foods: Their Role in the Prevention of Cardiovascular Disease and Cancer, Am. J. Med. 2002;113(9B):71S-88S.

Hu, H.L. et al., Antioxidants may contribute in the fight against ageing: an in vitro model, Mechanisms of Aging and Development, 2000, 121:217-230.

Graefe, E. U. et al., Pharmacokinetics and bioavailability of the flavonol quercetin in humans, Intl. J. of Clin. Pharmacology and Therapeutics, 1999;37(5):219-233.

Morino, M. et al., Specific Regulation of HSPs in Human Tumor Cell Lines by Flavonoids, In Vivo, 1997;11:265-270.

Nothwehr, S; et al., A Retention factor keeps death at bay, Nature Cell Biology, Apr. 2003;5:281-283.

Chua, K.F. et al., Mammalian SIRT1 limits replicative life span in response to chronic genotoxic street, Cell Metabolism, Jul. 2005;2:67-76.

Gallo et al., "Nicotinamide Clearance by Pnc1 Directly Regulates Sir2-Mediated Silencing and Longevity," Molecular and Cellular Biology, 24(3):1301-1312 (2004).

Balan, V. et al., "Lifespan Extension and Neuronal Cell Protection by *Drosophila* Nicotinamidase," The Journal of Biological Chemistry Published on Aug. 4, 2008 as Manuscript M804681200; JBC Papers in Press; printed from http://www.jbc.org/cgi/doi/10.1074/jbc.M8041681200.

Aksoy et al., Human liver nicotinamide N-methyltransferase. cDNA cloning, expression, and biochemical characterization. J Biol Chem. May 20, 1994;269(20):14835-40.

Balan et al., Life span extension and neuronal cell protection by *Drosophila nicotinamidase*. J Biol Chem Oct. 10, 2008;283(41):27810-9. Epub Aug. 4, 2008. Supplemental Materials Included.

Belenky et al., Nicotinamide riboside promotes Sir2 silencing and extends lifespan via Nrk and Urhl/Pnpl/Meu1pathways to NAD+. Cell. May 4, 2007;129(3):473-84.

Crowley et al., The NAD+ precursors, nicotinic acid and nicotinamide protect cells against apoptosis induced by a multiple stress inducer, deoxycholate. Cell Death Differ. Mar. 2000;7(3):314-26.

Dai et al., SIRT1 activation by small molecules: kinetic and biophysical evidence for direct interaction of enzyme and activator. J Biol Chem. Oct. 22, 2010;285(43):32695-703. Epub Aug. 11, 2010.

Dragovic et al., Phase I/II study of pentoxifylline and nicotinamide in combination with radiation therapy in locally advanced cancers. International Journal of Radiation Oncology Biology Physics. 1992;24(1):272-273. Abstract.

Emanuelli et al., Molecular cloning, chromosomal localization, tissue mRNA levels, bacterial expression, and enzymatic properties of human NMN adenylyltransferase. J Biol Chem. Jan. 5, 2001;276(1):406-12.

Gotoh, Inhibitory effects of nicotinamide on the growth of transplanted murine breast cancer and urethane-initiated lung tumorigenesis in mice. Vitamins (Japan). 1993;67(9):469-479, Y-English Abstract.

Knip et al., Safety of high-dose nicotinamide: a review. Diabetologia. Nov. 2000;43(11):1337-45. Review.

Ledford, Much ado about ageing. Nature. Mar. 2010;464:480-481.

Min et al., Crystal structure of a SIR2 homolog-NAD complex. Cell. Apr. 20, 2001;105(2):269-79.

Pacholec et al., SRT1720, SRT2183, SRT1460, and resveratrol are not direct activators of.

SIRT1. J Biol Chem. Mar. 12, 2010;285(11):8340-51. Epub Jan. 8, 2010. Supplemental Materials Included.

Pacholec et al., SRT1720, SRT2183 and SRT1460 do not activate Sirt1 with native substrates. Poster 30. FASEB Summer Research Conferences. Arizona. Jun. 21-26, 2009.

Raffaelli et al., Identification of a novel human nicotinamide mononucleotide adenylyltransferase. Biochem Biophys Res Commun Oct. 4, 2002;297(4):835-40.

Sasaski et al., Stimulation of nicotinamide adenine dinucleotide biosynthetic pathways delays axonal degeneration after axotomy. J Neurosci. Aug. 16, 2006;26(33):8484-91.

Sestili et al., Structural requirements for inhibitors of poly(ADP-ribose) polymerase. J Cancer Res Clin Oncol. 1990;116(6):615-22.

Van Der Horst et al., The *Caenorhabditis elegans* nicotinamidase PNC-1 enhances survival. Mech Ageing Dev. Apr. 2007;128(4):346-9. Epub Feb. 2, 2007.

Van Der Veer et al., Extension of human cell lifespan by nicotinamide phosphoribosyltransferase. J Biol Chem. Apr. 13, 2007;282(15):10841-5. Epub Feb. 16, 2007.

Wang et al., Nicotinamidase participates in the salvage pathway of NAD biosynthesis in *Arabidopsis*. Plant J. Mar. 2007;49(6):1020-9.

Yang et al., Nampt/PBEF/Visfatin: a regulator of mammalian health and longevity? Exp Gerontol. Aug. 2006;41(8):718-26. Epub Jul. 13, 2006.Review.

Yang et al., Nutrient-sensitive mitochondrial NAD+ levels dictate cell survival. Cell. Sep. 21, 2007;130(6):1095-107.

Genbank Submission; NIH/NCBI, Accession No. AAH20691; Strausberg.; Jan. 22, 2002.

Genbank Submission; NIH/NCBI, Accession No. AAH85681; Strausberg et al.; Nov. 12, 2004.

Genbank Submission; NIH/NCBI, Accession No. AAT72933; Revollo et al.; Nov. 29, 2004.

Genbank Submission; NIH/NCBI, Accession No. EAA35311; Galagan et al.; Mar. 12, 2003.

Genbank Submission; NIH/NCBI, Accession No. EAK92917; Jones et al.; Apr. 21, 2004.

Genbank Submission; NIH/NCBI, Accession No. NP_001011388; Strausberg et al.; Jan. 30, 2005.

Genbank Submission; NIH/NCBI, Accession No. NP_986013; Dietrich et al.; Mar. 5, 2004.

Genbank Submission; NIH/NCBI, Accession No. NP_997833; Strausberg et al.; May 9, 2004.

Genbank Submission; NIH/NCBI, Accession No. XP_444840; Dujon et al.; Jul. 14, 2004.

Genbank Submission; NIH/NCBI, Accession No. XP_456073; Dujon et al.; Jul. 15, 2004.

Genbank Submission; NIH/NCBI, Accession No. XP_500320; Dujon et al.; Jul. 23, 2004.

Genbank Submission; NIH/NCBI, Accession No. XP_567125; Loftus et al.; Jan. 28, 2005.

* cited by examiner

Figure 2
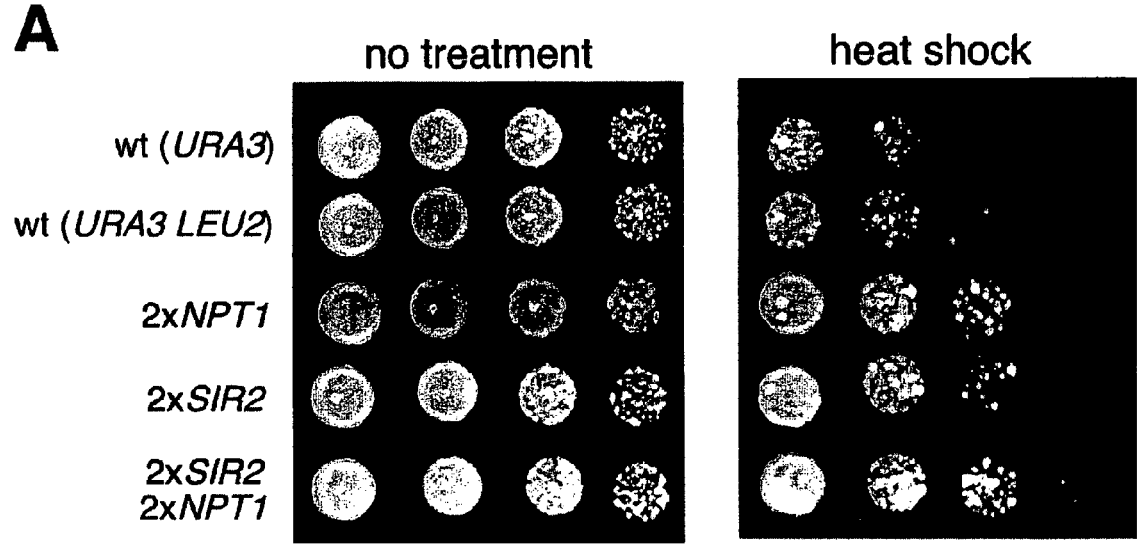
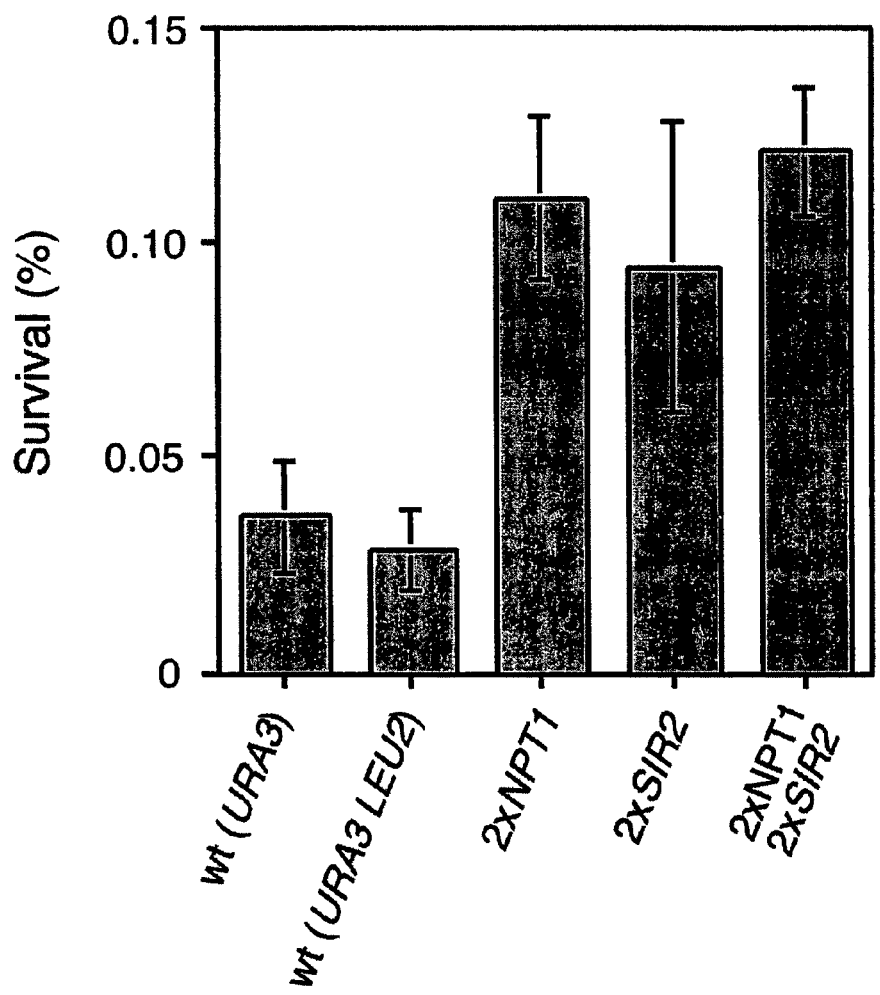

Figure 5
A
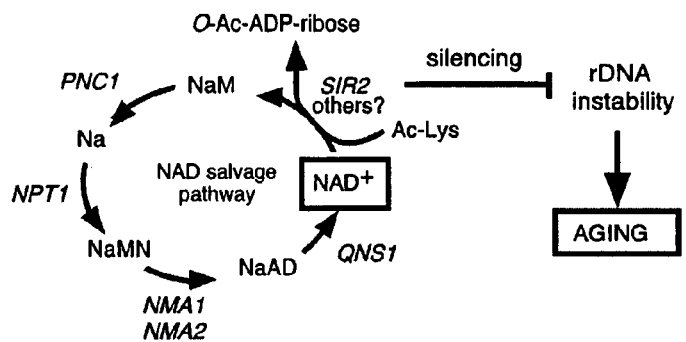
B
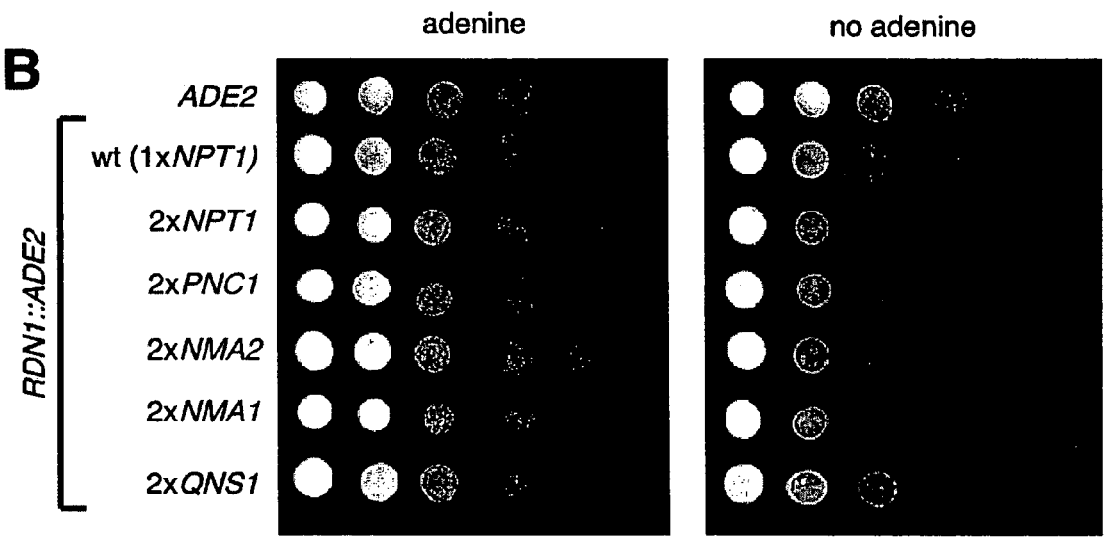
C
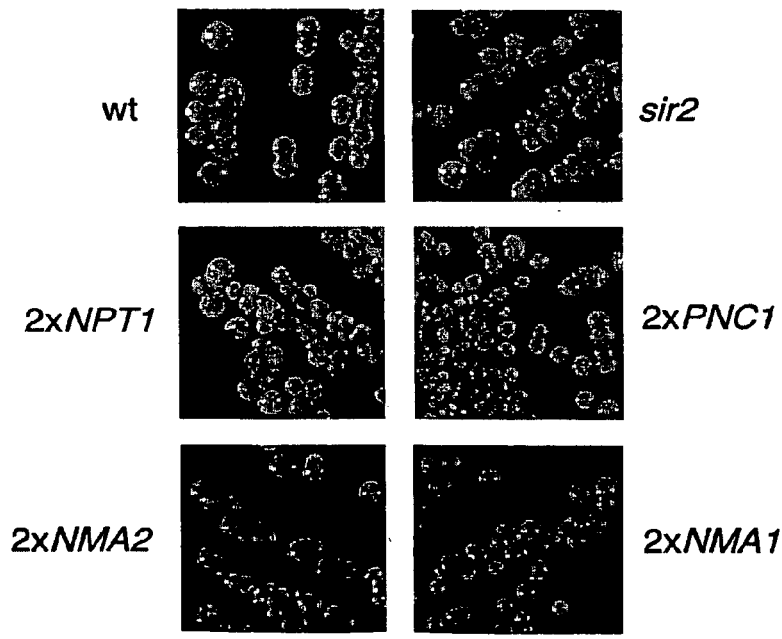

Figure 8
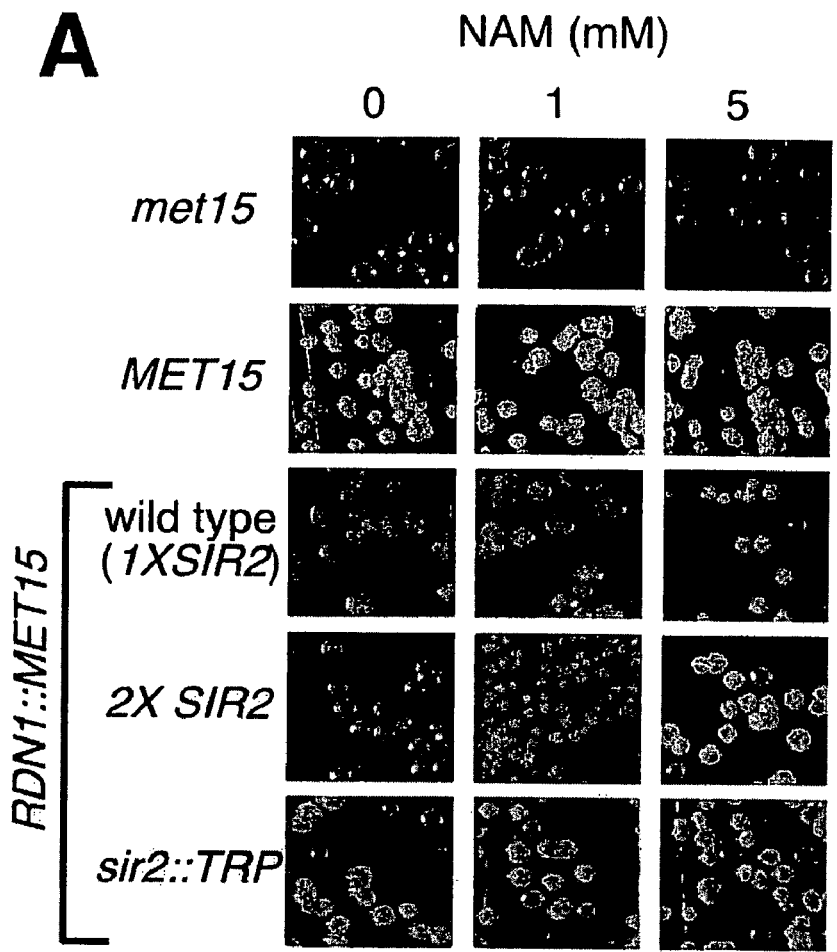
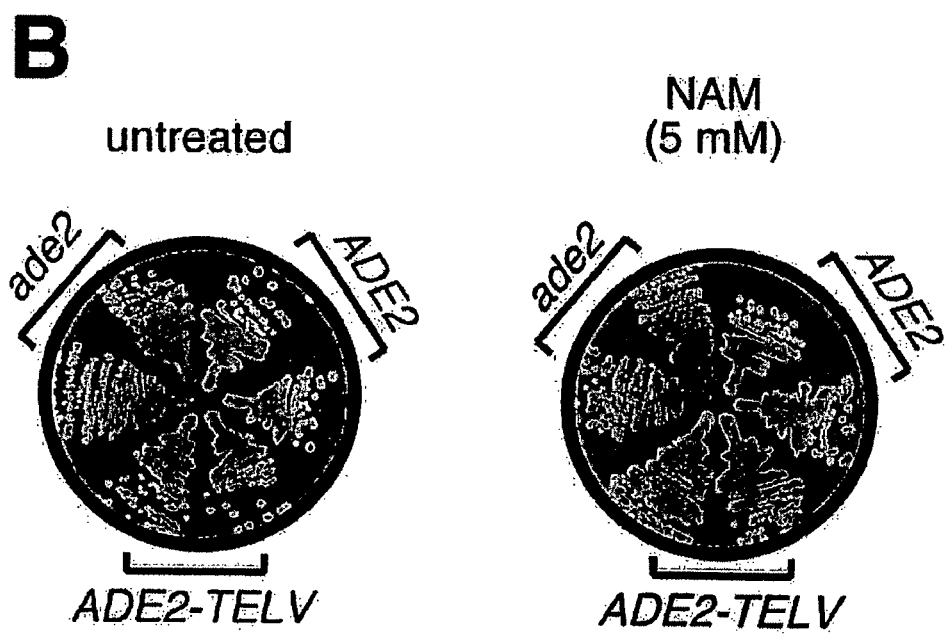

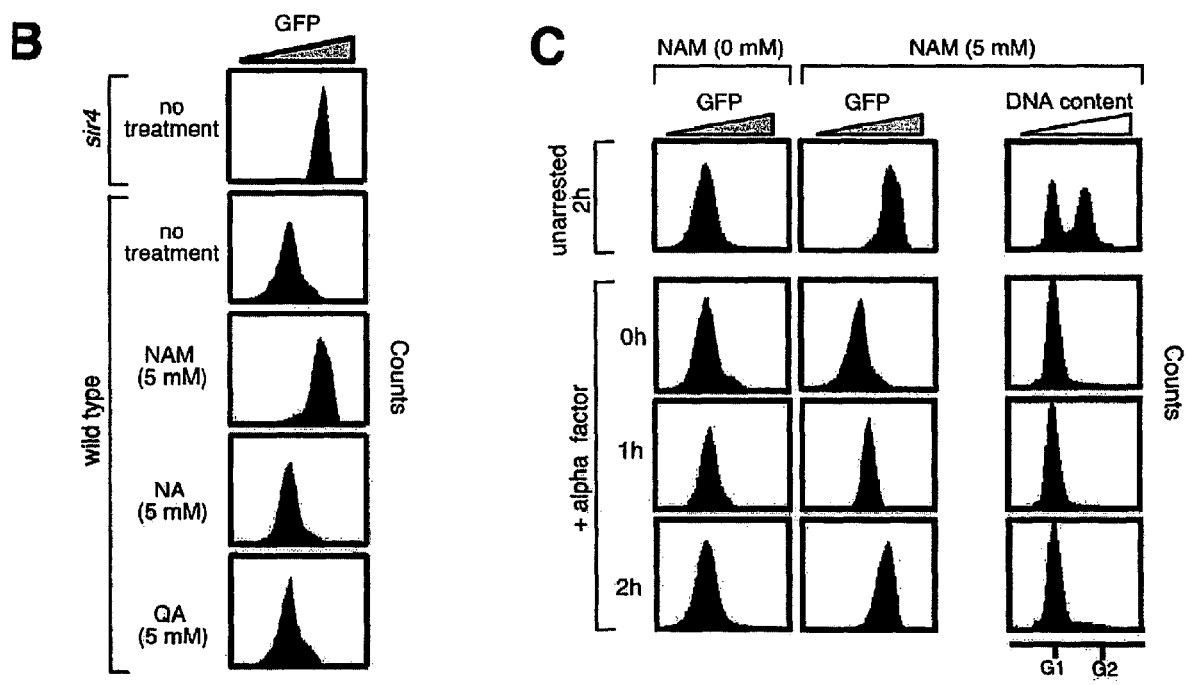
Figure 10B & C

Figure 16

```
humanAAH17344      1   - - - - - - - - - - - - - - - - - - - - - - - - - - - - - - -   0
humanNP_078986     1   - - - - - - - - - - - - - - - - - - - - - - - - - - - - - - -   0
humanXP_041059    58   Y G D Q I D M H R K F V V Q L F A E E W G Q Y V D L P - K G F A  88
humanNP_05712      1   - - - - - - M H R K F V V Q L F A E E W G Q Y V D L P - K G F A  25
flyAAF55694       45   S Q D S N D N L T S C S L C V C V C Q S L R I V R P V - N A F L  71
S.cerevisiaePnc1  -1   - - - - - - - - - - - - - - - - - - - - - - - M - K T L          5 humanAAH17344     -1   - - - - - - -                                                    17
humanNP_078986     1   - - - - - - -                                                    17
humanXP_041059    89   V S E R C K V R L V P - - - - Q Q L     N                       116
humanNP_05712     26   V S E R C K V R L V P - - - - Q Q L     N                        53
flyAAF55694       72   I V S G S N D F S N             A Q Q Q   H E   L E   I N      103
S.cerevisiaePnc1   6   V S P M Q N D F I                 T V K G E E   I N   I S        33 humanAAH17344     18                                                                    49
humanNP_078986    18                                                                    49
humanXP_041059   117                           R   P A K   D       V   Q     Q         148
humanNP_05712     54                           R   P A K   D       V   Q     Q          85
flyAAF55694      104   K     D T D - -   D A V     D W H P   D H   S     N V K         133
S.cerevisiaePnc1  34   D   M Q D A D R D W H R I V V R D W H P   R H   S     N H K      65 humanAAH17344     50   - - - - - - - - -                                                73
humanNP_078986    50   - - - - - - - - -                                                73
humanXP_041059   149   - - - - - - - G                     K       G       Q E   D    172
humanNP_05712     86   - - - - - - - G                   Y K       G   S   Q E   D    109
flyAAF55694      134   M R P M D E S S A L   D   A K V F D   V I F A G   P M K Q R    165
S.cerevisiaePnc1  66   D K - - - - - - -   P   S Y T   Y   S R   G D D   T Q   S        89 humanAAH17344     74       G L R -   L   A K   G   S M V -   A   Q Q E   D S R   Q L S 103
humanNP_078986    74       G L R -   L   A K   G   S M V -   A   Q Q E   D S R   Q L S 103
humanXP_041059   173     T C V K L V     K T K   S M V L   E V E A A   A E I   G V     204
humanNP_05712    110     T C V K L V     K T K   S M V L   E V E A A   A E I   G V     141
flyAAF55694      166   W   R H C V Q D S   G A E T H - - - K D L K V V D H G   I K V   194
S.cerevisiaePnc1  90   W P V H C V K N T   G S Q L V D Q   M D Q V   T K H I K   V D  121 humanAAH17344    104                             N - - - - - - - - - - - - - - -   T  119
humanNP_078986   104                             N D P R S Y P G L A L T S L Y P Q N    135
humanXP_041059   205                             Q Q - - - - - - - - - - - - - - - T A 220
humanNP_05712    142                             Q Q - - - - - - - - - - - - - - - T A 157
flyAAF55694      195   K C   N   E V D S   S V   W - - - - - - - - - - - - - - - D N  210
S.cerevisiaePnc1 122   K G     D R E Y   S A     - - - - - - - - - - - - - - - - D    137 humanAAH17344    120                                                                   151
humanNP_078986   136                                                                   167
humanXP_041059   221         G   V E           A T S S R S   M D R M   A L E R        252
humanNP_05712    158         G   G V E         A T S S R S M M D R M   A - - R        187
flyAAF55694      211   K     D T   N A   K M K     D I   V G - -   A   D V G          240
S.cerevisiaePnc1 138   W N   H K T D M K Y   E K H H   D E V   I   G - -   A   E Y     167 humanAAH17344    152                                     - - - - - - - - -            174
humanNP_078986   168                                     - - - - - - - - -            190
humanXP_041059   253   A R         T   S E A V   Q L V A D K D - - - - - - - - -      275
humanNP_05712    188   T S R - - - - - - - - - - - - - - - - - - - - S N C D H        195
flyAAF55694      241   V G   A T A V D A   A G Y R T I     D D C R G T D V H D I E H  272
S.cerevisiaePnc1 168   V K     A     S A A E L G   K T T V   D V   R - - - - - - -    190 humanAAH17344    175   - - - - - - - - - - - - - - - - - - - - - P Q E K E I Q K L    183
humanNP_078986   191   - - - - - - - - - - - - - - - - - - - - - P Q E K E I Q K L    199
humanXP_041059   276   - - - - - - - - - - - - - - - - - - - - -   K E   Q N          284
humanNP_05712    196   - - - - - - - - - - - - - - - - - - - - - S D H   - - - -      199
flyAAF55694      273   T K E K V N T S D G V I V H T N Q V K A M A E   R D R R P E L G 304
S.cerevisiaePnc1 191   - - - - - - - - - - - - - - - - - - - - - P   I S D D P E V     199 humanAAH17344    184         - -   A P D S G   L G   T     G Q N S   H - - - - - -    205
humanNP_078986   200         - -   A P D S G   L G   T     G Q N S   H - - - - - -    221
humanXP_041059   285         A S - -   A P   S G     L S K V - - - - - - - - -        298
humanNP_05712      0   - - - - - - - - - - - - - - - - - - - - - - - - - - - - -     199
flyAAF55694      305     K L A - - M E L K   P D   V   S Q R   N G   R P S Y - - - - - 328
S.cerevisiaePnc1 200   N   V K - - E E L K   H N   N V V D K - - - - - - - - -        216
```

Figure 21
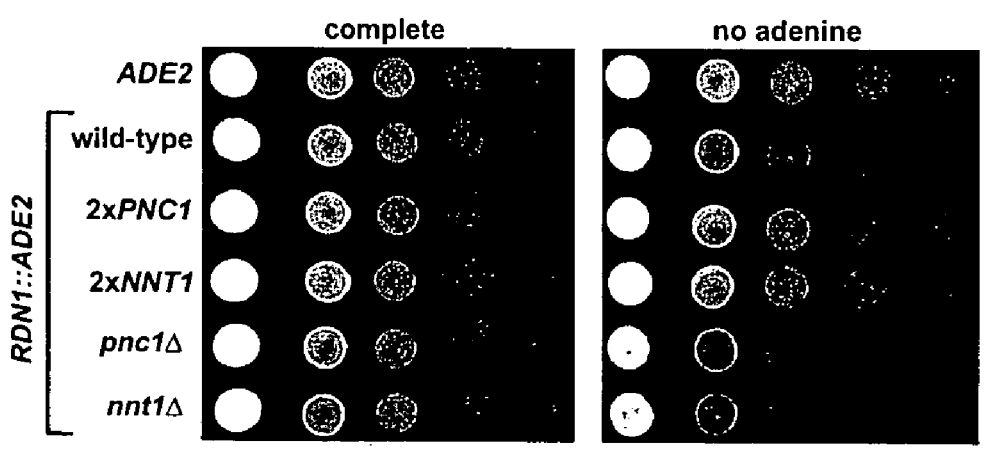
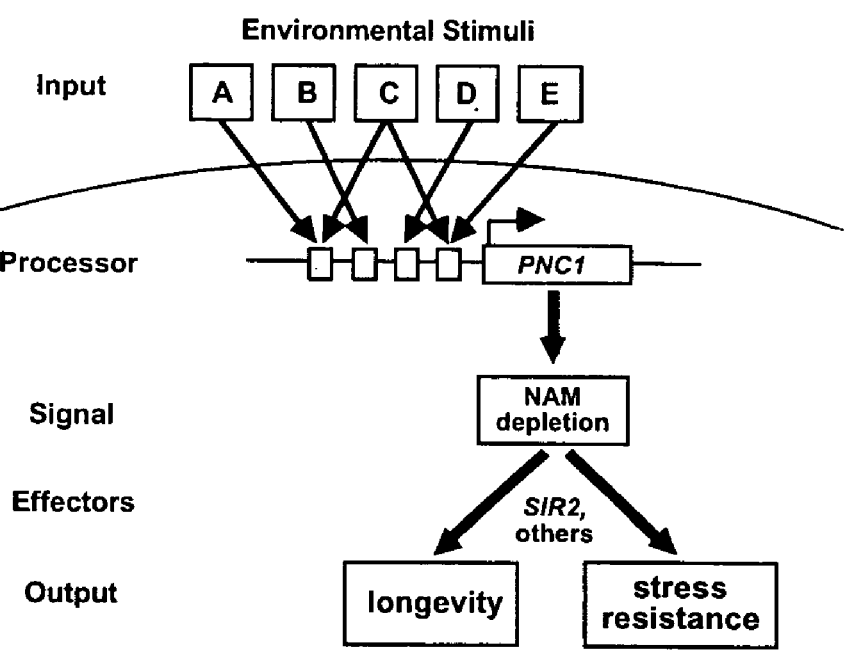

PBEF is higher in the serum of rats subjected to caloric restriction

Western Blot B rat serum - mAb

AL — Ad Libitum Fed
CR — Caloric Restriction

PBEF is up-regulated by serum starvation and oxidative stress in MEFs
Figure 23
A. Western blot
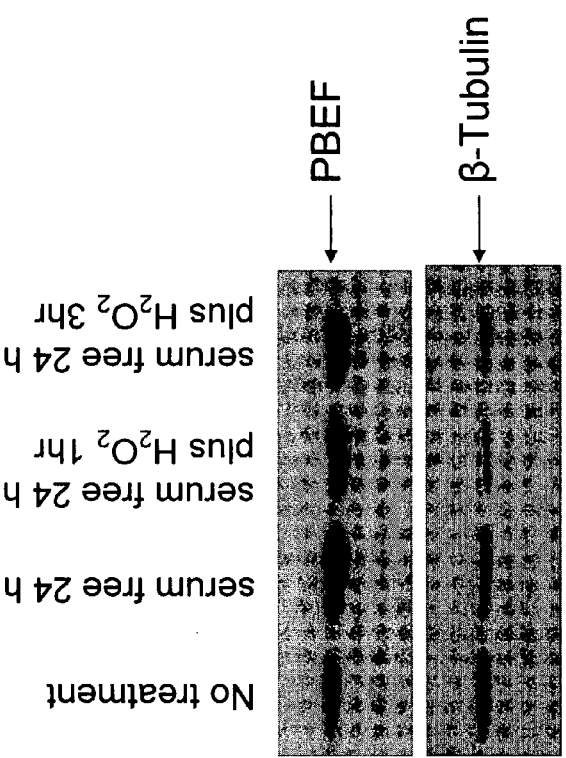
B. Relative folds of PBEF in MEFs upon stresses by integration
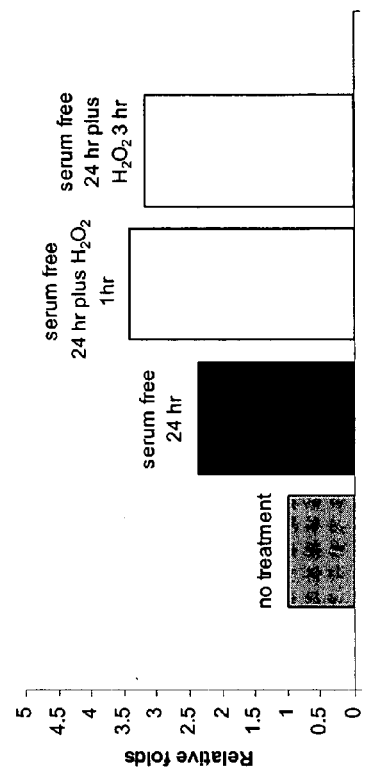

PBEF is up-regulated in cardiomyocytes by serum starvation and hypoxia
Figure 24
A. Western blot
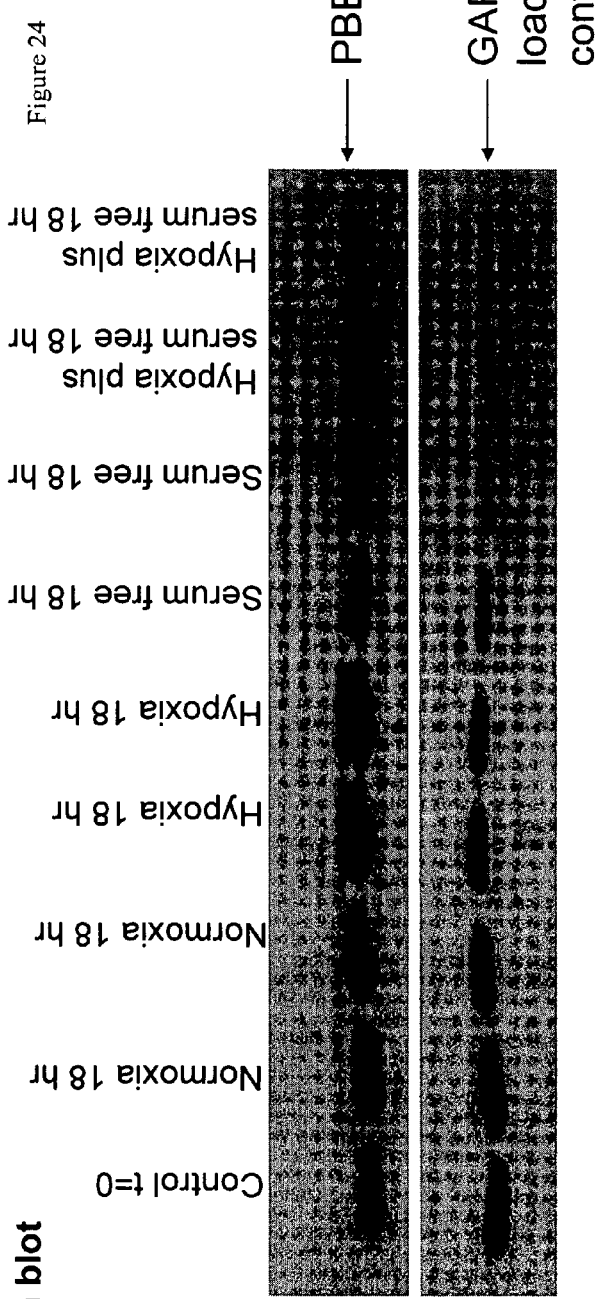
B. Relative fold increase in of PBEF in cardiomyocytes by stress
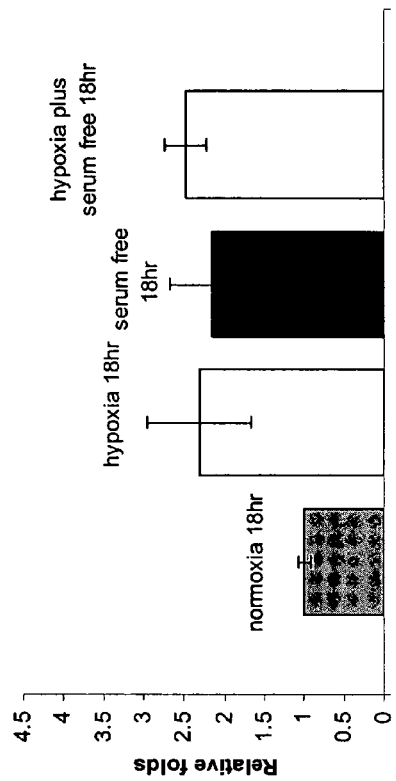

**PBEF transcription is up-regulated by fasting *in vivo* in rats**

The relative PBEF mRNA copies were measured by real time RT-PCR compared with mRNA copies of beta-actin.

METHODS AND COMPOSITIONS FOR EXTENDING THE LIFE SPAN AND INCREASING THE STRESS RESISTANCE OF CELLS AND ORGANISMS

CROSS-REFERENCE TO RELATED APPLICATIONS

This application claims the benefit of International Application No. PCT/US2003/025016, filed Aug. 8, 2003 and published in English under PCT article 21(2), which claims the benefit of U.S. Provisional Application No. 60/402,254, filed Aug. 9, 2002 and U.S. Provisional Application 60/428,614, filed Nov. 22, 2002. These applications are specifically incorporated by reference herein.

STATEMENT OF RIGHTS

This invention was made with government support under RO1 GM068072 awarded by the National Institutes of Health. The government has certain rights in the invention.

BACKGROUND OF THE INVENTION

Physiological studies and, more recently, DNA array analysis of gene expression patterns have confirmed that aging is a complex biological process. In contrast, genetic studies in model organisms have demonstrated that relatively minor changes to an organism's environment or genetic makeup can dramatically slow the aging process. For example, the life span of many diverse organisms can be greatly extended simply by limiting calorie intake, in a dietary regime known as caloric restriction (1-3).

How can simple changes have such profound effects on a complex process such as aging? A picture is emerging in which all eukaryotes possess a surprisingly conserved regulatory system that governs the pace of aging (4,5). Such a regulatory system may have arisen in evolution to allow organisms to survive in adverse conditions by redirecting resources from growth and reproduction to pathways that provide stress resistance (4,6).

One model that has proven particularly useful in the identification of regulatory factors of aging is the budding yeast, *S. cerevisiae*. Replicative life span in *S. cerevisiae* is typically defined as the number of buds or "daughter cells" produced by an individual "mother cell" (7). Mother cells undergo age-dependent changes including an increase in size, a slowing of the cell cycle, enlargement of the nucleolus, an increase in steady-state NAD$^+$ levels, increased gluconeogenesis and energy storage, and sterility resulting from the loss of silencing at telomeres and mating-type loci (8-13). An alternative measure of yeast life span, known as chronological aging, is the length of time a population of non-dividing cells remains viable when deprived of nutrients (14). Increased chronological life span correlates with increased resistance to heat shock and oxidative stress, suggesting that cumulative damage to cellular components is a major cause of this type of aging (14,15). The extent of overlap between replicative and chronological aging is currently unclear.

One cause of yeast replicative aging has been shown to stem from the instability of the repeated ribosomal DNA (rDNA) locus (16). This instability gives rise to circular forms of rDNA called ERCs that replicate but fail to segregate to daughter cells. Eventually, ERCs accumulate to over 1000 copies, which are thought to kill cells by titrating essential transcription and/or replication factors. (16-18). Regimens that reduce DNA recombination such as caloric restriction or a fob1 deletion extend replicative life span (17,19,20).

A key regulator of aging in yeast is the Sir2 silencing protein (17), a nicotinamide adenine dinucleotide (NAD$^+$)-dependent deacetylase (21-24). Sir2 is a component of the heterotrimeric Sir2/3/4 complex that catalyzes the formation of silent heterochromatin at telomeres and the two silent mating-type loci (25). Sir2 is also a component of the RENT complex that is required for silencing at the rDNA locus and exit from telophase (26,27). This complex has also recently been shown to directly stimulate transcription of rRNA by Pol I and to be involved in regulation of nucleolar structure (28).

Biochemical studies have shown that Sir2 can readily deacetylate the amino-terminal tails of histones H3 and H4, resulting in the formation of 1-O-acetyl-ADP-ribose and nicotinamide (21-23,29). Strains with additional copies of SIR2 display increased rDNA silencing (30) and a 30% longer life span (17). It has recently been shown that additional copies of the *C. elegans* SIR2 homolog, sir-2.1, greatly extend life span in that organism (31). This implies that the SIR2-dependent regulatory pathway for aging arose early in evolution and has been well conserved (4). Yeast life span, like that of metazoans, is also extended by interventions that resemble caloric restriction (19,32). Mutations that reduce the activity of the glucose-responsive cAMP (adenosine 3'5'-monophosphate)-dependent (PKA) pathway extend life span in wild type cells but not in mutant sir2 strains, demonstrating that SIR2 is a key downstream component of the caloric restriction pathway (19).

In most organisms, there are two pathways of NAD+ biosynthesis (see FIG. 1). NAD+ may be synthesized de novo from tryptophan or recycled in four steps from nicotinamide via the NAD+ salvage pathway. The first step in the bacterial NAD$^+$ salvage pathway, the hydrolysis of nicotinamide to nicotinic acid and ammonia, is catalyzed by the pncA gene product (33). An *S. cerevisiae* gene with homology to pncA, YGL037, was recently assigned the name PNC1 (SGD) (34). A nicotinate phosphoribosyltransferase, encoded by the NPT1 gene in *S. cerevisiae*, converts the nicotinic acid from this reaction to nicotinic acid mononucleotide (NaMN) (35-38). At this point, the NAD$^+$ salvage pathway and the de novo NAD$^+$ pathway converge and NaMN is converted to desamido-NAD$^+$ (NaAD) by a nicotinate mononucleotide adenylyltransferase (NaMNAT). In *S. cerevisiae*, there are two putative ORFs with homology to bacterial NaMNAT genes, YLR328 (39) and an uncharacterized ORF, YGR010 (23,39). We refer to these two ORFs as NMA1 and NMA2, respectively. In *Salmonella*, the final step in the regeneration of NAD$^+$ is catalyzed by an NAD synthetase (40). An as yet uncharacterized ORF, QNS1, is predicted to encode a NAD synthetase (23).

In yeast, null mutations in NPT1 reduce steady-state NAD$^+$ levels by ~2-fold (23) and abolish the longevity provided by limiting calories (19). One current hypothesis explaining how caloric restriction extends replicative life span is that decreased metabolic activity causes an increase in NAD$^+$ levels, which then stimulate Sir2 activity (reviewed in Campisi, 2000 and Guarente, 2000).

Transcriptional silencing involves the heritable modification of chromatin at distinct sites in the genome. Silencing is referred to as long-range repression as it is promoter non-specific and often encompasses an entire genomic locus (1', 2'). In yeast these silent regions of DNA, which are similar to the heterochromatin of higher eukaryotes, are subject to a wide variety of modifications (3'). Among the most well studied of these modifications is the reversible acetylation of histones (reviewed in 4',5').

There are two classes of enzymes that affect the acetylation state of histones: histone acetyltransferases (HATs) and the opposing histone deacetylases (HDACs). Compared with more transcriptionally active areas of the genome, histones within silent regions of chromatin are known to be hypoacetylated, specifically on the $NH_2$-terminal tails of core histones H3 and H4 (6'). Three classes of histone deacetylases have been described and classified based on homology to yeast proteins. Proteins in class I (Rpd3-like) and class II (Hda1-like) are characterized by their sensitivity to the inhibitor trichostatin A (TSA) (7',8'). Studies using this inhibitor have provided a wealth of information regarding the cellular function of these proteins, including their involvement in the expression of regulators of cell cycle, differentiation, and apoptosis (reviewed in 9').

Yeast Sir2 is the founding member of Class III HDACs. Sir2-like deacetylases are not inhibited by TSA and have the unique characteristic of being $NAD^+$-dependent (10'-13'). Proteins of this class are found in a wide array of organisms, ranging from bacteria to humans. At least two Sir2 homologues, yeast Hst2 and human SIRT2, are localized to the cytoplasm and human SIRT1 has recently been shown to target p53 for deacetylation (11',13'-15'). These results indicate that not all members of this family are specific for histones or other nuclear substrates.

The term, silent information regulator (SIR), was first coined to describe a set of non-essential genes required for repression of the mating type loci (HML and HMR) in S. cerevisiae (16'). Silencing in yeast is also observed at telomeres and the ribosomal DNA (rDNA) locus (2',17'). The formation of heterochromatin at mating type loci and the poly $(TG_{1-3})$ tracts of yeast telomeres is mediated by a heterotrimeric complex of Sir2, Sir3 and Sir4 (18',19'). At the rDNA locus, Sir2 is part of the RENT (regulator of nuleolar silencing and telophase exit) complex, which includes Net1 and Cdc14 (20',21'). Of these proteins, Sir2 is the only factor that is indispensable for silencing at all three silent regions (22'-24').

The yeast rDNA locus (RLN1) consists of 100-200 tandemly-repeated 9 kb units encoding ribosomal RNAs. A major cause of yeast aging has been shown to stem from recombination between these repeats (25'-27') which can lead to the excision of an extrachromosomal rDNA circle (ERC). ERCs are replicated but they fail to segregate to daughter cells, resulting in their exponential amplification as cells divide. ERCs can accumulate to a DNA content greater than that of the entire yeast genome in old cells and are thought to kill cells by titrating essential transcription and/or replication factors (28'). Although Sir2 silences Pol II-transcribed genes integrated at the rDNA, there is evidence that its primary function at this locus is to suppress recombination. Deletion of SIR2 eliminates rDNA silencing and increases the frequency that a marker gene is recombined out of the rDNA 10-fold (29'). This results in increased ERC formation and a dramatic shortening of life span (29',30').

Sir2 is a limiting component of yeast longevity. A single extra copy of the SIR2 gene suppresses recombination and extends life span by 40% (26',31',32'). Recently, it has been shown that SIR2 is essential for the increased longevity provided by calorie restriction (31"), a regimen that extends the life span of every organism it has been tested on. Moreover, increased dosage of the Sir2 homologue sir2.1 has been shown to extend the life span of the nematode C. elegans (33') and the nearest human homologue SIRT1, has been shown to inhibit apoptosis through deacetylation of p53 (34',35').

These findings suggest that Sir2 and its homologues have a conserved role in the regulation of survival at the cellular and organismal level.

Recently, a great deal of insight has been gained into the biochemistry of Sir2-like deacetylases (reviewed by 36'). In vitro, Sir2 has specificity for lysine 16 of histone H4 and lysines 9 and 14 of histone H3 (10',12',13'). Although TSA sensitive HDACs catalyze deacetylation without the need of a cofactor, the Sir2 reaction requires $NAD^+$. This allows for regulation of Sir2 activity through changes in availability of this co-substrate (10'-13'). Sir2 deacetylation is coupled to cleavage of the high-energy glycosidic bond that joins the ADP-ribose moiety of $NAD^+$ to nicotinamide. Upon cleavage, Sir2 catalyzes the transfer of an acetyl group to ADP-ribose (10',11',15',37'). The product of this transfer reaction is O-acetyl-ADP-ribose, a novel metabolite, which has recently been shown to cause a delay/block in the cell cycle and oocyte maturation of embryos (38').

The other product of deacetylation is nicotinamide, a precursor of nicotinic acid and a form of vitamin B3 (39'). High doses of nicotinamide and nicotinic acid are often used interchangeably to self-treat a range of conditions including anxiety, osteoarthritis, psychosis, and nicotinamide is currently in clinical trials as a therapy for cancer and type I diabetes (40'). The long-term safety of the high doses used in these treatments has been questioned (41') and the possible effects of these compounds at the molecular level are not clear.

SUMMARY OF THE INVENTION

In one embodidment, the invention provides methods for modulating the life span of a cell or its resistance to stress, comprising modulating the flux through the NAD+ salvage pathway in the cell. The method may comprise increasing or extending the life of a cell or increasing its resistance against stress, comprising increasing the flux through the NAD+ salvage pathway in the cell. Modulating the flux through the NAD+ salvage pathway may occur essentially without changing steady state levels of NAD+ and NADH and essentially by maintaining the NAD+/NADH ratio in the cell.

Increasing the flux through the NAD+ salvage pathway may comprise increasing the level or activity of a protein selected from the group consisting of NPT1, PNC1, NMA1 and NMA2. The method may comprise introducing into the cell at least one nucleic acid encoding a protein selected from the group consisting of NPT1, PNC1, NMA1 and NMA2, or a nucleic acid comprising at least 5 copies of a gene. Alternatively, the method may comprise introducing into the cell at least one protein selected from the group consisting of NPT1, PNC1, NMA1 and NMA2. The method may comprise contacting the cell with an agent that upregulates the expression of a gene selected from the group consisting of NPT1, PNC1, NMA1 and NMA2. The cell may live at least about 40% longer, or at least about 60% longer.

The invention also provides methods for increasing the resistance of the cell against stress, e.g., heat shock, osmotic stress, DNA damaging agents (e.g., U.V.), and inadequate nitrogen levels, comprising increasing the flux through the NAD+ salvage pathway in the cell.

In one embodiment, modulating the life span of a cell comprises modulating silencing in the cell. Silencing may include telomeric silencing and rDNA recombination.

The cell whose life span can be extended or who can be protected against stress can be a eukaryotic cell, such as a yeast cell or a prokaryotic cell, such as a bacterial cell. The cell can be in vitro or in vivo.

In another embodiment, modulating the life span of a cell or its resistance to stress comprises modulating the amount of nicotinamide and/or the ratio of NAD:nicotinamide in the cell. The ratio of NAD:nicotinamide may be modulated by a factor of at least about 50%, 2, 3, 5, 10 or more. For example, reducing the life span of a cell or rendering a cell more sensitive to stress may comprise increasing the level of nicotinamide in the cell. This may comprise contacting the cell with an amount of nicotinamide of about 1 to 20 mM, preferably of about 2 to 10 mM. The level of nicotinamide in a cell may also be increased by increasing the level or activity of enzymes involved in the biosynthesis of nicotinamide or by decreasing the level or activity of enzymes that degrade or inactivate nicotinamide. Enzymes which directly or indirectly inactivate nicotinamide include PNC1; nicotinamide N-methyl transferase (NNMT and NNT1); NPT1, and human homologs thereof; nicotinamide phosphoribosyltransferase (NAMPRT); and optionally nicotinamide mononucleotide adenylyltransferase (NMNAT-1 and 2); NMA1 and 2 and human homologs thereof.

On the contrary, extending the life span of a cell or rendering the cell more resistant (i.e., less sensitive) to stress may comprise decreasing the level of nicotinamide in the cell. This may be achieved by decreasing the level or activity of enzymes involved in the biosynthesis of nicotinamide or by increasing the level or activity of enzymes that degrade or inactivate nicotinamide. Accordingly, increasing lifespan or stress resistance in a cell can be achieved by increasing the activity or level of expression of a protein selected from the group consisting of NPT1, PNC1, NMA1, NMA2, NNMT, NAMPRT, NMNAT-1, and NMNAT-2. Increasing lifespan or stress resistance can also be achieved by contacting the cell with nicotinamide riboside, an NAD+ precursor, or a biologically active analog thereof or prodrug thereof, and optionally increasing the protein level or activity of nicotinamide riboside kinase, e.g., Nrk1 and Nrk2 (see, Bieganowski et al. (2004) Cell 117:495).

The invention further provides methods for identifying compounds that modulate the life span of a cell or its resistance to stress, comprising (i) contacting a protein selected from the group consisting of NPT1, PNC1, NMA1, NMA2, NNMT, NAMPRT, NMNAT-1, and NMNAT-2 with a test compound for an amount of time that would be sufficient to affect the activity of the protein; and (ii) determining the activity of the enzyme, wherein a difference in the activity of the enzyme in the presence of the test compound relative to the absence of the test compound indicates that the test compound is a compound that modulates the life span of the cell or its resistance to stress. The method may further comprise contacting a cell with the test compound and determining whether the life span of the cell has been modulated. The method may also further comprise contacting a cell with the test compound and determining whether the resistance of the cell to stress has been modulated.

In another embodiment, the invention provides a method for identifying a compound that modulates the life span of a cell or its resistance to certain types of stresses, comprising (i) contacting a cell or a lysate, comprising a transcriptional regulatory nucleic acid of a gene selected from the group consisting of NPT1, PNC1, NMA1, NMA2, NNMT, NAMPRT, NMNAT-1, and NMNAT-2 operably linked to a reporter gene, with a test compound for an amount of time that would be sufficient to affect the transcriptional regulatory nucleic acid; and (ii) determining the level or activity of the reporter gene, wherein a difference in the level or activity of the reporter gene in the presence of the test compound relative to the absence of the test compound indicates that the test compound is a compound that modulates the life span of the cell or its resistance to certain types of stresses. The method may further comprise contacting a cell with the test compound and determining whether the life span of the cell has been modulated. The method may also further comprise contacting a cell with the test compound and determining whether the resistance of the cell to stress has been modulated.

Also provided herein are methods for identifying an agent, e.g., a small molecule that modulates the nicotinamide level in a cell. The method may comprise (i) providing a cell or cell lysate comprising a reporter construct that is sensitive to the level of nicotinamide in a cell; (ii) contacting the cell with a test agent; and (iii) determining the level of nicotinamide in the cell contacted with the test agent, wherein a different level of nicotinamide in the cell treated with the test agent relative to a cell not treated with the test agent indicates that the test agent modulates the level of nicotinamide in the cell. The cell may further comprise a vector encoding a fusion protein that can bind to a DNA binding element operably linked to the reporter gene. The fusion protein may comprise at least an NAD+ binding pocket of a nicotinamide sensitive enzyme, e.g., a Sir2 family member, and a heterologous polypeptide. The heterologous polypeptide may be a transactivation domain of a transcription factor. The method may further comprise contacting a cell with the test compound and determining whether the life span of the cell or its resistance to stress has been modulated.

Also within the scope of the invention are computer-assisted methods for identifying an inhibitor of the activity of a Sir2 family member comprising: (i) supplying a computer modeling application with a set of structure coordinates of a molecule or molecular complex, the molecule or molecular complex including at least a portion of a Sir2 family member comprising a C pocket; (ii) supplying the computer modeling application with a set of structure coordinates of a chemical entity; and (iii) determining whether the chemical entity is an inhibitor expected to bind to or interfere with the molecule or molecular complex, wherein binding to or interfering with the molecule or molecular complex is indicative of potential inhibition of the activity of the Sir2 family member. The chemical entity may be an analog of nicotinamide. Another method for identifying an inhibitor of the activity of a Sir2 family member comprises: (i) contacting a protein of the Sir2 family comprising at least the C pocket with a test compound for a time sufficient for the test compound to potentially bind to the C pocket of the protein of the Sir2 family; and (ii) determining the activity of protein; wherein a lower activity of the protein in the presence of the test compound relative to the absence of the test compound indicates that the test compound is an inhibitor of the activity of a Sir2 family member.

In addition, the invention provides methods for treating or preventing diseases that are associated with aging or cell death (e.g., apoptosis) in a subject or diseases that may benefit from the effects of calorie restriction. A method may comprise administering to a subject in need thereof an agent that increases the flux through the NAD+ salvage pathway or reduces nicotinamide levels or the ratio of nicotinamide/NAD+ in the cells susceptible or subject to cell death. Diseases can be chronic or acute and include Alzheimer's disease, Parkinson's disease, stroke, myocardial infarction or a metabolic disease, such as insulin resistance. The methods of the invention for extending life span or increasing resistance to stress can also be used to reduce aging, e.g., for cosmetic purposes. The agent can be administered locally or systemically. Methods for extending life span or increasing resistance to stress can also be used on cells, tissues or organs outside of a subject, e.g., in an organ or tissue prior to transplantation.

The invention also provides methods for treating or preventing diseases in which reducing the life span of cells or rendering cells sensitive to stress is beneficial. Such diseases include those in which cells are undesirable, e.g., cancer and autoimmune diseases. Methods may also sensitize cells to killing by other agents, e.g., chemotherapeutic agents.

The methods of the invention can also be used to modulate the lifespan and stress resistance of organisms other than mammals. For example, the method can be used in microorganisms and plants. In particular, the methods of the invention permit to increase the resistance of plants to high salt, drought or disease, e.g., by treating these with a chemical that lowers nicotinamide levels or by genetically modifying genes that modulate the NAD+ salvage pathway or the level of nicotinamide in cells.

Also provided are diagnostic methods, e.g., a method for determining the general health of a subject or whether a subject has been exposed, e.g., unknowingly exposed, to a stress condition. A diagnostic method may also be used for diagnosing the presence or likelihood of developing cancer. A method may comprise (i) providing a sample of cells or bodily fluid, e.g., blood or serum, from a subject; and (ii) determining the level of expression of a gene or level of protein or activity thereof encoded thereby selected from the group consisting of NPT1, PNC1, NMA1, NMA2, NNMT, NAMPRT, NMNAT-1, and NMNAT-2, wherein a higher level of expression of a gene or the level of protein encoded thereby or activity thereof relative to a control sample indicates that the general health of the subject is not adequate, acceptable or optimal. A diagnostic method may also comprise determining the level of NAD+, NADH, nicotinamide or other intermediate compound of the NAD+ salvage pathway. In one embodiment, the method comprises determining the level of NAMPRT in serum of a subject.

BRIEF DESCRIPTION OF THE DRAWINGS

FIG. 2. NPT1 and SIR2 provide resistance to heat shock. A, Strains were grown for three days post-diauxic shift in SC medium and incubated for 1 h at 55° C. before plating 10-fold dilutions on SC plates. B, Strains were treated as in A and plated on SC at low density. Colonies that aroze after 24 hours were scored and expressed as a percentage of colonies arizing from the untreated sample. Values represent the avarage of three independent experiments (+/−s.d.). Strains: W303AR URA3 (YDS1568), W303AR URA3 LEU2 (YDS1563) and isogenic derivatives of W303AR, 2×NPT1-URA3 (YDS1503), 2×SIR2-URA3 (YDS1572) and 2×NPT1-URA3 2×SIR2-LEU2 (YDS1561).

FIG. 5. Multiple limiting components in the NAD+ salvage pathway. A, The putative steps in NAD+ biosynthesis in *S. cerevisiae* based on the known steps in *Salmonella*. The yeast genes that are thought to mediate each step are shown in italics. NaMN, nicotinic acid mononucleotide; NaAD, desamido-NAD+; NaM, nicotinamide; Na, nicotinic acid. Adapted from Smith et al. (2000). B, Silencing of ADE2 at the rDNA locus in strains ADE2 (YDS1596), wild type (W303AR5), 2×NPT1 (YDS1503), 2×PNC1 (YDS1588), 2×NMA2 (YDS1589), 2×NMA1 (YDS1590), and 2×QNS1 (YDS1614). Increased silencing is indicated by growth retardation on media lacking adenine. C, Strains with an ADE2 marker at the telomere were streaked onto SC medium containing limiting amounts of adenine. Silencing is indicated by the accumulation of a red pigment. Strains tested: wild type (PSY316AT), 2×NPT1 (YDS1544), 5×NPT1 (YDS 1548), sir2::TRP1 (YDS1594), 2×PNC1 (YDS1591), 2×NMA2 (YDS1592) and 2×NMA1 (YDS1593).

FIG. 8. Nicotinamide inhibits telomeric and rDNA silencing. A, Silencing at the rDNA locus was assayed by streaking isogenic derivatives of JS237 (RDN1::MET15) on rich medium containing 0.07% PbNO$_3$ and either 0, 1, or 5 mM nicotinamide. Silencing of the MET15 marker is indicated by the accumulation of a brown pigment. Single dark brown colonies in RDN1::MET15 strains represent marker loss events. Relevant genotypes: met15Δ (JS209), MET15 (JS241), RDN1::MET15 (JS237), sir2::TRP1 (JS218), 2×SIR2 (YDS1583). B, Strains with an ADE2 marker at the telomere were streaked onto SC medium containing limiting amounts of adenine and either 0 or 5 mM nicotinamide. Silencing of the ADE2 marker results in the accumulation of a red pigment. Relevant genotypes: (PSY316AT), W303-1 A ADE2 (YDS1596) and W303-1A ade2 (YDS 1595).

FIG. 16 shows an alignment of PNC1 homologs (SEQ ID NOS 16, 45-48, and 4, respectively in order of appearance).

FIG. 21A-B. Manipulation of nicotinamide metabolism affects SIR2 dependent silencing. (A) To measure silencing, an ADE2 reporter was integrated at the ribosomal DNA (rDNA) locus. In this system, increased growth on media lacking adenine indicates decreased ADE2 silencing. Strains were spotted in 10-fold serial dilutions on plates with or without adenine. An Ade⁺ strain served as a control. (B) Model for regulation of lifespan and stress resistance by nicotinamide. Disparate environmental stimuli including calorie restriction, heat and osmotic stress serve as inputs to a common pathway of longevity and stress resistance. Cells coordinate a response to these inputs by inducing transcription of PNC1, which encodes an enzyme that converts nicotinamide to nicotinic acid. In addition to alleviating inhibition of Sir2 and promoting longevity, depletion of nicotinamide activates a number of additional target proteins involved in stress resistance and possibly other cellular processes.

FIG. 23A is a Western blot showing the intracellular level of NAMPRT and beta-tubulin in MEF cells subjected to no treatment, serum starvation or oxidative stress with $H_2O_2$.

FIG. 23B is a diagram showing the relative levels of intracellular NAMPRT from the Western blot of FIG. 23A.

FIG. 24A is a Western blot showing the level of intracellular NAMPRT and GAPDH in cardiomyocytes subjected to no treatment, serum starvation or hypoxia.

FIG. 24B is a diagram showing the relative levels of NAMPRT from the Western blot of FIG. 24A.

DETAILED DESCRIPTION OF THE INVENTION

Figure 1:
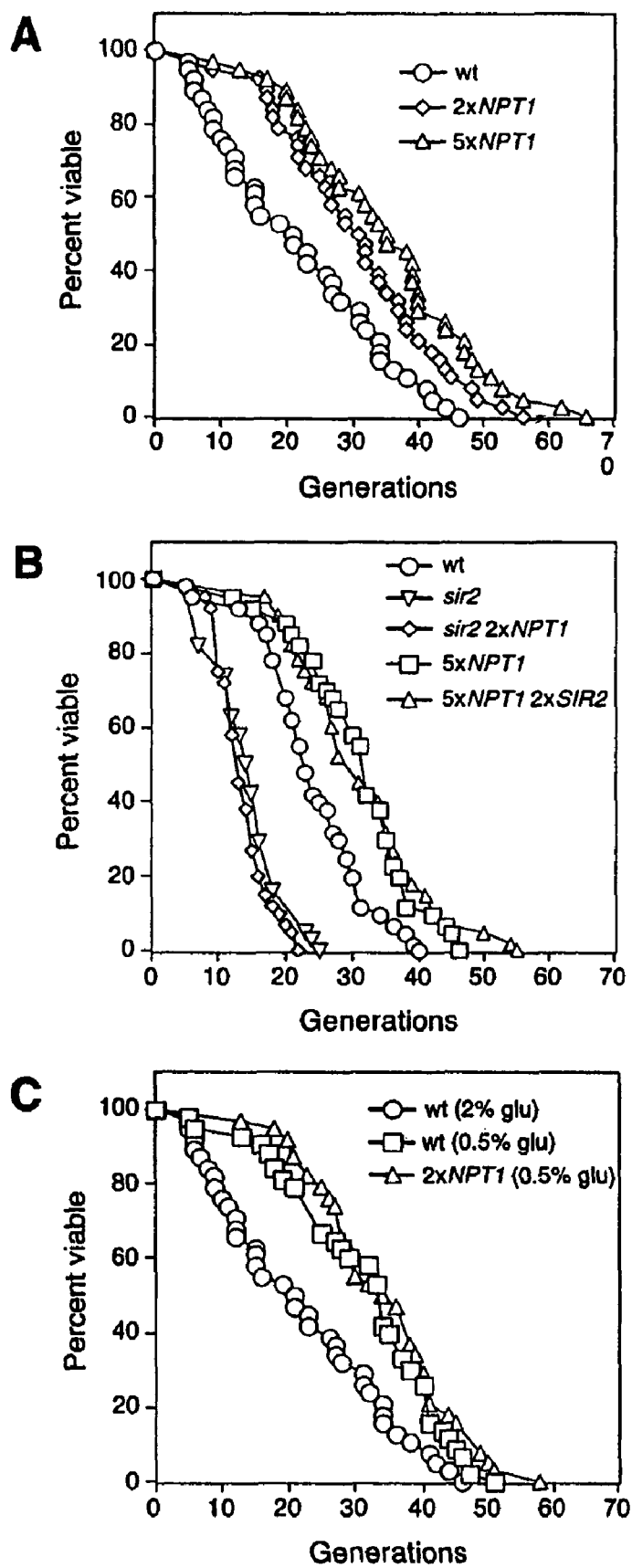
FIG. 1. Increased dosage of NPT1 delays aging by mimicking caloric restriction. Life span was determined by scoring the number of daughter cells produced by each mother cell before cessation of cell division (7,10). Cells were pre-grown for a minimum of 48 h on complete glucose medium.
A, Mortality curves for wild type (PSY316AT, circles), 2×NPT1 (YDS1544, diamonds) and 5×NPT1 (YDS1548, triangles) on medium with 2% glucose. Average life spans are 21.9, 30.8 and 35.1 generations respectively.
B, Mortality curves for wild type (PSY316AT, circles), sir2::TRP1 (YDS1594, downward triangles), 2×NPT1 (YDS1544, squares), sir2::TRPP 2×NPT1 (YDS1573, diamonds) and 5×NPT1 2×SIR2 (YDS1577, upward triangles) on 2% glucose medium. Average life spans were 23.7, 14.4, 13.9, 31.0 and 31.9 generations respectively.
C, Mortality curves for wild type on 2% glucose (PSY316AT, circles) and 0.5% glucose medium (PSY316AT, squares) and for 2×NPT1 on 0.5% glucose medium (YDS1544, triangles). Average life spans are 21.9, 31.7 and 34.5 generations respectively.

The invention is based at least in part on the discovery that the life span of yeast cells can be extended by at least about 60% by increasing the flux through the nicotinamide adenine dinucleotide (NAD)+ salvage pathway (shown in FIG. 1). In addition, it was shown herein that this increase in flux through the NAD+ salvage pathway occurs essentially without increase in NAD+ and NADH levels and essentially by maintaining the ratio of NAD+/NADH constant. As shown in the Examples, increasing the flux through the NAD+ salvage pathway and thereby increasing the life span of cells can be achieved by introducing into the cells additional copies of a gene involved in the NAD+ salvage pathway, e.g., NPT1, PNC1, NMA1 and NMA2. It has also been shown in the Examples, that increasing the flux through the NAD+ salvage pathway protects yeast cells against certain types of stresses, e.g., heatshock. In addition, overexpression of PNC1 increases silencing, lifespan, as well as stress resistance, e.g., protects cells from DNA breakage caused by ultraviolet (U.V.) light and ethidium bromide and osmotic stress. On the other hand, deletion of PNC1 prevents lifespan extension and renders cells sensitive to stress.

The invention is also based at least in part on the discovery that nicotinamide inhibits silencing in yeast and thereby decreases the life span of cells. Nicotinamide was also shown to render cells more sensitive to stress. In particular, it was shown that overexpression of nicotinamide methyl transferase (NNMT), an enzyme that is involved in the secretion of nicotinamide from cells, stimulated silencing and thus extended life span, and increased tolerance to stress (e.g., radiation exposure), whereas the deletion of this enzyme had the opposite effect.

Based at least on the strong conservation of the NAD+ salvage pathway and de novo pathways and silencing events from prokaryotes to eukaryotes, the methods of the invention are expected to be applicable to any eukaryotic cell, in addition to yeast cells, and to prokaryotic cells.

1. Definitions

As used herein, the following terms and phrases shall have the meanings set forth below. Unless defined otherwise, all technical and scientific terms used herein have the same meaning as commonly understood to one of ordinary skill in the art to which this invention belongs.

The singular forms "a," "an," and "the" include plural reference unless the context clearly dictates otherwise.

The term "agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues. The activity of such agents may render it suitable as a "therapeutic agent" which is a biologically, physiologically, or pharmacologically active substance (or substances) that acts locally or systemically in a subject.

"Diabetes" refers to high blood sugar or ketoacidosis, as well as chronic, general metabolic abnormalities arising from a prolonged high blood sugar status or a decrease in glucose tolerance. "Diabetes" encompasses both the type I and type II (Non Insulin Dependent Diabetes Mellitus or NIDDM) forms of the disease. The risk factors for diabetes include the following factors: waistline of more than 40 inches for men or 35 inches for women, blood pressure of 130/85 mmHg or higher, triglycerides above 150 mg/dl, fasting blood glucose greater than 100 mg/dl or high-density lipoprotein of less than 40 mg/dl in men or 50 mg/dl in women.

The term "$ED_{50}$" is art-recognized. In certain embodiments, $ED_{50}$ means the dose of a drug which produces 50% of its maximum response or effect, or alternatively, the dose which produces a pre-determined response in 50% of test subjects or preparations. The term "$LD_{50}$" is art-recognized. In certain embodiments, $LD_{50}$ means the dose of a drug which is lethal in 50% of test subjects. The term "therapeutic index" is an art-recognized term which refers to the therapeutic index of a drug, defined as $LD_{50}/ED_{50}$.

The term "insulin resistance" refers to a state in which a normal amount of insulin produces a subnormal biologic response relative to the biological response in a subject that does not have insulin resistance.

An "insulin resistance disorder," as discussed herein, refers to any disease or condition that is caused by or contributed to by insulin resistance. Examples include: diabetes, gestational diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholescystitis and cholelithiasis, gout, obstructive sleep apnea and respiratory problems, osteoarthritis, and prevention and treatment of bone loss, e.g. osteoporosis.

The term "isolated" as used herein with respect to nucleic acids, such as DNA or RNA, refers to molecules separated from other DNAs, or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

"Modulating the flux through the NAD+ salvage pathway of a cell" refers to an action resulting in increasing or decreasing the number of NAD+ molecules that are generated by the NAD+ salvage pathway, e.g. shown in FIG. 1.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. ESTs, chromosomes, cDNAs, mRNAs, and rRNAs are representative examples of molecules that may be referred to as nucleic acids.

The phrase "nucleic acid corresponding to a gene" refers to a nucleic acid that can be used for detecting the gene, e.g., a nucleic acid which is capable of hybridizing specifically to the gene.

The term "percent identical" refers to sequence identity between two amino acid sequences or between two nucleotide sequences. Identity can each be determined by comparing a position in each sequence which may be aligned for purposes of comparison. When an equivalent position in the compared sequences is occupied by the same base or amino acid, then the molecules are identical at that position; when the equivalent site occupied by the same or a similar amino acid residue (e.g., similar in steric and/or electronic nature), then the molecules can be referred to as homologous (similar) at that position. Expression as a percentage of homology, similarity, or identity refers to a function of the number of identical or similar amino acids at positions shared by the compared sequences. Various alignment algorithms and/or programs may be used, including FASTA, BLAST, or ENTREZ. FASTA and BLAST are available as a part of the GCG sequence analysis package (University of Wisconsin, Madison, Wis.), and can be used with, e.g., default settings. ENTREZ is available through the National Center for Biotechnology Information, National Library of Medicine, National Institutes of Health, Bethesda, Md. In one embodiment, the percent identity of two sequences can be determined by the GCG program with a gap weight of 1, e.g., each amino acid gap is weighted as if it were a single amino acid or nucleotide mismatch between the two sequences. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Preferably, an alignment program that permits gaps in the sequence is utilized to align the sequences. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases. Databases with individual sequences are described in Methods in Enzymology, ed. Doolittle, supra. Databases include Genbank, EMBL, and DNA Database of Japan (DDBJ).

"Obese" individuals or individuals suffering from obesity are generally individuals having a body mass index (BMI) of at least 25 or greater. Obesity may or may not be associated with insulin resistance.

"Replicative life span" which is used interchangeably herein with "life span" or "lifespan" of a cell refers to the number of daughter cells produced by an individual "mother cell." "Chronological aging," on the other hand, refers to the length of time a population of non-dividing cells remains viable when deprived of nutrients. The life span of cells can be increased by at least about 20%, 30%, 40%, 50%, 60% or between 20% and 70%, 30% and 60%, 40 and 60% or more using the methods of the invention.

"Sir2 family members" or "Sir2 protein family members" refers to *S. cerevisiae* Sir2 protein as well as any histone deacetylases having substantial structural similarities to Sir2, e.g., the human homologs hSIRT1, hSIRT2, hSIRT3, hSIRT4, hSIRT5, hSIRT6 and hSIRT7; and Sir-2.1.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays described herein.

The term "specific hybridization" of a probe to a target site of a template nucleic acid refers to hybridization of the probe predominantly to the target, such that the hybridization signal can be clearly interpreted. As further described herein, such conditions resulting in specific hybridization vary depending on the length of the region of homology, the GC content of the region, the melting temperature "Tm" of the hybrid. Hybridization conditions will thus vary in the salt content, acidity, and temperature of the hybridization solution and the washes.

"Stress" refers to any non-optimal condition for growth, development or reproduction. A "stress condition" can be exposure to heatshock; osmotic stress; a DNA damaging agent; inadequate salt level; inadequate nitrogen levels; inadequate nutrient level; radiation or a toxic compound, e.g., a toxin or chemical warfare agent (such as dirty bombs and other weapons that may be used in bioterrorism). "Inadequate levels" refer to levels that result in non-optimal condition for growth, development or reproduction.

"Treating" a condition or disease refers to curing as well as ameliorating at least one symptom of the condition or disease.

The term "therapeutic agent" is art-recognized and refers to any chemical moiety that is a biologically, physiologically, or pharmacologically active substance that acts locally or systemically in a subject. The term also means any substance intended for use in the diagnosis, cure, mitigation, treatment or prevention of disease or in the enhancement of desirable physical or mental development and/or conditions in an animal or human.

The term "therapeutic effect" is art-recognized and refers to a local or systemic effect in animals, particularly mammals, and more particularly humans caused by a pharmacologically active substance. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease or condition being treated, the weight and age of the subject, the severity of the disease or condition, the manner of administration and the like, which can readily be determined by one of ordinary skill in the art. For example, certain compositions described herein may be administered in a sufficient amount to produce a desired effect at a reasonable benefit/risk ratio applicable to such treatment.

A "variant" of a polypeptide refers to a polypeptide having the amino acid sequence of the polypeptide in which is altered in one or more amino acid residues. The variant may have "conservative" changes, wherein a substituted amino acid has similar structural or chemical properties (e.g., replacement of leucine with isoleucine). A variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to that of a particular gene or the coding sequence thereof. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variantion is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The term "aliphatic" is art-recognized and refers to a linear, branched, cyclic alkane, alkene, or alkyne. In certain embodiments, aliphatic groups in the present invention are linear or branched and have from 1 to about 20 carbon atoms.

The term "alkyl" is art-recognized, and includes saturated aliphatic groups, including straight-chain alkyl groups, branched-chain alkyl groups, cycloalkyl(alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure. The term "alkyl" is also defined to include halosubstituted alkyls.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "heteroatom" is art-recognized and refers to an atom of any element other than carbon or hydrogen. Illustrative heteroatoms include boron, nitrogen, oxygen, phosphorus, sulfur and selenium.

The term "aryl" is art-recognized and refers to 5-, 6-and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3-and 1,4-disubstituted benzenes, respectively. For example, the names 1,2-dimethylbenzene and ortho-dimethylbenzene are synonymous.

The terms "heterocyclyl" or "heterocyclic group" are art-recognized and refer to 3-to about 10-membered ring structures, alternatively 3-to about 7-membered rings, whose ring structures include one to four heteroatoms. Heterocycles may also be polycycles. Heterocyclyl groups include, for example, thiophene, thianthrene, fluran, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on 560 of "*Advanced Inorganic Chemistry*" by Cotton and Wilkinson.

The terms "amine" and "amino" are art-recognized and refer to both unsubstituted and substituted amines, e.g., a moiety that may be represented by the general formulas:

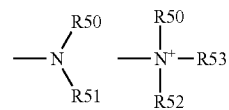

wherein R50, R51 and R52 each independently represent a hydrogen, an alkyl, an alkenyl, —$(CH_2)_m$—R61, or R50 and R51, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In certain embodiments, only one of R50 or R51 may be a carbonyl, e.g., R50, R51 and the nitrogen together do not form an imide. In other embodiments, R50 and R51 (and optionally R52) each independently represent a hydrogen, an alkyl, an alkenyl, or —(CH$_2$)$_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

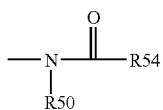

wherein R50 is as defined above, and R54 represents a hydrogen, an alkyl, an alkenyl or —(CH$_2$)$_m$—R61, where m and R61 are as defined above.

The term "amido" is art recognized as an amino-substituted carbonyl and includes a moiety that may be represented by the general formula:

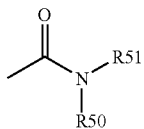

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—(CH$_2$)$_m$—R61, wherein m and R61 are defined above. Representative alkylthio groups include methylthio, ethyl thio, and the like.

The term "carbonyl" is art recognized and includes such moieties as may be represented by the general formulas:

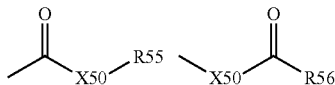

wherein X50 is a bond or represents an oxygen or a sulfur, and R55 and R56 represents a hydrogen, an alkyl, an alkenyl, —(CH$_2$)$_m$—R61 or a pharmaceutically acceptable salt, R56 represents a hydrogen, an alkyl, an alkenyl or —(CH$_2$)$_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The definition of each expression, e.g. alkyl, m, n, and the like, when it occurs more than once in any structure, is intended to be independent of its definition elsewhere in the same structure.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, *Handbook of Chemistry and Physics*, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The definition of each expression, e.g. lower alkyl, m, n, p and the like, when it occurs more than once in any structure, is intended to be independent of its definition elsewhere in the same structure.

The term "pharmaceutically-acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The terms "systemic administration," "administered systemically," "peripheral administration" and "administered peripherally" are art-recognized and refer to the administration of a subject composition, therapeutic or other material other than directly into the central nervous system, such that it enters the patient's system and, thus, is subject to metabolism and other like processes, for example, subcutaneous administration. The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrastemal injection and infusion.

2. Methods for Increasing the Life Span of a Cell or Protecting it Against Certain Stresses In one embodiment, the life span of a cell is increased and/or the cell is protected against certain stresses by increasing the flux through the NAD+ salvage pathway. This can be achieved, e.g., increasing the level or activity of at least one protein involved in the NAD+ salvage pathway, such as a protein selected from the group consisting of NPT1, PNC1, NMA1 and NMA2.

The level of protein can be increased in a cell, e.g., by introducing into the cell a nucleic acid encoding the protein operably linked to a transcriptional regulatory sequence directing the expression of the protein in the cell. Methods for expressing nucleic acids in cells and appropriate transcriptional regulatory elements for doing so are well known in the art. Alternatively, a protein can be introduced into a cell, usually in the presence of a vector facilitating the entry of the protein into the cells, e.g., liposomes. Proteins can also be linked to transcytosis peptides for that purpose. Yet in other methods, an agent that stimulates expression of the endogenous gene is contacted with a cell. Such agents can be identified as further described herein.

Figure 15:
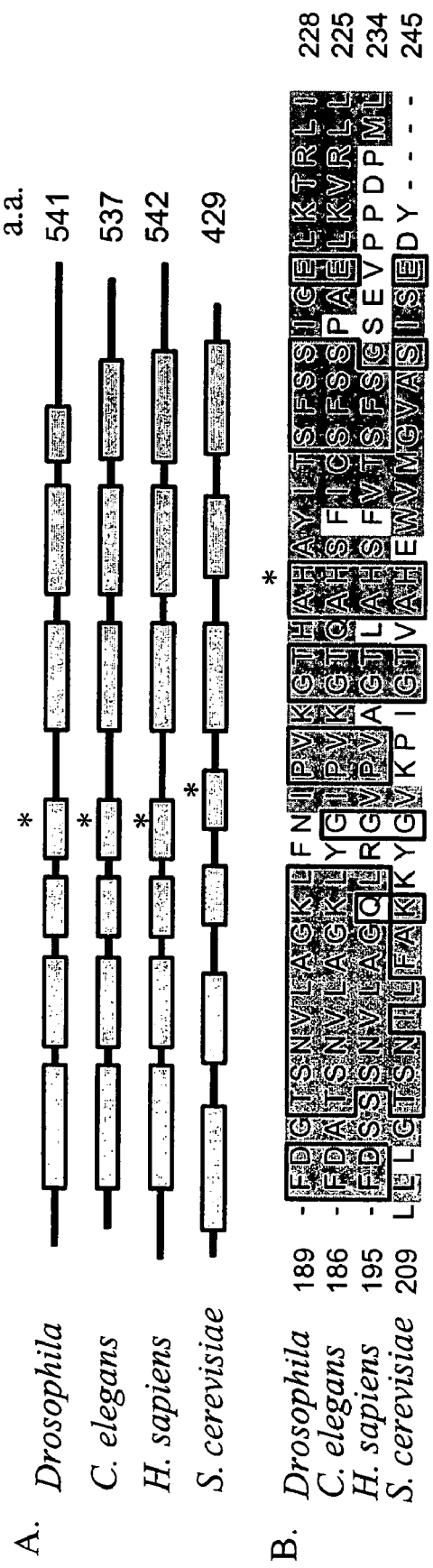
FIG. 15 shows an alignment of NPT1 homologs (SEQ ID NOS 41-44, respectively in order of appearance).

A nucleotide sequence encoding *S. cerevisiae* nicotinate phosphoribosyltransferase (NPT1) and the protein encoded thereby are set forth as SEQ ID Nos: 1 and 2, respectively. NPT1 is also known as "LSR2." The *S. cerevisiae* NPT1 complete cDNA and encoded protein are provided by GenBank Accession numbers NC_001147 and AAB59317, respectively, which are set forth as SEQ ID NOs: 1 and 2, respectively. Accession numbers L11274 and AAB59317 also appear to refer to *S. cerevisiae* nucleotide and amino acid sequences, respectively. The NPT1 homolog in bacteria is PncB (35, 37 and 38). The *E. coli* NPT1 is provided as GenBank accession number J05568. The human nucleotide and amino acid sequences are provided by GenBank Accession numbers BC006284 and AAH06284, respectively, and X71355 and CAA50490, respectively, AAH32466 and BC032466 and are described in Chong et al. (1993) Genomics 18:355. The human nucleotide and amino acid sequences are also set forth as SEQ ID NOs: 13 and 14, respectively (and correspond to GenBank Accession No. BC032466). The human protein is also referred to as a "renal sodium phosphate transport protein." A mouse NPT1 nucleotide and amino acid sequences are provided by GenBank Accession numbers X77241 and CAA54459 and are described in Chong et al. (1995) Am. J. Physiol. 268:1038. The promoter region of mouse NPT1 is provided as GenBank Accession number AF361762 and is described in Soumounou et al. (2001) Am J. Physiol. 281: F1082. NPT1 is also set forth as an IMAGE Clone, under number 3957135. An alignment of NPT1 homologs is set forth in FIG. 15.

A nucleotide sequence encoding *S. cerevisiae* PNC1 and the protein encoded thereby are set forth as SEQ ID NOs: 3 and 4, respectively, which correspond to GenBank Accession numbers NC_001139 and NP_011478, respectively. PNC1 is the yeast homologue of the bacterial protein pncA, which catalyzes the hydrolysis of nicotinamide to nicotinic acid and ammonia. *S. cerevisiae* PNC 1, also referred to as open reading frame (ORF) YGL037 is described in Ghislain et al. (2002) Yeast 19:215. The nucleotide and amino acid sequences of an Arachis hypogaea PNC1 is provided by GenBank Accession numbers M37636 and AAB06183 and are described in Buffard et al. (1990) PNAS 87:8874. Nucleotide and amino acid sequences of potential human homologs are provided by GenBank Accession numbers BC017344 and AAH17344, respectively; AK027122 and NP_078986, respectively; XM_041059 and XP_041059, respectively; and NM_016048 and NP_057132, respectively. The nucleotide and amino acid sequences of a potential human PNC1 are set forth as SEQ ID NOs: 15 and 16, respectively and correspond to GenBank Accession No. BC017344. An alignment of human, fly and S. cerevisiae PNC1 is set forth in FIG. 16. A human functional homolog of PNC1 is NAMPRT, further described herein.

A nucleotide sequence encoding S. cerevisae NMA1 and the protein encoded thereby are set forth as SEQ ID Nos: 5 and 6, respectively, which correspond to GenBank Accession Numbers NC_001144.2 and NP_013432, respectively. The S. cerevisiae NMA1 corresponds to ORF YLR328, described in Smith et al. (2000) PNAS 97:6658. NMA1 is the S. cerevisae homolog of the bacterial NaMNAT gene. Nucleotide and amino acid sequences of human homologs are provided by GenBank Accession numbers NM_022787 and NP_073624, respectively; AK026065 and BAB15345, respectively; AF459819 and AAL76934, respectively; XM_087387 and XP_087387, respectively; and AF345564 and AAK52726, respectively, and NP-073624; AAL76934; NP_073624; and AF3 14163. The nucleotide and amino acid sequence of human NMA1 is set forth as SEQ ID NOs: 17 and 18, respectively, and correspond to GenBank Accession number NM_022787. An IMAGE Clone is provided under number 4874147 and HRC clone hrc08458. Bacterial homologs are described, e.g., in Zhang et al. (2002) Structure 10:69.

A nucleotide sequence encoding S. cerevisiae NMA2 and the protein encoded thereby are set forth as SEQ ID Nos: 7 and 8, respectively, which correspond to GenBank Accession numbers NC_001139 and NP_011524, respectively. The S. cerevisiiae NMA2 corresponds to ORF YGR010, described in Emanuelli et al. (1999) FEBS Lett. 455:13. NMA2 is the S. cerevisiae homolog of the bacterial NaMNAT gene. Nucleotide and amino acid sequences of human homologs are provided by GenBank Accession numbers NM_015039 and NP_055854, respectively. The nucleotide and amino acid sequences of human NMA2 are set forth as SEQ ID NOs: 19 and 20, respectively, and correspond to GenBank Accession number NM_015039.

It will be apparent to a person of skill in the art that a full length protein or nucleic acid encoding such or a portion thereof can be used according to the methods described herein. A portion of a protein is preferably a biologically active portion thereof. Portions that are biologically active can be identified according to methods known in the art and using an assay that can monitor the activity of the particular protein. Assays for determining the activity of an NPT1 protein are described, e.g., in Pescanglini et al. (1994) Clin. Chim. Acta 229: 15-25 and Sestini et al. (2000) Archives of Biochem. Biophys. 379:277. Assays for determining the activity of a PNC1 protein are described, e.g., in Ghislain et al. Yeast 19:215. Assays for determining the activity of an NMA1 and NMA2 protein are described, e.g., in Sestini et al., supra. Alternatively, the activity of such a protein can be tested in an assay in which the life span of a cell is determined. For example, a cell is transfected with a nucleic acid comprising one or more copies of a sequence encoding a portion of an NPT1, PNC1, NMA1 or NMA2 protein or a control nucleic acid, and the life span of the cells is compared. A longer life span of a cell transfected with a portion of one of the proteins indicates that the portion of the protein is a biologically active portion. Assays for determining the life span of a cell are known in the art and are also further described herein. In particular, assays for determining the life span of a mammalian cell can be conducted as described, e.g., in Cell Growth, Differentiation and Senescence: A Practical Approach. George P. Studzinski (ed.). Instead of measuring the life span, one can also measure the resistance of a transfected cell to certain stresses, e.g., heatshock, for determining whether a portion of a protein is a biologically active portion. Methods for measuring resistance to certain stresses are known in the art and are also further described herein. In particular, assays for determining the resistance of a mammalian cell to heatshock can be conducted as described, e.g., in Bunelli et al. (1999) Exp. Cell Res. 262: 20.

In addition to portions of NPT1, PNC1, NMA1 or NMA2 proteins, other variants, such as proteins containing a deletion, insertion or addition of one or more amino acids can be used, provided that the protein is biologically active. Exemplary amino acid changes include conservative amino acid substitutions. Other changes include substitutions for non-naturally occurring amino acids. Proteins encoded by nucleic acids that hybridize to a nucleic acid encoding NPT1, PNC1, NMA1 or NMA2 under high or medium stringency conditions and which are biologically active can also be used. For example, nucleic acids that hybridize under high stringency conditions of 0.2 to 1×SSC at 65° C. followed by a wash at 0.2×SSC at 65° C. to a gene encoding NPT1, PNC1, NMA1 or NMA2 can be used. Nucleic acids that hybridize under low stringency conditions of 6×SSC at room temperature followed by a wash at 2×SSC at room temperature to a gene encoding NPT1, PNC1, NMA1 or NMA2 can be used. Other hybridization conditions include 3×SSC at 40 or 50° C., followed by a wash in 1 or 2×SSC at 20, 30, 40, 50, 60, or 65° C. Hybridizations can be conducted in the presence of formaldehyde, e.g., 10%, 20%, 30% 40% or 50%, which further increases the stringency of hybridization. Theory and practice of nucleic acid hybridization is described, e.g., in S. Agrawal (ed.) Methods in Molecular Biology, volume 20; and Tijssen (1993) Laboratory Techniques in biochemistry and molecular biology-hybridization with nucleic acid probes, e.g., part I chapter 2 "Overview of principles of hybridization and the strategy of nucleic acid probe assays," Elsevier, N.Y. provide a basic guide to nucleic acid hybridization.

Exemplary proteins may have at least about 50%, 70%, 80%, 90%, preferably at least about 95%, even more preferably at least about 98% and most preferably at least 99% homology or identity with a wild-type NPT1, PNC1, NMA1 or NMA2 protein or a domain thereof, e.g., the catalytic domain. Other exemplary proteins may be encoded by a nucleic acid that is at least about 90%, preferably at least about 95%, even more preferably at least about 98% and most preferably at least 99% homology or identity with a wild-type NPT1, PNC1, NMA1 or NMA2 nucleic acid, e.g., those described herein.

In other embodiments proteins are fusion proteins, e.g., proteins fused to a transcytosis peptide. Fusion proteins may also comprise a heterologous peptide that can be used to purify the protein and/or to detect it.

In other embodiments, non-naturally occurring protein variants are used. Such variants can be peptidomimetics.

In yet other embodiments, the activity of one or more proteins selected from the group consisting of NPT1, PNC1, NMA1 and NMA2 is enhanced or increased. This can be achieved, e.g., by contacting a cell with a compound that increases the activity, e.g., enzymatic activity, of one of these proteins. Assays for identifying such compounds are further described herein.

In preferred embodiments, the flux through the NAD+ salvage pathway is increased without substantially changing the level of NAD+, NADH and the ratio of NAD+/NADH in a cell. Levels of NAD+ and NADH and ratios of these two molecules can be determined, e.g., as described in the Examples.

Any means for the introduction of polynucleotides into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

In a preferred method of the invention, the DNA constructs are delivered using viral vectors. The transgene may be incorporated into any of a variety of viral vectors useful in gene therapy, such as recombinant retroviruses, adenovirus, adeno-associated virus (AAV), and herpes simplex virus-1, or recombinant bacterial or eukaryotic plasmids. While various viral vectors may be used in the practice of this invention, AAV- and adenovirus-based approaches are of particular interest. Such vectors are generally understood to be the recombinant gene delivery system of choice for the transfer of exogenous genes in vivo, particularly into humans. The following additional guidance on the choice and use of viral vectors may be helpful to the practitioner. As described in greater detail below, such embodiments of the subject expression constructs are specifically contemplated for use in various in vivo and ex vivo gene therapy protocols.

A viral gene delivery system useful in the present invention utilizes adenovirus-derived vectors. Knowledge of the genetic organization of adenovirus, a 36 kB, linear and double-stranded DNA virus, allows substitution of a large piece of adenoviral DNA with foreign sequences up to 8 kB. In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use as a gene transfer vector because of its mid-sized genome, ease of manipulation, high titer, wide target-cell range, and high infectivity. The virus particle is relatively stable and amenable to purification and concentration, and as above, can be modified so as to affect the spectrum of infectivity. Additionally, adenovirus is easy to grow and manipulate and exhibits broad host range in vitro and in vivo. This group of viruses can be obtained in high titers, e.g., $10^9$-$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors. Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109-127). Expression of the inserted polynucleotide of the invention can be under control of, for example, the E1A promoter, the major late promoter (MLP) and associated leader sequences, the viral E3 promoter, or exogenously added promoter sequences.

The genome of an adenovirus can be manipulated such that it encodes a gene product of interest, but is inactivated in terms of its ability to replicate in a normal lytic viral life cycle (see, for example, Berkner et al., (1988) BioTechniques 6:616; Rosenfeld et al., (1991) Science 252:431-434; and Rosenfeld et al., (1992) Cell 68:143-155). Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482-6486), hepatocytes (Herz and Gerard, (1993) PNAS USA 90:2812-2816) and muscle cells (Quantin et al., (1992) PNAS USA 89:2581-2584).

Adenoviruses can also be cell type specific, i.e., infect only restricted types of cells and/or express a transgene only in restricted types of cells. For example, the viruses comprise a gene under the transcriptional control of a transcription initiation region specifically regulated by target host cells, as described e.g., in U.S. Pat. No. 5,698,443, by Henderson and Schuur, issued Dec. 16, 1997. Thus, replication competent adenoviruses can be restricted to certain cells by, e.g., inserting a cell specific response element to regulate a synthesis of a protein necessary for replication, e.g., E1A or E1B.

DNA sequences of a number of adenovirus types are available from Genbank. For example, human adenovirus type 5 has GenBank Accession No.M73260. The adenovirus DNA sequences may be obtained from any of the 42 human adenovirus types currently identified. Various adenovirus strains are available from the American Type Culture Collection, Rockville, Md., or by request from a number of commercial and academic sources. A transgene as described herein may be incorporated into any adenoviral vector and delivery protocol, by restriction digest, linker ligation or filling in of ends, and ligation.

Adenovirus producer cell lines can include one or more of the adenoviral genes E1, E2a, and E4 DNA sequence, for packaging adenovirus vectors in which one or more of these genes have been mutated or deleted are described, e.g., in PCT/US95/15947 (WO 96/18418) by Kadan et al.; PCT/US95/07341 (WO 95/346671) by Kovesdi et al.; PCT/FR94/00624 (WO94/28152) by Imler et al.;PCT/FR94/00851 (WO 95/02697) by Perrocaudet et al., PCT/US95/14793 (WO96/14061) by Wang et al.

Yet another viral vector system useful for delivery of the subject polynucleotides is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97-129).

AAV has not been associated with the cause of any disease. AAV is not a transforming or oncogenic virus. AAV integration into chromosomes of human cell lines does not cause any significant alteration in the growth properties or morphological characteristics of the cells. These properties of AAV also recommend it as a potentially useful human gene therapy vector.

AAV is also one of the few viruses that may integrate its DNA into non-dividing cells, e.g., pulmonary epithelial cells, and exhibits a high frequency of stable integration (see for example Flotte et al., (1992) Am. J. Respir. Cell. Mol. Biol. 7:349-356; Samulski et al., (1989) J. Virol. 63:3822-3828; and McLaughlin et al., (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251-3260 can be used to introduce DNA into cells. A variety of nucleic acids have been introduced into different cell types using AAV vectors (see for example Hermonat et al., (1984) PNAS USA 81:6466-6470; Tratschin et al., (1985) Mol. Cell. Biol. 4:2072-2081; Wondisford et al., (1988) Mol. Endocrinol. 2:32-39; Tratschin et al., (1984) J. Virol. 51:611-619; and Flotte et al., (1993) J. Biol. Chem. 268:3781-3790).

The AAV-based expression vector to be used typically includes the 145 nucleotide AAV inverted terminal repeats (ITRs) flanking a restriction site that can be used for subcloning of the transgene, either directly using the restriction site available, or by excision of the transgene with restriction enzymes followed by blunting of the ends, ligation of appropriate DNA linkers, restriction digestion, and ligation into the site between the ITRs. The capacity of AAV vectors is about 4.4 kb (Kotin, R.M., Human Gene Therapy 5:793-801, 1994 and Flotte, et al. J. Biol. Chem. 268:3781-3790, 1993).

AAV stocks can be produced as described in Hermonat and Muzyczka (1984) PNAS 81:6466, modified by using the pAAV/Ad described by Samulski et al. (1989) J. Virol. 63:3822. Concentration and purification of the virus can be achieved by reported methods such as banding in cesium chloride gradients, as was used for the initial report of AAV vector expression in vivo (Flotte, et al. J. Biol. Chem. 268: 3781-3790, 1993) or chromatographic purification, as described in O'Riordan et al., WO97/08298. Methods for in vitro packaging AAV vectors are also available and have the advantage that there is no size limitation of the DNA packaged into the particles (see, U.S. Pat. No. 5,688,676, by Zhou et al., issued Nov. 18, 1997). This procedure involves the preparation of cell free packaging extracts.

Hybrid Adenovirus-AAV vectors represented by an adenovirus capsid containing a nucleic acid comprising a portion of an adenovirus, and 5' and 3' ITR sequences from an AAV which flank a selected transgene under the control of a promoter. See e.g. Wilson et al, International Patent Application Publication No. WO 96/13598. This hybrid vector is characterized by high titer transgene delivery to a host cell and the ability to stably integrate the transgene into the host cell chromosome in the presence of the rep gene. This virus is capable of infecting virtually all cell types (conferred by its adenovirus sequences) and stable long term transgene integration into the host cell genome (conferred by its AAV sequences).

The adenovirus nucleic acid sequences employed in this vector can range from a minimum sequence amount, which requires the use of a helper virus to produce the hybrid virus particle, to only selected deletions of adenovirus genes, which deleted gene products can be supplied in the hybrid viral process by a packaging cell. For example, a hybrid virus can comprise the 5' and 3' inverted terminal repeat (ITR) sequences of an adenovirus (which function as origins of replication). The left terminal sequence (5') sequence of the Ad5 genome that can be used spans bp 1 to about 360 of the conventional adenovirus genome (also referred to as map units 0-1) and includes the 5' ITR and the packaging/enhancer domain. The 3' adenovirus sequences of the hybrid virus include the right terminal 3' ITR sequence which is about 580 nucleotides (about bp 35,353—end of the adenovirus, referred to as about map units 98.4-100).

The preparation of the hybrid vector is further described in detail in published PCT application entitled "Hybrid Adenovirus-AAV Virus and Method of Use Thereof", WO 96/13598 by Wilson et al. For additional detailed guidance on adenovirus and hybrid adenovirus-AAV technology which may be useful in the practice of the subject invention, including methods and materials for the incorporation of a transgene, the propagation and purification of recombinant virus containing the transgene, and its use in transfecting cells and mammals, see also Wilson et al, WO 94/28938, WO 96/13597 and WO 96/26285, and references cited therein.

In order to construct a retroviral vector, a nucleic acid of interest is inserted into the viral genome in the place of certain viral sequences to produce a virus that is replication-defective. In order to produce virions, a packaging cell line containing the gag, pol, and env genes but without the LTR and psi components is constructed (Mann et al. (1983) Cell 33:153). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas and Rubenstein (1988) "Retroviral Vectors", In: Rodriguez and Denhardt ed. Vectors: A Survey of Molecular Cloning Vectors and their Uses. Stoneham:Butterworth; Temin, (1986) "Retrovirus Vectors for Gene Transfer: Efficient Integration into and Expression of Exogenous DNA in Vertebrate Cell Genome", In: Kucherlapati ed. Gene Transfer. New York: Plenum Press; Mann et al., 1983, supra). The media containing the recombinant retroviruses is then collected, optionally concentrated, and used for gene transfer. Retroviral vectors are able to infect a broad variety of cell types. Integration and stable expression require the division of host cells (Paskind et al. (1975) Virology 67:242). This aspect is particularly relevant for the treatment of PVR, since these vectors allow selective targeting of cells which proliferate, i.e., selective targeting of the cells in the epiretinal membrane, since these are the only ones proliferating in eyes of PVR subjects.

A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a protein of the present invention, e.g., a transcriptional activator, rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F.M. et al., (eds.) Greene Publishing Associates, (1989), Sections 9.10-9.14 and other standard laboratory manuals. Examples of suitable retroviruses include pLJ, pZIP, pWE and pEM which are well known to those skilled in the art. A preferred retroviral vector is a pSR MSVtkNeo (Muller et al. (1991) Mol. Cell Biol. 11:1785 and pSR MSV(XbaI) (Sawyers et al. (1995) J. Exp. Med. 181: 307) and derivatives thereof. For example, the unique BamHI sites in both of these vectors can be removed by digesting the vectors with BamHI, filling in with Klenow and religating to produce pSMTN2 and pSMTX2, respectively, as described in PCT/US96/09948 by Clackson et al. Examples of suitable packaging virus lines for preparing both ecotropic and amphotropic retroviral systems include Crip, Cre, 2 and Am.

Retroviruses, including lentiviruses, have been used to introduce a variety of genes into many different cell types, including neural cells, epithelial cells, retinal cells, endothelial cells, lymphocytes, myoblasts, hepatocytes, bone marrow cells, in vitro and/or in vivo (see for example, review by Federico (1999) Curr. Opin. Biotechnol. 10:448; Eglitis et al., (1985) Science 230:1395-1398; Danos and Mulligan, (1988) PNAS USA 85:6460-6464; Wilson et al., (1988) PNAS USA 85:3014-3018; Armentano et al., (1990) PNAS USA 87:6141-6145; Huber et al., (1991) PNAS USA 88:8039-8043; Ferry et al., (1991) PNAS USA 88:8377-8381; Chowdhury et al., (1991) Science 254:1802-1805; van Beusechem et al., (1992) PNAS USA 89:7640-7644; Kay et al., (1992) Human Gene Therapy 3:641-647; Dai et al., (1992) PNAS USA 89:10892-10895; Hwu et al., (1993) J. Immunol. 150:4104-4115; U.S. Pat. No. 4,868,116; 4,980, 286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079-9083; Julan et al., (1992) J. Gen Virol 73:3251-3255; and Goud et al., (1983) Virology 163:251-254); or coupling cell surface ligands to the viral env proteins (Neda et al., (1991) J. Biol. Chem. 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Other viral vector systems that can be used to deliver a polynucleotide of the invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth,; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68: 1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988, supra; Horwich et al.(1990) J. Virol., 64:642-650).

The expression of a protein, e.g., a protein selected from the group consisting of NPT1, PNC1, NMA1 and NMA2 or a biologically active variant thereof in cells of a subject to whom, e.g., a nucleic acid encoding the protein was administered, can be determined, e.g., by obtaining a sample of the cells of the patient and determining the level of the protein in the sample, relative to a control sample.

In another embodiment, a protein or biologically active variant thereof, is administered to the subject such that it reaches the target cells, and traverses the cellular membrane. Polypeptides can be synthesized in prokaryotes or eukaryotes or cells thereof and purified according to methods known in the art. For example, recombinant polypeptides can be synthesized in human cells, mouse cells, rat cells, insect cells, yeast cells, and plant cells. Polypeptides can also be synthesized in cell free extracts, e.g., reticulocyte lysates or wheat germ extracts. Purification of proteins can be done by various methods, e.g., chromatographic methods (see, e.g., Robert K Scopes "Protein Purification: Principles and Practice" Third Ed. Springer-Verlag, N.Y. 1994). In one embodiment, the polypeptide is produced as a fusion polypeptide comprising an epitope tag consisting of about six consecutive histidine residues. The fusion polypeptide can then be purified on a $Ni^{++}$ column. By inserting a protease site between the tag and the polypeptide, the tag can be removed after purification of the peptide on the Ni$^{++}$ column. These methods are well known in the art and commercial vectors and affinity matrices are commercially available.

Administration of polypeptides can be done by mixing them with liposomes, as described above. The surface of the liposomes can be modified by adding molecules that will target the liposome to the desired physiological location.

In one embodiment, a protein is modified so that its rate of traversing the cellular membrane is increased. For example, the polypeptide can be fused to a second peptide which promotes "transcytosis," e.g., uptake of the peptide by cells. In one embodiment, the peptide is a portion of the HIV transactivator (TAT) protein, such as the fragment corresponding to residues 37-62 or 48-60 of TAT, portions which are rapidly taken up by cell in vitro (Green and Loewenstein, (1989) Cell 55:1179-1188). In another embodiment, the internalizing peptide is derived from the *Drosophila antennapedia* protein, or homologs thereof. The 60 amino acid long homeodomain of the homeo-protein antennapedia has been demonstrated to translocate through biological membranes and can facilitate the translocation of heterologous polypeptides to which it is couples. Thus, polypeptides can be fused to a peptide consisting of about amino acids 42-58 of *Drosophila antennapedia* or shorter fragments for transcytosis. See for example Derossi et al. (1996) J Biol Chem 271:18188-18193; Derossi et al. (1994) J Biol Chem 269:10444-10450; and Perez et al. (1992) J Cell Sci 102:717-722.

In another embodiment, the amount of nicotinamide is decreased in a cell. This can be achieved, e.g., by inhibiting the expression of genes of the NAD+ salvage pathway or other pathway that produce nicotinamide. Inhibition of the genes can be conducted, e.g., as further described herein, such as by performing RNAi on the NAD+ salvage pathway genes that produce nicotinamide. One can also inhibit genes that are involved in the de novo synthesis of nicotinamide. For example, nicotinamide levels in cells can be regulated by regulating the level or activity of poly(adenosine diphosphate-ribose) polymerase-1 (PARP). In particular, nicotinamide levels can be reduced by reducing the level or activity of PARP, since this enzyme generates nicotinamide. Nicotinamide levels may also be decreased in cells by reducing the level or activity of glycohydrolases (e.g., human CD38, an ectoenzyme that is expressed on the surface of immune cells, such as neutrophils; gi:4502665 and GenBank Accession No. NP_001766), which cleave NAD to nicotinamide.

Nicotinamide levels may also be decreased by inhibiting the de novo nicotinamide synthesis pathway. Genes involved in this pathway include the BNA genes in *S. cerevisiae* (BNA1-6). Alternatively, poly(adenosine diphosphate-ribose) polymerase (PARP) family members, e.g., PARP-1 and PARPv and tankyrase can also be inhibited to decrease nicotinamide levels.

It is also possible to reduce the level or activity of nicotinamide transporters to reduce the level of nicotinamide that is imported into cells. For example, in yeast, nicotinic acid is transported by the Tna1 (nicotinate/nicotinamide mononucleotide transport) protein. Human homologues of yeast TNA1 have the following GenBank Accession numbers: gi:9719374 and AAF97769; gi:6912666 and NP_036566; gi: 18676562 and AB84933; gi:12718201 and CAC28600; gi:19263934 and AAH25312; gi:9966811 and NP_065079; and gi:22761334 and BAC11546. Other nucleoside transporters that can be modulated include bacterial and fly nucleoside transporter and the following human genes that are homologous thereto: gi:8923160 and NP_060164; gi:14336678 and AAK61212; gi: 22749231 and NP_689812; and gi: 18603939 and XP_091525.

Alternatively, nicotinamide levels can be decreased or nicotinamide inactivated, e.g., by stimulating the activity or increase the level of enzymes that metabolize, degrade or inhibit nicotinamide, e.g., nicotinamide N-methyl transferase, also referred to as nicotinamide methyltransferase (NNMT; EC 2.1.1.1; CAS registry number 9029-74-7). This enzyme catalyzes the reaction S-adenosyl-L-methionine+nicotinamide=S-adenosyl-L-homocysteine+1-methylnicotinamide and promotes excretion of nicotinamide from the cell (see also, Cantoni (1951) *J. Biol. Chem.* 203-216). The human enzyme is referred to as NNMT and its complete sequence can be found at GenBank Accession number U08021 and as SEQ ID NO: 9 for the nucleotide sequence and SEQ ID NO: 10 for the protein (Aksoy et al. (1994) *J. Biol. Chem.* 269: 14835). The yeast version of this enzyme is referred to as NNT1 (also referred to as YLR258w).

Yet another enzyme that metabolizes nicotinamide and thereby reduces the level of nicotinamide is nicotinamide phosphribosyltransferase (NAMPRT; E.C.2.4.2.12). The human gene is also referred to as pre-B-cell colony enhancing factor 1(PBEF1) and visfatin and exists as two isoforms (see, e.g., Samal et al. (1994) Mol. Cell. Biol. 14:1431, Rongwaux et al. (2002) Euro. J. Immunol. 32:3225 and Fukuhara et al. Science 307:426-30 (2005); U.S. Pat. Nos. 5,874,399 and 6,844,163). The sequence of isoform a is available under GenBank Accession numbers NM_005746, NP_005737 and U02020 and the sequence of isoform b is available under GenBank Accession numbers NM_182790, NP_877591 and BC020691. The nucleotide and amino acid sequences of human NAMPRT isoform a (NM_005746) are set forth as SEQ ID NOs: 21 and 22. The nucleotide and amino acid sequences of human NAMPRT isoform b (BC020691) are set forth as SEQ ID NOs: 11 and 12, respectively. The sequence of a genomic clone of human NAMPRT is provided in GenBank Accession No. AC007032. The structure of the human gene is described in Ognjanovic et al. (2001) J. Mol. Endocrinol. 26:107. In yeast and human cells, the level of PNC1 or functional human homolog or equivalent thereof can be increased to reduce nicotinamide levels.

Another enzyme that metabolizes nicotinamide and may thereby modulate, e.g., reduce, the level of nicotinamide is nicotinamide mononucleotide (NMN) adenylyltransferase in human cells. The human enzyme is referred to as NMNAT-1 (E.C.2.7.7.18). The following GenBank Accession numbers are provided for the human enzyme: NP_073624; NM_022787; AAL76934; AF459819; and NP_073624; AF314163. A variant of this gene is NMNAT-2 (KIAA0479), the human version of which can be found under GenBank Accession numbers NP_055854 and NM_015039 (Raffaelli et al. (2002) *Biochem Biophys Res Commun* 297:835). In yeast cells, the equivalent enzymes in the NAD+ salvage pathway are nicotinate mononucleotide adenyltransferase 1 and 2 (NMA1 and NMA2, respectively) (E.C. 2.7.7.1).

Yet another enzyme that may be increased to decrease nicotinamide levels is phosphoribosyl pyrophosphate (PRPP) synthase (PRPS), which converts ribose 5-phosphate to PRPP, the substrate of NPT1. There are several related enzymes, having the following GenBank Accession numbers: gi:4506127 and NP_002755 (Prps1); gi:4506129 and NP_002756 (Prps2); gi:20539448; gi:4506133 and NP_002758 (Prps associated protein 2); gi:24418495 and Q14558 (Prps associated protein 1); gi:17644236 and CAD18892; gi:2160401 and BAA05675 (Prps isoform 1); and gi:2160402 and BAA05676 (Prps isoform 2).

Reducing nicotinamide levels in cells may also provide other advantages, such as stimulating DNA break repair. Indeed, PARP is regulated by nicotinamide (nicotinamide negatively regulates PARP). Thus, regulating the level of nicotinamide in cells, e.g., as further described herein, will regulate the activity of PARP. Accordingly, since PARP is involved in numerous cellular functions, such as DNA break repair, telomere-length regulation, and histone modification, modulating nicotinamide levels will modulate these activities. For example, reducing nicotinamide levels in cells will increase the activity of PARP and thereby further enhance the DNA break repair mechanism of cells.

In addition to applying the methods of the invention in eukaryotic cells, such as mammalian cells and yeast cells, the methods can also be applied to plant cells, based at least on the fact that Sir2 family members are present in plants. Accordingly, the invention also provides methods for extending the life span of plants and plant cells and for rendering the plant and plant cells more resistant to stress, e.g., excessive salt conditions. This can be achieved, e.g., by modulating the level or activity of proteins in the plant cells that are essentially homologous to the proteins described herein in the yeast and mammalian systems as increasing the life span and/or the stress resistance of cells. Alternatively, the level of nicotinamide in plant cells can be reduced, in particular, as described herein for modulating their level in other eukaryotic cells. Nucleic acids can be introduced into plant cells according to methods known in the art.

For example, the following are genes form *Arabidopsis thalainia* that are homologous to the genes described above that can be modulated to modulate the flux through the NAD+ salvage pathway or nicotinamide levels in cells. Homologues of yeast PNC1: gi 18401044 NP_566539.1 (a putative hydrolase); gi 15237256 NP_1977131; and gi 15237258 NP_197714.1. Homologues of yeast NPT1: gi 2026021 AAM13003.1; gi 15234571 NP_195412.1; gi 25054896 AAN71931.1; and gi 15227832 NP_179923.1. Homologues of yeast NMA1/2: gi 22327861 NP_200392.2 and gi 9758615 BAB09248.1. Homologues of yeast NNT1 (YL285W): gi 20197178 AAC14529; gi 22325900 NP_565619.2; gi 15219438 NP_177475.1 (a Tumor related Protein); gi 12324311 AA652120.1; gi:22330409 NP_683465; gi:15240506 NP_199767; gi 8778835 AAF79834.1; and gi 15231011 NP_188637. Homologue of human NNMT: gi 15238203 NP_196623. Homologue of yeast QNS1 (gene downstream of NMA1/2 in the NAD+ salvage pathway): gi:15221990 NP_175906. Homologues of yeast BNA6: gi:18379203 NP_565259 and gi:21555686 AAM63914.

The methods of the invention can also be used to increase the lifespan and stress resistance in microorganisms, such as prokaryotes, based on the fact that Sir2 family members are also present in these organisms.

As set forth above, a full length protein described above (e.g., PARP, TNA1, NNMT, PBEF, NMN, NMNAT-1, PRPP, and homologs and equivalents of these proteins), or nucleic acid encoding such, or any portion thereof, preferably a biologically active portion, can be used. Homologs can be homologous proteins from other species or proteins or nucleic acids that have a certain degree or percentage identity with a particular protein, as further describe above. Fusion proteins, such as those comprising a peptide described above, or nucleic acids encoding such can also be used. The proteins or nucleic acids can be contacted with a cell, introduced into a cell or expressed in a cell. For example, a nucleic acid encoding a protein can be introduced into a cell, such as decribed above. Alternatively, the level of a protein or its activity can be increased in a cell. For example, an agent that stimulates the expression of the gene encoding the protein, or an agent that increases the activity of a protein, can be contacted with a cell.

In a particular embodiment, NAMPRT or homolog or equivalent thereof or biologically active fragment (included in the term "variant") thereof is contacted with a cell. As described in the Examples, NAMPRT is present in serum of animals under certain conditions, and thus is presumed to act on a cell. Accordingly, to extend the lifespan of a cell or to protect it from stress or to induce any of the other biological activities described herein, the cell may be contacted with an effective amount of NAMPRT or variant thereof. In animals, NAMPRT may be administered by any of the conventional means for administration of pharmaceuticals, e.g., as further described herein.

Exemplary biologically active portions of NAMPRT that may be used include NAMPRT proteins or peptide fragments capable of modulating the life span of a cell or its resistance to stress; those having enzymatic activity and those capable of binding and/or activating the insulin receptor ala Visfatin. Fragments may also consist of about at least 20, 50, 100, 200 or 300 amino acids of either isoform. Exemplary fragments of NAMPRT proteins include amino acids 15 or 32 to 491 of isoform a (SEQ ID NO: 22), which is believed to be the mature form of the protein (see, U.S. Pat. No. 5,874,399). NAMPRT may be glycosylated, e.g., on Asn 29 and/or Asn 396, or non-glycosylated.

A NAMPRT protein or other extracellular protein described herein may also be modified with a water soluble polymer such as polyethylene glycol. Covalent attachment of water soluble polymers to proteins may be carried out using techniques known to those skilled in the art and have been described in U.S. Pat. No. 4,179,937. The modified polypeptide may have desirable properties such as increased solubility in aqueous solutions, increased stability, longer in vivo half-life and increased biological activity.

In addition, compounds or agents that stimulate the level of expression of the NAMPRT gene or the activity of the protein can be used. Known inducers include pokeweek mitogen, lipopolysaccharide (LPS), interleukin (IL)-1β, tumor necrosis factor (TNF)α and IL-6 (Ognjanovic et al. (2001) J. Mol. Endocrinol. 26:107). Additional inducers of NAMPRT expression levels can be identified in assays using the promoter region of the gene, that is, e.g., included in the genomic clone described above.

In another embodiment, stimulating the NAD+ salvage pathway in a cell comprises contacting the cell with nicotinamide riboside, a precursor of NAD+, or a biologically active analog and/or prodrug thereof. Nicotinamide riboside can be prepared by treating NMN (from, e.g., Sigma) with a phosphatase, as described, e.g., in Bieganowski et al. (2004) Cell 117:495. Nicotinamide riboside can be in the oxidized or reduced form, the latter of which appears to be more stable (Friedlos et al. (1992) Biochem Pharmacol. 44:631. Nicotinamide riboside (1) is depicted below.

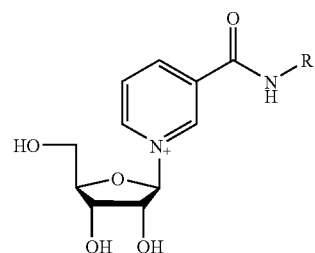

1

Nicotinamide riboside and some of its analogs are represented by formula A:

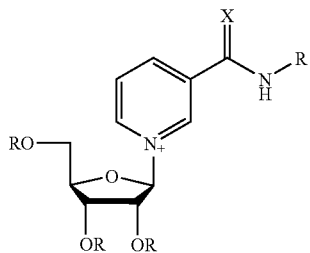

wherein

R represents independently for each occurrence H, acetyl, benzoyl, acyl, phosphate, sulfate, (alkyoxy)methyl, triarylmethyl, (trialkyl)silyl, (dialkyl)(aryl)silyl, (alkyl)(diaryl)silyl, or (triaryl)silyl; and X represents O or S.

Nicotinamide riboside can be contacted with the cell at a concentration of about 1 nM to 10 μM. A cell may be optionally contacted with an agent that increases protein or activity levels of a nicotinamide riboside kinase (Nrk) enzyme, that phosphorylates nicotinamide riboside to form nicotinamide mononucleotide (NMN). Nrk exits in one form in yeast, Nrk1, and in two forms in humans, Nrk1 (GenBank Accession Noa. NM_017881.1; NP_060351; SEQ ID NOs: 27 and 28, respectively) and Nrk2 (GenBank Accession Nos. NM_170678; NP_733778; SEQ ID NOs: 29 and 30, respectively).

3. Methods for Reducing the Life Span of a Cell or Rendering it More Susceptible to Certain Stresses In one embodiment, the level of expression or activity of a protein selected from the group consisting of NPT1, PNC1, NMA1 and NMA2 is decreased in a cell. This can be achieved by introducing into the cell an agent that inhibits the expression of the corresponding gene. An agent can be a small molecule that acts directly or indirectly on the promoter of the corresponding gene to reduce or inhibit its transcription. An agent can also be a compound that inhibits the biological activity of the protein. An agent can also be an antisense molecule, a triplex molecule or a si RNA. Yet other agents are nucleic acids encoding a protein, such as a dominant negative mutant or an intracellular antibody or other protein that interferes with the biological activity of the protein. Such methods are well known in the art. Exemplary methods are set forth below.

One method for decreasing the level of expression of a gene in a cell is to introduce into the cell antisense molecules which are complementary to at least a portion of the target gene or RNA. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

Preferably, antisense nucleic acids are of at least six nucleotides and are preferably oligonucleotides (ranging from 6 to about 200 oligonucleotides). In specific aspects, the oligonucleotide is at least 10 nucleotides, at least 15 nucleotides, at least 100 nucleotides, or at least 200 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., 1989, Proc. Natl. Acad. Sci. U.S.A. 86: 6553-6556; Lemaitre et al., 1987, Proc. Natl. Acad. Sci. 84: 648-652: PCT Publication No. WO 88/09810, published Dec. 15, 1988), hybridization-triggered cleavage agents (see, e.g., Krol et al., 1988, BioTechniques 6: 958-976) or intercalating agents (see, e.g., Zon, 1988, Pharm. Res. 5: 539-549).

In a preferred aspect of the invention, an antisense oligonucleotide is provided, preferably as single-stranded DNA. The oligonucleotide may be modified at any position on its structure with constituents generally known in the art. For example, the antisense oligonucleotides may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil,(acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is a 2-α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625-6641).

The oligonucleotide may be conjugated to another molecule, e.g., a peptide, hybridization triggered cross-linking agent transport agent, hybridization-triggered cleavage agent, etc. An antisense molecule can be a "peptide nucleic acid" (PNA). PNA refers to an antisense molecule or antigene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The antisense nucleic acids of the invention comprise a sequence complementary to at least a portion of a target RNA species. However, absolute complementarity, although preferred, is not required. A sequence "complementary to at least a portion of an RNA," as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a target RNA it may contain and still form a stable duplex (or triplex, as the case may be). One skilled in the art can ascertain a tolerable degree of mismatch by use of standard procedures to determine the melting point of the hybridized complex. The amount of antisense nucleic acid that will be effective in the inhibiting translation of the target RNA can be determined by standard assay techniques.

The synthesized antisense oligonucleotides can then be administered to a cell in a controlled manner. For example, the antisense oligonucleotides can be placed in the growth environment of the cell at controlled levels where they may be taken up by the cell. The uptake of the antisense oligonucleotides can be assisted by use of methods well known in the art.

In an alternative embodiment, the antisense nucleic acids of the invention are controllably expressed intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequences encoding the antisense RNAs can be by any promoter known in the art to act in a cell of interest. Such promoters can be inducible or constitutive. Most preferably, promoters are controllable or inducible by the administration of an exogenous moiety in order to achieve controlled expression of the antisense oligonucleotide. Such controllable promoters include the Tet promoter. Other usable promoters for mammalian cells include, but are not limited to: the SV40 early promoter region (Bemoist and Chambon, 1981, Nature 290: 304-310), the promoter contained in the 3' long terminal repeat of Rous sarcoma virus (Yamamoto et al., 1980, Cell 22: 787-797), the herpes thymidine kinase promoter (Wagner et al., 1981, Proc. Natl. Acad. Sci. U.S.A. 78: 1441-1445), the regulatory sequences of the metallothionein gene (Brinster et al., 1982, Nature 296: 39-42), etc.

Antisense therapy for a variety of cancers is in clinical phase and has been discussed extensively in the literature. Reed reviewed antisense therapy directed at the Bcl-2 gene in tumors; gene transfer-mediated overexpression of Bcl-2 in tumor cell lines conferred resistance to many types of cancer drugs. (Reed, J. C., N.C.I. (1997) 89:988-990). The potential for clinical development of antisense inhibitors of ras is discussed by Cowsert, L. M., Anti-Cancer Drug Design (1997) 12:359-371. Additional important antisense targets include leukemia (Geurtz, A. M., Anti-Cancer Drug Design (1997) 12:341-358); human C-ref kinase (Monia, B. P., Anti-Cancer Drug Design (1997) 12:327-339); and protein kinase C (McGraw et al., Anti-Cancer Drug Design (1997) 12:315-326).

In another embodiment, the level of a particular mRNA or polypeptide in a cell is reduced by introduction of a ribozyme into the cell or nucleic acid encoding such. Ribozyme molecules designed to catalytically cleave mRNA transcripts can also be introduced into, or expressed, in cells to inhibit expression of a gene (see, e.g., Sarver et al., 1990, Science 247:1222-1225 and U.S. Pat. No. 5,093,246). One commonly used ribozyme motif is the hammerhead, for which the substrate sequence requirements are minimal. Design of the hammerhead ribozyme is disclosed in Usman et al., Current Opin. Struct. Biol. (1996) 6:527-533. Usman also discusses the therapeutic uses of ribozymes. Ribozymes can also be prepared and used as described in Long et al., FASEB J. (1993) 7:25; Symons, Ann. Rev. Biochem. (1992) 61:641; Perrotta et al., Biochem. (1992) 31:16-17; Ojwang et al., Proc. Natl. Acad. Sci. (USA) (1992) 89:10802-10806; and U.S. Pat. No. 5,254,678. Ribozyme cleavage of HIV-I RNA is described in U.S. Pat. No. 5,144,019; methods of cleaving RNA using ribozymes is described in U.S. Pat. No. 5,116,742; and methods for increasing the specificity of ribozymes are described in U.S. Pat. No. 5,225,337 and Koizumi et al., Nucleic Acid Res. (1989) 17:7059-7071. Preparation and use of ribozyme fragments in a hammerhead structure are also described by Koizumi et al., Nucleic Acids Res. (1989) 17:7059-7071. Preparation and use of ribozyme fragments in a hairpin structure are described by Chowrira and Burke, Nucleic Acids Res. (1992) 20:2835. Ribozymes can also be made by rolling transcription as described in Daubendiek and Kool, Nat. Biotechnol. (1997) 15(3):273-277.

Another method for decreasing or blocking gene expression is by introducing double stranded small interfering RNAs (siRNAs), which mediate sequence specific mRNA degradation. RNA interference (RNAi) is the process of sequence-specific, post-transcriptional gene silencing in animals and plants, initiated by double-stranded RNA (dsRNA) that is homologous in sequence to the silenced gene. In vivo, long dsRNA are cleaved by ribonuclease III to generate 21-and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. Nature 2001;411(6836):494-8). Accordingly, translation of a gene in a cell can be inhibited by contacting the cell with short doublestranded RNAs having a length of about 15 to 30 nucleotides, preferably of about 18 to 21 nucleotides and most preferably 19 to 21 nucleotides. Alternatively, a vector encoding such siRNAs or hairpin RNAs that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550. Vectors that can be used are commercially available, e.g., from OligoEngine under the name pSuper RNAi System™.

Gene expression can also be reduced by targeting deoxyribonucleotide sequences complementary to the regulatory region of the target gene (i.e., the gene promoter and/or enhancers) to form triple helical structures that prevent transcription of the gene in target cells in the body. (See generally, Helene, C. 1991, Anticancer Drug Des., 6(6):569-84; Helene, C., et al., 1992, Ann, N.Y. Accad. Sci., 660:27-36; and Maher, L. J., 1992, Bioassays 14(12):807-15).

In a further embodiment, RNA aptamers can be introduced into or expressed in a cell. RNA aptamers are specific RNA ligands for proteins, such as for Tat and Rev RNA (Good et al., 1997, Gene Therapy 4: 45-54) that can specifically inhibit their translation.

Yet another method of decreasing the biological activity of a polypeptide is by introducing into the cell a dominant negative mutant. A dominant negative mutant polypeptide will interact with a molecule with which the polypeptide normally interacts, thereby competing for the molecule, but since it is biologically inactive, it will inhibit the biological activity of the polypeptide. A dominant negative mutant of a protein can be created, e.g., by mutating the substrate-binding domain, the catalytic domain, or a cellular localization domain of the polypeptide. Preferably, the mutant polypeptide will be overproduced. Point mutations are made that have such an effect. In addition, fusion of different polypeptides of various lengths to the terminus of a protein can yield dominant negative mutants. General strategies are available for making dominant negative mutants. See Herskowitz, *Nature* (1987) 329:219-222.

In another embodiment, the activity of one or more proteins selected from the group consisting of NPT1, PNC1, NMA1 and NMA2 is decreased. This can be accomplished, e.g., by contacting a cell with a compound that inhibits the activity, e.g., enzymatic activity, of one of these proteins. Assays for identifying such compounds are further described herein.

In another embodiment, the flux through the NAD+ salvage pathway in a cell is decreased by contacting the cell with nicotinamide or a variant thereof having substantially the same biological activity. In a preferred embodiment, a cell is contacted with an amount of nicotinamide of about 0.1 mM to about 100 mM, preferably about 1 mM to about 20 mM, even more preferably 2 mM to about 10 mM, and most preferably about 5 mM. Nicotinamide is commercially available (see, e.g., the source provided in the Examples). A cell is contacted with nicotinamide for a time sufficient to exert the desired effect. For example, a cell can be contacted for at least about 60 minutes or at least about 24 hours with nicotinamide. A cell may also be contacted continously with nicotinamide.

In addition to nicotinamide, cells can be contacted with analogs thereof. Exemplary analogs include Pyrazinamide, which is sold as an antituberculous agent. Analogs can be identified, e.g., by screening of combinatorial libraries of analogs for those having the desired activity. For example, an assay for measuring life span can be used. Alternatively, analogs of nicotinamide or agents that interact with the C pocket of Sir2 family members can be identified by rational drug design, as further described herein.

Exemplary analogs or derivatives of nicotinamide include compounds of formula I:

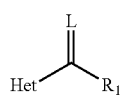

wherein,
L is O, NR, or S;
R is alkyl or phenyl;
$R_1$ is —$NH_2$, —O-alkyl, —$N(R)_2$, or —NH(R); and
Het is heteroaryl or heterocycloalkyl.

Particular analogs that may be used include compounds of formula I and the attendant definitions, wherein L is O; compounds of formula I and the attendant definitions, wherein $R_1$ is —$NH_2$; compounds of formula I and the attendant definitions, wherein Het is selected from the group consisting of pyridine, furan, oxazole, imidazole, thiazole, isoxazole, pyrazole, isothiazole, pyridazine, pyrimidine, pyrazine, pyrrole, tetrahydrofuran, 1:4 dioxane, 1,3,5-trioxane, pyrrolidine, piperidine, and piperazine; compounds of formula I and the attendant definitions, wherein Het is pyridine; compounds of formula I and the attendant definitions, wherein L is O and $R_1$ is —$NH_2$; compounds of formula I and the attendant definitions, wherein L is O and Het is pyridine; compounds of formula I and the attendant definitions, wherein $R_1$ is —$NH_2$ and Het is pyridine; and compounds of formula I and the attendant definitions, wherein L is O, $R_1$ is —$NH_2$, and Het is pyridine.

Other exemplary analogs or derivatives of nicotinamide that can be used include compounds of formula II:

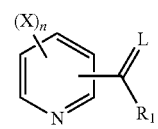

wherein,
L is O, NR, or S;
R is alkyl or phenyl;
$R_1$ is —$NH_2$, —O-alkyl, —$N(R)_2$, or —NH(R);
X is H, alkyl, —O-alkyl, OH, halide, or $NH_2$; and
n is an integer from 1 to 4 inclusive.

Particular analogs that may be used include compounds of formula II and the attendant definitions, wherein L is O; compounds of formula II and the attendant definitions, wherein $R_1$ is —$NH_2$; compounds of formula II and the attendant definitions, wherein X is H and n is 4; compounds of formula II and the attendant definitions, wherein L is O and $R_1$ is —$NH_2$; compounds of formula II and the attendant definitions, wherein L is O, X is H, and n is 4; compounds of formula II and the attendant definitions, wherein $R_1$ is —$NH_2$, X is H, and n is 4; and compounds of formula II and the attendant definitions, wherein L is O, $R_1$ is —$NH_2$, X is H, and n is 4.

Pharmaceutically acceptable salts and prodrugs of the compounds described herein may also be used.

Generally, any inhibitor of a Sir2 family member can be used to reduce the life span of cells. Preferred inhibitors are molecules that bind to the C pocket of a Sir2 family member, e.g., nicotinamide or analogs thereof.

Alternatively, the level or activity of enzymes that produce nicotinamide can be increased in a cell in which it is desired to reduce its lifespan or render it more susceptible to stress. For example, the level or activity of enzymes involved in the biosynthesis of nicotinamide in the NAD+ salvage pathway or in de novo synthesis pathways can be increased. Exemplary enzymes are set forth above in the previous section. Yet another method for increasing the level of nicotinamide in cells includes inhibiting enzymes that directly or indirectly inactivate or degrade nicotinamide, e.g., nicotinamide methyl transferase in yeast and human cells; nicotinamide phosphoribosyltransferase in human cells (discussed above) and yeast NPT1 or human homologs thereof (also described above). Methods for modulating gene expression levels or protein activity are further described herein and also known in the art.

Inhibitors of NAMPRT include FK866 (Hasmann and Schemainda, Cancer Research, 63:7436-7442, 2003) and compounds described in WO97/48397 and in WO03/080054.

In yet other embodiments, nicotinamide levels can be increased in cells by increasing the level or activity of glycohydrolases, which cleave NAD to nicotinamide. It is also possible to increase the level or activity of nicotinamide transporters to increase the level of nicotinamide in cells.

Decreasing the lifespan of cells or their resistance to stress can also be achieved in plant cells and microorganisms, by modulating plant genes that correspond to the genes described above. These genes have been described in the previous section.

4. Methods for Identifying Agents that Modulate the Flux Through the NAD+ Salvage Pathway or the Level of Nicotinamide in Cells Agents include small molecules, e.g., small organic molecules, or any biological macromolecule, e.g., a nucleic acid, such as DNA or RNA, single stranded or double stranded; a protein or peptide; a polysaccharide; a lipid; or molecular combinations thereof.

In one embodiment, a method for identifying a compound that modulates the life span of a cell or its resistance to certain types of stresses, comprises (i) contacting a protein selected from the group consisting of NPT1, PNC1, NMA1 and NMA2 with a test compound for an amount of time that would be sufficient to affect the activity of the protein; and (ii) determining the activity of the enzyme, wherein a difference in the activity of the enzyme in the presence of the test compound relative to the absence of the test compound indicates that the test compound is a compound that modulates the life span of the cell. The method may further comprise contacting a cell with the test compound and determining whether the life span of the cell has been modulated. Alternatively, the method may further comprise contacting a cell with the test compound and determining whether the resistance of the cell to certain stresses, e.g., heatshock, osmotic stress, high temperature, calorie restriction, DNA damaging agents (e.g., U.V. and the mitochondrial mutagen ethidium bromide), inappropriate nitrogen conditions, has been modulated. Determining the activity of the enzyme can be conducted as further described herein. It can also consist of measuring the effect of the test compounds on the life span of a cell or on its resitance to stress, e.g., heatshock, osmotic stress, etc.

As will be understood by a person of skill in the art, the above-assay can also be conducted with a biologically active portion or variant of one of the above-described proteins, such as those described above. For example, a portion of a protein can consist of its catalytic site. The catalytic site of S. cerevisae and human NPT1 is located between about amino acids 209 and 240. The catalytic site of S. cerevisiae PNC1 is located at about amino acids 150-186. The catalytic site of human NMNAT (homolog of NMA1 and NMA2) is located at about amino acids 100-110 and 280-310 (both sequences contribute to the active site).

In another embodiment, the invention provides a method for identifying a compound that modulates the life span of a cell or its resistance to certain types of stresses, comprising (i) contacting a cell or a lysate, comprising a transcriptional regulatory nucleic acid of a gene selected from the group consisting of NPT1, PNC1, NMA1 and NMA2 operably linked to a reporter gene, with a test compound for an amount of time that would be sufficient to affect the transcriptional regulatory nucleic acid; and (ii) determining the level or activity of the reporter gene, wherein a difference in the level or activity of the reporter gene in the presence of the test compound relative to the absence of the test compound indicates that the test compound is a compound that modulates the life span of the cell or its resistance to certain types of stresses.

The method may further comprise contacting a cell with the test compound and determining whether the life span of the cell has been modulated. The method may also further comprise contacting a cell with the test compound and determining whether the resistance of the cell to certain stresses, e.g., heatshock, has been modulated. Transcriptional regulatory nucleic acids are either known in the art or can easily be isolated according to methods well known in the art. The reporter gene can be any gene encoding a protein whose expression can be detected, e.g., by fluorescence activated cell sorting. The cell can be a prokaryotic or eukaryotic cell. The lysate can be a complete lysate of a cell, prepared according to methods known in the art, or it can be a fraction of a cell lysate or a combination of several cell lysates or fractions of cell lysates. A lysate may also comprise one or more recombinant proteins.

The invention also provides methods for regulating the level of nicotinamide in cells. Such methods may comprising identifying agents that modulate an enzyme that directly or indirectly increases or decreases nicotinamide levels in a cell. Exemplary enzymes are described herein. Assays can be conducted essentially as described above for identifying agents that modulate the NAD+ salvage pathway.

5. Methods for Identifying Inhibitors of Sir2 and Sir2 Family Members

As shown herein, nicotinamide inhibits Sir2 and human SRT1. It has also been shown that nicotinamide inhibits Sir2 non-competitively by binding to the C pocket of Sir2. Accordingly, the invention provides assays, e.g., based on rational drug design, for identifying analogs of nicotinamide that are also inhibitors of Sir2 and other members of the Sir2 family of proteins which comprise a C pocket.

Accordingly, the present invention provides methods of identifying agents that can be used for reducing the life span of cells, such as to treat conditions that may benefit from reducing the life span of certain cells. One such embodiment comprises a method of identifying an agent for use as an inhibitor of a Sir2 family member using a dataset comprising the three-dimensional coordinates of at least a portion a Sir2 family member comprising the C pocket. The crystal structure of a Sir2 homolog is described in Min et al. (2001) Cell 105 269 and the structure is provided in Protein Data Bank ID code 1ICI. The C pocket is located at about amino acids 70-90 and 127-167 of human SIRT1. The C pocket of Sir2 is located at about amino acids 250-270 and 310-350. The coordinates may further comprise the coordinates of nicotinamide or an analog thereof. In a particular embodiment the three-dimensional coordinates are those of a Sir2 homolog. In other embodiments, assays comprise co-crystallizing at least a portion of a Sir2 family member comprising the C pocket with a compound, e.g., a nicotinamide analog. Co-crystallization may be in the presence or absence of NAD+.

In one embodiment a potential agent is selected by performing rational drug design with the three-dimensional coordinates of a portion of a Sir2 family member comprising at least the C pocket. As noted above, preferably the selection is performed in conjunction with computer modeling. The potential agent is then contacted with the Sir2 family member and the activity of the Sir2 family member is determined (e.g., measured). A potential agent is identified as an agent that inhibits a Sir2 family member when there is a decrease in the activity determined for the Sir2 family member.

In a preferred embodiment the method further comprises preparing a supplemental crystal containing at least a portion of a Sir2 family member comprising the C pocket bound to the potential agent. Preferably the supplemental crystal effectively diffracts X-rays for the determination of the atomic coordinates to a resolution of better than 5.0 Angstroms, more preferably to a resolution equal to or better than 3.5 Angstroms, and even more preferably to a resolution equal to or better than 3.3 Angstroms. The three-dimensional coordinates of the supplemental crystal are then determined with molecular replacement analysis and a second generation agent is selected by performing rational drug design with the three-dimensional coordinates determined for the supplemental crystal. Preferably the selection is performed in conjunction with computer modeling. The second generation agent can be an analog of nicotinamide.

As should be readily apparent the three-dimensional structure of a supplemental crystal can be determined by molecular replacement analysis or multiwavelength anomalous dispersion or multiple isomorphous replacement. A candidate drug can then selected by performing rational drug design with the three-dimensional structure determined for the supplemental crystal, preferably in conjunction with computer modeling. The candidate drug can then be tested in a large number of drug screening assays using standard biochemical methodology exemplified herein.

The method can further comprise contacting the second generation agent with a Sir2 family member or portion thereof of a different species and determining (e.g., measuring) the activity of the Sir2 family member or portion thereof of the other species. A potential agent is then identified as an agent for use as an essentially specific inhibitor of a Sir2 family member of a first species when there is significantly less change (a factor of two or more) in the activity of the Sir2 family member of other species relative to that observed for the Sir2 family member of the first species. Preferably no, or alternatively minimal change (i.e., less than 15%) in the activity of the other species is observed.

In one aspect, the present invention provides a computer-assisted method for identifying an inhibitor of the activity of a Sir2 family member including: supplying a computer modeling application with a set of structure coordinates of a molecule or molecular complex, the molecule or molecular complex including at least a portion of a Sir2 family member comprising a C pocket; supplying the computer modeling application with a set of structure coordinates of a chemical entity, e.g., an analog of nicotinamide; and determining whether the chemical entity is an inhibitor expected to bind to or interfere with the molecule or molecular complex, wherein binding to or interfering with the molecule or molecular complex is indicative of potential inhibition of the activity of the Sir2 family member. Preferably determining whether the chemical entity is an inhibitor expected to bind to or interfere with the molecule or molecular complex includes performing a fitting operation between the chemical entity and a binding pocket of the molecule or molecular complex, followed by computationally analyzing the results of the fitting operation to quantify the association between the chemical entity and the binding pocket. The method may further includes screening a library of chemical entities. The method may also further include supplying or synthesizing the potential inhibitor, then assaying the potential inhibitor to determine whether it inhibits the activity of a Sir2 family member.

In another aspect, the present invention provides a method for making an inhibitor of a Sir2 family member, the method including chemically or enzymatically synthesizing a chemical entity to yield an inhibitor of the activity of a Sir2 family member, the chemical entity having been designed during a computer-assisted process, e.g., as described above.

The present invention further provides an apparatus that comprises a representation of a complex between Sir2 family member and nicotinamide or analog thereof. One such apparatus is a computer that comprises the representation of the complex in computer memory. In one embodiment, the computer comprises a machine-readable data storage medium which contains data storage material that is encoded with machine-readable data which comprises the atomic coordinates of the complex. The computer may further comprise a working memory for storing instructions for processing the machine-readable data, a central processing unit coupled to both the working memory and to the machine-readable data storage medium for processing the machine readable data into a three-dimensional representation of the complex. In a preferred embodiment, the computer also comprises a display that is coupled to the central-processing unit for displaying the three-dimensional representation.

6. Uses of the Invention

As further described herein, increasing the flux through the NAD+ salvage pathway, e.g., by increasing the activity or level of proteins in the pathway, or reducing nicotinamide levels mimics calorie restriction and thereby promotes cell survival and health in cells and organisms.

In one embodiment, increasing the flux through the NAD+ salvage pathway or decreasing nicotinamide levels is used to increase the life span of cells and protect cells against at least certain stresses in vitro. For example, cells in culture can be treated as described herein, such as to keep them proliferating longer. This is particularly useful for primary cell cultures (i.e., cells obtained from an organism, e.g., a human), which are known to have only a limited life span in culture. Treating such cells according to methods of the invention, e.g., by integrating one or more additional copies of one or more genes selected from the group consisting of NPT1, PNC1, NMA1, NMA2, nicotinamide N-methyl transferase (NNMT and NNT 1), nicotinamide phosphoribosyltransferase (NAMPRT), and optionally human nicotinamide mononucleotide adenylyltransferase (NMNAT, NMAT-1 and 2), will result in increasing the amount of time that the cells are kept alive in culture. Embryonic stem (ES) cells and pluripotent cells, and cells differentiated therefrom, can also be modified according to the methods of the invention such as to keep the cells or progeny thereof in culture for longer periods of time. Primary cultures of cells, ES cells, pluripotent cells and progeny thereof can be used, e.g., to identify compounds having particular biological effects on the cells or for testing the toxicity of compounds on the cells (i.e., cytotoxicity assays).

Instead of introducing one or more copies of the above-cited genes into a cell, a cell may also be contacted with the protein encoded by these genes. For example, NAMPRT or a variant thereof can be added to the culture medium of cells, from where it will interact with the cell and exert its activities on the cell. NAMPRT may be added at a concentration sufficient for inducing a biological effect on cells, e.g., at a concentration of about 1 to 1000 ng/ml, more preferably about 1 to 300 ng/ml and most preferably about 3 to 100 ng/ml. Concentrations of about 10 and 100 ng/ml may also be used. NAMPRT may be produced in vitro, e.g., in a bacterial expression system or in an in vitro transcription and/or translation system, or in vivo, e.g., in cells, according to methods known in the art.

In another embodiment, nicotinamide riboside or a functional homolog or prodrug thereof is added to the culture.

In other embodiments, cells that are intended to be preserved for long periods of time are treated as described herein. The cells can be cells in suspension, e.g., blood cells, or tissues or organs. For example, blood collected from an individual for administering to an individual can be treated according to the invention, such as to preserve the blood cells for longer periods of time. Other cells that one may treat for extending their lifespan and/or protect them against certain types of stresses include cells for consumption, e.g., cells from non-human mammals (such as meat), or plant cells (such as vegetables).

In another embodiment, cells obtained from a subject, e.g., a human or other mammal, are treated according to the methods of the invention and then administered to the same or a different subject. Accordingly, cells or tissues obtained from a donor for use as a graft can be treated as described herein prior to administering to the recipient of the graft. For example, bone marrow cells can be obtained from a subject, treated ex vivo to extend their life span and protect the cells against certain types of stresses and then administered to a recipient. In certain embodiments, the cells of the graft, e.g., bone marrow, are transfected with one or more copies of one or more genes selected from the group consisting of NPT1, PNC1, NMA1, NMA2, NMNAT, NNT1, NAMPRT, and optionally NMAT-1 or 2. In other embodiments, a graft is incubated with a solution comprising the protein, e.g., NAMPRT. The graft can be an organ, a tissue or loose cells.

In yet other embodiments, cells are treated in vivo to increase their life span and/or protect them against certain types of stresses. For example, skin can be protected from aging, e.g., developing wrinkles, by treating skin, e.g., epithelial cells, as described herein. In an exemplary embodiment, skin is contacted with a pharmaceutical or cosmetic composition comprising a compound that is capable of increasing the transcription of one or more genes selected from the group consisting of NPT1, PNC1, NMA1, NMA2, NMNAT, NNT1, NAMPRT, and optionally NMAT-1 or 2. In another embodiment, skin cells are contacted with a composition comprising a protein selected from the group consisting of NPT1, PNC1, NMA1, NMA2, NMNAT, NNT1, NAMPRT, and optionally NMAT-1 or 2, or a nucleic acid encoding such, and a vehicle for delivering the nucleic acid or protein to the cells. Nicotinamide riboside or a functional homolog or prodrug thereof can also be administered in vivo.

Compounds, nucleic acids and proteins can also be delivered to a tissue or organ within a subject, such as by injection, to extend the life span of the cells or protect the cells against certain stresses.

In yet another embodiment, an agent of the invention, e.g. an NPT1, PNC1, NMA1, NMA2, NMNAT, NNT1, NAMPRT, and/or NMAT-1 or 2 protein or nucleic acid or agent increasing the level of expression or activity of these proteins, is administered to subjects, such as to generally increase the life span of its cells, protect its cells against certain types of stresses, to prevent or treat diseases of aging, the process of aging itself, diseases or afflictions associate with cell death, infection and toxic agents. For example, an agent can be taken by subjects as food supplements. In one embodiment, such an agent is a component of a multi-vitamin complex.

All animals typically go through a period of growth and maturation followed by a period of progressive and irreversible physiological decline ending in death. The length of time from birth to death is known as the life span of an organism, and each organism has a characteristic average life span. Aging is a physical manifestation of the changes underlying the passage of time as measured by percent of average life span.

In some cases, characteristics of aging can be quite obvious. For example, characteristics of older humans include skin wrinkling, graying of the hair, baldness, and cataracts, as well as hypermelanosis, osteoporosis, cerebral cortical atrophy, lymphoid depletion, thymic atrophy, increased incidence of diabetes type II, atherosclerosis, cancer, and heart disease. Nehlin et al. (2000), Annals NY Acad Sci 980:176-79. Other aspects of mammalian aging include weight loss, lordokyphosis (hunchback spine), absence of vigor, lymphoid atrophy, decreased bone density, dermal thickening and subcutaneous adipose tissue, decreased ability to tolerate stress (including heat or cold, wounding, anesthesia, and hematopoietic precursor cell ablation), liver pathology, atrophy of intestinal villi, skin ulceration, amyloid deposits, and joint diseases. Tyner et al. (2002), Nature 415:45-53.

Careful observation reveals characteristics of aging in other eukaryotes, including invertebrates. For example, characteristics of aging in the model organism *C. elegans* include slow movement, flaccidity, yolk accumulation, intestinal autofluorescence (lipofuscin), loss of ability to eat food or dispel waste, necrotic cavities in tissues, and germ cell appearance.

Those skilled in the art will recognize that the aging process is also manifested at the cellular level, as well as in mitochondria. Cellular aging is manifested in loss of doubling capacity, increased levels of apoptosis, changes in differentiated phenotype, and changes in metabolism, e.g., decreased levels of protein synthesis and turnover.

Given the programmed nature of cellular and organismal aging, it is possible to evaluate the "biological age" of a cell or organism by means of phenotypic characteristics that are correlated with aging. For example, biological age can be deduced from patterns of gene expression, resistance to stress (e.g., oxidative or genotoxic stress), rate of cellular proliferation, and the metabolic characteristics of cells (e.g., rates of protein synthesis and turnover, mitochondrial function, ubiquinone biosynthesis, cholesterol biosynthesis, ATP levels within the cell, levels of a Krebs cycle intermediate in the cell, glucose metabolism, nucleic acid metabolism, ribosomal translation rates, etc.). As used herein, "biological age" is a measure of the age of a cell or organism based upon the molecular characteristics of the cell or organism. Biological age is distinct from "temporal age," which refers to the age of a cell or organism as measured by days, months, and years.

The rate of aging of an organism, e.g., an invertebrate (e.g., a worm or a fly) or a vertebrate (e.g., a rodent, e.g., a mouse) can be determined by a variety of methods, e.g., by one or more of: a) assessing the life span of the cell or the organism; (b) assessing the presence or abundance of a gene transcript or gene product in the cell or organism that has a biological age-dependent expression pattern; (c) evaluating resistance of the cell or organism to stress, e.g., genotoxic stress (e.g., etopicide, UV irradition, exposure to a mutagen, and so forth) or oxidative stress; (d) evaluating one or more metabolic parameters of the cell or organism; (e) evaluating the proliferative capacity of the cell or a set of cells present in the organism; and (f) evaluating physical appearance or behavior of the cell or organism. In one example, evaluating the rate of aging includes directly measuring the average life span of a group of animals (e.g., a group of genetically matched animals) and comparing the resulting average to the average life span of a control group of animals (e.g., a group of animals that did not receive the test compound but are genetically matched to the group of animals that did receive the test compound). Alternatively, the rate of aging of an organism can be determined by measuring an age-related parameter. Examples of age-related parameters include: appearance, e.g., visible signs of age; the expression of one or more genes or proteins (e.g., genes or proteins that have an age-related expression pattern); resistance to oxidative stress; metabolic parameters (e.g., protein synthesis or degradation, ubiquinone biosynthesis, cholesterol biosynthesis, ATP levels, glucose metabolism, nucleic acid metabolism, ribosomal translation rates, etc.); and cellular proliferation (e.g., of retinal cells, bone cells, white blood cells, etc.).

Agents that extend the life span of cells and protect them from stress can also be administered to subjects for treatement of diseases, e.g., chronic diseases, associated with cell death, such as to protect the cells from cell death, e.g., diseases associated with neural cell death or muscular cell death. In particular, based at least on the fact that SIRT1 protects neurons from axonal degeneration (Araki et al. (2004) Science 305:1010), the methods may be used to prevent or alleviate neurodegeneration and peripheral neuropathies associated with chemotherapy, such as cancer chemotherapy (e.g., taxol or cisplatin treatment). Neurodegenerative diseases include Parkinson's disease, Alzheimer's disease, multiple sclerosis, amniotropic lateral sclerosis (ALS), Huntington's disease and muscular dystrophy. Thus, the agents may be used as neuroprotective agents. The agent may be administered in the tissue or organ likely to encounter cell death.

Such agents can also be administered to a subject suffering from an acute damage to an organ or tissue, e.g., a subject suffering from stroke or myocardial infarction or a subject suffering from a spinal cord injury. Agents can also be used to repair an alcoholic's liver.

More generally, agents described herein may be administered to subjects in which caloric restriction or the effects thereof would be beneficial. Subjects may be subjects suffering from an aging disease, e.g., stroke, heart disease, arthritis, high blood pressure. They may also be administered for treating a metabolic disease, such as insulin-resistance or other precursor symptom of type II diabetes, type II diabetes or complications thereof. Methods may increase insulin sensitivity or decrease insulin levels in a subject. A method may comprise administering to a subject, such as a subject in need thereof, a pharmaceutically effective amount of an agent that increases the activity or protein level of a protein involved in the NAD+ salvation pathway, i.e., in the synthesis of NAD+ and the degradation of nicotinamide. A subject in need of such a treatment may be a subject who has insulin resistance or other precusor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and lipodystrophy.

Based at least in part on the facts that NAMPRT is upregulated in cells exposed to hypoxia and extra copies of the NAMPRT gene boost SIRT1 activity, other subject that may be treated include patients suffering from a cardiac disease, e.g., ischemia, cardiovascular diseases, myocardial infarction, congestive heart disease. Cardiovascular diseases that can be treated or prevented include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to the retinal arterioles, the glomerular arterioles, the vasa nervorum, cardiac arterioles, and associated capillary beds of the eye, the kidney, the heart, and the central and peripheral nervous systems. The methods may also be used for increasing HDL levels in plasma of an individual.

Yet other disorders that may be treated with sirtuin activators include restenosis, e.g., following coronary intervention, and disorders relating to an abnormal level of high density and low density cholesterol. The methods may also be used for treating or preventing viral infections, such as infections by influenza, herpes or papilloma virus.

The agents may also be used to help prevent the spread of disease/infection on an individual or population level, e.g. during a SARS or influenza outbreak.

Based at least on the fact that SIRT1 deacetylates and regulates NF-kB, the methods described herein may be used to treat inflammatory conditions, such as arthritis, Crohn's disease, inflammatory bowel disease, rheumatoid arthritis, asthma, atherosclerosis, coronary heart disease, reperfusion injury from heart attack or stroke, ulcerative colitis, and active inflammatory bowel disease (IBD).

They may also be used as antifungal agents.

Other conditions that can be treated include ocular disorders, e.g., associated with the aging of the eye, such as cataracts, glaucoma, and macular degeneration. They can also be used for treatment of diseases, e.g., AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections.

Based at least on the fact that sirtuins have been shown to be involved in fat mobilization, e.g., by repressing PPAR-γ (Picard et al. (2004) Nature 430:921), methods described herein for mimicking calorie restriction can also be used for stimulating fat mobilization, e.g., for treating obesity and any condition resulting therefrom or for reducing weight gain. Alternatively, stimulating weight gain can be achieved by the methods described herein that counter calorie restriction.

In addition, the agents described herein may be administered to subjects for protection against or treatment of exposure to toxic agents, radiation or any warfare chemical. For example, the agents may be administered to subjects who have recently received or are likely to receive a dose of radiation. In one embodiment, the dose of radiation is received as part of a work-related or medical procedure, e.g., working in a nuclear power plant, flying an airplane, an X-ray, CAT scan, or the administration of a radioactive dye for medical imaging; in such an embodiment, the agent is administered as a prophylactic measure. In another embodiment, the radiation exposure is received unintentionally, e.g., as a result of an industrial accident, terrorist act, or act of war involving radioactive material. In such a case, the agent would be administered as soon as possible after the exposure to inhibit apoptosis and the subsequent development of acute radiation syndrome. The agents described herein could also be used to protect non-cancerous cells from the effects of chemotherapy, such as to protect neurons in the case of preventing neuropathies, hematoxicity, renal toxicity, and gastrointestinal toxicity due to chemotherapy.

Since DNA repair is also inhibited by nicotinamide, agents that reduce nicotinamide levels in cells can be used to promote DNA repair in cells. Accordingly, cells exposed to conditions that may trigger DNA damage, e.g., U.S. radiation and ethidium bromide, may be protected by contacting them before, during and/or after exposure to the DNA damaging agent, with an agent that reduces nicotinamide levels in the cell.

In other embodiments, the methods of the invention are applied to yeast cells. Situations in which it may be desirable to extend the life span of yeast cells and to protect them against certain types of stress include any process in which yeast is used, e.g., the making of beer, yogurt, and bakery, e.g., making of bread. Use of yeast having an extended life span can result in using less yeast or in having the yeast be active for longer periods of time.

The agents described herein may also be used to mimic calorie restriction in plants, e.g., to increase lifespan, stress resistance, and resistance to apoptosis in plants. In one embodiment, an agent is applied to plants, either on a periodic basis or in times of stress, e.g., drought, frost, or an infestation of insects or fungi. In another embodiment, plants are genetically modified to produce an agent. In another embodiment, plants and fruits are treated with an agent prior to picking and shipping to increase resistance to damage during shipping.

The agents may also be used to increase lifespan, stress resistance and resistance to apoptosis in insects. In this embodiment, the agents would be applied to useful insects, e.g., bees and other insects that are involved in pollination of plants. In a specific embodiment, an agent would be applied to bees involved in the production of honey.

Higher doses of the agents may also be used as a pesticide by interfering with the regulation of silenced genes and the regulation of apoptosis during development. In this embodiment, an agent is applied to plants using a method known in the art that ensures the compound is bio-available to insect larvae, and not to plants.

The invention also provides methods for reducing the life span of a cell or rendering it more susceptible to certain stresses, e.g., heatshock, radioactivity, osmotic stress, DNA damage, e.g., from U.V, and chemotherapeutic drugs. Such methods can be used whenever it is desired to reduce the life span of a cell. Exemplary methods include decreasing the level or activity of a protein selected from the group consisting of NPT1, PNC1, NMA1, NMA2, NMNAT, NNT1, NAMPRT, and optionally NMAT-1 or 2.

Another method includes increasing the level of nicotinamide in the cell and/or decreasing the ratio of NAD+/nicotinamide, e.g., by contacting the cell with nicotinamide, or by increasing the level or activity of an enzyme stimulating nicotinamide biosynthesis or decreasing the level or activity of an enzyme inhibiting or degrading nicotinamide, e.g., by decreasing the level or activity of NPT1, PNC1, NMA1, NMA2, NMNAT, NNT1, NAMPRT, and optionally NMAT-1 or 2. Exemplary situations in which one may wish to reduce the life span of a cell or render it more susceptible to certain stresses include treatment of cancer, autoimmune diseases or any other situation in which it is desirable to eliminate cells in a subject. Nicotinamide or other compounds or agents of the invention can be administered directly to the area containing the undesirable cells, e.g., in a tumor, such as in a cancer patient. These methods can also be used to eliminate cells or prevent further proliferation of undesirable cells of non-malignant tumors, e.g., warts, beauty spots and fibromas. For example, nicotinamide can be injected into a wart, or alternatively be included in a pharmaceutical composition for applying onto the wart. The methods may also be used to make tumor cells more sensitive to agents that rely on killing them, e.g., chemotherapeutic drugs.

Methods for decreasing the life span of cells or increasing their susceptibility to certain stresses can be applied to yeast, e.g., yeast infecting subjects. Accordingly, a composition comprising an agent, e.g., nicotinamide, can be applied to the location of the yeast infection.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells.

Also provided herein are diagnostic methods, e.g., methods for determining the general health of a subject. Based at least in part on the fact that expression of the genes described herein is elevated in subjects that are fasting and in cells submitted to various stresses, the measurement of the level of gene expression could be indicative of whether a subject is or has been exposed to stress or has or is likely to develop a disease associated with stress or any of the diseases described herein. In addition, based at least in part on the fact that NAMPRT is produced in response to cell stress, the level of NAMPRT may be an early marker for cancer. In an illustrative embodiment, a diagnostic method comprises providing a sample from a subject and determining the level of gene expression, such as protein level, of one or more of NPT1, PNC1, NMA1, NMA2, NNMT, NNT1, NAMPRT, NMNAT, NMAT-1 and NMAT-2 is determined. A higher level of gene expression in a cell or level of the protein in serum, relative to a control is indicative that the subject tested is or has been exposed to stress or a disease related thereto, such as the diseases described herein. A control may be a value representing an average level obtained from two or more individuals that are not believed to be under any conditions that would elevate or decrease the particular factor that is evaluated in the diagnosis. A control value may be an average value obtained from 10 or more or from 100 or more individuals. A difference of a factor of at least about 50%, 2 fold, 3 fold, 5 fold, 10 fold or more may be significant.

A diagnostic assay may comprise obtaining a sample of a bodily fluid, e.g., blood or serum, if the protein to be measured exists in soluble extracellular form, e.g., NAMPRT. A diagnostic assay may also comprise obtaining a cell sample and determining the level of gene transcript, e.g., mRNA, or protein. The sample of cells may be a sample of blood cells, e.g., peripheral blood mononuclear cells, skin cells, or cells of hair follicles, cheek swabs, tissue biopsies, and lumpectomies. Methods for determining protein or transcript levels are well known in the art. Methods for determining protein levels may, e.g., involve the use of antibodies.

Diagnostic methods may also be used to determine the presence of likelihood of development of a particular disease or disorder, e.g., those described herein. In addition, the diagnostic methods described herein may be used to identify individuals who have been or are subject to stress conditions, e.g., as a result of irradiation.

A diagnostic method may also be used to identify individuals who may be more sensitive to stress conditions, relative to other individuals. Such a diagnostic method may involve exposing a subject to a stress condition, and evaluating a characteristic of the subject before and after exposure to the stress condition. The characteristic may be the level or activity of a protein described herein, e.g., NAMPRT, or the level of NAD+/NADH or nicotinamide.

A subject having been diagnosed with elevated levels of one or more of NPT1, PNC1, NMA1, NMA2, NNMT, NNT1, NAMPRT, NMNAT, NMAT-1 and NMAT-2, may then be treated accordingly, following which a second sample may be obtained and subjected to the diagnostic method.

7. Pharmaceutical Compositions and Methods

Compounds, nucleic acids, proteins, cells and other compositions can be administered to a subject according to methods known in the art. For example, nucleic acids encoding a protein or an antisense molecule can be administered to a subject as described above, e.g., using a viral vector. Cells can be administered according to methods for administering a graft to a subject, which may be accompanied, e.g., by administration of an immunosuppressant drug, e.g., cyclosporin A. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000.

Pharmaceutical agents for use in accordance with the present methods may be formulated in conventional manner using one or more physiologically acceptable carriers or excipients. Thus, proteins and nucleic acids described herein as well as compounds or agents that increase the protein or expression level of nucleic acids described herein, and their physiologically acceptable salts and solvates may be formulated for administration by, for example, injection, inhalation or insufflation (either through the mouth or the nose) or oral, buccal, parenteral or rectal administration. In one embodiment, the agent is administered locally, e.g., at the site where the target cells are present, such as by the use of a patch.

Agents can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the agents can be formulated in liquid solutions, preferably in physiologically compatible buffers such as Hank's solution or Ringer's solution. In addition, the agents may be formulated in solid form and redissolved or suspended immediately prior to use. Lyophilized forms are also included.

For oral administration, the pharmaceutical compositions may take the form of, for example, tablets, lozanges, or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

Agents that may oxidize and lose biological activity, especially in a liquid or semi-solid form, may be prepared in a nitrogen atmosphere or sealed in a type of capsule and/or foil package that excludes oxygen (e.g. Capsugel™).

For administration by inhalation, the agents may be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin, for use in an inhaler or insufflator may be formulated containing a powder mix of the agent and a suitable powder base such as lactose or starch.

The agents may be formulated for parenteral administration by injection, e.g., by bolus injection or continuous infusion. Formulations for injection may be presented in unit dosage form, e.g., in ampoules or in multi-dose containers, with an added preservative. The agents may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The agents may also be formulated in rectal compositions such as suppositories or retention enemas, e.g., containing conventional suppository bases such as cocoa butter or other glycerides.

In addition to the formulations described previously, the agents may also be formulated as a depot preparation. Such long acting formulations may be administered by implantation (for example subcutaneously or intramuscularly) or by intramuscular injection. Thus, for example, the agents may be formulated with suitable polymeric or hydrophobic materials (for example as an emulsion in an acceptable oil) or ion exchange resins, or as sparingly soluble derivatives, for example, as a sparingly soluble salt. Controlled release formula also include patches, e.g., transdermal patches. Patches may be used with a sonic applicator that deploys ultrasound in a unique combination of waveforms to introduce drug molecules through the skin that normally could not be effectively delivered transdermally.

Pharmaceutical compositions (including cosmetic preparations) may comprise from about 0.00001 to 100% such as from 0.001 to 10% or from 0.1% to 5% by weight of one or more agents described herein.

In one embodiment, an agent described herein, is incorporated into a topical formulation containing a topical carrier that is generally suited to topical drug administration and comprising any such material known in the art. The topical carrier may be selected so as to provide the composition in the desired form, e.g., as an ointment, lotion, cream, microemulsion, gel, oil, solution, or the like, and may be comprised of a material of either naturally occurring or synthetic origin. It is preferable that the selected carrier not adversely affect the active agent or other components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like.

Formulations may be colorless, odorless ointments, lotions, creams, microemulsions and gels.

Agents may be incorporated into ointments, which generally are semisolid preparations which are typically based on petrolatum or other petroleum derivatives. The specific ointment base to be used, as will be appreciated by those skilled in the art, is one that will provide for optimum drug delivery, and, preferably, will provide for other desired characteristics as well, e.g., emolliency or the like. As with other carriers or vehicles, an ointment base should be inert, stable, nonirritating and nonsensitizing. As explained in Remington's, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Exemplary water-soluble ointment bases are prepared from polyethylene glycols (PEGs) of varying molecular weight; again, reference may be had to Remington's, supra, for further information.

Agents may be incorporated into lotions, which generally are preparations to be applied to the skin surface without friction, and are typically liquid or semiliquid preparations in which solid particles, including the active agent, are present in a water or alcohol base. Lotions are usually suspensions of solids, and may comprise a liquid oily emulsion of the oil-in-water type. Lotions are preferred formulations for treating large body areas, because of the ease of applying a more fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethylcellulose, or the like. An exemplary lotion formulation for use in conjunction with the present method contains propylene glycol mixed with a hydrophilic petrolatum such as that which may be obtained under the trademark Aquaphor™ from Beiersdorf, Inc. (Norwalk, Conn.).

Agents may be incorporated into creams, which generally are viscous liquid or semisolid emulsions, either oil-in-water or water-in-oil. Cream bases are water-washable, and contain an oil phase, an emulsifier and an aqueous phase. The oil phase is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington's, supra, is generally a nonionic, anionic, cationic or amphoteric surfactant.

Agents may be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono-di-and triglycerides, mono-and di-esters of PEG (e.g., oleoyl macrogol glycerides), etc.

Agents may be incorporated into gel formulations, which generally are semisolid systems consisting of either suspensions made up of small inorganic particles (two-phase systems) or large organic molecules distributed substantially uniformly throughout a carrier liquid (single phase gels). Single phase gels can be made, for example, by combining the active agent, a carrier liquid and a suitable gelling agent such as tragacanth (at 2 to 5%), sodium alginate (at 2-10%), gelatin (at 2-15%), methylcellulose (at 3-5%), sodium carboxymethylcellulose (at 2-5%), carbomer (at 0.3-5%) or polyvinyl alcohol (at 10-20%) together and mixing until a characteristic semisolid product is produced. Other suitable gelling agents include methylhydroxycellulose, polyoxyethylene-polyoxypropylene, hydroxyethylcellulose and gelatin. Although gels commonly employ aqueous carrier liquid, alcohols and oils can be used as the carrier liquid as well.

Various additives, known to those skilled in the art, may be included in formulations, e.g., topical formulations. Examples of additives include, but are not limited to, solubilizers, skin permeation enhancers, opacifiers, preservatives (e.g., anti-oxidants), gelling agents, buffering agents, surfactants (particularly nonionic and amphoteric surfactants), emulsifiers, emollients, thickening agents, stabilizers, humectants, colorants, fragrance, and the like. Inclusion of solubilizers and/or skin permeation enhancers is particularly preferred, along with emulsifiers, emollients and preservatives. An optimum topical formulation comprises approximately: 2 wt. % to 60 wt. %, preferably 2 wt. % to 50 wt. %, solubilizer and/or skin permeation enhancer; 2 wt. % to 50 wt. %, preferably 2 wt. % to 20 wt. %, emulsifiers; 2 wt. % to 20 wt. % emollient; and 0.01 to 0.2 wt. % preservative, with the active agent and carrier (e.g., water) making of the remainder of the formulation.

A skin permeation enhancer serves to facilitate passage of therapeutic levels of active agent to pass through a reasonably sized area of unbroken skin. Suitable enhancers are well known in the art and include, for example: lower alkanols such as methanol ethanol and 2-propanol; alkyl methyl sulfoxides such as dimethylsulfoxide (DMSO), decylmethylsulfoxide ($C_{10}$ MSO) and tetradecylmethyl sulfboxide; pyrrolidones such as 2-pyrrolidone, N-methyl-2-pyrrolidone and N-(-hydroxyethyl)pyrrolidone; urea; N,N-diethyl-m-toluamide; $C_2$-$C_6$ alkanediols; miscellaneous solvents such as dimethyl formamide (DMF), N,N-dimethylacetamide (DMA) and tetrahydrofurfuryl alcohol; and the 1-substituted azacycloheptan-2-ones, particularly 1-n-dodecylcyclazacycloheptan-2-one (laurocapram; available under the trademark Azone® from Whitby Research Incorporated, Richmond, Va.).

Examples of solubilizers include, but are not limited to, the following: hydrophilic ethers such as diethylene glycol monoethyl ether (ethoxydiglycol, available commercially as Transcutol™) and diethylene glycol monoethyl ether oleate (available commercially as Softcutol™); polyethylene castor oil derivatives such as polyoxy 35 castor oil, polyoxy 40 hydrogenated castor oil, etc.; polyethylene glycol, particularly lower molecular weight polyethylene glycols such as PEG 300 and PEG 400, and polyethylene glycol derivatives such as PEG-8 caprylic/capric glycerides (available commercially as Labrasol™); alkyl methyl sulfoxides such as DMSO; pyrrolidones such as 2-pyrrolidone and N-methyl-2-pyrrolidone; and DMA. Many solubilizers can also act as absorption enhancers. A single solubilizer may be incorporated into the formulation, or a mixture of solubilizers may be incorporated therein.

Suitable emulsifiers and co-emulsifiers include, without limitation, those emulsifiers and co-emulsifiers described with respect to microemulsion formulations. Emollients include, for example, propylene glycol, glycerol, isopropyl myristate, polypropylene glycol-2 (PPG-2) myristyl ether propionate, and the like.

Other active agents may also be included in formulations, e.g., anti-inflammatory agents, analgesics, antimicrobial agents, antifungal agents, antibiotics, vitamins, antioxidants, and sunblock agents commonly found in sunscreen formulations including, but not limited to, anthranilates, benzophenones (particularly benzophenone-3), camphor derivatives, cinnamates (e.g., octyl methoxycinnamate), dibenzoyl methanes (e.g., butyl methoxydibenzoyl methane), p-aminobenzoic acid (PABA) and derivatives thereof, and salicylates (e.g., octyl salicylate).

In certain topical formulations, the active agent is present in an amount in the range of approximately 0.25 wt. % to 75 wt. % of the formulation, preferably in the range of approximately 0.25 wt. % to 30 wt. % of the formulation, more preferably in the range of approximately 0.5 wt. % to 15 wt. % of the formulation, and most preferably in the range of approximately 1.0 wt. % to 10 wt. % of the formulation.

Topical skin treatment compositions can be packaged in a suitable container to suit its viscosity and intended use by the consumer. For example, a lotion or cream can be packaged in a bottle or a roll-ball applicator, or a propellant-driven aerosol device or a container fitted with a pump suitable for finger operation. When the composition is a cream, it can simply be stored in a non-deformable bottle or squeeze container, such as a tube or a lidded jar. The composition may also be included in capsules such as those described in U.S. Pat. No. 5,063,507. Accordingly, also provided are closed containers containing a cosmetically acceptable composition.

In an alternative embodiment, a pharmaceutical formulation is provided for oral or parenteral administration, in which case the formulation may comprise an activating compound-containing microemulsion as described above, and may contain alternative pharmaceutically acceptable carriers, vehicles, additives, etc. particularly suited to oral or parenteral drug administration. Alternatively, an activating compound-containing microemulsion may be administered orally or parenterally substantially as described above, without modification.

Administration of an agent may be followed by measuring a factor in the subject, such as measuring the protein or transcript level of a gene described herein, or the level of NAD+, NADH or nicotinamide. In an illustrative embodiment, a cell is obtained from a subject following administration of an agent to the subject, such as by obtaining a biopsy, and the factor is determined in the biopsy. Alternatively, biomarkers, such as plasma biomarkers may be followed. The cell may be any cell of the subject, but in cases in which an agent is administered locally, the cell is preferably a cell that is located in the vicinity of the site of administration.

Other factors that may be monitored include a symptom of aging, weight, body mass, blood glucose sugar levels, blood lipid levels and any other factor that may be measured for monitoring diseases or conditions described herein.

8. Kits

Also provided herein are kits, e.g., kits for therapeutic purposes, including kits for modulating aging, apoptosis, and for treating diseases, e.g., those described herein. A kit may comprise one or more agent described herein, and optionally devices for contacting cells with the agents. Devices include syringes, stents and other devices for introducing an agent into a subject or applying it to the skin of a subject.

Further, a kit may also contain components for measuring a factor, e.g., described above, such as a protein or transcript level, e.g., in tissue samples.

Other kits include kits for diagnosing the likelihood of having or developing an aging related disease, weight gain, obesity, insulin-resistance, diabetes, cancer, precursors thereof or secondary conditions thereof. A kit may comprise an agent for measuring the activity and or expression level of NPT1, PNC1, NMA1, NMA2, NNMT, NNT1, NAMPRT, NMNAT, NMAT-1 and NMAT-2 or the level of NAD+, NADH, nicotinamide, and/or other intermediary compound in the NAD+ salvage pathway.

Kits for screening assays are also provided. Exemplary kits comprise one or more agents for conducting a screening assay, such as a protein described herein or a biologically active portion thereof, or a cell or cell extract comprising such. Any of the kits may also comprise instructions for use.

The present invention is further illustrated by the following examples which should not be construed as limiting in any way. The contents of all cited references (including literature references, issued patents, published patent applications and GenBank Accession numbers as cited throughout this application) are hereby expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization(B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Manipulation of a Nuclear NAD$^+$ Salvage Pathway Delays Aging

Yeast deprived of nutrients exhibit a marked life span extension that requires the activity of the NAD$^+$-dependent histone deacetylase, Sir2p. Here we show that increased dosage of NPT1, encoding a nicotinate phosphoribosyltranfserase critical for the NAD$^+$ salvage pathway, increases Sir2-dependent silencing, stabilizes the rDNA locus and extends yeast replicative life span by up to 60%. Both NPT1 and SIR2 provide resistance against heat shock, demonstrating that these genes act in a more general manner to promote cell survival. We show that Npt1 and a previously uncharacterized salvage pathway enzyme, Nma2, are both concentrated in the nucleus, indicating that a significant amount of NAD$^+$ is regenerated in this organelle. Additional copies of the salvage pathway genes, PNC1, NMA1 and NMA2 increase telomeric and rDNA silencing, implying that multiple steps affect the rate of the pathway. Although SIR2-dependent processes are enhanced by additional NPT1, steady-state NAD$^+$ levels and NAD$^+$/NADH ratios remain unaltered. This finding suggests that yeast life span extension may be facilitated by an increase in the availability of NAD$^+$ to Sir2, though not through a simple increase in steady-state levels. We propose a model in which increased flux through the NAD$^+$ salvage pathway is responsible for the Sir2-dependent extension of life span.

Experimental Procedures

Plasmids and strains—Strains used in this study are listed in Table 2. W303AR5 sir3::URA3 (16), W303AR5 sir4.: HIS3, W303AR5 sir2::TRP1 and PSY316AT are described (41). Deletion of SIR2 in PSY316AT was performed using ScaI/PvuII linearized pC369 (41). JS209, JS241, JS237 and JS218 were gifts from J. Smith (42). The coding region and 1.1 kb of upstream sequence of NPT1 were amplified by PCR (43) and the 2.4 kb product fragment was subcloned into the pRS306 based vector pSP400 between NotI and SacI (gift from L. Guarente, M.I.T.) and the 2μ-based vector pDB20 (44) to generate pSPNPT1 and pDBNPT1 respectively.

TABLE 2

Yeast strains used in this study.

| Strain | Genotype |
|---|---|
| W303AR5 | W303 MATa, ade2-1, leu2-3,112, can1-100, trp1-1, ura3-52, his3-11,15, RDN1::ADE2, RAD5 |
| YDS878 | W303 MATa,, ade2-1, leu2-3,112, can1-100, trp1-1,, ura3-52, his3-11,15, RDN1::ADE2, RAD5, sir2:TRP1 |
| YDS924 | W303AR5 MATa, ade2-1, leu2-3,112, can1-100, trp1-1, ura3-52, his3-11,15, RDN1::ADE2, RAD5, sir3:HIS3 |
| YDS882 | W303 MATa, ade2-1, leu2-3,112, can1-100, trp1-1, ura3-52, his3-11,15, RDN1::ADE2, RAD5, sir4:HIS3 |
| YDS1503 | W303 MATa, ade2-1, leu2-3,112, can1-100, trp1-1, ura3-52, his3-11,15, RDN1::ADE2, RAD5, URA3/NPT1 |
| YDS1504 | W303 MATa, ade2-1, leu2-3,112, can1-100, trp1-1, ura3-52, his3-11,15, RDN1::ADE2, RAD5, sir2:TRP1, URA3/NPT1 |
| YDS1505 | W303 MATa, ade2-1, leu2-3,112, can1-100, trp1-1, ura3-52, his3-11,15, RDN1::ADE2, RAD5, sir3:HIS3, URA3/NPT1 |
| YDS1506 | W303 MATa, ade2-1, leu2-3,112, can1-100, trp1-1, ura3-52, his3-11,15, RDN1::ADE2, RAD5, sir4:HIS3, URA3/NPT1 |
| YDS1496 | W303 MATa, ade2-1, leu2-3,112, can1-100, trp1-1, ura3-52, his3-11,15, RDN1::ADE2, RAD5, pDBNPT1 |
| YDS1494 | W303 MATa, ade2-1, leu2-3,112, can1-100, trp1-1, ura3-52, his3-11,15, RDN1::ADE2, RAD5, sir2:TRP1, pDBNPT1 |
| YDS1587 | W303 MATa, ade2-1, leu2-3,112, can1-100, trp1-1, ura3-52, his3-11,15, RDN1::ADE2, RAD5, sir3:HIS3, pDBNPT1 |
| YDS1495 | W303 MATa, ade2-1, leu2-3,112, can1-100, trp1-1, ura3-52, his3-11,15, RDN1::ADE2, RAD5, sir4:HIS3, pDBNPT1 |
| YDS1572 | W303 MATa, ade2-1, leu2-3,112, can1-100, trp1-1, ura3-52, his3-11,15, RDN1::ADE2, RAD5, LEU2/SIR2 |
| YDS1561 | W303 MATa, ade2-1, leu2-3,112, can1-100, trp1-1, ura3-52, his3-11,15, RDN1::ADE2, RAD5, URA3/NPT1, LEU2/SIR2 |
| YDS1595 | W303 MATa, ade2-1, leu2-3,112, can1-100, trp1-1, ura3-52, his3-11,15, RAD5 |
| YDS1596 | W303 MATa, ADE2, leu2-3,112, can1-100, trp1-1, ura3-52, his3-11,15, RAD5 |
| YDS1568 | W303 MATa, ade2-1, leu2-3,112, can1-100, trp1-1, URA3-52, his3-11,15, RDN1::ADE2, RAD5 |
| YDS1563 | W303 MATa, ade2-1, LEU2, can1-100, trp1-1, URA3, his3-11,15, RDN1::ADE2, RAD5 |
| YDS1588 | W303 MATa, ade2-1, leu2-3,112, can1-100, trp1-1, ura3-52, his3-11,15, RDN1::ADE2, RAD5, pSPYGL037 |
| YDS1589 | W303 MATa, ade2-1, leu2-3,112, can1-100, trp1-1, ura3-52, his3-11,15, RDN1::ADE2, RAD5, pSPYGR010 |
| YDS1590 | W303 MATa, ade2-1, leu2-3,112, can1-100, trp1-1, ura3-52, his3-11,15, RDN1::ADE2, RAD5, p306YLR328 |
| YDS1614 | W303 MATa, ade2-1, leu2-3,112, can1-100, trp1-1, ura3-52, his3-11,15, RDN1::ADE2, RAD5, p306YHR074 |
| YDS1531 | W303 MATa, ade2-1, leu2-3,112, can1-100, trp1-1, ura3-52, his3-11,15, RDN1::ADE2, RAD5, NPT1-HA |
| W303cdc25-10 | W303 MATa, ade2-1, leu2-3,112, can1-100, trp1-1, ura3-52, his3-11,15, RDN1::ADE2, RAD5, cdc25-10 |
| YDS1537 | W303 MATa, ade2-1, leu2-3,112, can1-100, trp1-1, ura3-52, his3-11,15, RDN1::ADE2, RAD5, cdc25-10, NPT1-HA |
| YDS1611 | W303 MATa, ade2-1, leu2-3,112, can1-100, trp1-1, ura3-52, his3-11,15, RDN1::ADE2, RAD5, NPT1-GFP |
| YDS1625 | W303 MATa, ade2-1, leu2-3,112, can1-100, trp1-1, ura3-52, his3-11,15, RDN1::ADE2, RAD5, NMA1-GFP |
| YDS1624 | W303 MATa, ade2-1, leu2-3,112, can1-100, trp1-1, ura3-52, his3-11,15, RDN1::ADE2, RAD5, NMA2-GFP |
| PSY316AT | MATα, ura3-53 leu2-3,112 his3-Δ200 ade2-1,01 can1-100 ADE2-TEL V-R |
| YDS1594 | PSY316 MATα, ura3-53 leu2-3,112 his3-Δ200 ade2-1,01 can1-100 ADE2-TEL V-R, sir2:TRP1 |
| YDS1544 | PSY316 MATα, ura3-53 leu2-3,112 his3-Δ200 ade2-1,01 can1-100 ADE2-TEL V-R, URA3/NPT1 |
| YDS1548 | PSY316 MATα, ura3-53 leu2-3,112 his3-Δ200 ade2-1,01 can1-100 ADE2-TEL V-R, (4x)URA3/NPT1 |
| YDS1527 | PSY316 MATα, ura3-53 leu2-3,112 his3-Δ200 ade2-1,01 can1-100 ADE2-TEL V-R, pDBNPT1 |
| YDS1577 | PSY316 MATα, ura3-53 leu2-3,112 his3-Δ200 ade2-1,01 can1-100 ADE2-TEL V-R, (4x)URA3/NPT1, LEU2/SIR2 |
| YDS1573 | PSY316 MATα, ura3-53 leu2-3,112 his3-Δ200 ade2-1,01 can1-100 ADE2-TEL V-R, sir2::HIS3, URA3/NPT1 |
| YDS1591 | PSY316 MATα, ura3-53 leu2-3,112 his3-Δ200 ade2-1,01 can1-100 ADE2-TEL V-R, pSPYGL037 |
| YDS1592 | PSY316 MATα, ura3-53 leu2-3,112 his3-Δ200 ade2-1,01 can1-100 ADE2-TEL V-R, pSPYGR010 |
| YDS1593 | PSY316 MATα, ura3-53 leu2-3,112 his3-Δ200 ade2-1,01 can1-100 ADE2-TEL V-R, p306YLR328 |
| JS209 | MATα, his3Δ200, leu2Δ1, met15Δ200, trp1Δ63, ura3-167 |
| JS241 | JS209 MATα, his3Δ200, leu2Δ1, met15Δ200, trp1Δ63, ura3-167, MET15 |
| JS237 | JS209 MATα, his3Δ200, leu2Δ1, met15Δ200, trp1Δ63, ura3-167, RDN1::Ty-MET15 |
| JS218 | JS237 MATα, his3Δ200, leu2Δ1, met15Δ200, trp1Δ63, ura3-167, RDN1::Ty-MET15, sir2::HIS3 |
| YDS1583 | JS237 MATα, his3Δ200, leu2Δ1, met15Δ200, trp1Δ63, ura3-167, RDN1::Ty-MET15, LEU2/SIR2 |
| YDS1522 | JS237 MATα, his3Δ200, leu2Δ1, met15Δ200, trp1Δ63, ura3-167, RDN1::Ty-MET15, p2μSIR2 |
| YDS1580 | JS237 MATα, his3Δ200, leu2Δ1, met15Δ200, trp1Δ63, ura3-167, RDN1::Ty-MET15, npt1Δ::kan$^r$ |
| YDS1581 | JS237 MATα, his3Δ200, leu2Δ1, met15Δ200, trp1Δ63, ura3-167, RDN1::Ty-MET1, URA3/NPT1 |
| YDS1493 | JS237 MATα, his3Δ200, leu2Δ1, met15Δ200, trp1Δ63, ura3-167, RND1::Ty-MET15, pDBNPT1 |

Additional copies of NPT1 were integrated at the URA3 locus using plasmid pSPNPT1 linearized with StuI. Integrants were first identified by PCR. NPT1 copy-number was then determined by probing for NPT1 and ACT1 DNA on Southern blots. The density of the NPT1 band was compared to an ACT1 band using ImageQuant software (Molecular Dynamics, Sunnyvale, Calif.). Strains carrying an additional copy of SIR2 were generated by integrating plasmids p306SIR2 or p305SIR2 (17) linearized with XcmI. High copy SIR2 was introduced on the 2μ-based plasmid p2μSIR2 (gift of L. Pillus, UCSD). W303AR5 was transformed to Ura$^+$ and Leu$^+$ prototrophy by integrating pRS306 or pRS305 (45) linearized with StuI and XcmI respectively. YDS1595 was generated from W303AR5 by selecting a colony that had experienced an ADE2 loss event. YDS1595 was transformed with StuI-cut pRS402 (carrying the ADE2 gene) to create YDS1596. W303cdc25-10 was a gift from S. Lin (M.I.T) (19). The NPT1 deletion strain, YDS1580, was generated by replacing the wildtype gene with the kanr marker as described (46). The coding region and 650 bp upstream of PNC1/YGL037 was amplified by PCR from genomic DNA. The 1350 bp SacI/NotI fragment was cloned into the vector pSR400 to generate pSPYGL037. The coding region and 500 bp upstream of NMA2/YGR010 were amplified by PCR from genomic template and the 1730 bp SacI/NotI fragment was cloned into pSP400 to generate pSPYGR010. The coding region of NMA1/YLR328 and 450 bp upstream were amplified from genomic template by PCR and the 2150 bp fragment was cloned into pRS306 to generate p306YLR328. The coding region and 600 bp upstream of QNS1/YHR074 was amplified by PCR and the 2.8 kb SacI/NotI fragment was cloned into pSP400 to make pSPYHR074. Additional copies of PNC1/YGL037, NMA1/YLR328, NMA2/YGR010, and QNS1/YHR074 were integrated at the URA3 locus of W303AR5 and PSY316AT by transformation. All amplified DNA was confirmed to be free of mutations by sequencing.

HA-tagged NPT1 was generated using a tag-kan$^r$ integration method (47) in strains W303AR5 and W303cdc25-10 (19). A green fluorescent protein (GFP) cassette was introduced at the carboxy-terminus of Npt1, Nma1 and Nma2 as described (48). The functionality of tagged proteins was confirmed by assaying rDNA silencing.

Life span determination—Replicative life span determination was performed as described (16). Cells were grown on YPD medium (1% yeast extract, 2% bactopeptone, 2% glucose w/v) unless otherwise stated with a minimum of 40 cells per experiment. Each experiment was performed at least twice independently. Statistical significance of life span differences was determined using the Wilcoxon rank sum test. Differences are stated to be different when the confidence is higher than 95%.

mRNA and protein determination—Northern and Western blots were performed using standard techniques. NPT1 transcripts were detected using a probe derived from the complete open reading frame of the NPT1 gene. ACT1 mRNA was detected using a full-length ACT1 probe (gift of G. Fink, M.I.T). The HA epitope tag was detected using monoclonal antibody HA.11 (CRP, Richmond, Calif.). Actin was detected with monoclonal antibody MAB1501R (Chemicon, Temecula, Calif.).

Yeast assays and GFP localization—Yeast strains were grown at 30° C. unless otherwise stated. The extent of silencing at the ribosomal DNA locus was determined using two assays. For the ADE2 silencing assay, cells were pre-grown on synthetic complete (SC) medium (1.67% yeast nitrogen base, 2% glucose, 40 mg/l of histidine, uridine, tryptophan, adenine and leucine) for 3 days. Cells were resuspended in SD medium and serially diluted 10-fold in phosphate-buffered saline and spotted onto SC medium lacking adenine. MET15 silencing assays were performed on $Pb^{2+}$-containing plates as previously described (42). Telomeric silencing was assayed on SC medium containing 0.7 mg/l adenine. Cells were grown for 3 days and placed at 4° C. for 3 days to enhance color. Heat shock assays were performed essentially as described (14). Strains were pre-grown overnight in SC-complete medium with limiting histidine (20 mg/ml), diluted to $1 \times 10^5$ cells/ml in 3 ml of the same medium and grown for 5 days. Cultures were diluted 10-fold in expired medium, incubated for 1 h at 55° C. and spotted on SC plates. Ribosomal DNA recombination rates were determined as previously described (49). At least 10,000 colonies were examined for each strain and each experiment was performed in triplicate.

$NAD^+$ and NADH determinations were measured as described elsewhere (50). Cells expressing a GFP fusions were grown to mid log phase in YPD medium or YPD low glucose (0.5% w/v) then incubated in PBS containing 20 μM Hoechst 33342 DNA stain (Sigma) for 5 min. Images were captured under a 100× magnification on a Nikon E600 fluorescence microscope and analyzed using Photoshop 6.0 software.

Results

Increased dosage of NPT1 increases longevity but not steady-state $NAD^+$ levels—SIR2 is a limiting component of longevity in yeast and requires $NAD^+$ for catalysis. Studies in *E. coli* have shown that PncB catalyzes a rate-limiting step in the salvage pathway that recycles $NAD^+$ (35,37,38). We asked whether additional copies of the yeast pncB homolog, NPT1, could increase $NAD^+$ production to Sir2 and hence extend yeast life span. NPT1 was integrated at the URA3 locus under the control of its native promoter. Strains that carried one or four tandem copies of NPT1 were then identified by Southern blotting. We refer to the resulting genotypes as 2×NPT1 and 5×NPT1 respectively.

For the replicative life span assay, cells were grown for at least two days on fresh yeast extract/peptone/glucose (YPD) medium to ensure that they had fully recovered from conditions of caloric restriction prior to the assay. Daughter cells that emerged from previously unbudded mother cells were then micro-manipulated away and scored. As shown in FIG. 1A, the 2×NPT1 strain lived an average of ~40% longer than the wild type strain and the 5×NPT1 strain lived a striking ~60% longer. The NPT1-induced life span extension was completely abrogated by a sir2 deletion and not significantly enhanced by an additional copy of SIR2 (FIG. 1B) indicating that the life span extension provided by NPT1 is mediated by Sir2.

It has recently been shown that wild type cells grown in low glucose medium (0.5% w/v) have an average life span significantly greater than those grown on standard (2%) glucose medium (19,32). As shown in FIG. 1C, on low glucose medium the life span of the 5×NPT1 strain was not significantly greater than the wild type strain. The fact that the effect of NPT1 and low glucose were not additive suggests that these two regimens act via the same pathway.

Biochemical studies have shown that Sir2 requires $NAD^+$ as a cofactor. This has led to the hypothesis that replicative life span may be extended by increased $NAD^+$ levels. Consistent with this idea, $NAD^+$ levels have been shown to increase significantly in old cells, perhaps as a defense against aging or as the result of decreased metabolic activity (50). To date the intracellular levels of $NAD^+$ in any long-lived strain have not been reported. We found that steady-state $NAD^+$ levels and $NAD^+$/NADH ratios in the 2×NPT1 strain were not significantly different from the wild type (Table 1). We also examined Δsir2 and 2×NPT1 Δsir2 strains and again found no difference from wild type, indicating that the failure to detect increased $NAD^+$ levels was not due to the activity of Sir2.

TABLE 1

Steady-state $NAD^+$ and NADH levels in various long-and short-lived strains.

| Genotype | $NAD^+$ (amol/pg protein)[1] | NADH (amol/pg protein)[1] | $NAD^+$/ NADH ratio | ATP (amol/pg protein)[1] |
|---|---|---|---|---|
| 1×NPT1 (wild type) | 23.7 (3.2) | 9.3 (0.8) | 2.8 (0.5) | 15.5 (3) |
| 2×NPT1 | 21.9 (2.0) | 6.0 (0.6) | 3.3 (0.3) | 7.6 (1.6) |
| 2×NPT1 sir2::TRP1 | 22.5 (1.6) | 7.0 (0.3) | 2.4 (0.9) | 5.3 (1.1) |
| sir2::TRP1 | 23.6 (1.2) | 7.0 (0.6) | 2.8 (1.2) | 7.9 (1.9) |

[1]average of five independent experiments (s.e.)

NPT1 and SIR2 increase resistance to heat shock but not to other stresses—Mutations in components of the C. elegans and Drosophila insulin/IGF-1 pathway allow animals to live up to twice as long as controls (5). In C. elegans this longevity is coupled to stress resistance (4). In contrast, the chico mutation in Drosophila, which extends life span by ~50% in homozygotes, does not protect against heat shock or oxidative stress (51). The link between sir2.1 life span extension and stress resistance in C. elegans has not been examined, though there is evidence from yeast that the Sir2/3/4 complex may be involved in such a response. The yeast sir4-42 mutation increases replicative life span as well as resistance to starvation and heat shock (52). This raises the possibility that the SIR2 longevity pathway may also influence stress resistance.

To explore this, we examined the ability of extra copies of NPT1 and SIR2 to confer resistance to a variety of stresses including heat shock, starvation, and exposure to methylmethane sulfonate (MMS) or paraquat. MMS is a DNA damaging agent that causes a variety of DNA lesions, whereas paraquat induces oxidative stress by generating reactive oxygen species. Additional copies of either NPT1, SIR2, or both did not provide resistance against paraquat or MMS, nor did they enhance the ability to survive in stationary phase.

To assay heat shock resitance, strains with an additional copy of NPT1 or SIR2 were grown to stationary phase in SC medium, heat shocked for 1 hour at 55° C., then spotted in 10-fold serial dilutions onto SC plates. As shown in FIG. 2A, stains with a single additional copy of NPT1 or SIR2 were significantly more resistant to heat shock than the otherwise isogenic wild type control strain. No additive effect of NPT1 and SIR2 was apparent, consistent with these two genes acting in the same pathway. To provide a more quantitative measure of this phenotype, strains were subjected to 1 hour heat shock, plated for single colonies and the number of colonies after 24 hours was scored as a percentage of the untreated sample. As shown in FIG. 2B, additional copies of NPT1 and SIR2, or both provided ~8-fold greater survival than wild type, consistent with our earlier finding.

Additional NPT1 increases silencing and rDNA stability— We wished to determine the molecular basis of the SIR2-dependent life span extension provided by additional NPT1. A simple model predicts that increased dosage of NPT1 would stimulate the NAD$^+$ salvage pathway, which would in turn increase Sir2 activity. We thus examined the effect of additional copies of NPT1 on the SIR2-dependent processes of silencing and stability at the rDNA locus.

Figure 3:
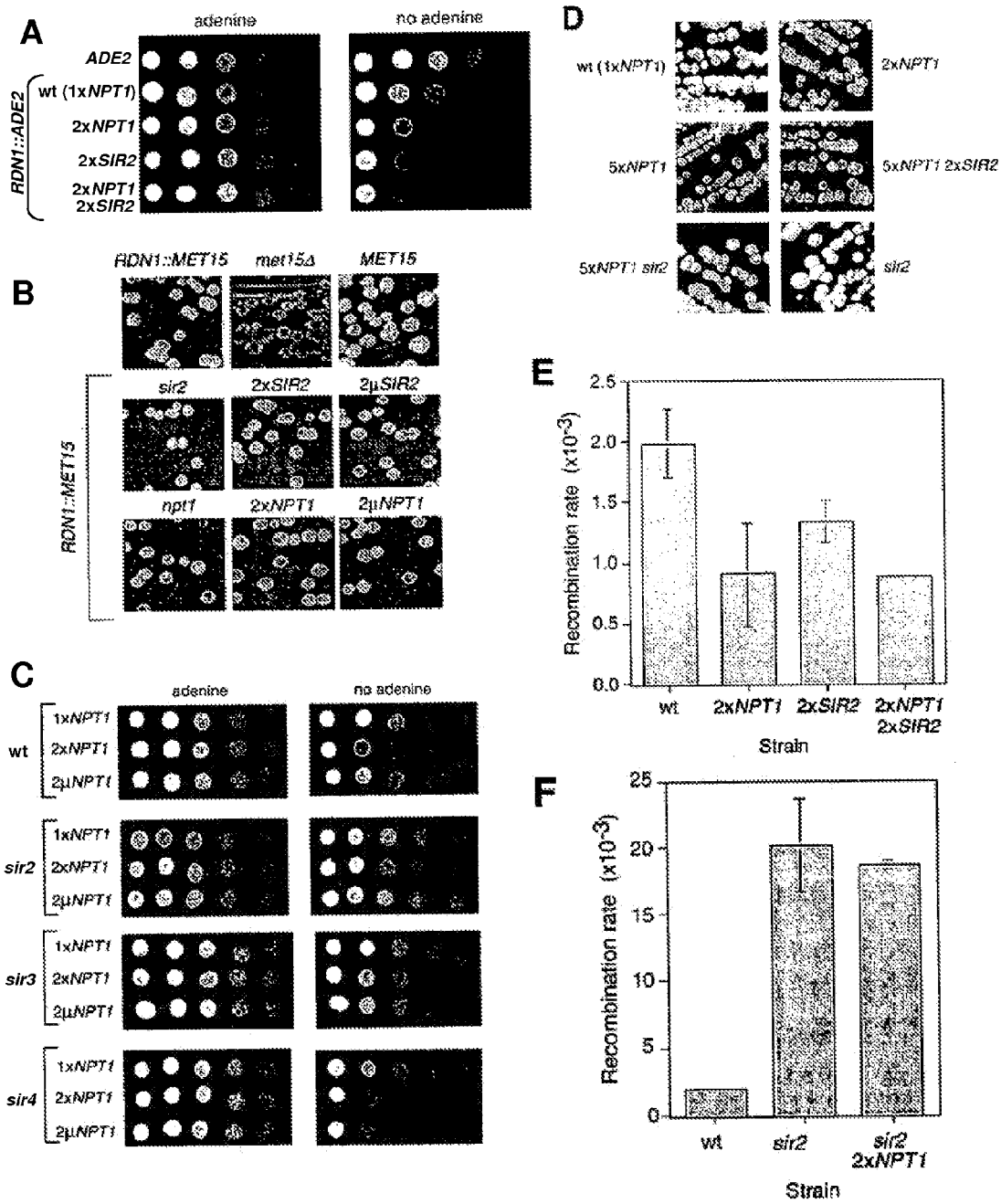
FIG. 3. Additional NPT1 increases silencing and rDNA stability. A, Strains with an ADE2 marker at the rDNA were pre-grown on SC plates and spotted as 10-fold serial dilutions on SC plates. Increased silencing is indicated by growth retardation on media lacking adenine. Strains: W303-1A ADE2 (YDS1596), W303-1A RDN1:.ADE2 (W303AR5) and W303AR5 derivatives 2×NPT1 (YDS1503), 2×SIR2 (YDS1572) and 2×NPT1 2×SIR2 (YDS1561). B, Silencing of MET15 at the rDNA locus was assayed by streaking isogenic derivatives of JS237 on rich medium containing 0.07% PbNO$_3$ and incubating for 5 days at 30° C. Increased silencing is indicated by accumulation of a brown pigment. Relevant genotypes: met15Δ (JS209), MET15 (JS241), RND1::MET15 (JS237), sir2::TRP1 (JS218), 2×SIR2 (YDS1583), 2μSIR2 (YDS1522), npt1::kan$^r$ (YDS1580), 2×NPT1 (YDS1581) and 2 μNPT1 (YDS1493). C, Silencing of an ADE2 marker at the rDNA locus was determined in strains with 1×NPT1, 2×NPT1, and 2 μNPT1 in the following backgrounds: wild type (W303AR5, YDS1503, YDS1496), sir2::TRP1 (YDS878, YDS1504, YDS1494), sir3::HIS3 (YDS924, YDS1505, YDS1587), and sir4::HIS3 (YDS882, YDS1506, YDS1495). D, Strains with an ADE2 marker at the telomere were streaked onto SC medium containing limiting amounts of adenine. Increased silencing is indicated by accumulation of red pigment. Relevant genotypes: (PSY316AT), 2×NPT1 (YDS1544), 5×NPT1 (YDS1548), 5×NPT1 2×SIR2 (YDS1577) and 5×NPT1 SIR2::TRP1 (YDS1573). sir2::TRP1 (YDS1594). E, Strains in A were assayed for rDNA stability by examining the rate of loss of an ADE2 marker integrated at the rDNA locus. Cells were plated on YPD medium and the frequency of half-sectored colonies, reflecting a marker loss event at the first cell division, was measured. More than 10,000 colonies were examined for each strain and each experiment was performed in triplicate. Average recombination frequencies (+/−s.d.) per cell division are shown. F, Ribosomal DNA recombination rates for wild type (W303AR), sir2::TRP1 (YDS878) and 2×NPT1 sir2::TRP1 (YDS1504) strains. Assays were performed as in (E).

To determine the effect of NPT1 on rDNA silencing, we utilized strains with either an ADE2 or MET15 marker integrated at the rDNA locus (RDN1). We used two marker genes to ensure that the effects we observed were not simply due to changes in adenine or methionine biosynthesis. Silencing of ADE2 results in slower growth of cells on media lacking adenine and the accumulation of a red pigment on plates with limiting adenine. Silencing of MET15 leads to production of a brown pigment on Pb$^{2+}$-containing medium. Strains with additional copies of SIR2 were included for comparison. The 2×NPT1 strains showed higher levels of rDNA silencing than wild type in the ADE2 assay (FIG. 3A, compare growth on adenine with growth on no adenine) and the MET15 assay (FIG. 3B). Introduction of an additional copy of NPT1 into the 2×SIR2 strain did not further increase silencing, again consistent with the placement of these two genes in the same pathway. Strains carrying SIR2 and NPT1 on high-copy 2μ-based plasmids also showed increased levels of rDNA silencing (FIGS. 3B and C). An additional copy of NPT1 also increased silencing in sir3 and sir4 null strains (FIG. 3C). High-copy NPT1 had a disruptive effect on rDNA silencing in the sir3 strain, whereas this effect was not observed in the sir4 strain. This can be explained by the fact that sir4 mutants relocalize Sir2 to the rDNA, which may counteract the high levels of Npt1. Additional copies of NPT1 in a sir2 mutant caused a slight increase in rDNA silencing that was considerably weaker than SIR2-dependent silencing. The basis of this apparent increase is unclear. To determine whether this was a global effect on silencing, we examined silencing at a telomeric locus. An additional copy of NPT1 was introduced into PSY316AT, which has an ADE2 marker inserted in the subtelomeric region of chromosome V (53). As shown in FIG. 3D, additional copies of NPT1 increased telomeric silencing in a SIR2-dependent manner.

Instability of the rDNA has been shown to be a major cause of yeast replicative aging. To test whether NPT1 extends life span by increasing stability at this locus, we determined the rate of rDNA recombination in 2×NPT1 and 2×SIR2 strains. This was achieved by measuring the rate of loss of an ADE2 marker inserted at the rDNA. As shown in FIG. 3E, an additional copy of NPT1 decreased rDNA recombination by 2-fold, similar to the 2×SIR2 and 2×NPT1 2×SIR2 strains. When sir2 was deleted from the 2×NPT1 strain, rDNA recombination increased dramatically to the levels of a sir2 null strain (FIG. 3F). These results are consistent with a model in which NPT1 extends replicative life span by increasing the ability of Sir2 to inhibit rDNA recombination.

One plausible explanation for the increase in rDNA silencing associated with additional copies of NPT1 is that the telomeric Sir2 in these strains is relocalized to the rDNA, which would result in the loss of telomeric silencing. We have shown that additional copies of NPT1 increase telomeric silencing in a SIR2-dependent manner, arguing against relocalization of Sir2 from telomeres as the mechanism of life span extension. Another possible explanation is that additional NPT1 upregulates Sir2 expression. By Western blotting we found that the steady-state levels of Sir2 did not change in response to additional NPT1. A third possibility for the increase in rDNA silencing is that additional NPT1 stimulates overall Sir2 activity. Although it is not currently possible to measure this activity in vivo, this idea is consistent with our findings that additional NPT1 enhances each of the SIR2-dependent processes thus far examined.

Figure 4:
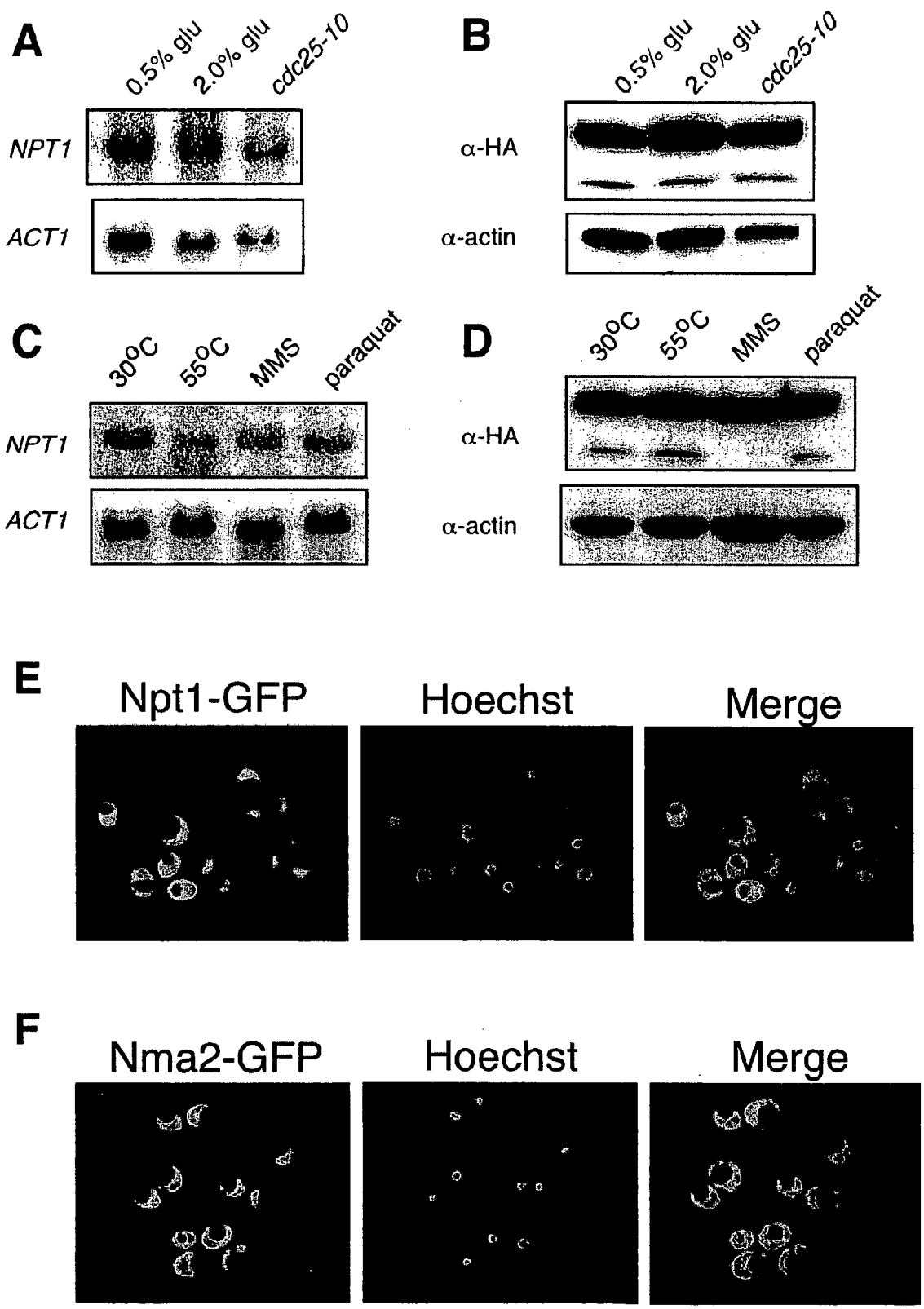
FIG. 4. Expression of NPT1 in response to caloric restriction and stress. A, 3×HA Tag sequence (SEQ ID NO: 49) was inserted in frame with the 3' end of the native NPT1 ORF in W303AR5 (YDS1531) and W303cdc10-25 (YDS1537). Cells were grown in YPD medium at 30° C. and treated as described. Levels of NPT1 mRNA were examined for W303AR5 grown in YPD (0.5% and 2.0% glucose) and W303cdc25-10 grown in YPD (2% glucose). A 1.8 kb NPT1 transcript was detected and levels were normalized to actin (ACT1) control. Similar results were obtained in the PSY316 strain background (not shown). B, Protein extracts from cultures in A were analyzed by Western blot to detect the HA-tagged Npt1 using α-HA antibody. Two bands of 53 kD and 40 kD were detected in the Npt1-HA strains and no bands were detected in the untagged control strain (not shown). Actin levels served as a loading control. Similar results were obtained in the PSY316 strain background (not shown). C, Levels of NPT1 mRNA were examined in wild type W303AR5 (YDS1531) log phase cultures after 1 h exposure to the following: MMS (0.02% v/v), paraquat (5 mM), or heat shock (55° C.). D, Protein extracts of cultures in C were analyzed as in B. E and F. A green fluorescent protein (GFP) sequence was inserted in-frame at the 3' end of the native NPT1 and NMA2 ORFs in W303AR5 (YDS1611 and YDS1624, respectively). Cells were grown in YPD medium at 30° C. to mid log phase and photographed live. Regions of overlap between GFP (green) and Hoechst DNA stain (false color red) appear yellow in the merged image. Regions of overlap between GFP (green) and Hoechst DNA stain (false color red) appear yellow in the merged image.

Caloric restriction does not alter NPT1 expression or localization—Given that additional NPT1 and caloric restriction appear to extend life span via the same pathway, we tested whether caloric restriction acts by increasing NPT1 expression. A triple hemagglutinin epitope (3×HA) tag (SEQ ID NO: 49) was added to the carboxy-terminus of Npt1 by integrating an 3×HA-kanamycin resistance cassette into the native NPT1 locus (3×HA tag disclosed as SEQ ID NO: 49). We confirmed that the fusion protein was functional by assaying its ability to maintain wild type levels of rDNA silencing. NPT1 levels were then determined in strains grown on (0.5%) glucose medium and in the long-lived cdc25-10 strain, which is considered a genetic mimic of caloric restriction (19). As shown in FIGS. 4A and B, no increase in NPT1 expression was detected at the mRNA or protein level. In fact under low glucose conditions a consistent ~2-fold decrease in NPT1 expression was observed. We did not detect significant changes in NPT1 expression after heat shock or exposure to MMS or paraquat (FIGS. 4C and D). We conclude that caloric restriction does not increase longevity by upregulating NPT1 expression.

Given that NPT1 expression was not enhanced in response to caloric restriction, we examined the possibility that the activity of this protein may be modulated by other means.

Specifically, we examined the subcellular localization of GFP-tagged Npt1 in live cells grown in complete or low glucose medium. To our surprise, Npt1 was observed throughout the cell with an apparent concentration of the protein in the nucleus of most cells (FIG. 4E). The large regions of exclusion correspond to vacuoles. These findings raise the intriguing possibility that a significant fraction of $NAD^+$ is regenerated in the nucleus. In low glucose medium the localization pattern of Npt1-GFP was unaltered, indicating that there is no gross relocalization of Npt1 in response to caloric restriction.

If our hypothesis that the entire $NAD^+$ salvage pathway exists in the nuclear compartment, then we should expect that the other enzymes in the pathway will show a similar localization pattern to Npt1. Based on the bacterial salvage pathway, the step immediately downstream of NPT1 is predicted to be catalyzed by a nicotinate mononucleotide adenylyltransferase (NaMAT). There are two yeast ORFs with similar homology to NaMATs from other species, YLR0328 and YGR010, which we have designated NMA1 and NMA2, respectively. To localize these two proteins, a GFP cassette was integrated in frame prior to the stop codon of each ORF to generate C-terminal fusions. As shown in FIG. 4F, Nma2-GFP was concentrated in the nucleus in the majority of cells, in a pattern identical to that of Npt1-GFP. This finding further supports our hypothesis that $NAD^+$ is recycled from nicotinamide entirely within the nucleus. The localization pattern of Nma1 was unable to be determined due to low expression levels.

Identification of other putative longevity genes in the $NAD^+$ salvage pathway—The discovery that Nma2 shows a similar localization to Npt1 prompted us to test whether other genes in the $NAD^+$ salvage pathway could have similar effects to Npt1 when overexpressed. While the bacterial genes in $NAD^+$ salvage pathway have been studied in detail, in *S. cerevisiae* some of the key genes in the pathway remain to be characterized. PNC1, a recently identified gene, encodes a nicotinamidase which catalyses the conversion of nicoinamide to nicotinic acid, the step immediately upstream of NPT1. As discussed above, the two genes NMA1 and NMA2 encode NaMNATs which catalyze the step immediately downstream of NPT1. In bacteria, the next step in the pathway, the generation of $NAD^+$, is catalyzed by an NAD synthetase. An uncharacterized ORF, QNS1/YHR074, shows high homolgy to NAD synthetases. Each of these salvage pathway genes was integrated as a single copy into the URA3 locus of W303AR5 and PSY316AT and assayed for silencing as previously described. Additional copies of either PNC1, NMA1 or NMA2 increased rDNA and telomeric silencing to levels similar to those in a 2×NPT1 strain (FIGS. 5B and C). In contrast, additional copies of QNS1 had no effect on either rDNA silencing (FIG. 5B) or telomeric silencing. As discussed below, these results indicate there are multiple steps that can affect the rate of the pathway and that the two homologs NMA1 and NMA2 may have overlapping functions.

DISCUSSION

NPT1 encodes a key component of the yeast salvage pathway that recycles $NAD^+$, a cofactor of Sir2. We have shown that additional copies of NPT1 increase life span by up to 60% in a SIR2-dependent manner. It has been proposed that longevity in yeast may be associated with increased $NAD^+$ levels. However we have shown that in strains with additional copies of NPT1, steady-state $NAD^+$ levels are unaltered. Furthermore, the $NAD^+$/NADH ratios are also similar to wild type cells, indicating that total cellular redox state is not dramatically altered either.

Figure 6:
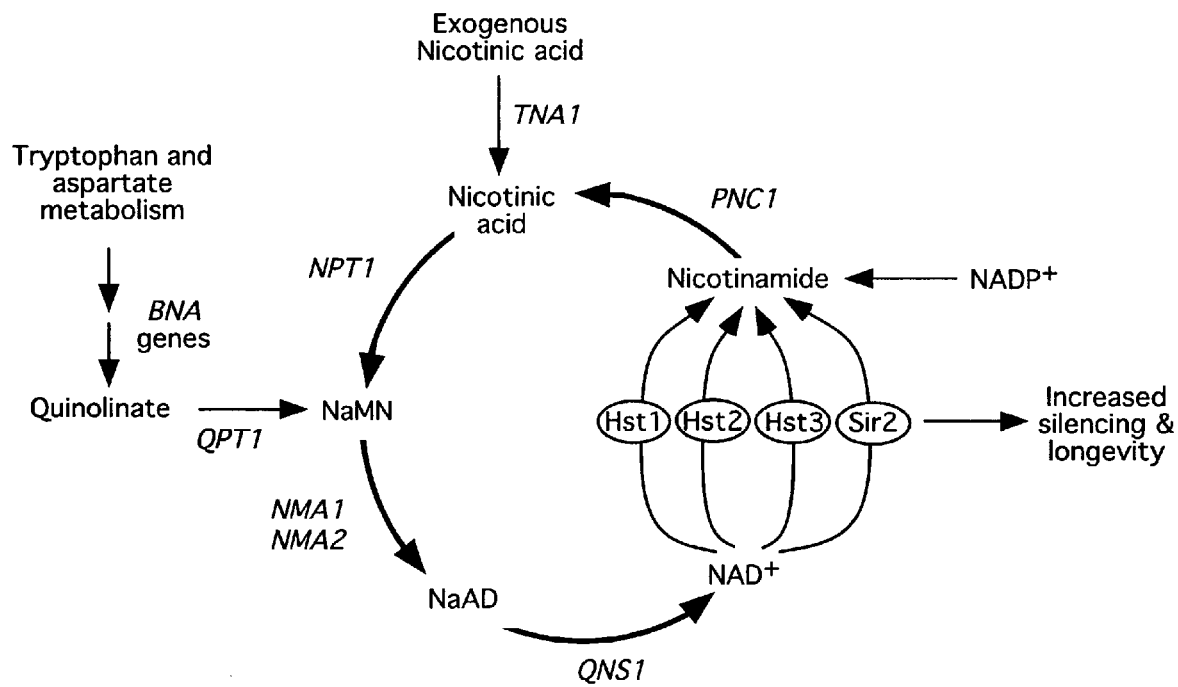
FIG. 6. Model for life span extension via increased flux through the NAD+ salvage pathway. Type III histone deacetylases such as Sir2 and Hst1-4 catalyze a key step in the salvage pathway by converting NAD+ to nicotinamide. Additional copies of PNC1, NPT1, NMA1 and NMA2 increase flux through the NAD+ salvage pathway, which stimulates Sir2 activity and increases life span. Additional copies of QNS1 fail to increase silencing because, unlike other steps in the pathway, its substrate cannot be supplied from a source outside the salvage pathway and is therefore limiting for the reaction. Abbreviations: NAD+, nicotinamide adenine dinucleotide; NaMN, nicotinic acid mononucleotide; NaAD, desamido-NAD+.

We have also shown that sir2 mutants have wild type $NAD^+$ levels, implying that Sir2 is not a major consumer of $NAD^+$. Nevertheless, by virtue of its ability to convert $NAD^+$ to nicotinamide, Sir2 should be responsive to increased flux through the salvage pathway (FIG. 6). Thus, while steady-state levels of $NAD^+$ remain constant, the turnover of this molecule may be elevated. Localization of GFP-tagged enzymes indicated that at least two of the enzymes in the $NAD^+$ salvage pathway are concentrated in the nucleus. Consistent with this, Nma1 and Nma2 have been shown by high-throughput 2-hybrid screening to interact with Srp1, a protein that acts as a receptor for nuclear localization sequences (NLS) (54). The same 2-hybrid screen also found that Nma1 and Nma2 can interact with themselves and with each other. Perhaps Nma proteins exist as dimers, as is the case for the *Bacillus subtilis* NaMNAT (55), or as hexamers, as is the case for *Methanococcus jannaschii* (56) and *Methanobacterium thermoautotrophicum* NaMNATs (57). It is worth nothing that strains disrupted for either NMA1 or NMA2 are viable (58), arguing that they are functionally redundant.

In vertebrates, NaMNAT/NMNAT activity is primarily observed in the nuclear fraction of liver cell extracts (59), suggesting that nuclear compartmentalization of the pathway may be a universal property of eukaryotic cells. Having the salvage pathway in proximity to chromatin may allow $NAD^+$ to be rapidly regenerated for silencing proteins. Alternatively, it may permit the coordination of a variety of nuclear activities via the alteration of nuclear $NAD^+$ pools. Testing of these hypotheses will not be a simple task but one that will be greatly assisted by the development of a molecular probe for intracellular $NAD^+$.

In yeast and many metazoans, a number of long-lived mutants display increased stress resistance. However, there are many examples of mutations that extend life span but provide little protection against stress, indicating that this relationship is not straightforward (4). For example, in yeast the life span extension provided by a cdc25-10 mutation is not accompanied by heat shock resistance (19). We have shown that additional copies of NPT1 or SIR2 extend life span but do not provide protection against MMS, paraquat or starvation. Thus, in *S. cerevisiae* longevity is not linked to a general increase in stress resistance. The only stress-related phenotype that we found correlated with longevity was heat shock resistance. Based on genome-wide analyses of gene expression in sir2Δ strains, it has been proposed that Sir2 regulates genes other than those at the three silent loci (60), although this interpretation is debated (61). If the interpretation is correct, then it is plausible that the heat shock resistance we observed in 2×NPT1 and 2×SIR2 strains results from Sir2-mediated silencing of genes that suppress heat shock resistance.

In bacteria, the Npt1 homolog PncB catalyzes a rate-limiting step in the $NAD^+$ salvage pathway (35,37,38). In this study we show that additional copies of PNC1, NPT1, NMA1 or NMA2 all increase rDNA and telomeric silencing. The implication is that, in yeast, multiple steps can affect the rate of the pathway. Such a proposal is consistent with Metabolic Control Analysis, a theory based on the observation that flux through most metabolic pathways is controled by multiple enzymes, rather than by a single rate-liming step (62). Of all the genes in the salvage pathway, only QNS1 had no effect on silencing, suggesting that it is the only enzyme in the pathway limited by substrate availability. This is likely due to the fact that the predicted substrate for Qns1, desamido-$NAD^+$, is the only intermediate that can not be supplied from a source outside the salvage pathway (see FIG. 6).

In yeast and metazoans there are multiple members of the Sir2 family, many of which have been shown (or are predicted) to be NAD$^+$-dependent deacetylases (24,63). This finding, combined with the fact that some Sir2 family members are cytoplasmic (64,65), suggests that reversible acetylation may be a much more prevalent regulatory mechanism than previously thought (66). This would place the NAD$^+$ salvage pathway in a pivotal position, coordinating the activity of this group of effector proteins in response to cellular energy status It is now widely accepted that there are conserved pathways for the regulation of longevity (4,5). The extent of this conservation is exemplified by the discovery that additional copies of *C. elegans* sir-2.1 also extend life span in that organism (31). Our findings show that several SIR2-dependent processes can be enhanced by manipulation of the NAD$^+$ salvage pathway in yeast and this may hold true for higher organisms. We have identified NPT1 homologs in every genome we have examined and all possess a highly conserved region around a histidine residue that, in *Salmonella*, greatly stimulates catalysis when phosphorylated (67). This mode of regulation may permit the design of mutations or small molecules that increase Npt1 activity. Together, our findings show that Npt1 and other members of the salvage pathway are attractive targets for small molecules that may mimic the beneficial effects of caloric restriction.

REFERENCES

1. Masoro, E. J. (2000) *Exp Gerontol* 35(3), 299-305.
2. Vanfleteren, J. R., and Braeckman, B. P. (1999) *Neurobiol Aging* 20(5), 487-502
3. Zainal, T. A., Oberley, T. D., Allison, D. B., Szweda, L. I., and Weindruch, R. (2000) *Faseb J* 14(12), 1825-36.
4. Kenyon, C. (2001) *Cell* 105,165-168
5. Guarente, L., and Kenyon, C. (2000) *Nature* 408(6809), 255-62.
6. Kirkwood, T. B., and Rose, M. R. (1991) *Philos Trans R Soc Lond B Biol Sci* 332(1262), 15-24.
7. Barton, A. (1950) *J Gen Microbiol* 4, 84-86
8. Sinclair, D. A., Mills, K., and Guarente, L. (1997) *Science* 277(5330), 1313-6.
9. Mortimer, R. K., and Johnston, J. R. (1959) *Nature* 183, 1751-1752
10. Kennedy, B. K., Austriaco, N. R., Jr., and Guarente, L. (1994) *J Cell Biol* 127(6 Pt 2), 1985-93.
11. Kim, S., Villeponteau, B., and Jazwinski, S. M. (1996) *Biochem Biophys Res Commun* 219(2), 370-6.
12. Ashrafi, K., Lin, S. S., Manchester, J. K., and Gordon, J. I. (2000) *Genes Dev* 14(15), 1872-85.
13. Lin, S. S., Manchester, J. K., and Gordon, J. I. (2001) *J. Biol. Chem.,*
14. Longo, V. D. (1999) *Neurobiol Aging* 20(5), 479-86.
15. Jazwinski, S. M. (2001) *Mech Ageing Dev* 122(9), 865-82.
16. Sinclair, D. A., and Guarente, L. (1997) *Cell* 91(7), 1033-42.
17. Kaeberlein, M., McVey, M., and Guarente, L. (1999) *Genes Dev* 13(19), 2570-80.
18. Park, P. U., Defossez, P. A., and Guarente, L. (1999) *Mol Cell Biol* 19(5), 3848-56
19. Lin, S. J., Defossez, P. A., and Guarente, L. (2000) *Science* 289(5487), 2126-8.
20. Defossez, P. A., Prusty, R., Kaeberlein, M., Lin, S. J., Ferrigno, P., Silver, P. A., Keil, R. L., and Guarente, L. (1999) *Mol Cell* 3(4), 447-55
21. Tanner, K. G., Landry, J., Sternglanz, R., and Denu, J. M. (2000) *Proc Natl Acad Sci USA* 97(26), 14178-82.
22. Imai, S., Armstrong, C. M., Kaeberlein, M., and Guarente, L. (2000) *Nature* 403(6771), 795-800
23. Smith, J. S., Brachmann, C. B., Celic, I., Kenna, M. A., Muhammad, S., Starai, V. J., Avalos, J. L., Escalante-Semerena, J. C., Grubmeyer, C., Wolberger, C., and Boeke, J. D. (2000) *Proc Natl Acad Sci USA* 97(12), 6658-63.
24. Landry, J., Sutton, A., Tafrov, S. T., Heller, R. C., Stebbins, J., Pillus, L., and Sternglanz, R. (2000) *Proc Natl Acad Sci USA* 97(11), 5807-11.
25. Laurenson, P., and Rine, J. (1992) *Microbiol Rev* 56(4), 543-60.
26. Straight, A. F., Shou, W., Dowd, G. J., Turck, C. W., Deshaies, R. J., Johnson, A. D., and Moazed, D. (1999) *Cell* 97(2), 245-56.
27. Shou, W., Seol, J. H., Shevchenko, A., Baskerville, C., Moazed, D., Chen, Z. W., Jang, J., Charbonneau, H., and Deshaies, R. J. (1999) *Cell* 97(2), 233-44.
28. Shou, W., Sakamoto, K. M., Keener, J., Morimoto, K. W., Traverso, E. E., Azzam, R., Hoppe, G. J., Feldman, R. M. R., DeModena, J., Moazed, D., Charbonneaux, H., Nomura, M., and Deshaies, R. J. (2001) Mol. Cell. 8(1), 45-55
29. Tanny, J. C., and Moazed, D. (2001) *Proc Natl Acad Sci USA* 98(2), 415-20.
30. Smith, J. S., Caputo, E., and Boeke, J. D. (1999) *Mol Cell Biol* 19(4), 3184-97.
31. Tissenbaum, H. A., and Guarente, L. (2001) *Nature* 410 (6825), 227-30.
32. Jiang, J. C., Jaruga, E., Repnevskaya, M. V., and Jazwinski, S. M. (2000) *Faseb J* 14(14),2135-7.
33. Foster, J. W., Kinney, D. M., and Moat, A. G. (1979) *J Bacteriol* 137(3), 1165-75.
34. Ghislain, M., Talla, E., and Francois, J. M. (2002) *Yeast* 19(3), 215-224.
35. Wubbolts, M. G., Terpstra, P., van Beilen, J. B., Kingma, J., Meesters, H. A., and Witholt, B. (1990) *J Biol Chem* 265(29), 17665-72.
36. Vinitsky, A., Teng, H., and Grubmeyer, C. T. (1991) *J Bacteriol* 173(2), 536-40.
37. Imsande, J. (1964) *Biochim. Biophys. Acta* 85, 255-273
38. Grubmeyer, C. T., Gross, J. W., and Rajavel, M. (1999) *Methods Enzymol* 308, 28-48
39. Emanuelli, M., Carnevali, F., Lorenzi, M., Raffaelli, N., Amici, A., Ruggieri, S., and Magni, G. (1999) *FEBS Lett* 455(1-2), 13-7.
40. Hughes, K. T., Olivera, B. M., and Roth, J. R. (1988) *J Bacteriol* 170(5), 2113-20.
41. Mills, K. D., Sinclair, D. A., and Guarente, L. (1999) *Cell* 97(5), 609-20.
42. Smith, J. S., and Boeke, J. D. (1997) *Genes Dev* 11(2), 241-54.
43. Lalo, D., Carles, C., Sentenac, A., and Thuriaux, P. (1993) *Proc Natl Acad Sci USA* 90(12), 5524-8.
44. Becker, D. M., Fikes, J. D., and Guarente, L. (1991) *Proc Natl Acad Sci USA* 88(5), 1968-72.
45. Sikorski, R. S., and Hieter, P. (1989) *Genetics* 122(1), 19-27.
46. Guldener, U., Heck, S., Fielder, T., Beinhauer, J., and Hegemann, J. H. (1996) *Nucleic Acids Res* 24(13), 2519-24.
47. De Antoni, A., and Gallwitz, D. (2000) *Gene* 246(1-2), 179-85.

48. Longtine, M. S., McKenzie, A., 3rd, Demarini, D. J., Shah, N. G., Wach, A., Brachat, A., Philippsen, P., and Pringle, J. R. (1998) *Yeast* 14(10), 953-61.
49. Keil, R. L., and McWilliams, A. D. (1993) *Genetics* 135 (3), 711-8.
50. Ashrafi, K., Sinclair, D., Gordon, J. I., and Guarente, L. (1999) *Proc Natl Acad Sci USA* 96(16), 9100-5.
51. Clancy, D. J., Gems, D., Harshman, L. G., Oldham, S., Stocker, H., Hafen, E., Leevers, S. J., and Partridge, L. (2001) *Science* 292(5514), 104-6.
52. Kennedy, B. K., and Guarente, L. (1996) *Trends Genet* 12(9), 355-9.
53. Gottschling, D. E., Aparicio, O. M., Billington, B. L., and Zakian, V. A. (1990) *Cell* 63(4), 751-62.
54. Uetz, P., Giot, L., Cagney, G., Mansfield, T. A., Judson, R. S., Knight, J. R., Lockshon, D., Narayan, V., Srinivasan, M., Pochart, P., Qureshi-Emili, A., Li, Y., Godwin, B., Conover, D., Kalbfleisch, T., Vijayadamodar, G., Yang, M., Johnston, M., Fields, S., and Rothberg, J. M. (2000) *Nature* 403(6770), 623-7.
55. Olland, A. M., Underwood, K. W., Czerwinski, R. M., Lo, M. C., Aulabaugh, A., Bard, J., Stahl, M. L., Somers, W. S., Sullivan, F. X., and Chopra, R. (2002) *J Biol Chem* 277(5), 3698-707.
56. D'Angelo, I., Raffaelli, N., Dabusti, V., Lorenzi, T., Magni, G., and Rizzi, M. (2000) *Structure Fold Des* 8(9), 993-1004.
57. Saridakis, V., Christendat, D., Kimber, M. S., Dharamsi, A., Edwards, A. M., and Pai, E. F. (2001) *J Biol Chem* 276(10), 7225-32.
58. Winzeler, E. A., Shoemaker, D. D., Astromoff, A., Liang, H., Anderson, K., Andre, B., Bangham, R., Benito, R., Boeke, J. D., Bussey, H., Chu, A. M., Connelly, C., Davis, K., Dietrich, F., Dow, S. W., El Bakkoury, M., Foury, F., Friend, S. H., Gentalen, E., Giaever, G., Hegemann, J. H., Jones, T., Laub, M., Liao, H., Davis, R. W., and et al. (1999) *Science* 285(5429), 901-6.
59. Hogeboom, G., and Schneider, W. (1950) *J. Biol. Chem.* 197, 611-620
60. Wyrick, J. J., Holstege, F. C., Jennings, E. G., Causton, H. C., Shore, D., Grunstein, M., Lander, E. S., and Young, R. A. (1999) *Nature* 402(6760), 418-21.
61. Bedalov, A., Gatbonton, T., Irvine, W. P., Gottschling, D. E., and Simon, J. A. (2001) *Proc Natl Acad Sci USA* 98(26), 15113-8.
62. Fell, D. (1997) *Understanding the Control of Metabolism*. Frontiers in Metabolism (Snell, K., Ed.), Portland Press, London
63. Landry, J., Slama, J. T., and Stemglanz, R. (2000) *Biochem Biophys Res Commun* 278(3), 685-90.
64. Perrod, S., Cockell, M. M., Laroche, T., Renauld, H., Ducrest, A. L., Bonnard, C., and Gasser, S. M. (2001) *Embo J* 20(1-2), 197-209.
65. Afshar, G., and Murnane, J. P. (1999) *Gene* 234(1), 161-8.
66. Shore, D. (2000) *Proc Natl Acad Sci USA* 97(26), 14030-2.
67. Rajavel, M., Lalo, D., Gross, J. W., and Grubmeyer, C. (1998) *Biochemistry* 37(12), 4181-8.

Example 2

Increased Genomic Instability and Accelerated Aging by Nicotinamide

The *Saccharomyces cerevisiae* Sir2 protein is an $NAD^+$-dependent histone deacetylase that plays a critical role in transcriptional silencing, genome stability and longevity. A human homologue of Sir2, SIRT1, regulates the activity of the p53 tumor suppressor and inhibits apoptosis. The Sir2 deacetylation reaction generates two products: O-acetyl-ADP-ribose and nicotinamide, a precursor of nicotinic acid and a form of niacin/vitamin B3. We show here that nicotinamide completely abolishes yeast silencing and shortens replicative life span to that of a sir2 mutant. Nicotinamide, but not nicotinic acid, strongly inhibits silencing at the telomeres, rDNA and mating type loci of yeast. Nicotinamide also increases instability of the rDNA locus and shortens yeast life span to that of a sir2 mutant. Nicotinamide also abolishes silencing in G1-arrested cells, demonstrating that continual Sir2 activity is required to maintain silencing. In the presence of nicotinamide, Sir2 no longer associates with either telomeres or mating type loci, but remains associated with the rDNA. Sir2 no longer co-immunoprecipitates with chromatin at telomeres and mating-type loci in the presence of nicotinamide, though the Sir2 localization pattern is unaltered. We show that physiological concentrations of nicotinamide non-competitively inhibit both Sir2 and SIRT1 in vitro. The degree of inhibition of SIRT1 by nicotinamide ($IC_{50}$<50 µM) is equal to or better than the most effective known inhibitors of this class of proteins. We propose that nicotinamide and $NAD^+$ can bind simultaneously to Sir2 preventing catalysis and discuss the possibility that inhibition of Sir2 by nicotinamide is physiologically relevant.

We discuss the possibility that nuclear nicotinamide negatively regulates Sir2 activity in vivo. Our findings suggest that the clinical use of nicotinamide should be given careful consideration.

Experimental Procedures

Yeast assays—All yeast strains used in this study are listed in Table 3. Cells were grown at 30° C. on YPD medium (1% yeast extract, 2% bactopeptone, 2% glucose w/v) unless otherwise stated. The extent of silencing at the ribosomal DNA locus was determined by growing RDN1::MET15 strains on $Pb^{2+}$-containing medium (0.3% peptone, 0.5% yeast extract, 4% glucose, 0.02% (w/v) ammonium acetate, 0.07% $Pb(NO_3)_2$ and 2% agar). ADE2-based telomeric and HM locus silencing assays were performed as described previously (see, Example 1). Ribosomal DNA recombination frequencies were determined as previously described (44').

TABLE 3

Yeast strains used in this study.

| Strain | Genotype |
| --- | --- |
| W303AR5 | W303 MATa, ade2-1, leu2-3,112, can1-100, trp1-1, ura3-52, his3-11,15, RDN1::ADE2, RAD5 |
| YDS878 | W303 MATa,, ade2-1, leu2-3,112, can1-100, trp1-1,, ura3-52, his3-11,15, RDN1::ADE2, RAD5, sir2:TRP1 |
| YDS1572 | W303 MATa, ade2-1, leu2-3,112, can1-100, trp1-1, ura3-52, his3-11,15, RDN1::ADE2, RAD5, LEU2/SIR2 |
| YDS1595 | W303 MATa, ade2-1, leu2-3,112, can1-100, trp1-1, ura3-52, his3-11,15, RAD5 |

TABLE 3-continued

Yeast strains used in this study.

| Strain | Genotype |
| --- | --- |
| YDS1596 | W303 MATa, ADE2, leu2-3,112, can1-100, trp1-1, ura3-52, his3-11,15, RAD5 |
| YDS1097 | W303 MATa, ade2-1, leu2-3,112, can1-100, trp1-1, ura3-52, his3-11,15, RDN, RAD5, GFP-Sir4::URA3 |
| YDS1099 | W303 MATa, ade2-1, leu2-3,112, can1-100, trp1-1, ura3-52, his3-11,15, RDN, RAD5, GFP-Sir3::LEU2 |
| YDS1109 | W303 MATa, ade2-1, leu2-3,112, can1-100, trp1-1, ura3-52, his3-11,15, RDN, RAD5, GFP-Sir3::LEU2, sir2:TRP1 |
| YDS1078 | W303 MATa, ade2-1, leu2-3,112, can1-100, trp1-1, ura3-52, his3-11,15, RDN1::ADE2, RAD5, GFP-Sir2::LEU2, sir2:TRP1 |
| PSY316AT | MATα, ura3-53 leu2-3,112 his3-Δ200 ade2-1,01 can1-100 ADE2-TEL V-R |
| YDS1594 | PSY316 MATα, ura3-53 leu2-3,112 his3-Δ200 ade2-1,01 can1-100 ADE2-TEL V-R, sir2:TRP1 |
| YDS970 | PSY316 MATα, ura3-53 leu2-3,112 his3-Δ200 ade2-1,01 can1-100 ADE2-TEL V-R, HMR::GFP |
| YDS1005 | PSY316 MATa, ura3-53 leu2-3,112 his3-Δ200 ade2-1,01 can1-100 ADE2-TEL V-R, HMR::GFP |
| YDS1499 | PSY316 MATα, ura3-53 leu2-3,112 his3-Δ200 ade2-1,01 can1-100 ADE2-TEL V-R, HMR::GFP, sir4:HIS3 |
| YDS1690 | PSY316 MATα, ura3-53 leu2-3,112 his3-Δ200 ade2-1,01 can1-100 ADE2-TEL V-R, HMR::GFP, Δhml::LEU2 |
| JS209 | MATα, his3Δ200, leu2Δ1, met15Δ200, trp1Δ63, ura3-167 |
| JS241 | JS209 MATa, his3Δ200, leu2Δ1, met15Δ200, trp1Δ63, ura3-167, Ty1-MET15 |
| JS237 | JS209 MATα, his3Δ200, leu2Δ1, met15Δ200, trp1Δ63, ura3-167, RDN1::Ty1-MET15 |
| JS218 | JS237 MATα, his3Δ200, leu2Δ1, met15Δ200, trp1Δ63, ura3-167, RDN1::Ty1-MET15, sir2::HIS3 |
| YDS1583 | JS237 MATα, his3Δ200, leu2Δ1, met15Δ200, trp1Δ63, ura3-167, RDN1::Ty1-MET15, LEU2/SIR2 |

Replicative life span determination was performed by micromanipulation as described (25'). A minimum of 40 cells were examined per experiment and each experiment was performed at least twice independently. Statistical significance of life span differences was determined using the Wilcoxon rank sum test. Differences are stated to be significant when the confidence is higher than 95%.

GFP fluorescence was quantified by fluorescence-activated cell sorting (FACS) using a FACSCalibur flow cytometer (Becton Dickinson, Calif.) as described (45'). For G1-arrest experiments, cells were treated with 10 μg/ml alpha factor for 3 hours. DNA content was determined by FACS analysis of fixed cells stained with propidium iodide (Sigma) as described (45'). Typically 20,000 cells were analyzed per sample. Data acquisition and analysis were performed using CELLQuest software (Becton Dickenson).

Fluorescence Microscopy and Chomatin immunoprecipitation—GFP fluorescence was visualized in live cells grown to log phase in synthetic complete (SC) medium (1.67% yeast nitrogen base, 2% glucose, 40 mg/liter each of histidine, uridine, tryptophan, adenine and leucine). Images were captured using a Nikon Eclipse E600 microscope at a magnification of 1000× and analyzed with Scion Image software. Chromatin immunoprecipitation (ChIP) was performed as described (45') using the primer pairs listed in Table 2 (46'). PCR reactions were carried out in a 50 μl volume using a 1/5000 or a 1/12500 dilution of input DNA from precleared whole-cell extracts and a 1/50 dilution of immunoprecipitated DNA. PCR parameters were as follows. For CUP1 and 5S rDNA primer pairs, 26 cycles of PCR were performed with an annealing temperature of 55° C. For Tel 0.6, Tel 1.4 and HM primer pairs 32 cycles at an annealing temperature of 50° C. were used. PCR products were separated by gel electrophoresis on a 2.3% agarose gel and visualized by ethidium bromide staining.

| Oligonucleotide | Sequence | SEQ ID NO |
| --- | --- | --- |
| TEL-0.6.Fwd | CAGGCAGTCCTTTCTATTTC | 31 |
| TEL-0.6.Rev | GCTTGTTAACTCTCCGACAG | 32 |
| TEL-1.4.Fwd | AATGTCTTATCAAGACCGAC | 33 |
| TEL-1.4.Rev | TACAGTCCAGAAATCGCTCC | 34 |
| RDN-5S.Fwd | GAAAGGATTTGCCCGGACAGTTTG | 35 |
| RDN-5S.Rev | CTTCTTCCCAGTAGCCTGTTCCTT | 36 |
| HMR-YA/ZL.Fwd | GTGGCATTACTCCACTTCAAGTAAG | 37 |
| HMR-YA/ZL.Rev | CAAGAGCAAGACGATGGGG | 38 |
| CUP1-Fwd | TTTTCCGCTGAACCGTTCCA | 39 |
| CUP1-Rev | CATTGGCACTCATGACCTTC | 40 |

In vitro deacetylation assays—Recombinant GST tagged yeast Sir2p (gift of D. Moazed) and recombinant human SIRT1 (47') were assayed for deacetylase activity using the HDAC Fluorescent Activity Assay/Drug Discovery Kit (AK-500, BIOMOL Research Laboratories). This assay system allows detection of a fluorescent signal upon deacetylation of a histone substrate when treated with developer. Fluorescence was measured on a fluorometric reader (Cytofluor II 400 series PerSeptive Biosystems) with excitation set at 360 nm and emission detection set at 460 nm. Reactions consisted of either 5 μg of GST-Sir2 or 2.5 μg of SIRT1, incubated with 250 μM acetylated histone substrate, 1 mM DTT and a range of NAD$^+$ concentrations as described, in 50 μl of assay buffer. Reactions with the yeast and human proteins were carried out at 30° C. and 37° C. respectively for 30 minutes.

For inhibitor assays, reactions were performed in the presence of 200 μM NAD$^+$ and either nicotinamide (0, 50, 150 or 300 μM) (Sigma), or 50 μM of the following inhibitors; nicotinic acid (Sigma), sirtinol, M15 (Chembridge), splitomicin (47), TSA (BIOMOL).

Results

Nicotinamide abolishes silencing at the rDNA, telomeres and mating type loci. Nicotinamide is a product of Sir2 deacetylation and is a key substrate in the NAD$^+$ salvage 20 pathway. Based on our previous observation that manipulation of NAD$^+$ biosynthesis can influence Sir2 dependent activities (see, Example 1), we wished to examine what effect NAD$^+$ precursors would have on silencing. Strains with either an ADE2 or MET15 marker integrated at the rDNA locus (RDN1) were examined. Silencing of ADE2 results in the accumulation of a red pigment on plates with limiting adenine, whereas silencing of MET15 leads to production of a brown pigment on Pb$^{2+}$-containing medium. We used two marker genes to ensure that the effects we observed were not simply due to changes in adenine or methionine biosynthesis. Strains with a single extra copy of SIR2 (2×SIR2) or lacking SIR2 (sir2::TRP1), were included as controls for increased silencing and lack of silencing, respectively. As shown in FIG. 8A, when grown in the presence of 5 mM nicotinamide, silencing is completely abolished. Silencing of an ADE2 marker at this locus was similarly abolished by addition of nicotinamide.

To test whether the effect of nicotinamide is specific to the rDNA or whether it influences other heterochromatic regions, we examined silencing at telomeres. To monitor telomeric silencing, we used a strain in which the ADE2 gene is integrated at the subtelomeric (Y') region of the right arm of chromosome V (22'). On plates with limiting adenine, colonies have red/white sectors due to variegated expression of the ADE2 marker. In the presence of 5 mM nicotinamide colonies were white, demonstrating a complete loss of repression (FIG. 8B). We also monitored silencing of mating type genes and found that nicotinamide completely abrogated silencing at this locus as well.

Figure 9:
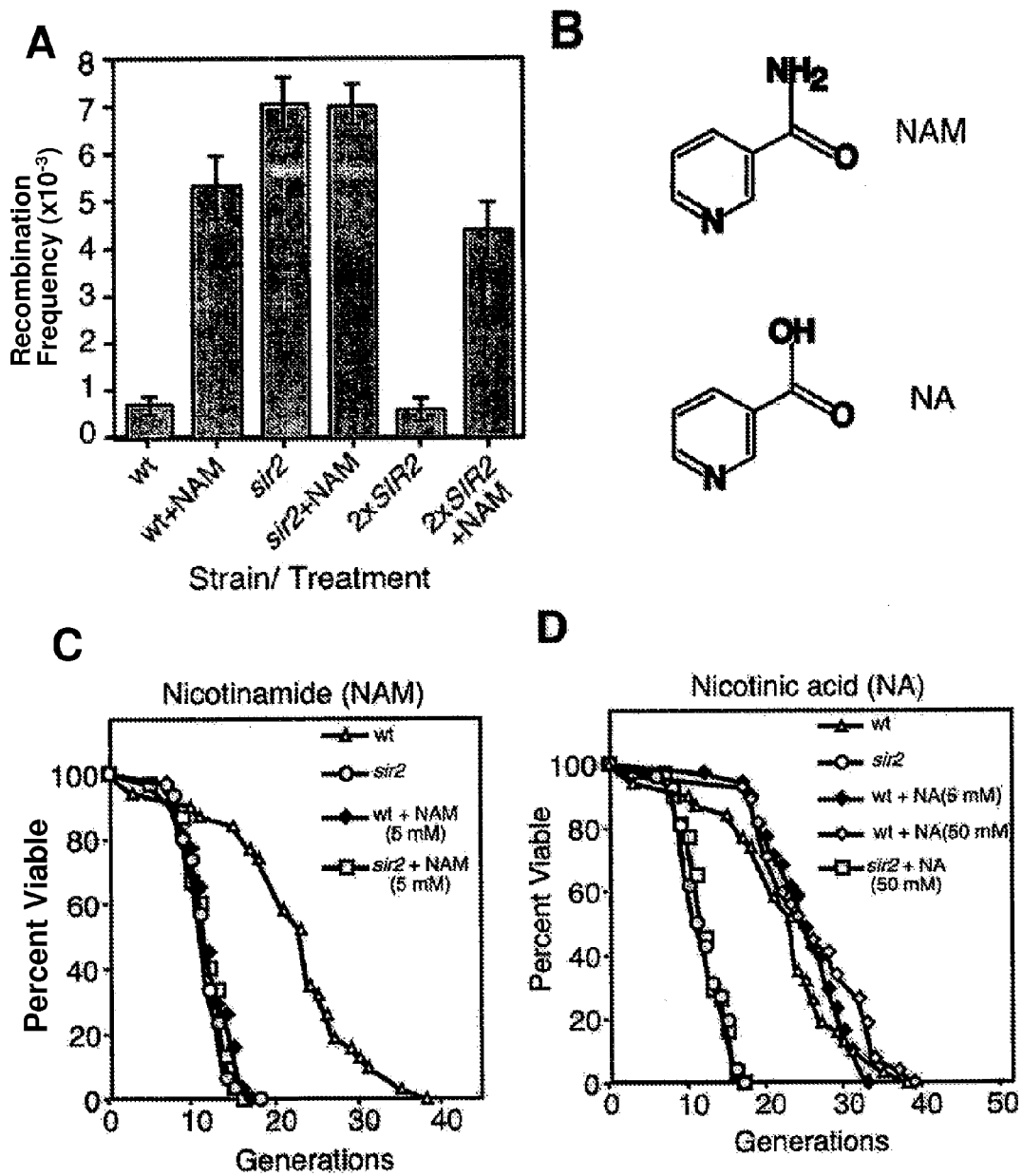
FIG. 9. Nicotinamide increases rDNA recombination and shortens yeast life span. A, Strains were assayed for rDNA stability by examining the rate of loss of an ADE2 marker integrated at the rDNA locus. Cells were plated on 2% glucose YPD medium with or without 5 mM nicotinamide (NAM) and the frequency of half-sectored colonies, reflecting a marker loss event at the first cell division, was measured. More than 10,000 colonies were examined for each strain and each experiment was performed in triplicate. Average recombination frequencies (+/−s.d.) per cell division are shown. Relevant strains: W303-1A RDN1::ADE2 (W303AR5) and W303AR5 derivatives 2×SIR2 (YDS1572) and sir2::TRP1 (YDS878). B, Comparison of structures for nicotinamide (NAM) and nicotinic acid (NA). C and D, Life spans were determined by scoring the number of daughter cells produced by each mother cell before cessation of cell division (68',69'). Cells were pre-grown for a minimum of 48 h on complete glucose medium. C, Mortality curves for wild type (PSY316AT) and sir2::TRP1 (YDS1594) strains in 0 or 5 mM nicotinamide (NAM). Average life spans were wt: 22.4, 12.1 and sir2: 12.1, 11.7 respectively. D, Mortality curves for wild type and sir2 strains from C, in the presence of either 0, 5 mM or 50 mM nicotinic acid (NA). Average life spans were wt: 22.4, 26, 25 and sir2: 12.1, 12.2.

Nicotinic acid, an intermediate in the NAD$^+$ salvage pathway, is structurally similar to nicotinamide (see FIG. 9B). Nicotinic acid is taken up efficiently by yeast cells and a specific transporter for this compound, Tna1, was recently identified (48',49'). In each of the above assays, we examined the effect of 5 mM nicotinic acid on Sir2-dependent silencing and in each case found that nicotinic acid had no effect.

Nicotinamide increases genomic instability and shortens yeast life span. We wished to determine whether the above loss of silencing was due to inhibition of Sir2 activity, in which case nicotinamide-treated cells should mimic a sir2Δ strain. Yeast lacking a functional Sir2 show increased frequencies of rDNA recombination. The loss of an ADE2 marker at the rDNA locus was monitored in wild type, 2×SIR2 and sir2 strains, in the presence and absence of nicotinamide. As shown in FIG. 9A, treatment of wild type and 2×SIR2 cells with nicotinamide increased the frequency of marker loss ~7-fold, similar to that of a sir2 mutant. Importantly, treatment of the sir2 strain did not further increase recombination, arguing that the observed marker loss was due to inhibition of Sir2.

Instability of the rDNA locus has been shown to be a major cause of yeast replicative aging (25',26'). We therefore examined the effect of nicotinamide on yeast life span. Cells were grown for two days on fresh yeast YPD medium to ensure that they had fully recovered from conditions of calorie restriction prior to the assay. Daughter cells that emerged from previously unbudded mother cells were then micro-manipulated away and scored. FIG. 9C shows representative life span curves of both wild type (triangles) and the short-lived sir2 mutant (circles). Cells grown on medium containing 5 mM nicotinamide (closed diamonds) had an average life span ~45% that of wild type, which was equivalent to that of the sir2 mutant. Treatment of the sir2 strain with nicotinamide did not further shorten life span (squares). In contrast to these results, we observed no detrimental effect on replicative life span in the presence of either 5 or 50 mM nicotinic acid (FIG. 9D, closed and open diamonds, respectively).

Figure 10A:
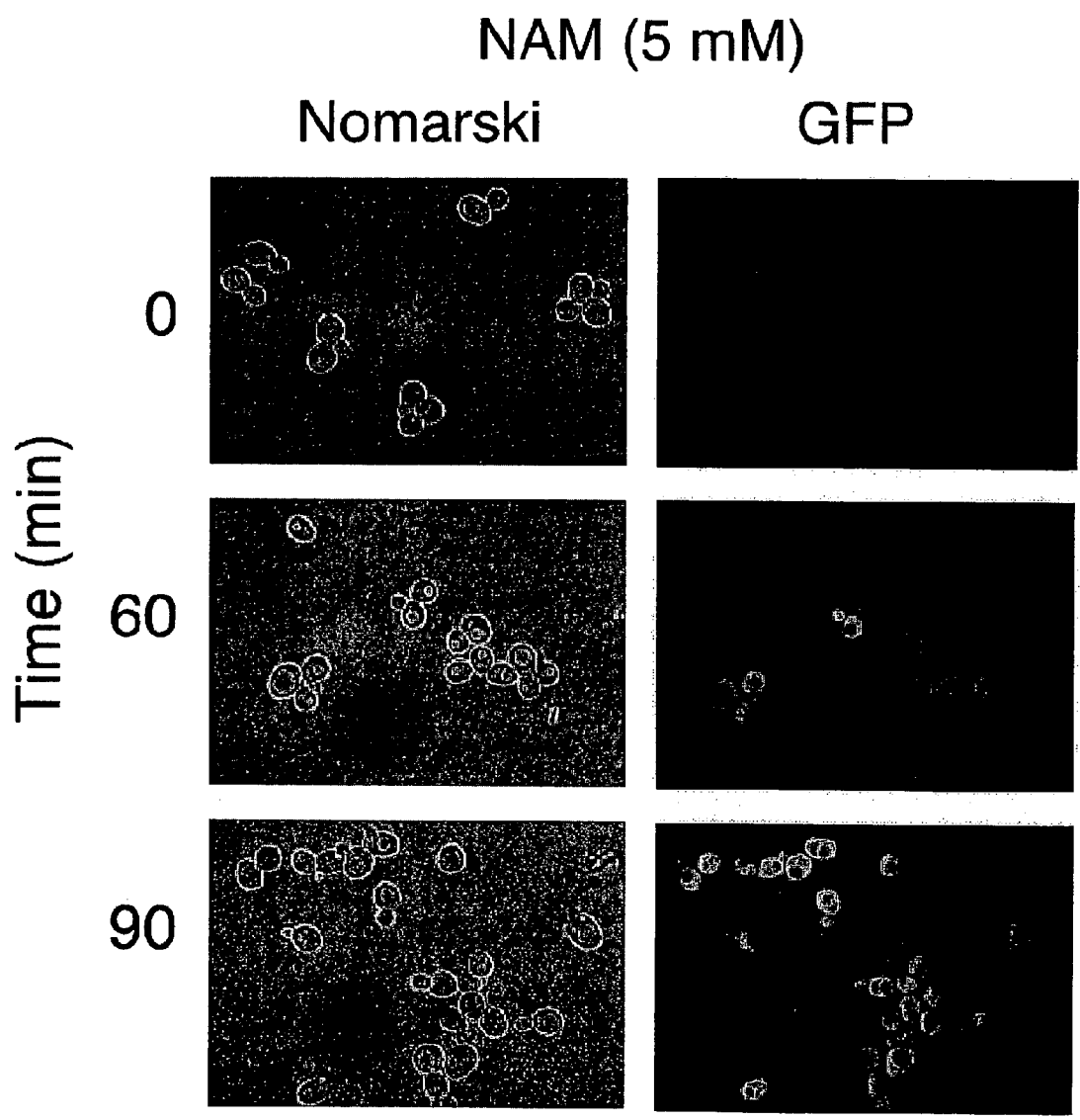
FIG. 10. Nicotinamide derepresses the silent mating type locus (HMR) in the both cycling and G1 arrested cells. A, PSY316 cells containing an ADH driven GFP transcript inserted at the HMR locus (YDS970) were grown in YPD medium at 30° C. to mid-log phase and treated with 5 mM nicotinamide (NAM) for the indicated times. Cells were photographed live. B, Strain YDS970 or the isogenic sir4Δ mutant (YDS1499) were treated with either 5 mM nicotinamide (NAM), 5 mM nicotinic acid (NA) or 5 mM quinolinic acid (QA). Cells were analyzed by fluorescent activated cell sorting (FACS) to determine the extent of ADH-GFP expression. C, A MATa derivative of strain YDS970 (YDS1005) was deleted for HML and treated with 10 μg/ml alpha-factor for 3 hours. Cells were then grown in the presence of 5 mM nicotinamide for the indicated times and examined by FACS as above. Cell cycle progression was monitored at each time point by FACS analysis of propidium iodide stained cells.

Nicotinamide inhibits silencing in non-dividing cells. The reestablishment of silent chromatin domains requires passage through S phase (50'), although the trigger does not appear to be DNA replication (51',52'). Experiments with a temperature-sensitive SIR3 allele suggest that the presence of the Sir2/3/4 complex is required to maintain a silenced state throughout the cell cycle (50'). We have shown that nicotinamide derepresses silent domains in cycling cells and attenuates replicative life span. We wondered whether nicotinamide treatment could have a similar effect on silencing in non-cycling, G1-arrested cells. We used a strain containing a GFP reporter integrated at the HMR locus allowing us to quantify the effects of nicotinamide on HM silencing in single cells. We first validated the system in cycling cells. As shown in FIG. 10A, GFP was not expressed in untreated cells due to the high degree of silencing at this locus. However, after 60 minutes in 5 mM nicotinamide we observed a dramatic increase in the level of expression, which became even more pronounced after 90 minutes (FIG. 10A, second and third panels respectively).

To gain a more quantitative measure of silencing, cells were analyzed by fluorescence activated cell sorting (FACS). The top two panels of FIG. 10B show the GFP expression profiles of asynchronous cultures of sir4 and wild type strains. Deletion of SIR4 disrupts the telomeric and mating type loci SIR complexes, leading to a redistribution of Sir2 away from these sites and to the rDNA locus. Thus, the profile of the sir4 strain represents complete derepression of the HMR locus. FIG. 10B shows that growth of wild type cells in 5 mM nicotinamide leads to complete derepression of this locus (third panel), as compared to the sir4 mutant. Cells treated with 5 mM nicotinic acid or the structurally related quinolinic acid (a substrate in the de novo NAD$^+$ synthesis pathway) showed no increase in GFP expression (FIG. 10B, bottom two panels) demonstrating that the desilencing effect is specific to nicotinamide.

Using this assay system we could monitor the effects of nicotinamide on heterochromatin in non-cycling cells. A MATa strain containing the GFP transgene was deleted for the HMLα locus to ensure that the cells did not escape G1-arrest due to the co-expression of a and α genes. After arrest in G1 by treatment with a factor, cells were exposed to 5 mM nicotinamide and examined by FACS every 30 min. FIG. 10C shows the expression profiles of arrested cells, in the presence and absence of nicotinamide. Surprisingly, cells arrested in G1 showed a loss of silencing when treated with nicotinamide. Measurement of DNA content by FACS confirmed that the cells remained in G1 for the duration of the experiment (FIG. 10C, right column). These results demonstrate that exogenous nicotinamide derepresses silent chromatin even in non-dividing cells and suggests that heterochromatin is an unstable and dynamic structure. This also indicates that continued deacetylation of histones is essential for the maintenance of silencing.

Nicotinamide causes Sir2 to dissociate from telomeres and mating type loci but not from rDNA. We have shown that nicotinamide derepresses heterochromatin at all three silent loci in yeast. Although the most likely explanation for our observations was that Sir2 is catalytically inactivated by nicotinamide, is was also possible that Sir2 was delocalized or that its expression was down-regulated. To address the latter possibility we determined Sir2 protein levels in the presence of nicotinamide (1-5 mM) and found that they were unaltered. Next, we examined the effect of nicotinamide on the localization of a GFP-tagged Sir2. Identical log-phase cultures were grown in the presence or absence of 5 mM nicotinamide for two hours, during which the localization of GFP-Sir2 was monitored by fluorescence microscopy. Under normal conditions, Sir2 can be visualized at distinct foci near the nuclear periphery, each focal point representing a cluster of several telomeres (53'). In a sir2 mutant background, Sir3 is released from telomeres and shows a diffuse nuclear pattern (FIG. 11A). This strain served as a reference for Sir delocalization. During growth in nicotinamide we observed no change in the Sir2-GFP pattern, even after two hours, a time at which treated cells show maximal derepression of silent loci (FIGS. 11C and D). We also examined the two other members of the Sir silencing complex, Sir3 and Sir4. FIGS. 5E and G show the localization pattern of Sir3-GFP and GFP-Sir4 in untreated cells, respectively. Treatment with 5 mM nicotinamide for two hours did not alter the pattern of GFP fluorescence for either of these proteins (FIGS. 11F and H). These results show for the first time that inhibition of Sir2 does not result in a gross relocalization of the SIR complex.

Figure 12:
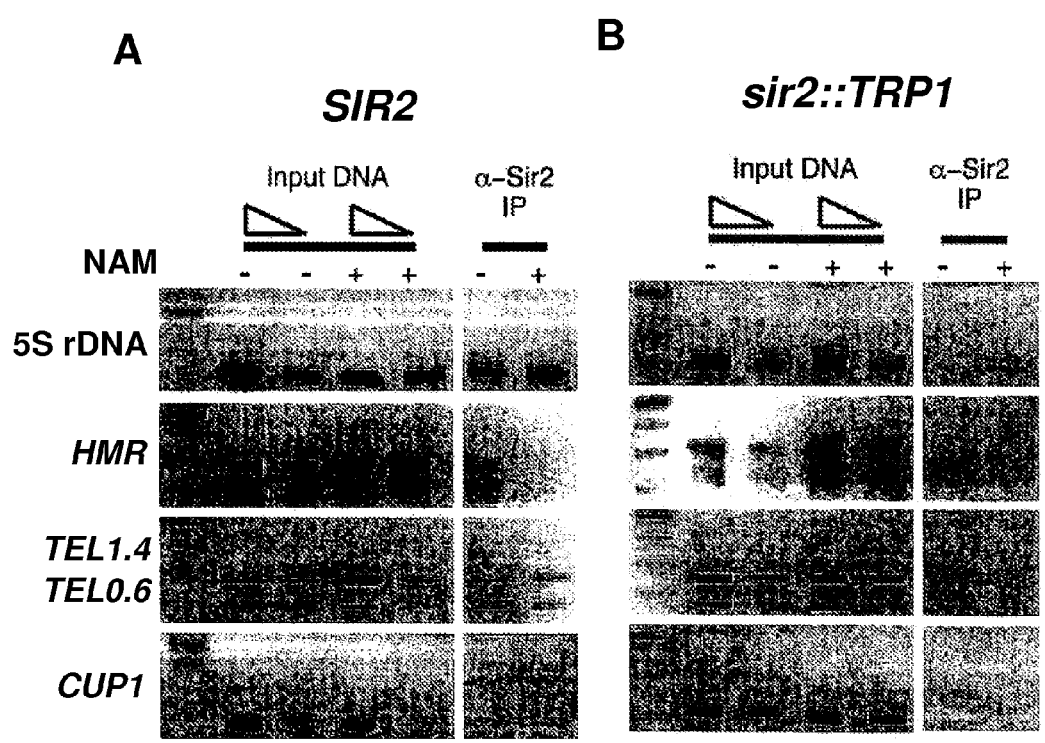
FIG. 12. Sir2 does not associate with DNA from telomeres or mating type loci in the presence of nicotinamide. A and B, Chromatin immunoprecipitation using a polyclonal α-Sir2 antibody was performed on extracts from either a sir2 (YDS878) (A) or wild type (W303AR5) (B) strains in the presence of 5 mM nicotinamide (NAM). PCR amplification of both input DNA from whole cell extracts and immunoprecipitated chromatin are shown. PCR was performed using primer pairs specific for the CUP1 gene (top panels), 5S rDNA (second panels), the HMR locus (third panels), or subtelomeric DNA 1.4 and 0.6 kb from telomeres (bottom panels). Primer sequences are listed in Table 4.

To more closely examine the association between Sir2 and silent loci in the presence of nicotinamide, we performed chromatin immunoprecipitation (ChIP) on both treated and untreated cells. A sir2 mutant strain and the non-silenced CUP1 gene served as controls. FIG. 12 shows PCR products from input and immunoprecipitated DNA using a 5S rDNA-specific primer pair. Treatment of cells with 5 mM nicotinamide did not alter the amount of PCR product obtained using these primers (compare lanes 5 and 6), demonstrating that Sir2 remains associated with rDNA in the presence of this compound.

Next, we examined the association of Sir2 with the silent HMRα locus and DNA 0.6 and 1.4 kb from the right telomere of chromosome VI. In the presence of nicotinamide, no PCR product was obtained using primers specific for HMR. Similarly, the amount of product from obtained from nicotinamide-treated cells using primers specific for sub-telomeric DNA was equivalent to background. These results demonstrate that Sir2 is not associated with HMR or sub-telomeric DNA in cells treated with nicotinamide. This presumably reflects a fundamental difference in the roles of Sir2 in the RENT complex at the rDNA and in the heterotrimeric SIR complex at telomeres and mating type loci.

Figure 13:
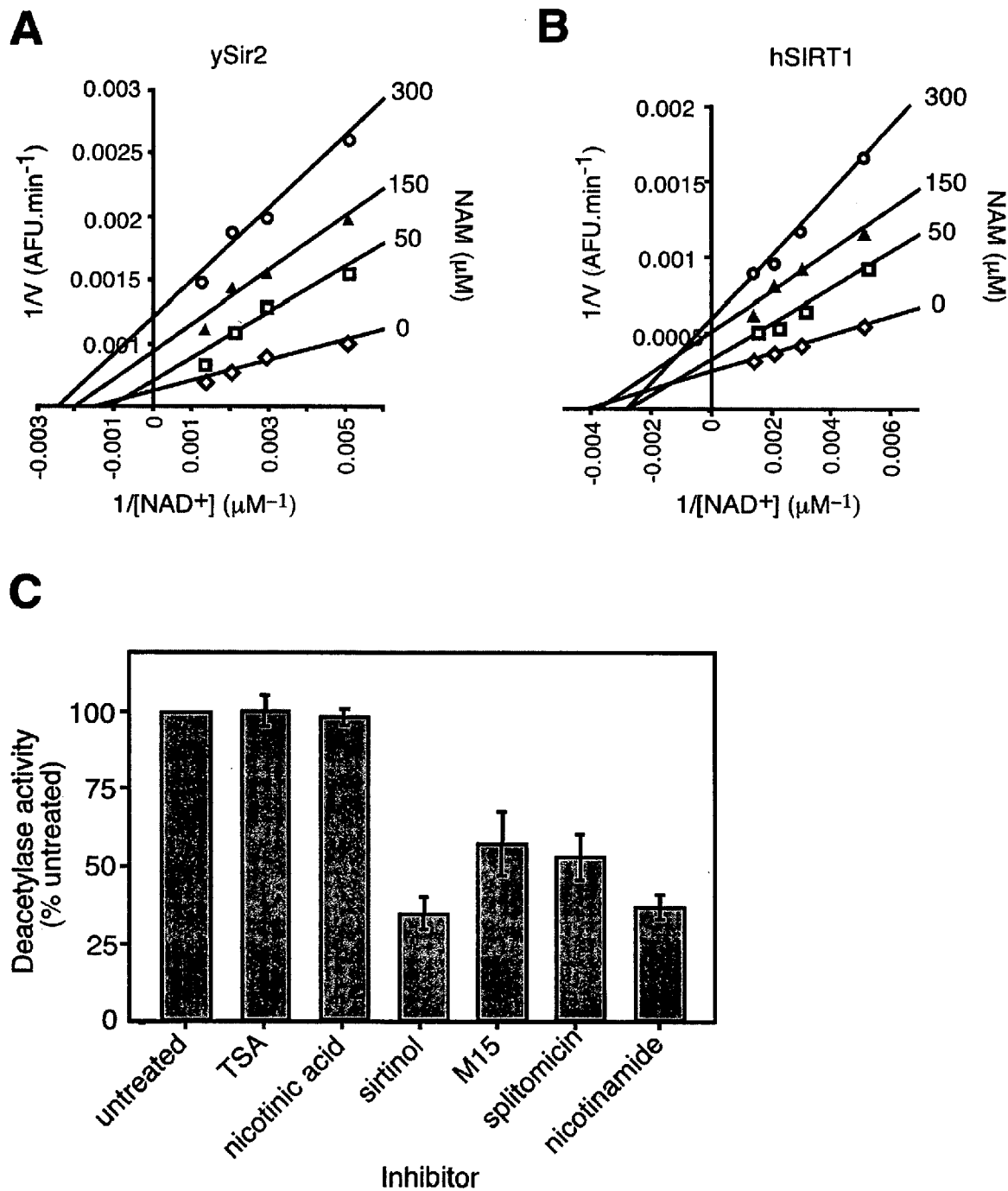
FIG. 13. Nicotinamide is a potent non-competitive inhibitor of yeast Sir2 and human SIRT1 in vitro. A, Recombinant GST-tagged Sir2 was incubated with acetylated substrate for 30 minutes at 30° C. in the presence of 1 mM DTT, 200, 350, 500 or 750 μM NAD+ and the indicated concentrations of nicotinamide. Reactions were terminated by the addition of developer and samples were analyzed by fluorometry (excitation set at 360 nm and emission at 460 nm). Experiments were performed in triplicate. Data is shown as a Lineweaver-Burk double reciprocal plot of arbitrary fluorescence units (AFUs) min$^{-1}$ versus NAD+ (μM). B, Experiments were performed as in A, except that recombinant human SIRT1 was used and reactions were carried out at 37° C. C, Deacetylation reactions were performed in triplicate with 2.5 μg of SIRT1, 1 mM DTT, 200 μM NAD+ and either 50 μM water blank, DMSO blank, nicotinic acid, sirtinol, M15, splitomicin or nicotinamide. Reactions were carried out at 37° C. for 30 minutes and fluorescence was measured as in A.

Nicotinamide is a potent non-competitive inhibitor of both yeast Sir2 and human SIRT1 in vitro. Since Sir2 was neither delocalized nor down-regulated in response to nicotinamide, the most plausible explanation for our results was that this compound acted as a direct inhibitor of Sir2 deacetylase activity. To further explore this, and to gain more insight into the mechanism of desilencing induced by nicotinamide, we directly measured Sir2 activity in vitro in the presence of varying amounts of this compound. We utilized a novel class III HDAC activity assay that generates a fluorescent signal upon deacetylation of a histone substrate. When incubated with acetylated substrate and $NAD^+$, recombinant GST-tagged Sir2 gives a strong fluorescent signal 10-fold greater than no enzyme and no $NAD^+$ controls. Using this assay, we tested the ability of nicotinamide to inhibit deacetylation in the presence of varying concentrations of $NAD^+$. A double reciprocal Lineweaver-Burk plot of the data (FIG. 13A) shows that nicotinamide is a strong non-competitive inhibitor of this reaction. A similar result has recently been obtained for Hst2, a cytoplasmic Sir2 homologue (54'). We wished to determine whether the inhibitory effects of nicotinamide could be extended to the Sir2 homologues of higher eukaryotes. Thus, we examined whether nicotinamide could also inhibit human SIRT1 in vitro. Using recombinant SIRT1, we monitored deacetylation of the substrate in the presence of varying amounts of nicotinamide and $NAD^+$. Similar to Sir2, a Lineweaver-Burk plot of the data shows that nicotinamide also inhibits SIRT1 in a non-competitive manner (FIG. 13B). These results imply that nicotinamide does not inhibit deacetylation by competing with $NAD^+$ for binding to Sir2/SIRT1 and that nicotinamide and $NAD^+$ can bind the enzyme simultaneously.

Recently several groups have isolated compounds that inhibit Sir2-like proteins both in vitro and in vivo (55',56'). Among these are sirtinol, M15 and splitomycin. These compounds were isolated in high-throughput phenotypic screens of small molecule libraries as inhibitors of silencing, though none has yet been examined for its ability to inhibit SIRT1 activity. To compare the efficacy of inhibition of these compounds to that of nicotinamide we measured recombinant SIRT1 activity in the presence of 50 µM of each of these inhibitors. We also included the class I/II HDAC inhibitor TSA as a negative control. As shown in FIG. 13C, nicotinamide inhibited SIRT1 with an $IC_{50} < 50$ µM, a value that was equal to, or lower than, that of all the other inhibitors we tested. Adding further support to our in vivo results, we showed that the structurally related compound, nicotinic acid, had no effect on the activity of SIRT1 in vitro (FIG. 13C).

Discussion

We have shown that nicotinamide, a product of the Sir2 deacetylation reaction, is a potent inhibitor of Sir2 activity both in vivo and in vitro. Addition of exogenous nicotinamide to yeast cells derepresses all three silent loci, increases instability at the ribosomal DNA locus and shortens yeast life span to that of a sir2 mutant. rDNA instability and short life span phenotypes of nicotinamide-treated cells are not augmented by a sir2 mutation indicating that these phenotypes are the consequence of Sir2 inhibtion. Importantly, these results also indicate that rDNA instability and life span are not influenced by the other yeast Sir2 family members, the Hst proteins.

We have recently shown that strains carrying extra copies of $NAD^+$ salvage pathway genes show increased silencing and are long lived, yet they do not have increased steady-state $NAD^+$ or NADH levels (see, Example 1). We hypothesized that the increased longevity is mediated by local increases in $NAD^+$ availability or increased flux through the salvage pathway. The latter model implies that that there may be continual recycling of $NAD^+$ to nicotinamide, via Sir2 family members and/or NMN adenylyl transferases. We show that nicotinamide abrogates silencing in G1 arrested cells, arguing that Sir2 activity is required constitutively for the maintenance of heterochromatin and that Sir2 consumes $NAD^+$ even in non-cycling cells. This is consistent with the recent finding of Bedelov et al. that the MATα gene at the silenced HML locus is expressed in G1 cells treated with splitomycin (56').

Figure 11:
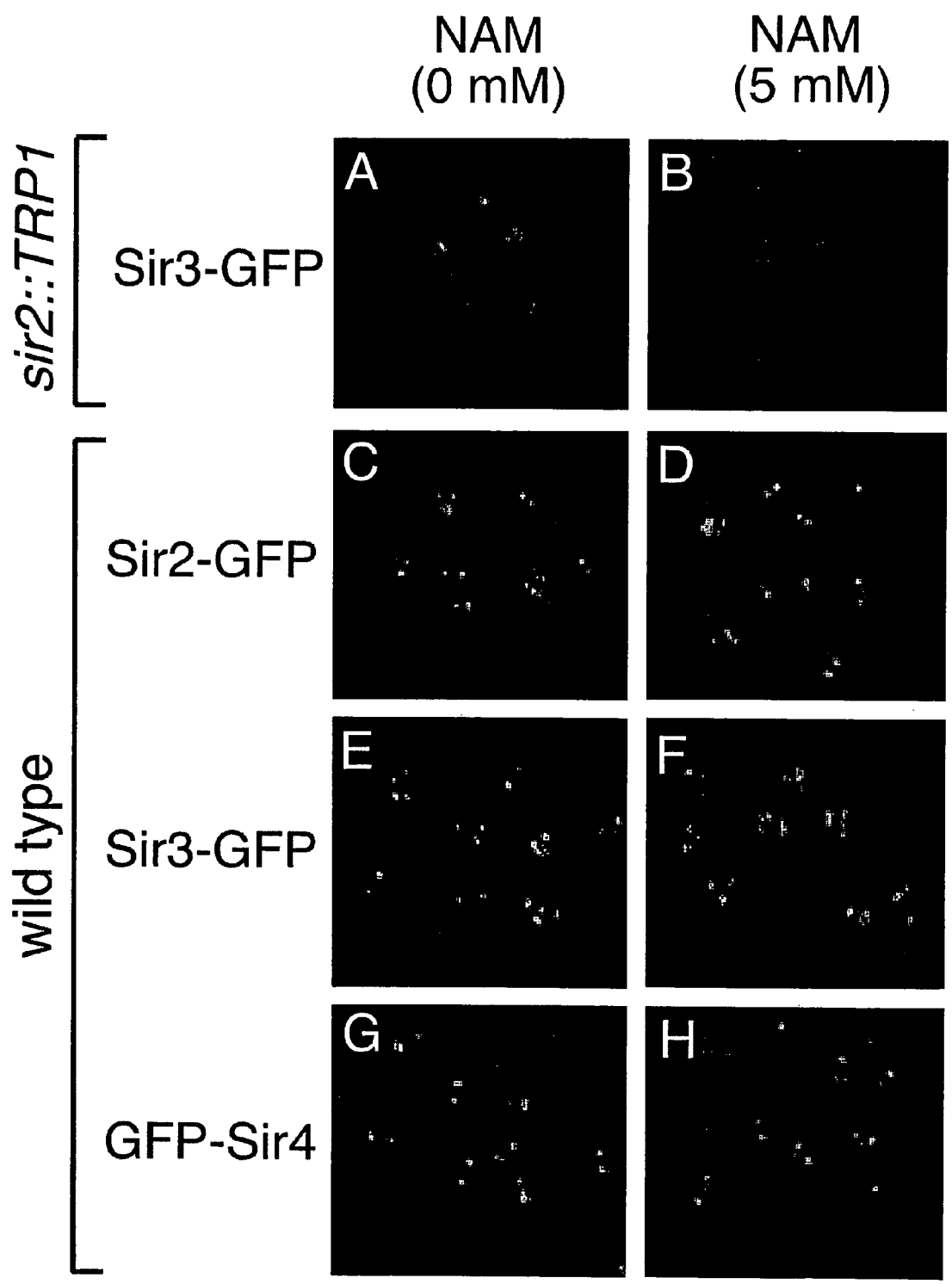
FIG. 11. Nicotinamide does not alter the localization of Sir proteins. Wild type strains containing either SIR2-GFP (YDS1078) (C and D), SIR3-GFP (YDS1099) (E and F), or GFP-SIR4 (YDS1097) (G and H) and an isogenic sir2 derivative expressing SIR3-GFP (YDS1109) (A and B), were grown for 2 hours in the presence of 5 mM nicotinamide. GFP fluorescence was detected in live cells.

Addition of nicotinamide to cells does not alter the localization pattern of any of the Sir-GFP fusion proteins we examined (FIG. 11). This suggests that there are interactions that maintain the localization of Sir2 independently of its activity. Closer examination using ChIP shows that while Sir2 is still bound to the rDNA, it no longer associates with either telomeres or mating type loci in the presence of this compound (FIG. 12). It has previously been shown that Net1, the DNA binding subunit of the RENT complex, can associate with chromatin independently of Sir2 (57'). These findings indicate that this complex can assemble on ribosomal DNA in the absence of Sir2 deacetylase activity. In contrast, we show that the heterotrimeric Sir2/3/4 complex can not assemble on chromatin in the absence of Sir2 catalytic activity. These results are consistent with recent data from two other groups using catalytically inactive Sir2 mutants (46',58'). Both groups find that mutation of the conserved histidine in the catalytic domain (His-364) prevents Sir2 from interacting with telomeres and mating type loci in vivo. However, there remains the possibility that these mutations also affect the ability of Sir2 to interact with other proteins. Our results show conclusively that the deacetylase activity of Sir2 is required for its proper association with telomeres and mating type loci.

We have shown that nicotinamide strongly inhibits the deacetylase activity of both yeast Sir2 and the human homologue, SIRT1 in vitro. The fact that nicotinamide acts non-competitively to inhibit Sir2 suggests that this compound does not compete with NAD+ for binding. Examination of the reaction mechanism for Sir2 deacetylation and the crystal structure of an archeal Sir2 homologue provides clues as to a possible mechanism of inhibition. Sir2-catalyzed deacetylation consists of two hydrolysis steps which are thought to be coupled. Cleavage of the glycosidic bond connecting nicotinamide to the ADP-ribose moiety of $NAD^+$ is followed by cleavage of the C—N bond between an acetyl group and lysine. A recent structural analysis indicates that Sir2 enzymes contain two spatially distinct $NAD^+$ binding sites (the B site and the C site), both of which are involved in catalysis (59'). The authors propose that in the presence of an acetyl lysine, $NAD^+$ bound to the B site can undergo a conformational change bringing the nicotinamide group in proximity to the C site where it is cleaved. The ADP-ribose product of this reaction then returns to the B site where deacetylation of the acetyl lysine occurs. We propose that at elevated concentrations, nicotinamide binds to and blocks the internal C site, which prevents the conformational change and subsequent cleavage of $NAD^+$. This would explain the non-competitive nature of the mode of inhibition of this compound.

We have shown that the potency of nicotinamide rivals that of the most effective library-isolated compounds used in our assay. The fact that SIRT1 is inhibited by such low concentrations of nicotinamide in vitro, raises the possibility that this mode of inhibition may be physiologically relevant. Levels of nicotinamide in mammalian tissues have been reported to lie in the range of 11-400 µM (39',60'-62'). Recently, levels of nicotinamide in cerebrospinal fluid were determined with high accuracy to be 54.2 µM (63'), a value which is similar to the $IC_{50}$ for nicotinamide reported here. We propose that fluctuations in 4 cellular nicotinamide levels may directly control the activity of Sir2 proteins in vivo. These fluctuations may, in turn, be regulated by enzymes involved in nicotinamide metabolism.

Figure 7:
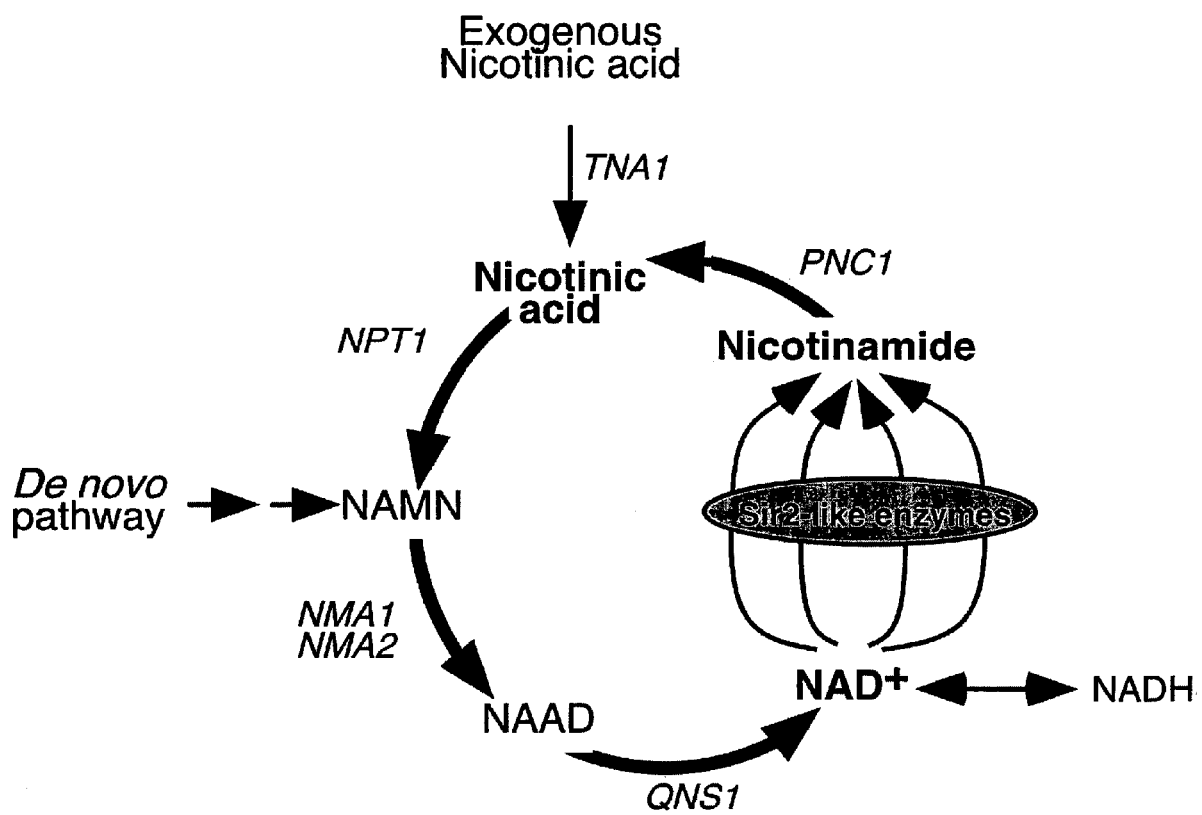
FIG. 7. The NAD+ salvage pathway. Nicotinamide generated by Sir2 is converted into nicotinic acid by Pnc1 and subsequently back to NAD+ in three steps. Abbreviations: NAD+, nicotinamide adenine dinucleotide; NaMN, nicotinic acid mononucleotide; NaAD, desamido-NAD+.

The yeast PNC1 gene encodes a nicotinamidase that is situated in a key position to regulate $NAD^+$-dependent deacetylases. By converting nicotinamide into nicotinic acid, Pnc1 may reduce levels of this inhibitor and stimulate the rate at which $NAD^+$ is regenerated (see FIG. 7). Interestingly, PNC1 is one of the most highly induced genes in response to stress and conditions that resemble calorie restriction (64', 65'). Furthermore, PNC1 encodes the only salvage pathway enzyme whose transcript undergoes cell-cycle dependent fluctuations (66'). Levels of PNC1 are highest in M/G1 and drop off sharply in S-phase. Interestingly, this coincides with the establishment of Sir-dependent silencing (51',52',67'). These facts raise the possibility that high levels of Pnc1 induce silencing after S-phase or under conditions of stress and calorie restriction by removing the inhibitory effects of nicotinamide. Our previous finding, that a single extra copy of PNC1 increases Sir2-dependent silencing (see, Example 1), adds further support to this model. It will be interesting to determine if intracellular nicotinamide levels change during the cell cycle, stress or calorie restriction.

Nicotinamide and nicotinic acid are used at high doses (up to 10 g/day) to self-treat a wide variety of conditions (41'). Both are considered forms of vitamin B3 and are often used interchangeably, however nicotinamide has become preferred in many cases due to an apparent lack of side effects. In addition, nicotinamide is currently in trials as a therapy to prevent cancer recurrence and insulin-dependent (type I) diabetes. Our results, which clearly demonstrate that nicotinamide can disrupt heterochromatin, even in non-cycling cells, raise the concern that there may be deleterious consequences of long-term nicotinamide therapy in humans.

REFERENCES

1'. Courey, A. J., S. (2001) *Genes Dev* 15(21), 2786-96
2'. Moazed, D. (2001) *Mol Cell* 8(3), 489-98.
3'. Gasser, S. C. M. (2001) *Gene* 279(1), 1-16
4'. Eberharter, A. B., PB. (2002) *Embo Reports* 3(3), 224-9
5'. Kuo, M. A., CD. (1998) *Bioessays* 20(8), 615-26
6'. Bernstein, B. E., Tong, J. K., and Schreiber, S. L. (2000) *Proc Natl Acad Sci USA* 97(25), 13708-13.
7'. Fischle, W. K., V. Dequiedt, F. Verdin, E. (2001) *Biochem Cell Biol* 79(3), 337-48
8'. Marks, P. R., R A. Richon, V M. Breslow, R. Miller, T. Kelly, W K. (2001) *Nature Rev Cancer* 1(3), 194-202
9'. Yoshida, M. F., R. Nishiyama, M. Komatsu, Y. Nishino, N. Horinouchi, S. (2001) *Cancer Chemother Pharmacol* 48(suppl), S20-6
10'. Smith, J. S., Brachmann, C. B., Celic, I., Kenna, M. A., Muhammad, S., Starai, V. J., Avalos, J. L., Escalante-Semerena, J. C., Grubmeyer, C., Wolberger, C., and Boeke, J. D. (2000) *Proc Natl Acad Sci USA* 97(12), 6658-63.
11'. Tanner, K. G., Landry, J., Sternglanz, R., and Denu, J. M. (2000) *Proc Natl Acad Sci USA* 97(26),14178-82.
12'. Landry, J., Sutton, A., Tafrov, S. T., Heller, R. C., Stebbins, J., Pillus, L., and Sternglanz, R. (2000) *Proc Natl Acad Sci USA* 97(11), 5807-11.
13'. Imai, S., Armstrong, C. M., Kaeberlein, M., and Guarente, L. (2000) *Nature* 403(6771), 795-800
14'. Brachmann, C. B., Sherman, J. M., Devine, S. E., Cameron, E. E., Pillus, L., and Boeke, J. D. (1995) *Genes Dev* 9(23), 2888-902.
15'. Tanny, J. C., and Moazed, D. (2001) *Proc Natl Acad Sci USA* 98(2), 415-20.
16'. Rine, J. H. I. (1987) *Genetics* 116(1), 9-22
17'. Wood, J. G., and Sinclair, D. A. (2002) *Trends Pharmacol Sci* 23(1), 1-4.
18'. Strahl-Bolsinger S, H. A., Luo K, Grunstein M. (1997) *Genes Dev* (11), 1
19'. Hecht, A. S.-B. S., Grunstein M. (1996) *Nature* 383 (6595), 92-6
20'. Ghidelli, S. D. D., Dhillon N, Kamakaka RT. (2001) *EMBO* 20(16), 4522-35
21'. Shou, W., Sakamoto, K. M., Keener, J., Morimoto, K. W., Traverso, E. E., Azzam, R., Hoppe, G. J., Feldman, R. M. R., DeModena, J., Moazed, D., Charbonneaux, H., Nomura, M., and Deshaies, R. J. (2001) Mol. Cell. 8(1), 45-55
22'. Gottschling, D. E., Aparicio, O. M., Billington, B. L., and Zakian, V. A. (1990) *Cell* 63(4), 751-62.
23'. Smith, J. S., and Boeke, J. D. (1997) *Genes Dev* 11(2), 241-54.
24'. Bryk, M., Banedjee, M., Murphy, M., Knudsen, K. E., Garfinkel, D. J., and Curcio, M. J. (1997) *Genes Dev* 11(2), 255-69.
25'. Sinclair, D. A., and Guarente, L. (1997) *Cell* 91(7), 1033-42.

26'. Kaeberlein, M., McVey, M., and Guarente, L. (1999) *Genes Dev* 13(19), 2570-80.
27'. Park, P. U., Defossez, P. A., and Guarente, L. (1999) *Mol Cell Biol* 19(5), 3848-56
28'. Sinclair, D. A., Mills, K., and Guarente, L. (1998) *Trends Biochem Sci* 23(4), 131-4.
29'. Gottlieb, S., and Esposito, R. E. (1989) *Cell* 56(5), 771-6.
30'. Kennedy, B. K., Austriaco, N. R., Jr., Zhang, J., and Guarente, L. (1995) *Cell* 80(3), 485-96.
31'. Lin, S. J., Defossez, P. A., and Guarente, L. (2000) *Science* 289(5487), 2126-8.
32'. Anderson, R. M., Bitterman, K. J., Wood, J. G., Medvedik, O., Cohen, H., Lin, S. S., Manchester, J. K., Gordon, J. I., and Sinclair, D. A. (2002) *J Biol Chem* 277(21), 18881-90.
33'. Tissenbaum, H. A., and Guarente, L. (2001) *Nature* 410 (6825), 227-30.
34'. Vaziri, H., Dessain, S. K., Eaton, E. N., Imai, S. I., Frye, R. A., Pandita, T. K., Guarente, L., and Weinberg, R. A. (2001) *Cell* 107(2), 149-59.
35'. Luo, J., Nikolaev, A. Y., Imai, S., Chen, D., Su, F., Shiloh, A., Guarente, L., and Gu, W. (2001) *Cell* 107(2), 137-48.
36'. Moazed, D. (2001) *Curr Opin Cell Biol* 13(2), 232-8.
37'. Sauve, A. A., Celic, I., Avalos, J., Deng, H., Boeke, J. D., and Schramm, V. L. (2001) *Biochemistry* 40(51), 15456-63.
38'. Borra, M. T., O'Neill, F. J., Jackson, M. D., Marshall, B., Verdin, E., Foltz, K. R., and Denu, J. M. (2002) *J Biol Chem* 277(15), 12632-41.
39'. Dietrich, L. S. (1971) *Amer J Clin Nut* 24, 800-804
40'. Kaanders, J. P. L., Marres H A, Bruaset I, van den Hoogen F J, Merkx M A, van der Kogel A J. (2002) *Int J Radiat Oncol Biol Phys* 52(3), 769-78
41'. Knip, M. D. I., Moore W P, Gillmor H A, McLean A E, Bingley P J, Gale E A. (2000) *Diabetologia* 43(11), 1337-45
42'. Foster, J. W., Park, Y. K., Penfound, T., Fenger, T., and Spector, M. P. (1990) *J Bacteriol* 172(8), 4187-96.
43'. Ghislain, M., Talla, E., and Francois, J. M. (2002) *Yeast* 19(3), 215-224.
44'. Keil, R. L., and McWilliams, A. D. (1993) *Genetics* 135(3), 711-8.
45'. Mills, K. D., Sinclair, D. A., and Guarente, L. (1999) *Cell* 97(5), 609-20.
46'. Hoppe, G. T. J., Rudner A D, Gerber S A, Danaie S, Gygi S P, Moazed D. (2002) *Mol Cell Biol* 22(12), 4167-80
47'. Langley, E. P. M., Faretta M, Bauer U M, Frye R A, Minucci S, Pelicci P G, Kouzarides T. (2002) *EMBO J* 21 (10), 2383-2396
48'. Llorente, B., and Dujon, B. (2000) *FEBS Lett* 475(3), 237-41.
49'. Sandmeier, J. J., Celic, I., Boeke, J. D., and Smith, J. S. (2002) *Genetics* 160(3), 877-89.
50'. Miller, A. N. K. (1984) *Nature* 312(5991), 247-51
51'. Kirchmaier, A. L., and Rine, J. (2001) *Science* 291(5504), 646-50.
52'. Li, Y. C., Cheng, T. H., and Gartenberg, M. R. (2001) *Science* 291(5504), 650-3.
53'. Gasser, S. M., Gotta, M., Renauld, H., Laroche, T., and Cockell, M. (1998) *Novartis Found Symp* 214, 114-26
54'. Landry, J., Slama, J. T., and Sternglanz, R. (2000) *Biochem Biophys Res Commun* 278(3), 685-90.
55'. Grozinger, C. C. E., Blackwell H E, Moazed D, Schreiber S L. (2001) *J Biol Chem* 276(42), 38837-43
56'. Bedalov, A., Gatbonton, T., Irvine, W. P., Gottschling, D. E., and Simon, J. A. (2001) *Proc Natl Acad Sci USA* 98(26), 15113-8.
57'. Straight, A. F., Shou, W., Dowd, G. J., Turck, C. W., Deshaies, R. J., Johnson, A. D., and Moazed, D. (1999) *Cell* 97(2), 245-56.
58'. Armstrong, C. K. M., Imai S I, Guarente L. (2002) *Mol Biol Cell* 13(4), 1427-38
59'. Min, J. L. J., Stemglanz R, Xu R M. (2001) *Cell* 105(2), 269-79
60'. Hoshino, J., Schluter, U., and Kroger, H. (1984) *Biochim Biophys Acta* 801(2), 250-8.
61'. Ijichi, H. A. I., A. Hataishi, O. (1966) *J Biol Chem* 241, 3701
62'. Hagino, Y. L., J. Henderson, M. (1968) *J Biol Chem* 243, 4980
63'. Smythe, G. A., Braga, O., Brew, B. J., Grant, R. S., Guillemin, G. J., Kerr, S. J., and Walker, D. W. (2002) *Anal Biochem* 301(1), 21-6.
64'. Gasch, A. P., Spellman, P. T., Kao, C. M., Carnel-Harel, O., Eisen, M. B., Storz, G., Botstein, D., and Brown, P. O. (2000) *Mol Biol Cell* 11(12), 4241-57.
65'. Moskvina, E. S. C., Maurer C T, Mager W H, Ruis H. (1998) *Yeast* 14(11), 1041-50
66'. Spellman, P. T., Sherlock, G., Zhang, M. Q., Iyer, V. R., Anders, K., Eisen, M. B., Brown, P. O., Botstein, D., and Futcher, B. (1998) *Mol Biol Cell* 9(12), 3273-97.
67'. Laurenson, P., and Rine, J. (1992) *Microbiol Rev* 56(4), 543-60.
68'. Barton, A. (1950) *J Gen Microbiol* 4, 84-86
69'. Kennedy, B. K., Austriaco, N. R., Jr., and Guarente, L. (1994) *J Cell Biol* 127(6 Pt 2), 1985-93.

Example 3

Nicotinamide, but Not Nicotinic Acid, Bind to the C Pocket of Sir2

Figure 14:
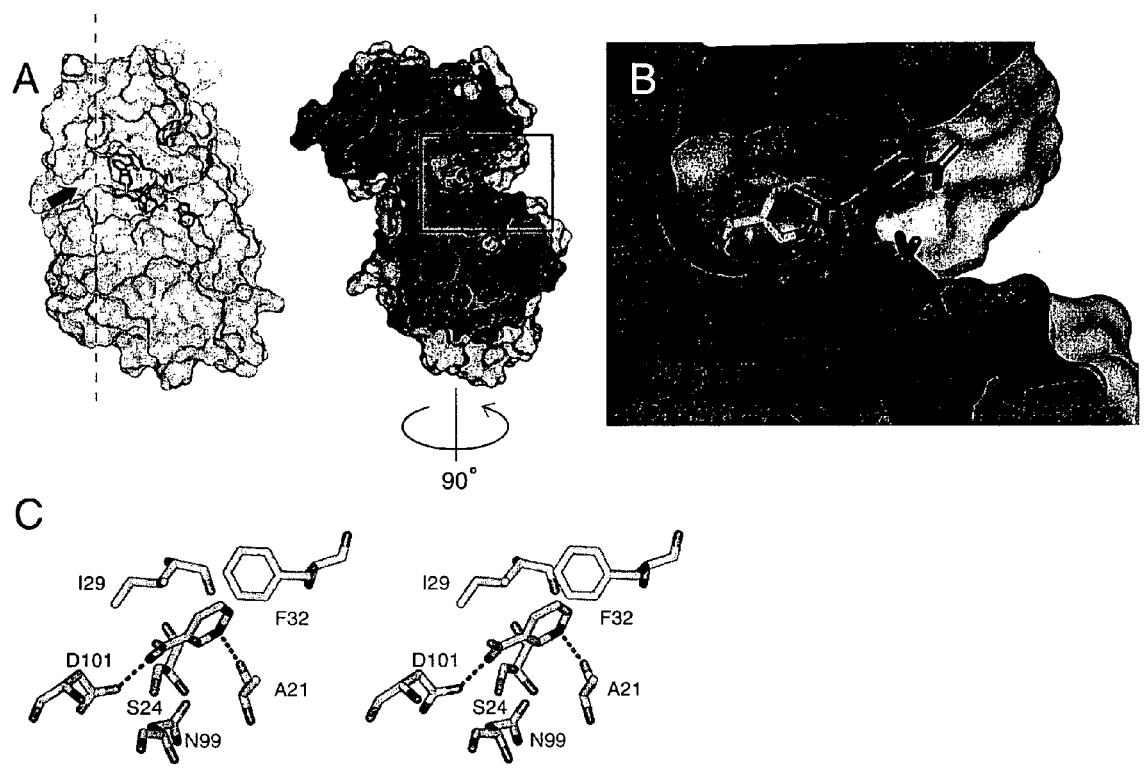
FIG. 14A-C. Nicotinamide docked in the conserved C pocket of Sir2-Af1. (A) The left panel shows a frontal view of the surface representation of Sir2-Af1, with bound NAD⁺ in purple and a red arrow pointing at the acetyl-lysine binding tunnel. The C site is traced with a dashed teal curve. The right panel shows the protein cut through the dashed line and rotated 90 degrees along its vertical axis. The surface of the conserved residues in the C site is colored teal. (B) Close-up view of the black rectangle drawn on the right panel of A, showing the nicotinamide docked deeply inside the C pocket of Sir2-Af1. (C) Stereo view of the docked nicotinamide (green) surrounded by the conserved residues in the C pocket. The putative interactions are shown as dashed lines, including H-bonds (blue), electrostatic (magenta) and Van der Waals (yellow).

The nicotinamide was docked in the crystal structure of Sir2 from *Archaeoglobus fulgidus* (Sir2-Af1) bound to NAD$^+$ (Protein Data Bank ID code 1ICI, Min et al. (2001). Crystal structure of a SIR2 homolog-NAD complex. Cell 105, 269-279). It was first manually docked in the C site of Sir2-Af1 using QUANTA (MSI, Inc.). Subsequently, an energy minimization calculation was done with CHARMM (Brooks et al. (1983) J. Comput. Chem. 4, 187-217) with harmonic constraint on Sir2-Af1 and NAD$^+$ (F=2.4 Kcal/mol Å$^2$). FIG. 14A-C were made with PYMOL (DeLano, W. L. The PyMOL Molecular Graphics System (2002) DeLano Scientific, San Carlos, Calif., USA).

These studies indicate that nicotinamide inhibits Sir2 (see FIGS. 14 A-C) and that nicotinic acid does not inhibit Sir2 because the presence of residue D101 (i.e., acidic) prevents nicotinic acid to dock into the C pocket of Sir2.

Example 4

PNC1 Mediates Lifespan Extension

Figure 17:
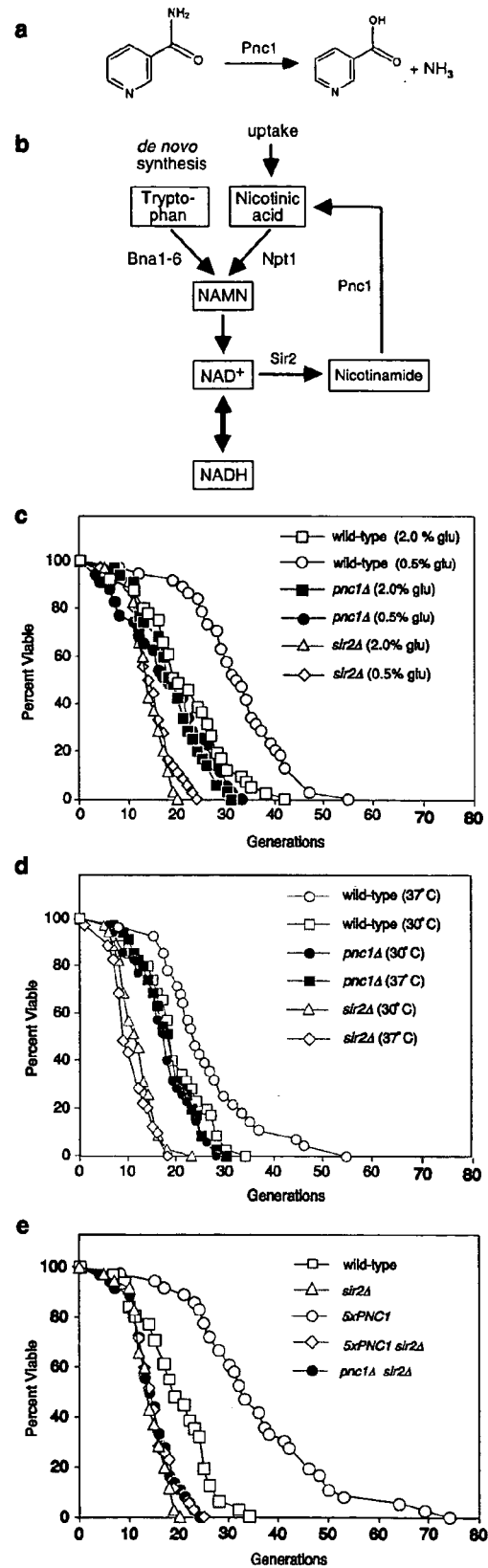
FIG. 17 A-E. Calorie restriction and heat stress extend lifespan in a PNC1-dependent manner. (A) Pnc1 catalyses the conversion of nicotinamide to nicotinic acid. (B) In yeast NAD⁺ is synthesised de novo from tryptophan and recycled from nicotinamide via the NAD⁺ salvage pathway. (C) Lifespan extension by glucose restriction requires PNC1. Average lifespan on complete media containing 2.0% (w/v) glucose were: wild-type, (21.6); pnc1Δ, (19.1); sir2Δ, (14.2). Average lifespans on 0.5% glucose were: wild-type, (32.7); pnc1Δ, (18.1); sir2Δ, (14.7). (D) Extension of life span by exposure to mild heat stress. At 30° C., average lifespans were: wild-type, (19.4);pnc1Δ, (18.5); sir2Δ, (12.0). At 37° C., average lifespans were: wild-type, (23.4); pnc1Δ, (17.5); sir2Δ, (10.6). (E) Additional PNC1 extends lifespan in a SIR2-dependent manner. Average lifespans on 2.0% glucose/ 30° C.: wild-type, (19.7); 5×PNC1, (36.1); sir2Δ, (14.2); 5×PNC1 sir2Δ, (15.1); pnc1Δsir2Δ, (14.4).

As shown in FIG. 17A, PNC1 catalyzes an amide hydrolysis, converting nicotinamide to nicotinic acid in the NAD$^+$ salvage pathway (FIG. 17B). Most wild-type yeast strains have an average lifespan of 21-23 divisions, with a maximum lifespan of ~40 divisions. A wild-type strain that was calorie restricted (0.5% glucose) or heat stressed (37° C.) exhibited a longer lifespan than an untreated control (2.0% glucose or 30° C., respectively) (FIGS. 17C and D). The sir2Δ strain had a short lifespan, consistent with previous reports[12,13], and neither calorie restriction nor heat extended lifespan in this strain (FIGS. 17C and D). The pnc1Δ strain did not exhibit a lifespan extension under either of these conditions, demonstrating that PNC1 is necessary for lifespan extension.

Strikingly, under non-stressing conditions (2% glucose, 30° C.), a strain with additional copies of PNC1 (5×PNC1) lived 70% longer than the wild-type and some cells lived over 70 divisions, which is the longest reported lifespan extension in this organism (FIG. 17E). Neither calorie restriction nor heat stress further increased the lifespan of the 5×PNC1 strain. Deletion of SIR2 in the 5×PNC1 background shortened lifespan to that of the sir2Δ strain (FIG. 17E). The pnc1Δ sir2Δ double mutant had a lifespan similar to the sir2Δ mutant as well (FIG. 17E) and its lifespan was unaffected by glucose restriction. This indicates that PNC1 and SIR2 function in the same pathway and that PNC1 increases lifespan via SIR2.

Thus, these results demonstrate that PNC1 is necessary for lifespan extension by both calorie restriction and heat stress, and that additional PNC1 is sufficient to mimic these stimuli. According to our model, additional copies of PNC1 extend lifespan by depleting nicotinamide, thus relieving inhibition of Sir2.

Example 5

PNC1 Expression is Increased in Response to Stress Conditions

Figure 18:
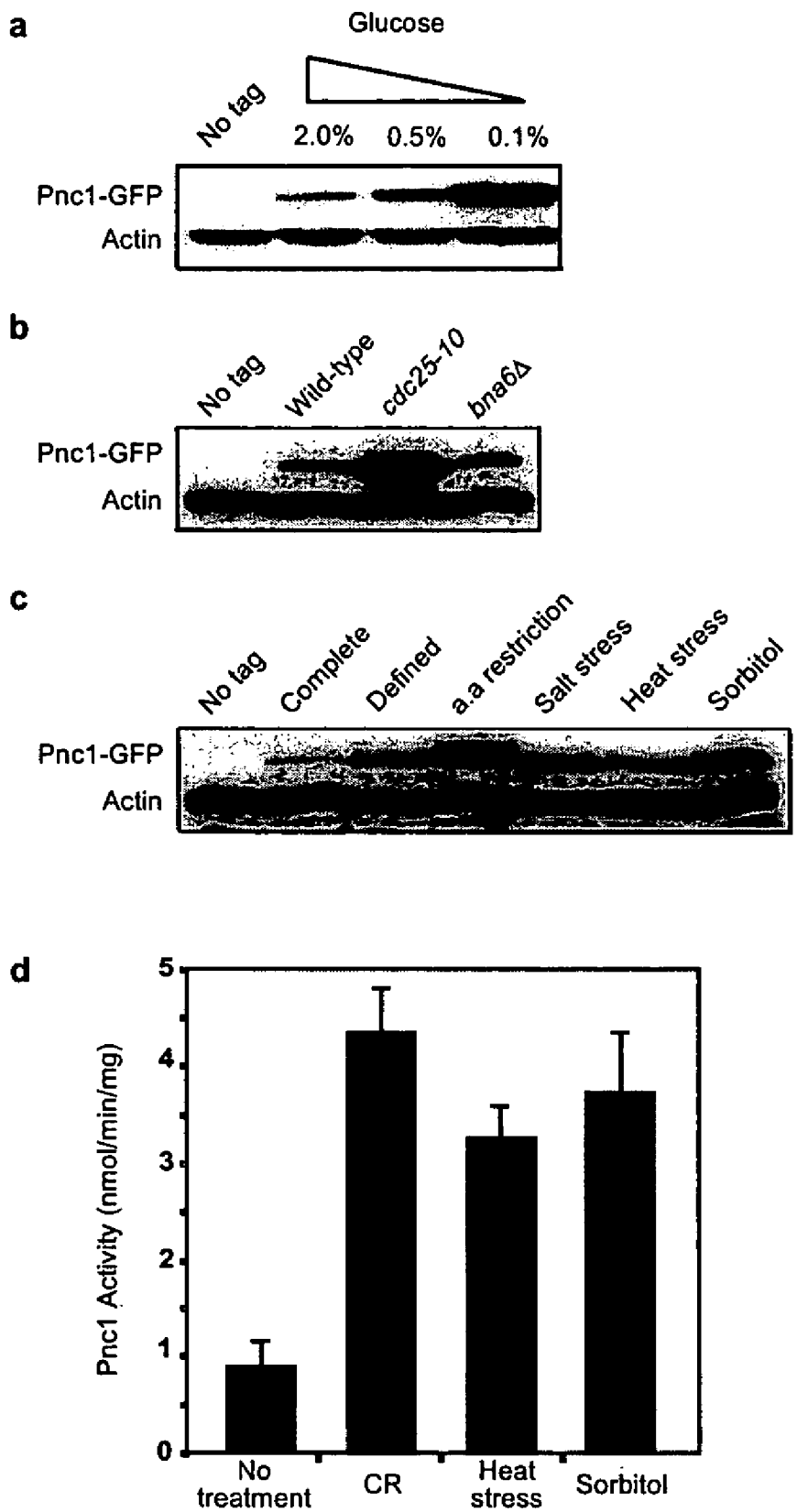
FIG. 18A-D. Pnc1 levels and activity are elevated in response to calorie restriction and stress. (A) Detection of Pnc1-GFP in yeast whole cell extracts using an anti-GFP antibody. Actin levels are included as a loading control. Extracts were made from mid-log phase wild-type cultures grown in complete media with 2.0%, 0.5% or 0.1% glucose (w/v). (B) Pnc1-GFP levels in extracts from mid-log phase wild-type, cdc25-10 or bna6Δ cultures detected as above. (C) Detection of Pnc1-GFP in extracts from mid-log phase wild-type cultures as described above. Cultures were grown under the following conditions: complete medium (no treatment), defined medium (SD), amino acid (a.a.) restriction (SD lacking non-essential amino acids), salt stress (NaCl, 300 mM), heat stress (37° C.), sorbitol (1M). (D) Measurement of nicotinamide deamination by Pnc 1 from cell extracts of mid-log phase wild-type cultures grown under the indicated conditions. Values shown are the average of three independent experiments. Activity is expressed as nmol ammonia produced/min/mg of total protein, ±s.d: 2.0% glucose 0.90±0.26, 0.1% glucose 4.38±0.43, 37° C. 3.28±0.32, sorbitol (1 M) 3.75±0.65.

*S. cerevisiae* were incubated in different stress conditions and the level of expression of PNC1 was measured by conducted Western blots. The amount of PNC1 measured in yeast cells grown in 2.0% glucose complete medium (YPD) was set at 1. The Table below and FIG. 18 show the fold induction in different growth conditions relative to this reference level of expression:

| Culture conditions | Fold comparison |
| --- | --- |
| 2.0% glucose complete meidum (YPD) | 1 |
| 0.5% glucose complete medium (YPD) | 15 |
| 0.1% glucose complete medium (YPD) | 25 |
| Defined complete medium (SD) + amino acids | 5 |
| Defined complete medium (SD) − amino acids | 20 |
| Heat shocked in 2% YPD (37 degrees for 4 hours) | 20 |
| Osmotic stress (0.1 M NaCl) | 15 |

It was also shown that nitrogen restriction greatly induced PNC1 expression. Since all of the above "stress conditions," i.e., not 2.0% glucose complete medium (YPD) extend the life span of *S. cerevisiae* (caloric restriction), an increase in PNC1 correlates with an extended life span in every condition tested and known to extend yeast lifespan, including amino acid restriction, salt stress and heat stress (FIG. 18C). Analysis of genome-wide mRNA profiles of the stress response (Gash) showed that PNC1 is one of the most highly responsive genes in response to stress and starvation in this organism. PNC1 levels were also greatly induced in cells carrying a cdc25-10 allele that mimics calorie restriction by lowering cAMP (FIG. 18B).

To test whether this response was specific to environmental stress, we examined Pnc1 levels in a strain deleted for BNA6/QPT1, which is required for the de novo synthesis of NAD$^+$ but not life span extension by calorie restriction[12] In this mutant Pnc1 levels were unaltered (FIG. 18B). Pnc1 activity in extracts from treated cells correlated with Pnc1 levels in Western blots (FIG. 18D), demonstrating that these cells have increased rates of nicotinamide hydrolysis. Thus, PNC1 is the first yeast longevity gene whose expression is modulated by stimuli that extend lifespan.

Accordingly, methods in which the level of PNC1 is increased to extend the life span of cells or protect them against stresses, as further described herein, mimics the natural events in cells.

Example 6

Additional PNC1 Confers Resistance to Acute Stress

Figure 19:
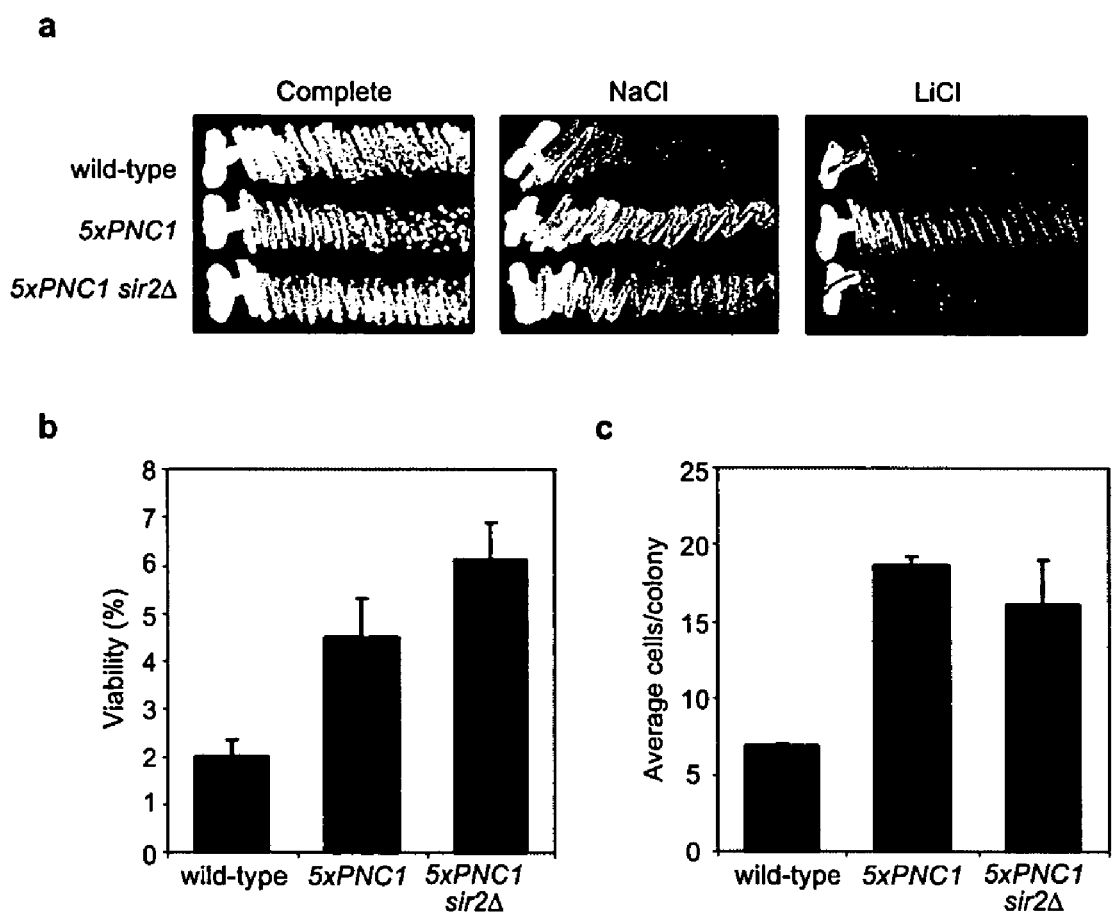
FIG. 19A-C. PNC1 confers resistance to acute stress. (A) Additional PNC1 confers resistance to salt stress. Cells from mid-log phase colonies were struck out on complete medium containing 600 mM NaCl or 200 mM LiCl and incubated for 4 d at 25° C. On standard yeast medium (2% glucose, 25° C.), there was no detectable difference in growth rate between wild-type, 5×PNC1, or 5×PNC1 sir2Δ strains. (B) Additional PNC1 protects against UV induced damage in a SIR2 independent manner. Cells from mid-log phase cultures were plated at low density on complete medium and exposed to UV (5 mJ/cm², 254 nm). Viability was determined by the ability to form colonies after 3 d growth in the dark at 30° C. Values are expressed as percent viable±s.e. (C) PNC1 provides SIR2-independent protection against mitochondrial DNA damage. Microcolony analysis of log-phase cells streaked on complete 3% (v/v) glycerol medium and 10 μg/ml ethidium bromide (EtBr). At least 100 microcolonies were scored after 3 d in two independent experiments. Number of cells per colony±s.e. were: wild-type 6.92±0.06, 5×PNC1 18.72±0.53, and 5×PNC1 sir2Δ 16.15±2.82. No difference in growth was detected between these strains on complete 2% (w/v) glucose medium with EtBr FIG. 20A-D. Pnc1-GFP is localized in the cytoplasm and nucleus and is concentrated in peroxisomes. (A) Pnc1-GFP fluorescence was detected in cells taken from mid-log phase wild-type cultures grown in complete media containing 2.0% glucose (unrestricted), or 0.5% or 0.1% glucose (Glu). (B) Detection of Pnc1-GFP in cells from wild-type cultures grown under the following conditions: amino acid (a.a) restriction (SD lacking non-essential amino acids), salt stress (300 mM NaCl), heat stress (37° C.). (C) Co-localisation of Pnc1-GFP (green) and RFP-PTS1 (Peroxisomal Targeting Signal 1) (red) in cells from mid-log phase wild-type cultures. Yellow indicates overlap. Cultures were grown in complete media containing 0.5% glucose to facilitate visualization of fluorescence. (D) Localisation of Pnc1-GFP in cells from mid-log phase cultures of peroxisomal mutant strains, pex6Δ, pex5Δ and pex7Δ. Cultures were grown in complete media containing 0.5% glucose to enhance visualization of fluorescence. All images were taken with the same exposure of 1 s.

Given the strong link between longevity and stress resistance in other species, we tested whether additional PNC1 could also confer resistance to a range of stresses. A well-characterized test of stress resistance in yeast is the ability of cells to tolerate high concentrations of salt[26]. We found that the 5×PNC1 strain was dramatically more resistant than wild-type to high levels of both NaCl (600 mM) and LiCl (200 mM) (FIG. 19A). We also tested survival following DNA damage by UV irradiation (5 mJ/cm$^2$) and found again that additional PNC1 conferred resistance (FIG. 19B). Because mitochondrial DNA damage has been implicated in mammalian aging[27], we also examined the ability of additional PNC1 to protect against this type of stress. Under conditions of obligate respiration (3% glycerol as carbon source), 5×PNC1 cells were more resistant than wild-type to mitochondrial mutagenesis by ethidium bromide (FIG. 19C). The increased resistance of the 5×PNC1 strain to LiCl was dependent on SIR2. Strikingly, the resistance of this strain to NaCl, UV and ethidium bromide was independent of SIR2 (FIGS. 19A-C). These results demonstrate that PNC1 promotes both longevity and stress resistance, and suggests that SIR2 is not the only downstream effector of this gene. It is thus likely that nicotinamide regulates proteins other than Sir2.

Example 7

Cellular Localization of PNC1 Under a Variety of Stress Conditions

Figure 20:
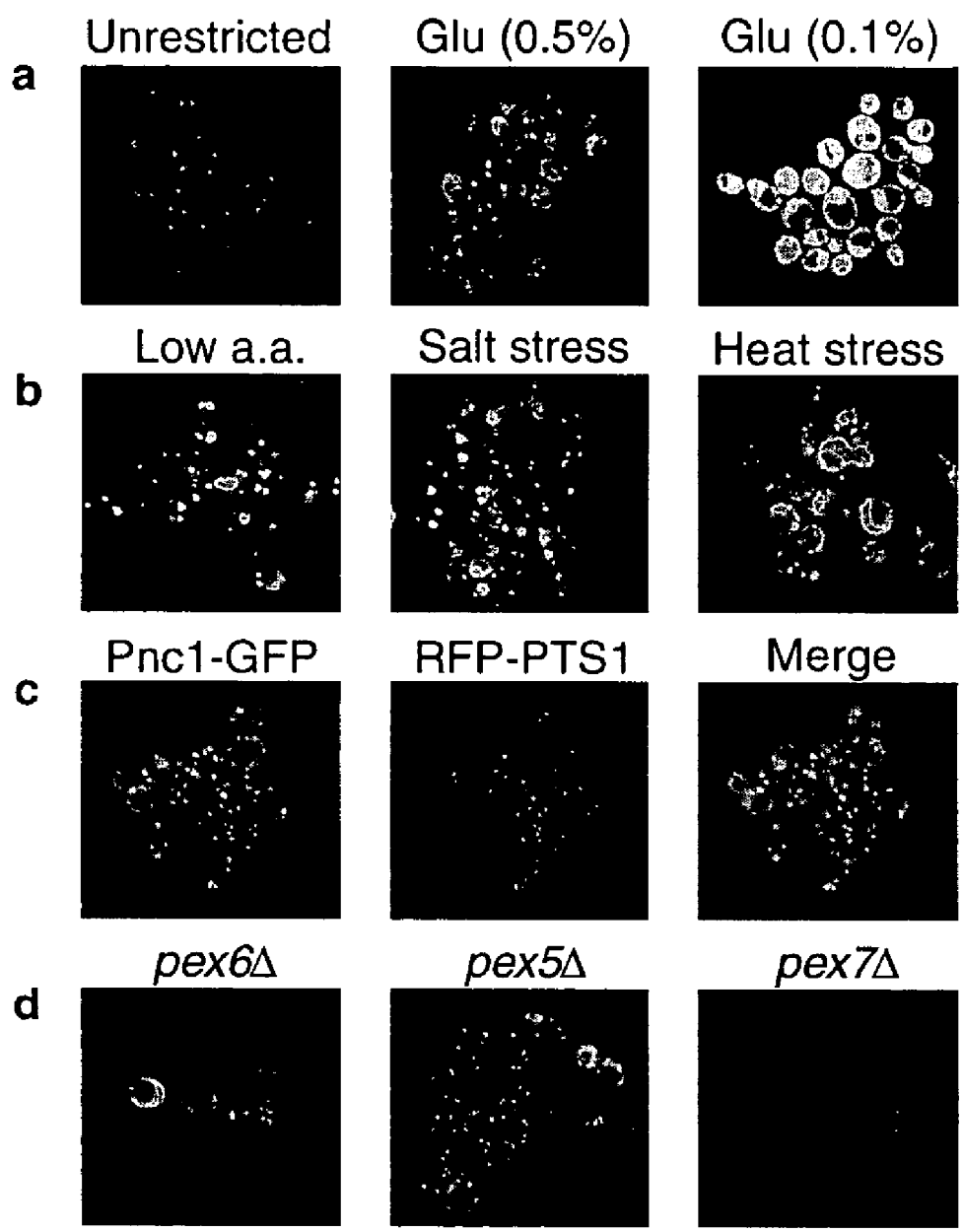

We have previously shown that two enzymes in the NAD$^+$ salvage pathway, Npt1 (nicotinamide phosphoribosyltransferase) and Nma2 (nicotinate mononucleotide adenylyltransferase), are concentrated in the nucleus[23]. We investigated whether Pnc1, another salvage pathway enzyme, had a similar cellular distribution. Surprisingly, on complete 2% glucose medium, Pnc 1-GFP was observed in the cytoplasm, the nucleus and in 3-6 discrete cytoplasmic foci per cell (FIG. 20A). Calorie-restricted or stressed cells showed a dramatic increase in the intensity of fluorescence, consistent with the Western data. Interestingly, under conditions of amino acid restriction or salt stress, this pattern was altered, with the fluorescence being predominately localized to the foci (FIG. 20B). This suggests that Pnc1 localization is regulated in distinct ways by different stresses.

To determine the identity of the foci, we searched for cellular markers that co-localized with Pnc1-GFP. We observed significant overlap with a peroxisomally-targeted red fluorescent protein (RFP) (FIG. 20C). Furthermore, the Pnc1-GFP foci were no longer observed in a pex6Δ mutant, which is unable to form peroxisomes (FIG. 20D). Because our stress studies indicated that the localisation of Pnc1 to peroxisomes might be regulated, we sought to identify the transporter responsible for its import into this organelle. Although Pex5 imports the vast majority of peroxisomal proteins, the localisation of Pnc1 to peroxisomes required the lesser-utilised transporter Pex7 (FIG. 20D). The localisation of Pnc1 to sites outside the nucleus is consistent with our stress results demonstrating that nicotinamide regulates proteins other than Sir2. The peroxisomal localisation is of particular interest because these organelles are a major source of reactive oxygen species and have been implicated in mammalian aging[28,29]. In addition, a number of crucial steps in lipid metabolism occur in peroxisomes and lipid signaling has recently been linked to salt tolerance[26]. The salt resistance of additional PNC1 maybe the result of a peroxisomal function of Pnc1.

Example 8

Life Span and Stress Resistance are Negatively Regulated by Intracellular Nicotinamide One prediction of our model is that any manipulation of intracelluar nicotinamide levels should be sufficient to alter Sir2 activity. A common indicator of Sir2 activity is the extent to which a reporter gene inserted at the rDNA (RDN1) is silenced. To exclude the possibility that $NAD^+$ levels were responsible for any silencing effect, we sought to manipulate intracellular nicotinamide levels using a gene outside the $NAD^+$ salvage pathway. In humans, the major route of nicotinamide metabolism is through nicotinamide N-methlytransferase (NNMT)[30]. NNMT converts nicotinamide to N'-methylnicotinamide, which is excreted via the kidneys[31]. By homology we identified the S. cerevisiae NNMT gene, which we have named NNT1. Nnt1 is 23% identical to a mammalian NNMT core domain[30] and contains the four signature motifs of S-adenosylmethionine(SAM)-dependent methyltranferases[32].

Deletion of NNT1 caused a desilencing phenotype similar to deletion of PNC1[33] (FIG. 21A). These results are consistent with our finding that rDNA silencing is abrogated in the presence of exogenous nicotinamide (Example 2). As predicted, strains with additional NNT1 showed increased silencing, similar to strains with additional PNC1[23]. We conclude that lifespan, stress resistance and Sir2 activity can be regulated by changes in intracellular nicotinamide and levels of NNT1. It is worth noting that although NNT1 can mimic PNC1 phenotypes, unlike PNC1, its expression is not apparently modulated by stimuli that extend lifespan[25].

We have identified PNC1 as a calorie restriction- and stress-responsive gene that increases lifespan and stress resistance of cells by depleting intracellular nicotinamide (FIG. 21B). We show that lifespan extension by calorie restriction is the result of an active cellular defense response coordinated by a specific regulatory gene. An attractive feature of this mechanism is that it is not based on the modulation of $NAD^+$, an essential co-factor involved in cellular homeostasis.

We do not yet know how a gene involved in nicotinamide metabolism confers resistance to numerous acute stresses. Presumably the benefits of increased Pnc1 come at an evolutionary cost but we have yet to identify any selective disadvantage. Both our stress and localisation results imply the existence of multiple nicotinamide-regulated effectors. Based on the enzymology of Sir2 inhibition by nicotinamide (Example 2 and [34]), proteins that cleave $NAD^+$ in a two-step reaction are plausible candidates. Examples include the homologues of Sir2 (Hst1-4) and Tpt1, an $NAD^+$-dependent 2'-phosphotransferase that facilitates the unfolded protein response[35]. Expression profiling of cells with altered nicotinamide metabolism should help identify these effectors and the downstream pathways of stress resistance.

In mammals, there is evidence for a link between nicotinamide metabolism and stress resistance. Poly(adenosine diphosphate-ribose) polymerase-1 (PARP) is a nuclear enzyme that cleaves $NAD^+$ to covalently attach poly(ADP-ribose) to acceptor proteins. This two-step reaction generates nicotinamide, which exerts an inhibitory effect on PARP-1 allowing for autoregulation[36]. PARP enzymes have been implicated in numerous cellular functions including DNA break repair, telomere-length regulation, histone modification, and the regulation at the transcriptional level of key proteins including ICAM-1 and nitric oxide synthase[36]. Our results suggest that PARP enzymes might be regulated by nicotinamide metabolism as part of a general stress response. Nicotinamide also inhibits human SIRT1 both in vitro (Example 2) and in vivo[17]. SIRT1 negatively controls p53 activity, indicating that nicotinamide levels may regulate apoptosis and DNA repair[17,18]. Consistent with this, the expression of NNMT in human cells and tissues correlates with tumorigenesis[37] and radioresistance[38].

Example 9

Materials and Methods for Examples 4-8

Media and Strains: All strains were grown at 30° C. in complete 2.0% (w/v) glucose (YPD) medium except where stated otherwise. In all experiments, we ensured that auxotrophic markers were matched between strains by integrating empty vector. All deletions were generated using a kanMX6 PCR-based technique[39] and confirmed by PCR. Additional copies of PNC1 were integrated as previously described[23]. The entire open reading frame and 700 bases of upstream sequence of NNT1 (YLR285w) were cloned from genomic DNA by PCR into pSP400[40], sequenced, and integrated into the yeast genome as described previously[23]. The copy number of integrated genes was determined by Southern blotting. A GFP cassette was introduced in-frame at the 3' end of the native PNC1 gene as previously described[39]. The RFP-PTS1 plasmid (pSG421) was a gift from S. J. Gould (Johns Hopkins U.). PSY316AT-derived strains were used for lifespan analysis and stress resistance assays. Strains derived from PSY316AT (MATα, ura3-53 leu2-3,112 his3-Δ200 ade2-1, 01 can1-100 ADE2-TEL V-R): pnc1Δ (YDS1741), sir2Δ (YDS1750), 5×PNC1 (YDS1853), 5×PNC1 sir2Δ (YDS1851), pnc1Δ sir2Δ (YDS1853). W303-derived strains were used for Western blot analysis, fluorescence microscopy and SMR2 dependent silencing assays. Strains derived from W303 (MATα, ade2-1, leu2-3,112, can1-100, trp1-1, ura3-52, his3-11,15, RDN1::ADE2, RAD5) include: PNC1-GFP (YDS1742), pnc1Δ (YDS1911), nnt1Δ (YDS1747), 2×PNC1 (YDS1588), 2×NNT1 (YDS1926), ADE2 (YDS1596). The following strains were derived from PNC1-GFP (YDS1742): bna6Δ (YDS1857), pSG421 (YDS1916), pex6Δ (YDS1869), pex5Δ (YDS1870) and pex7Δ (YDS1871). The cdc25-10 strain was a gift from L Guarente (M.I.T.).

Yeast assays were conducted as follows. Life span measurements were performed as previously described[23] except for the heat stress experiments where strains were incubated after each dissection at 37° C. Stress resistance assays were performed using mid-log phase cells. Silencing was assayed as previously described[23].

Protein expression analysis were conducted as follows. Strains were pretreated under the indicated conditions and grown to mid-log phase. Western blots were performed as described[23] using whole cell extracts (75 μg). Proteins were detected using anti-GFP antibodies (Santa Cruz) or anti-actin antibodies (Chemicon). Fluorescent microscopy images were captured at the same exposure (1 s) at 100× magnification with a Hamamatsu Orca100 CCD camera and processed with Openlab software.

Nicotinamidase activity assay was conducted as follows. Activity of Pnc1 in extracts obtained from pretreated mid-log phase cultures was determined as previously described[41]. Briefly, 0.16 mg of protein were incubated with either 0 or 8 mM nicotinamide for 45 min at 30° C. in a final volume of 400 µl consisting of 10 mM Tris pH 7.5, 150 mM NaCl and 1 mM $MgCl_2$. Pnc1 activity was determined by measuring the final concentration of the reaction product, ammonia, using the Sigma ammonia diagnostic kit. Baseline ammonia was accounted for by subtracting a no nicotinamide control. Nicotinamidase activity was expressed as nmol ammonia produced/min/mg total protein. Pnc1 activity was obtained by subtracting the background value for the pnc1Δ strain (0.06±0.004 nmol/min/mg).

REFERENCES FOR EXAMPLES 4-9

1. Masoro, E. J. *Exp Gerontol* 35, 299-305. (2000).
2. Masoro, E. J. *Exp Gerontol* 33, 61-6. (1998).
3. Kirkwood, T. B. & Holliday, R. *Proc R Soc Lond B Biol Sci* 205, 531-46. (1979).
4. Holliday, R. Food *Bioessays* 10, 125-7. (1989).
5. Kenyon, C. *Cell* 105, 165-168 (2001).
6. Guarente, L. & Kenyon, C. *Nature* 408, 255-62. (2000).
7. Kaeberlein, M. & Guarente, *Genetics* 160, 83-95. (2002).
8. Jiang et al. *Faseb J* 14, 2135-7. (2000).
9. Swiecilo et al. *Acta Biochim Pol* 47, 355-64 (2000).
10. Sinclair, D. A. *Mech Ageing Dev* in press. (2002).
11. Moazed, D. *Curr Opin Cell Biol* 13, 232-8. (2001).
12. Lin et al. *Science* 289, 2126-8. (2000).
13. Kaeberlein et al. *Genes Dev* 13, 2570-80. (1999).
14. Sinclair, D. A. & Guarente, L. *Cell* 91, 1033-42. (1997).
15. Tissenbaum, H. A. & Guarente, L. *Nature* 410, 227-30. (2001).
16. Rogina et al. *Science*, in press (2002).
17. Vaziri, H. et al. *Cell* 107, 149-59. (2001).
18. Luo, J. et al. *Cell* 107, 137-48. (2001).
19. Smith, J. S. et al. *Proc Natl Acad Sci USA* 97, 6658-63. (2000).
20. Imai et al. *Nature* 403, 795-800 (2000).
21. Tanny, J. C. & Moazed, D. *Proc Natl Acad Sci USA* 98, 415-20. (2001).
22. Landry, J. et al. *Proc Natl Acad Sci USA* 97, 5807-11. (2000).
23. Anderson, R. M. et al. *J Biol Chem* 277, 18881-90. (2002).
24. Bitterman et al. *J. Biol. Chem.* in press (2002).
25. Gasch, A. P. et al. *Mol Biol Cell* 11, 4241-57. (2000).
26. Betz et al. *Eur J Biochem* 269, 4033-9. (2002).
27. Melov, S. *Ann N Y Acad Sci* 908, 219-25. (2000).
28. Masters, C. J. & Crane, D. I. *Mech Ageing Dev* 80, 69-83. (1995).
29. Perichon et al. *Cell Mol Life Sci* 54, 641-52. (1998).
30. Aksoy et al. *J Biol Chem* 269, 14835-40. (1994).
31. Matsubara et al. *Neurotoxicol Teratol* 24, 593. (2002).
32. Niewmierzycka, A. & Clarke, S *J Biol Chem* 274, 814-24. (1999).
33. Sandmeier et al. *Genetics* 160, 877-89. (2002).
34. Landry et al. *Biochem Biophys Res Commun* 278, 685-90. (2000).
35. Spinelli et al. *J Biol Chem* 274, 2637-44. (1999).
36. Virag, L. & Szabo, C. *Pharmacol Rev* 54, 375-429. (2002).
37. Lal, A. et al. *Cancer Res* 59, 5403-7. (1999).
38. Kassem et al. *Int J Cancer* 101, 454-60. (2002).
39. Longtine, M. S. et al. *Yeast* 14, 953-61. (1998).
40. Mills et al. *Cell* 97, 609-20. (1999).
41. Ghislain et al. *Yeast* 19, 215-224. (2002).

Example 10

Human Nicotinamide Methyltransferase (NMNAT) Confers Radioresistance in Human Cells NMNAT (EC 2.1.1.1; CAS registry number 9029-74-7), which is also referred to as nicotinamide N-methyltransferase, is an enzyme that catalyzes the reaction S-adenosyl-L-methionine+nicotinamide=S-adenosyl-L-homocysteine+1-methylnicotinamide (see also, Cantoni (1951) J. Biol. Chem. 203-216). Overexpression of human NMNAT in radiosensitive human cells was found to increase the radioresistance of the cells.

Example 11

PBEF Levels are Upregulated in Serum of Rats During Caloric Restriction

This example describes that PBEF is present in higher levels in serum of rats subjected to caloric restiction.

Male Fischer-344 (F344) rats were bred and reared in a vivarium at the Gerontology Research Center (GRC, Baltimore, Md.). From weaning (2 weeks), the rats were housed individually in standard plastic cages with beta chip wood bedding. Control animals were fed a NIH-31 standard diet ad libitum (AL). At one month of age the calorie restricted (CR) animals were provided a vitamin and mineral fortified version of the same diet at a level of 40% less food (by weight) than AL rats consumed during the previous week. Filtered and acidified water was available AL for both groups. The vivarium was maintained at a temperature of 25° C., with relative humidity at 50% on a 12/12 h light/dark cycle (lights on at 6:00 a.m.) All serum was obtained from fasted, anesthetized animals. Rats were anesthetized and a 21-gauge catheter was inserted into the tail vein. 1.5 ml of whole blood was then collected and allowed to clot (20-30 min), then centrifuged for 20 min at 2500 rpm. Serum from AL or CR samples was removed from the centrifuge and pooled. Two different pools of AL serum and two different pools of CR serum were analyzed. Two microliters of serum from each pooled sample was denatured by boiling for 5 minutes in sample buffer containing SDS, then subjected to polyacrylamide gel electrophoresis (PAGE). Proteins were transferred to PVDF membrane (Immobilon™-P, Sigma, P2938), which was subsequently blocked for 1 hour at room temperature using 5% dry non-fat milk in TBST. Blots were then probed using a 1:1000 dilution of NAMPRT monoclonal or polyclonal antibodies (from Dr. Oberdan Leo) in 0.5% milk in TBST for 1 hour at room temperature. After three 5-minute washes in TBST, blots were probed with the appropriate secondary antibodies conjugated to horseradish peroxidase (Amersham Biosciences Anti-Mouse NA931V, or Molecular Probes Anti-Rabbit G21234) in 0.5% milk in TBST. Following three 10-minutes washes in TBST, blots were visualized by chemiluminescence using ECL reagents (Amersham Biosciences, RPN2105) and detected with X-Ray film (Kodak BioMax XAR,1651454).

Figure 22:
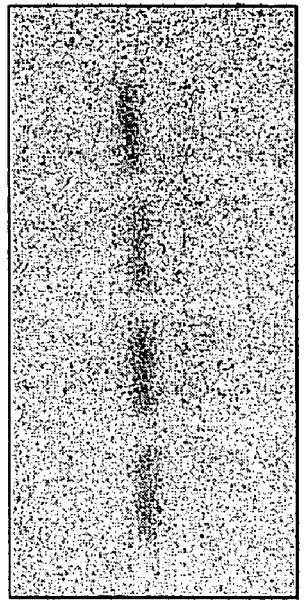
FIG. 22 shows that extracellular NAMPRT protein levels are higher in the serum of rats subjected to calorie restriction.

The results are shown in FIG. 22, which shows higher levels of NAMPRT in serum from calorie restricted rats.

Example 12

PBEF Levels are Up-Regulated in Response to Stress Conditions

This example shows that PBEF is up-regulated by serum starvation and oxidative stress in MEF cells and in cardiomyocytes by serum starvation and hypoxia.

Cardiomyocytes were prepared from 1- to 2-day-old rats by use of the Neonatal Cardiomyocyte Isolation System (Worthington Biochemical Corp) and cultured in 60 mm Petri dishes with RPMI 1640 medium containing 5% FCS, 10% horse serum (HS) for 72 hours. Then, medium was removed and replaced with medium with or without serum. For hypoxia, cells were placed in a 37° C. airtight box saturated with 95% N2/5% C02 for 18 hours. $O_2$ concentrations were 0.1% (Ohmeda oxygen monitor, type 5120). For normoxia, cells were placed in a 37° C./5% $CO_2$ incubator for 18 hours before harvest.

MEFs were generated from 13.5-d-old embryos from pregnant mice as described previously (Razani et al., 2001). Control MEF cells were cultured in DMEM supplemented with 10% FCS, 1% penicillin/streptomycin/0.5% fungizone for 24 hours. To starve the cells, MEFs were washed with PBS and cultured in DMEM containing 2% BSA, 1% penicillin/streptomycin/0.5% fungizone for 24 hours. Cells under further oxidative stress treatment were cultured in the same medium containing 150 micro moles $H_2O_2$ for 1 or 3 hours before harvest.

The results, which are shown in FIGS. 23 and 24, indicate that NAMPRT is upregulated by serum starvation, oxidative stress and hypoxia.

Example 13

PBEF Transcription is Up-Regulated by Fasting in vivo in Mice

Eight Sprague-Dawley male mice, four for each group (control versus fasting), were used to compare NAMPRT gene regulation by fasting. Control mice were fed ad libitum with 78% sucrose diet prepared by Research Diets. Experimental mice were fasted for 48 hours before sacrificed. Fresh liver tissues were removed, cut into small pieces and soaked in DNAlater reagent and stored at 4° C. till starting RNA preparation.

Total RNA was isolated from tissue by trizol (Invitrogen) according to the protocol recommended by manufacture. 1 µg RNA was used as template for reverse transcription to cDNA. Real-time PCR was carried out in LightCycler RT-PCR (Roche Molecular Biochemicals) using non-specific LightCycler DNA Master SYBR Green dye to monitor PCR product. The relative NAMPRT mRNA copies were normalized to that of β-actin. Primers used to amplify NAMPRT fragment were:
AAATCCGCTCGACACTGTCCTGAA (SEQ ID NO: 23),
TTGGGATCAGCAACTGGGTCCTTA (SEQ ID NO: 24).
Primers used to amplify β-actin fragment were: TTCCTC-CCTGGAGAAGAGCTATGA (SEQ ID NO: 25),
TACTCCTGCTTGCTGATCCACATC (SEQ ID NO: 26).

Figure 25:
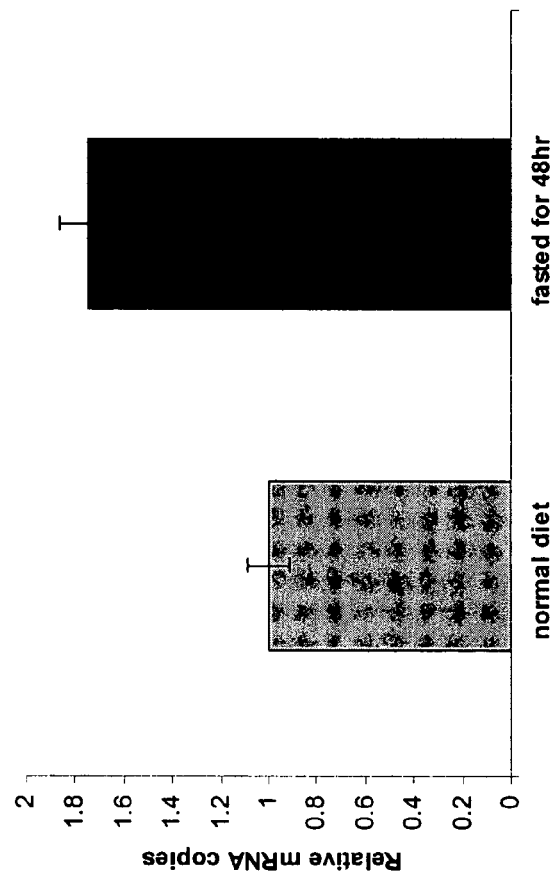
FIG. 25 is a histogram showing the relative number of NAMPRT mRNA copies measured by real time RT-PCR compared with number of beta-actin mRNA copies in cells of mice having a normal diet and mice fasted for 48 hours.

The results, which are shown in FIG. 25 show that NAMPRT transcription is upregulated in fasting mice relative to non-fasting mice.

Equivalents

Those skilled in the art will recognize, or be able to ascertain using no more than routine experimentation, many equivalents of the specific embodiments of the invention described herein. Such equivalents are intended to be encompassed by the following claims.

---

The invention claimed is:

1. A method for modulating the life span of a cell or its resistance to stress, comprising providing a cell having a flux through the NAD+ salvage pathway and modulating the flux through the NAD+ salvage pathway in the cell, wherein the step of modulating the flux through the NAD+ salvage pathway in the cell comprises introducing into the cell at least one nucleic acid encoding an enzyme that metabolizes nicotinamide selected from the group consisting of a nicotinamidase enzyme and a nicotinamide phosphoribosyltransferase enzyme, thereby modulating the life span of the cell or its resistance to stress.

2. The method of claim 1, wherein the stress is heatshock; osmotic stress; exposure to a DNA damaging agent; inadequate salt level; inadequate nitrogen levels; inadequate nutrient level; radiation; or exposure to a toxic compound.

3. The method of claim 1, wherein modulating the flux through the NAD+ salvage pathway occurs without changing steady state levels of NAD+ and NADH.

4. The method of claim 1, wherein the lifespan of the cell is extended by at least about 40%.

5. The method of claim 1, wherein the cell is in vitro.

6. The method of claim 1, wherein the cell is a eukaryotic cell.

7. The method of claim 6, wherein the cell is a mammalian cell.

8. The method of claim 6, wherein the cell is a yeast cell.

9. The method of claim 1, comprising introducing into the cell at least 5 copies of a nucleotide sequence encoding the enzyme.

10. A method for increasing stress resistance of a cell, comprising introducing into the cell at least one nucleic acid encoding an enzyme that metabolizes nicotinamide selected from the group consisting of a nicotinamidase enzyme and a nicotinamide phosphoribosyltransferase enzyme, thereby increasing stress resistance of the cell.

11. The method of claim 10, wherein the cell is in vitro.

12. The method of claim 10, wherein the cell is a eukaryotic cell.

13. The method of claim 12, wherein the cell is a mammalian cell.

14. The method of claim 12, wherein the cell is a yeast cell.

15. A method for increasing the life span of a cell, comprising introducing into the cell at least one nucleic acid encoding an enzyme that metabolizes nicotinamide selected from the group consisting of a nicotinamidase enzyme and a nicotinamide phosphoribosyltransferase enzyme, thereby increasing the life span of the cell.

16. The method of claim 15, wherein the cell is in vitro.

17. The method of claim 15, wherein the cell is a eukaryotic cell.

18. The method of claim 17, wherein the cell is a mammalian cell.

19. The method of claim 17, wherein the cell is a yeast cell.

20. A method for increasing stress resistance of a cell, comprising introducing into the cell at least one nucleic acid which hybridizes under high stringency conditions to SEQ ID NO:3 or SEQ ID NO:21, wherein high stringency conditions comprise hybridization in 0.2 to 1×SSC at 65° C. followed by a wash in 0.2×SSC at 65° C., wherein the nucleic acid that hybridizes under high stringency conditions to SEQ ID NO:3 encodes a nicotinamidase enzyme and wherein the nucleic acid that hybridizes under high stringency conditions to SEQ ID NO:21 encodes a nicotinamide phosphoribosyltransferase enzyme, thereby increasing stress resistance of the cell.

21. A method for increasing the life span of a cell, comprising introducing into the cell at least one nucleic acid which hybridizes under high stringency conditions to SEQ ID NO:3 or SEQ ID NO:21, wherein high stringency conditions comprise hybridization in 0.2 to 1×SSC at 65° C. followed by a wash in 0.2×SSC at 65° C., wherein the nucleic acid that hybridizes under high stringency conditions to SEQ ID NO:3 encodes a nicotinamidase enzyme and wherein the nucleic acid that hybridizes under high stringency conditions to SEQ ID NO:21 encodes a nicotinamide phosphoribosyltransferase enzyme, thereby increasing the life span of the cell.

22. The method of claim 20, wherein the cell is in vitro.

23. The method of claim 20, wherein the cell is a eukaryotic cell.

24. The method of claim 23, wherein the cell is a mammalian cell.

25. The method of claim 23, wherein the cell is a yeast cell.

26. The method of claim 21, wherein the cell is in vitro.

27. The method of claim 21, wherein the cell is a eukaryotic cell.

28. The method of claim 27, wherein the cell is a mammalian cell.

29. The method of claim 27, wherein the cell is a yeast cell.

30. The method of claim 1, wherein the nicotinamidase enzyme is PNC1.

31. The method of claim 30, wherein the nicotinamidase enzyme consists of SEQ ID NO:4.

32. The method of claim 1, wherein the nicotinamidase enzyme is at least 80% identical to SEQ ID NO:4.

33. The method of claim 32, wherein the nicotinamidase enzyme is at least 90% identical to SEQ ID NO:4.

34. The method of claim 1, wherein the nicotinamide phosphoribosyltransferase enzyme is NAMPRT.

35. The method of claim 34, wherein the nicotinamide phosphoribosyltransferase enzyme consists of SEQ ID NO:22.

36. The method of claim 1, wherein the nicotinamide phosphoribosyltransferase enzyme is at least 80% identical to SEQ ID NO:22.

37. The method of claim 36, wherein the nicotinamide phosphoribosyltransferase enzyme is at least 90% identical to SEQ ID NO:22.

38. The method of claim 10, wherein the nicotinamidase enzyme is PNC1.

39. The method of claim 38, wherein the nicotinamidase enzyme consists of SEQ ID NO:4.

40. The method of claim 10, wherein the nicotinamidase enzyme is at least 80% identical to SEQ ID NO:4.

41. The method of claim 40, wherein the nicotinamidase enzyme is at least 90% identical to SEQ ID NO:4.

42. The method of claim 10, wherein the nicotinamide phosphoribosyltransferase enzyme is NAMPRT.

43. The method of claim 42, wherein the nicotinamide phosphoribosyltransferase enzyme consists of SEQ ID NO:22.

44. The method of claim 10, wherein the nicotinamide phosphoribosyltransferase enzyme is at least 80% identical to SEQ ID NO:22.

45. The method of claim 44, wherein the nicotinamide phosphoribosyltransferase enzyme is at least 90% identical to SEQ ID NO:22.

46. The method of claim 15, wherein the nicotinamidase enzyme is PNC1.

47. The method of claim 46, wherein the nicotinamidase enzyme consists of SEQ ID NO:4.

48. The method of claim 15, wherein the nicotinamidase enzyme is at least 80% identical to SEQ ID NO:4.

49. The method of claim 48, wherein the nicotinamidase enzyme is at least 90% identical to SEQ ID NO:4.

50. The method of claim 15, wherein the nicotinamide phosphoribosyltransferase enzyme is NAMPRT.

51. The method of claim 50, wherein the nicotinamide phosphoribosyltransferase enzyme consists of SEQ ID NO:22.

52. The method of claim 15, wherein the nicotinamide phosphoribosyltransferase enzyme is at least 80% identical to SEQ ID NO:22.

53. The method of claim 52, wherein the nicotinamide phosphoribosyltransferase enzyme is at least 90% identical to SEQ ID NO:22.

54. The method of claim 50, wherein the nicotinamidase enzyme is PNC1.

55. The method of claim 54, wherein the nicotinamidase enzyme consists of SEQ ID NO:4.

56. The method of claim 20, wherein the nicotinamidase enzyme is at least 80% identical to SEQ ID NO:4.

57. The method of claim 56, wherein the nicotinamidase enzyme is at least 90% identical to SEQ ID NO:4.

58. The method of claim 20, wherein the nicotinamide phosphoribosyltransferase enzyme is NAMPRT.

59. The method of claim 58, wherein the nicotinamide phosphoribosyltransferase enzyme consists of SEQ ID NO:22.

60. The method of claim 20, wherein the nicotinamide phosphoribosyltransferase enzyme is at least 80% identical to SEQ ID NO:22.

61. The method of claim 60, wherein the nicotinamide phosphoribosyltransferase enzyme is at least 90% identical to SEQ ID NO:22.

62. The method of claim 21, wherein the nicotinamidase enzyme is PNC1.

63. The method of claim 62, wherein the nicotinamidase enzyme consists of SEQ ID NO:4.

64. The method of claim 21, wherein the nicotinamidase enzyme is at least 80% identical to SEQ ID NO:4.

65. The method of claim 64, wherein the nicotinamidase enzyme is at least 90% identical to SEQ ID NO:4.

66. The method of claim 21, wherein the nicotinamide phosphoribosyltransferase enzyme is NAMPRT.

67. The method of claim 66, wherein the nicotinamide phosphoribosyltransferase enzyme consists of SEQ ID NO:22.

68. The method of claim 21, wherein the nicotinamide phosphoribosyltransferase enzyme is at least 80% identical to SEQ ID NO:22.

69. The method of claim 68, wherein the nicotinamide phosphoribosyltransferase enzyme is at least 90% identical to SEQ ID NO:22.

70. The method of claim 20, wherein hybridization is conducted in the presence of formaldehyde.

71. The method of claim 21, wherein hybridization is conducted in the presence of formaldehyde.

* * * * *

UNITED STATES PATENT AND TRADEMARK OFFICE
CERTIFICATE OF CORRECTION

| | | |
|---|---|---|
| PATENT NO. | : 7,977,049 B2 | Page 1 of 1 |
| APPLICATION NO. | : 11/053185 | |
| DATED | : July 12, 2011 | |
| INVENTOR(S) | : David A. Sinclair et al. | |

It is certified that error appears in the above-identified patent and that said Letters Patent is hereby corrected as shown below:

In the Claims:

At column 160, line 1 (claim 54), "claim 50" should be replaced to read --claim 20--.

Signed and Sealed this
Sixth Day of December, 2011

David J. Kappos
*Director of the United States Patent and Trademark Office*

SEQUENCE LISTING

```
<160> NUMBER OF SEQ ID NOS: 49

<210> SEQ ID NO 1
<211> LENGTH: 1290
<212> TYPE: DNA
<213> ORGANISM: Saccharomyces cerevisiae
<220> FEATURE:
<221> NAME/KEY: CDS
<222> LOCATION: (1)..(1290)

<400> SEQUENCE: 1 atg tca gaa cca gtg ata aag tct ctt ttg gac aca gac atg tac aag      48
Met Ser Glu Pro Val Ile Lys Ser Leu Leu Asp Thr Asp Met Tyr Lys
 1               5                  10                  15 att acg atg cat gct gct gtc ttc act aat ttt cca gat gtt aca gtt      96
Ile Thr Met His Ala Ala Val Phe Thr Asn Phe Pro Asp Val Thr Val
             20                  25                  30 act tat aaa tat acc aac agg tcg tcc caa ttg acc ttc aat aag gaa     144
Thr Tyr Lys Tyr Thr Asn Arg Ser Ser Gln Leu Thr Phe Asn Lys Glu
         35                  40                  45 gcc att aat tgg ttg aaa gag caa ttt tcg tat ttg gga aat ttg agg     192
Ala Ile Asn Trp Leu Lys Glu Gln Phe Ser Tyr Leu Gly Asn Leu Arg
     50                  55                  60 ttc aca gaa gag gaa att gaa tac tta aaa cag gaa atc cca tat ttg     240
Phe Thr Glu Glu Glu Ile Glu Tyr Leu Lys Gln Glu Ile Pro Tyr Leu
 65                  70                  75                  80 cca tcg gca tat att aag tat att agc agt tct aat tac aaa cta cac     288
```

```
                Pro Ser Ala Tyr Ile Lys Tyr Ile Ser Ser Asn Tyr Lys Leu His
                                85                  90                  95 cct gaa gag cag att tcc ttc act tca gaa gaa atc gag ggc aag ccc         336
Pro Glu Glu Gln Ile Ser Phe Thr Ser Glu Glu Ile Glu Gly Lys Pro
                100                 105                 110 acc cac tac aaa ttg aaa att tta gtc agt ggt agt tgg aag gat act         384
Thr His Tyr Lys Leu Lys Ile Leu Val Ser Gly Ser Trp Lys Asp Thr
                115                 120                 125 atc ctt tat gag atc ccc tta ctg tcc cta ata tca gaa gcg tat ttt         432
Ile Leu Tyr Glu Ile Pro Leu Leu Ser Leu Ile Ser Glu Ala Tyr Phe
                130                 135                 140 aaa ttt gtt gac atc gac tgg gac tac gaa aac caa tta gaa caa gct         480
Lys Phe Val Asp Ile Asp Trp Asp Tyr Glu Asn Gln Leu Glu Gln Ala
145                 150                 155                 160 gag aag aag gcg gaa act ttg ttt gat aat ggt att aga ttc agt gaa         528
Glu Lys Lys Ala Glu Thr Leu Phe Asp Asn Gly Ile Arg Phe Ser Glu
                165                 170                 175 ttt ggt aca aga cgt cgt aga tct ctg aag gct caa gat cta att atg         576
Phe Gly Thr Arg Arg Arg Arg Ser Leu Lys Ala Gln Asp Leu Ile Met
                180                 185                 190 caa gga atc atg aaa gct gtg aac ggt aac cca gac aga aac aaa tcg         624
Gln Gly Ile Met Lys Ala Val Asn Gly Asn Pro Asp Arg Asn Lys Ser
                195                 200                 205 cta tta tta ggc aca tca aat att tta ttt gcc aag aaa tat gga gtc         672
Leu Leu Leu Gly Thr Ser Asn Ile Leu Phe Ala Lys Lys Tyr Gly Val
                210                 215                 220 aag cca atc ggt act gtg gct cac gag tgg gtt atg gga gtc gct tct         720
Lys Pro Ile Gly Thr Val Ala His Glu Trp Val Met Gly Val Ala Ser
225                 230                 235                 240 att agt gaa gat tat ttg cat gcc aat aaa aat gca atg gat tgt tgg         768
Ile Ser Glu Asp Tyr Leu His Ala Asn Lys Asn Ala Met Asp Cys Trp
                245                 250                 255 atc aat act ttt ggt gca aaa aat gct ggt tta gca tta acg gat act         816
Ile Asn Thr Phe Gly Ala Lys Asn Ala Gly Leu Ala Leu Thr Asp Thr
                260                 265                 270 ttt gga act gat gac ttt tta aaa tca ttc cgt cca cca tat tct gat         864
Phe Gly Thr Asp Asp Phe Leu Lys Ser Phe Arg Pro Pro Tyr Ser Asp
                275                 280                 285 gct tac gtc ggt gtt aga caa gat tct gga gac cca gtt gag tat acc         912
Ala Tyr Val Gly Val Arg Gln Asp Ser Gly Asp Pro Val Glu Tyr Thr
                290                 295                 300 aaa aag att tcc cac cat tac cat gac gtg ttg aaa ttg cct aaa ttc         960
Lys Lys Ile Ser His His Tyr His Asp Val Leu Lys Leu Pro Lys Phe
305                 310                 315                 320 tcg aag att atc tgt tat tcc gat tct ttg aac gtc gaa aag gca ata         1008
Ser Lys Ile Ile Cys Tyr Ser Asp Ser Leu Asn Val Glu Lys Ala Ile
                325                 330                 335 act tac tcc cat gca gct aaa gag aat gga atg cta gcc aca ttc ggt         1056
Thr Tyr Ser His Ala Ala Lys Glu Asn Gly Met Leu Ala Thr Phe Gly
                340                 345                 350 att ggc aca aac ttt act aat gat ttt cgt aag aag tca gaa ccc cag         1104
Ile Gly Thr Asn Phe Thr Asn Asp Phe Arg Lys Lys Ser Glu Pro Gln
                355                 360                 365 gtt aaa agt gag ccg tta aac atc gtt atc aaa cta tta gaa gta aat         1152
Val Lys Ser Glu Pro Leu Asn Ile Val Ile Lys Leu Leu Glu Val Asn
                370                 375                 380 ggt aat cac gct atc aaa att tct gat aac tta ggt aaa aat atg gga         1200
Gly Asn His Ala Ile Lys Ile Ser Asp Asn Leu Gly Lys Asn Met Gly
385                 390                 395                 400 gat cct gcc act gtg aag aga gtg aaa gag gaa ttg gga tat act gaa         1248
```

```
Asp Pro Ala Thr Val Lys Arg Val Lys Glu Glu Leu Gly Tyr Thr Glu
                405                 410                 415 cga agt tgg agt ggt gat aac gaa gcg cac aga tgg acc taa           1290
Arg Ser Trp Ser Gly Asp Asn Glu Ala His Arg Trp Thr
            420                 425
```

<210> SEQ ID NO 2
<211> LENGTH: 429
<212> TYPE: PRT
<213> ORGANISM: Saccharomyces cerevisiae

<400> SEQUENCE: 2

```
Met Ser Glu Pro Val Ile Lys Ser Leu Leu Asp Thr Asp Met Tyr Lys
 1               5                  10                  15

Ile Thr Met His Ala Ala Val Phe Thr Asn Phe Pro Asp Val Thr Val
                20                  25                  30

Thr Tyr Lys Tyr Thr Asn Arg Ser Ser Gln Leu Thr Phe Asn Lys Glu
            35                  40                  45

Ala Ile Asn Trp Leu Lys Glu Gln Phe Ser Tyr Leu Gly Asn Leu Arg
        50                  55                  60

Phe Thr Glu Glu Ile Glu Tyr Leu Lys Gln Glu Ile Pro Tyr Leu
 65                  70                  75                  80

Pro Ser Ala Tyr Ile Lys Tyr Ile Ser Ser Asn Tyr Lys Leu His
                85                  90                  95

Pro Glu Glu Gln Ile Ser Phe Thr Ser Glu Glu Ile Glu Gly Lys Pro
            100                 105                 110

Thr His Tyr Lys Leu Lys Ile Leu Val Ser Gly Ser Trp Lys Asp Thr
        115                 120                 125

Ile Leu Tyr Glu Ile Pro Leu Leu Ser Leu Ile Ser Glu Ala Tyr Phe
    130                 135                 140

Lys Phe Val Asp Ile Asp Trp Asp Tyr Glu Asn Gln Leu Glu Gln Ala
145                 150                 155                 160

Glu Lys Lys Ala Glu Thr Leu Phe Asp Asn Gly Ile Arg Phe Ser Glu
                165                 170                 175

Phe Gly Thr Arg Arg Arg Ser Leu Lys Ala Gln Asp Leu Ile Met
            180                 185                 190

Gln Gly Ile Met Lys Ala Val Asn Gly Asn Pro Asp Arg Asn Lys Ser
        195                 200                 205

Leu Leu Leu Gly Thr Ser Asn Ile Leu Phe Ala Lys Lys Tyr Gly Val
    210                 215                 220

Lys Pro Ile Gly Thr Val Ala His Glu Trp Val Met Gly Val Ala Ser
225                 230                 235                 240

Ile Ser Glu Asp Tyr Leu His Ala Asn Lys Asn Ala Met Asp Cys Trp
                245                 250                 255

Ile Asn Thr Phe Gly Ala Lys Asn Ala Gly Leu Ala Leu Thr Asp Thr
            260                 265                 270

Phe Gly Thr Asp Asp Phe Leu Lys Ser Phe Arg Pro Pro Tyr Ser Asp
        275                 280                 285

Ala Tyr Val Gly Val Arg Gln Asp Ser Gly Asp Pro Val Glu Tyr Thr
    290                 295                 300

Lys Lys Ile Ser His His Tyr His Asp Val Leu Lys Leu Pro Lys Phe
305                 310                 315                 320

Ser Lys Ile Ile Cys Tyr Ser Asp Ser Leu Asn Val Glu Lys Ala Ile
                325                 330                 335

Thr Tyr Ser His Ala Ala Lys Glu Asn Gly Met Leu Ala Thr Phe Gly
            340                 345                 350
```

```
Ile Gly Thr Asn Phe Thr Asn Asp Phe Arg Lys Lys Ser Glu Pro Gln
            355                 360                 365

Val Lys Ser Glu Pro Leu Asn Ile Val Ile Lys Leu Leu Glu Val Asn
    370                 375                 380

Gly Asn His Ala Ile Lys Ile Ser Asp Asn Leu Gly Lys Asn Met Gly
385                 390                 395                 400

Asp Pro Ala Thr Val Lys Arg Val Lys Glu Glu Leu Gly Tyr Thr Glu
                405                 410                 415

Arg Ser Trp Ser Gly Asp Asn Glu Ala His Arg Trp Thr
            420                 425

<210> SEQ ID NO 3
<211> LENGTH: 651
<212> TYPE: DNA
<213> ORGANISM: Saccharomyces cerevisiae
<220> FEATURE:
<221> NAME/KEY: CDS
<222> LOCATION: (1)..(651)

<400> SEQUENCE: 3 atg aag act tta att gtt gtt gat atg caa aat gat ttt att tca cct        48
Met Lys Thr Leu Ile Val Val Asp Met Gln Asn Asp Phe Ile Ser Pro
 1               5                  10                  15 tta ggt tcc ttg act gtt cca aaa ggt gag gaa tta atc aat cct atc        96
Leu Gly Ser Leu Thr Val Pro Lys Gly Glu Glu Leu Ile Asn Pro Ile
             20                  25                  30 tcg gat ttg atg caa gat gct gat aga gac tgg cac agg att gtg gtc       144
Ser Asp Leu Met Gln Asp Ala Asp Arg Asp Trp His Arg Ile Val Val
         35                  40                  45 acc aga gat tgg cac cct tcc aga cat att tcg ttc gca aag aac cat       192
Thr Arg Asp Trp His Pro Ser Arg His Ile Ser Phe Ala Lys Asn His
     50                  55                  60 aaa gat aaa gaa ccc tat tca aca tac acc tac cac tct cca agg cca       240
Lys Asp Lys Glu Pro Tyr Ser Thr Tyr Thr Tyr His Ser Pro Arg Pro
 65                  70                  75                  80 ggc gat gat tcc acg caa gag ggt att ttg tgg ccc gta cac tgt gtg       288
Gly Asp Asp Ser Thr Gln Glu Gly Ile Leu Trp Pro Val His Cys Val
                 85                  90                  95 aaa aac acc tgg ggt agt caa ttg gtt gac caa ata atg gac caa gtg       336
Lys Asn Thr Trp Gly Ser Gln Leu Val Asp Gln Ile Met Asp Gln Val
            100                 105                 110 gtc act aag cat att aag att gtc gac aag ggt ttc ttg act gac cgt       384
Val Thr Lys His Ile Lys Ile Val Asp Lys Gly Phe Leu Thr Asp Arg
        115                 120                 125 gaa tac tac tcc gcc ttc cac gac atc tgg aac ttc cat aag acc gac       432
Glu Tyr Tyr Ser Ala Phe His Asp Ile Trp Asn Phe His Lys Thr Asp
    130                 135                 140 atg aac aag tac tta gaa aag cat cat aca gac gag gtt tac att gtc       480
Met Asn Lys Tyr Leu Glu Lys His His Thr Asp Glu Val Tyr Ile Val
145                 150                 155                 160 ggt gta gct ttg gag tat tgt gtc aaa gcc acc gcc att tcc gct gca       528
Gly Val Ala Leu Glu Tyr Cys Val Lys Ala Thr Ala Ile Ser Ala Ala
                165                 170                 175 gaa cta ggt tat aag acc act gtc ctg ctg gat tac aca aga ccc atc       576
Glu Leu Gly Tyr Lys Thr Thr Val Leu Leu Asp Tyr Thr Arg Pro Ile
            180                 185                 190 agc gat gat ccc gaa gtc atc aat aag gtt aag gaa gag ttg aag gcc       624
Ser Asp Asp Pro Glu Val Ile Asn Lys Val Lys Glu Glu Leu Lys Ala
        195                 200                 205 cac aac atc aat gtc gtg gat aaa taa                                   651
```

His Asn Ile Asn Val Val Asp Lys
210                 215

<210> SEQ ID NO 4
<211> LENGTH: 216
<212> TYPE: PRT
<213> ORGANISM: Saccharomyces cerevisiae

<400> SEQUENCE: 4

Met Lys Thr Leu Ile Val Val Asp Met Gln Asn Asp Phe Ile Ser Pro
1               5                   10                  15

Leu Gly Ser Leu Thr Val Pro Lys Gly Glu Glu Leu Ile Asn Pro Ile
                20                  25                  30

Ser Asp Leu Met Gln Asp Ala Asp Arg Asp Trp His Arg Ile Val Val
            35                  40                  45

Thr Arg Asp Trp His Pro Ser Arg His Ile Ser Phe Ala Lys Asn His
        50                  55                  60

Lys Asp Lys Glu Pro Tyr Ser Thr Tyr Thr His Ser Pro Arg Pro
65                  70                  75                  80

Gly Asp Asp Ser Thr Gln Glu Gly Ile Leu Trp Pro Val His Cys Val
                85                  90                  95

Lys Asn Thr Trp Gly Ser Gln Leu Val Asp Gln Ile Met Asp Gln Val
                100                 105                 110

Val Thr Lys His Ile Lys Ile Val Asp Lys Gly Phe Leu Thr Asp Arg
            115                 120                 125

Glu Tyr Tyr Ser Ala Phe His Asp Ile Trp Asn Phe His Lys Thr Asp
        130                 135                 140

Met Asn Lys Tyr Leu Glu Lys His His Thr Asp Glu Val Tyr Ile Val
145                 150                 155                 160

Gly Val Ala Leu Glu Tyr Cys Val Lys Ala Thr Ala Ile Ser Ala Ala
                165                 170                 175

Glu Leu Gly Tyr Lys Thr Thr Val Leu Leu Asp Tyr Thr Arg Pro Ile
            180                 185                 190

Ser Asp Asp Pro Glu Val Ile Asn Lys Val Lys Glu Glu Leu Lys Ala
        195                 200                 205

His Asn Ile Asn Val Val Asp Lys
210                 215

<210> SEQ ID NO 5
<211> LENGTH: 1206
<212> TYPE: DNA
<213> ORGANISM: Saccharomyces cerevisiae
<220> FEATURE:
<221> NAME/KEY: CDS
<222> LOCATION: (1)..(1206)

<400> SEQUENCE: 5 atg gat ccc aca aga gct ccg gat ttc aaa ccg cca tct gca gac gag     48
Met Asp Pro Thr Arg Ala Pro Asp Phe Lys Pro Pro Ser Ala Asp Glu
1               5                   10                  15 gaa ttg att cct cca ccc gac ccg gaa tct aaa att ccc aaa tct att     96
Glu Leu Ile Pro Pro Pro Asp Pro Glu Ser Lys Ile Pro Lys Ser Ile
                20                  25                  30 cca att att cca tac gtc tta gcc gat gcg aat tcc tct ata gat gca    144
Pro Ile Ile Pro Tyr Val Leu Ala Asp Ala Asn Ser Ser Ile Asp Ala
            35                  40                  45 cct ttt aat att aag agg aag aaa aag cat cct aag cat cat cat cac    192
Pro Phe Asn Ile Lys Arg Lys Lys Lys His Pro Lys His His His His
        50                  55                  60

| | | |
|---|---|---|
| cat cat cac agt cgt aaa gaa ggc aat gat aaa aaa cat cag cat att<br>His His His Ser Arg Lys Glu Gly Asn Asp Lys Lys His Gln His Ile<br>65                                 70                       75                         80 | 240 |
| cca ttg aac caa gac gac ttt caa cca ctt tcc gca gaa gtg tct tcc<br>Pro Leu Asn Gln Asp Asp Phe Gln Pro Leu Ser Ala Glu Val Ser Ser<br>85                       90                       95 | 288 |
| gaa gat gat gac gcg gat ttt aga tcc aag gag aga tac ggt tca gat<br>Glu Asp Asp Asp Ala Asp Phe Arg Ser Lys Glu Arg Tyr Gly Ser Asp<br>100                     105                     110 | 336 |
| tca acc aca gaa tca gaa act aga ggt gtt cag aaa tat cag att gct<br>Ser Thr Thr Glu Ser Glu Thr Arg Gly Val Gln Lys Tyr Gln Ile Ala<br>             115                     120                     125 | 384 |
| gat tta gaa gaa gtt cca cat gga atc gtt cgt caa gca aga acc ttg<br>Asp Leu Glu Glu Val Pro His Gly Ile Val Arg Gln Ala Arg Thr Leu<br>130                     135                     140 | 432 |
| gaa gac tac gaa ttc ccc tca cac aga tta tcg aaa aaa tta ctg gat<br>Glu Asp Tyr Glu Phe Pro Ser His Arg Leu Ser Lys Lys Leu Leu Asp<br>145                     150                     155                     160 | 480 |
| cca aat aaa ctg ccg tta gta ata gta gca tgt ggg tct ttt tca cca<br>Pro Asn Lys Leu Pro Leu Val Ile Val Ala Cys Gly Ser Phe Ser Pro<br>                     165                     170                     175 | 528 |
| atc acc tac ttg cat cta aga atg ttt gaa atg gct tta gat gca atc<br>Ile Thr Tyr Leu His Leu Arg Met Phe Glu Met Ala Leu Asp Ala Ile<br>180                     185                     190 | 576 |
| tct gaa caa aca agg ttt gaa gtc ata ggt gga tat tac tcc cct gtt<br>Ser Glu Gln Thr Arg Phe Glu Val Ile Gly Gly Tyr Tyr Ser Pro Val<br>             195                     200                     205 | 624 |
| agt gat aac tat caa aag caa ggc ttg gcc cca tcc tac cat aga gta<br>Ser Asp Asn Tyr Gln Lys Gln Gly Leu Ala Pro Ser Tyr His Arg Val<br>210                     215                     220 | 672 |
| cgt atg tgt gaa ttg gcc tgc gaa aga acc tca tct tgg ttg atg gtg<br>Arg Met Cys Glu Leu Ala Cys Glu Arg Thr Ser Ser Trp Leu Met Val<br>225                     230                     235                     240 | 720 |
| gat gca tgg gag tca ttg caa cct tca tac aca aga act gcc aag gtc<br>Asp Ala Trp Glu Ser Leu Gln Pro Ser Tyr Thr Arg Thr Ala Lys Val<br>                     245                     250                     255 | 768 |
| ttg gat cat ttc aat cac gaa atc aat att aag aga ggt ggt gta gct<br>Leu Asp His Phe Asn His Glu Ile Asn Ile Lys Arg Gly Gly Val Ala<br>260                     265                     270 | 816 |
| act gtt act gga gaa aaa att ggt gtg aaa ata atg ttg ctg gct ggt<br>Thr Val Thr Gly Glu Lys Ile Gly Val Lys Ile Met Leu Leu Ala Gly<br>             275                     280                     285 | 864 |
| ggt gac cta ata gag tca atg ggt gaa cca aac gtt tgg gcg gac gcc<br>Gly Asp Leu Ile Glu Ser Met Gly Glu Pro Asn Val Trp Ala Asp Ala<br>290                     295                     300 | 912 |
| gat tta cat cac att ctc ggt aat tac ggt tgt ttg att gtc gaa cgt<br>Asp Leu His His Ile Leu Gly Asn Tyr Gly Cys Leu Ile Val Glu Arg<br>305                     310                     315                     320 | 960 |
| act ggt tct gat gta agg tct ttt ttg tta tcc cat gat att atg tat<br>Thr Gly Ser Asp Val Arg Ser Phe Leu Leu Ser His Asp Ile Met Tyr<br>             325                     330                     335 | 1008 |
| gaa cat aga agg aat att ctt atc atc aag caa ctc atc tat aat gat<br>Glu His Arg Arg Asn Ile Leu Ile Ile Lys Gln Leu Ile Tyr Asn Asp<br>340                     345                     350 | 1056 |
| att tct tcc acg aaa gtt cgt cta ttt atc aga cgc gcc atg tct gta<br>Ile Ser Ser Thr Lys Val Arg Leu Phe Ile Arg Arg Ala Met Ser Val<br>             355                     360                     365 | 1104 |
| caa tat ttg tta cct aat tcg gtc atc agg tat atc caa gaa cat aga<br>Gln Tyr Leu Leu Pro Asn Ser Val Ile Arg Tyr Ile Gln Glu His Arg<br>370                     375                     380 | 1152 |

```
cta tat gtg gac caa acc gaa cct gtt aag caa gtt ctt gga aac aaa    1200
Leu Tyr Val Asp Gln Thr Glu Pro Val Lys Gln Val Leu Gly Asn Lys
385                 390                 395                 400 gaa tga                                                            1206
Glu
```

<210> SEQ ID NO 6
<211> LENGTH: 401
<212> TYPE: PRT
<213> ORGANISM: Saccharomyces cerevisiae

<400> SEQUENCE: 6

```
Met Asp Pro Thr Arg Ala Pro Asp Phe Lys Pro Ser Ala Asp Glu
1               5                   10                  15

Glu Leu Ile Pro Pro Asp Pro Glu Ser Lys Ile Pro Lys Ser Ile
                20                  25                  30

Pro Ile Ile Pro Tyr Val Leu Ala Asp Ala Asn Ser Ser Ile Asp Ala
            35                  40                  45

Pro Phe Asn Ile Lys Arg Lys Lys His Pro Lys His His His
    50                  55                  60

His His His Ser Arg Lys Glu Gly Asn Asp Lys Lys His Gln His Ile
65                  70                  75                  80

Pro Leu Asn Gln Asp Asp Phe Gln Pro Leu Ser Ala Glu Val Ser Ser
                85                  90                  95

Glu Asp Asp Asp Ala Asp Phe Arg Ser Lys Glu Arg Tyr Gly Ser Asp
                100                 105                 110

Ser Thr Thr Glu Ser Gly Thr Arg Gly Val Gln Lys Tyr Gln Ile Ala
            115                 120                 125

Asp Leu Glu Glu Val Pro His Gly Ile Val Arg Gln Ala Arg Thr Leu
130                 135                 140

Glu Asp Tyr Glu Phe Pro Ser His Arg Leu Ser Lys Lys Leu Leu Asp
145                 150                 155                 160

Pro Asn Lys Leu Pro Leu Val Ile Val Ala Cys Gly Ser Phe Ser Pro
                165                 170                 175

Ile Thr Tyr Leu His Leu Arg Met Phe Glu Met Ala Leu Asp Ala Ile
            180                 185                 190

Ser Glu Gln Thr Arg Phe Glu Val Ile Gly Gly Tyr Tyr Ser Pro Val
        195                 200                 205

Ser Asp Asn Tyr Gln Lys Gln Gly Leu Ala Pro Ser Tyr His Arg Val
210                 215                 220

Arg Met Cys Glu Leu Ala Cys Glu Arg Thr Ser Ser Trp Leu Met Val
225                 230                 235                 240

Asp Ala Trp Glu Ser Leu Gln Pro Ser Tyr Thr Arg Thr Ala Lys Val
                245                 250                 255

Leu Asp His Phe Asn His Glu Ile Asn Ile Lys Arg Gly Gly Val Ala
            260                 265                 270

Thr Val Thr Gly Glu Lys Ile Gly Val Lys Ile Met Leu Leu Ala Gly
        275                 280                 285

Gly Asp Leu Ile Glu Ser Met Gly Glu Pro Asn Val Trp Ala Asp Ala
290                 295                 300

Asp Leu His His Ile Leu Gly Asn Tyr Gly Cys Leu Ile Val Glu Arg
305                 310                 315                 320

Thr Gly Ser Asp Val Arg Ser Phe Leu Leu Ser His Asp Ile Met Tyr
                325                 330                 335

Glu His Arg Arg Asn Ile Leu Ile Ile Lys Gln Leu Ile Tyr Asn Asp
            340                 345                 350
```

```
Ile Ser Ser Thr Lys Val Arg Leu Phe Ile Arg Arg Ala Met Ser Val
            355                 360                 365

Gln Tyr Leu Leu Pro Asn Ser Val Ile Arg Tyr Ile Gln Glu His Arg
        370                 375                 380

Leu Tyr Val Asp Gln Thr Glu Pro Val Lys Gln Val Leu Gly Asn Lys
385                 390                 395                 400

Glu

<210> SEQ ID NO 7
<211> LENGTH: 1188
<212> TYPE: DNA
<213> ORGANISM: Saccharomyces cerevisiae
<220> FEATURE:
<221> NAME/KEY: CDS
<222> LOCATION: (1)..(1188)

<400> SEQUENCE: 7 atg gat ccc acc aaa gca ccc gat ttt aaa ccg cca cag cca aat gaa      48
Met Asp Pro Thr Lys Ala Pro Asp Phe Lys Pro Pro Gln Pro Asn Glu
  1               5                  10                  15 gaa cta caa cca ccg cca gat cca aca cat acg ata cca aaa tct gga      96
Glu Leu Gln Pro Pro Pro Asp Pro Thr His Thr Ile Pro Lys Ser Gly
             20                  25                  30 ccc ata gtt cca tat gtt tta gct gat tat aat tct tcg atc gat gct     144
Pro Ile Val Pro Tyr Val Leu Ala Asp Tyr Asn Ser Ser Ile Asp Ala
         35                  40                  45 cct ttc aat ctc gac att tac aaa acc ctg tcg tca agg aaa aaa aac     192
Pro Phe Asn Leu Asp Ile Tyr Lys Thr Leu Ser Ser Arg Lys Lys Asn
     50                  55                  60 gcc aac tca agc aac cga atg gac cat att cca tta aat act agt gac     240
Ala Asn Ser Ser Asn Arg Met Asp His Ile Pro Leu Asn Thr Ser Asp
 65                  70                  75                  80 ttc cag cca cta tct cgg gat gta tca tcg gag gag gaa agt gaa ggg     288
Phe Gln Pro Leu Ser Arg Asp Val Ser Ser Glu Glu Glu Ser Glu Gly
                 85                  90                  95 caa tcg aat gga att gac gct act cta cag gat gtt acg atg act ggg     336
Gln Ser Asn Gly Ile Asp Ala Thr Leu Gln Asp Val Thr Met Thr Gly
            100                 105                 110 aat ttg ggg gta ctg aag agc caa att gct gat ttg gaa gaa gtt cct     384
Asn Leu Gly Val Leu Lys Ser Gln Ile Ala Asp Leu Glu Glu Val Pro
        115                 120                 125 cac aca att gta aga caa gcc aga act att gaa gat tac gaa ttt cct     432
His Thr Ile Val Arg Gln Ala Arg Thr Ile Glu Asp Tyr Glu Phe Pro
    130                 135                 140 gta cac aga ttg acg aaa aag tta caa gat cct gaa aaa ctg cct ctg     480
Val His Arg Leu Thr Lys Lys Leu Gln Asp Pro Glu Lys Leu Pro Leu
145                 150                 155                 160 atc atc gtt gct tgt gga tca ttt tct ccc ata aca tac cta cat ttg     528
Ile Ile Val Ala Cys Gly Ser Phe Ser Pro Ile Thr Tyr Leu His Leu
                165                 170                 175 aga atg ttt gaa atg gct tta gat gat atc aat gag caa acg cgt ttt     576
Arg Met Phe Glu Met Ala Leu Asp Asp Ile Asn Glu Gln Thr Arg Phe
            180                 185                 190 gaa gtg gtt ggt ggt tat ttt tct cca gta agt gat aac tat caa aag     624
Glu Val Val Gly Gly Tyr Phe Ser Pro Val Ser Asp Asn Tyr Gln Lys
        195                 200                 205 cga ggg tta gcc cca gct tat cat cgt gtc cgc atg tgc gaa tta gca     672
Arg Gly Leu Ala Pro Ala Tyr His Arg Val Arg Met Cys Glu Leu Ala
    210                 215                 220 tgc gag cgg aca tca tct tgg tta atg gtt gat gcc tgg gaa tct tta     720
```

-continued

```
Cys Glu Arg Thr Ser Ser Trp Leu Met Val Asp Ala Trp Glu Ser Leu
225                 230                 235                 240 caa tca agt tat aca agg aca gca aaa gtc ttg gac cat ttc aat cat       768
Gln Ser Ser Tyr Thr Arg Thr Ala Lys Val Leu Asp His Phe Asn His
                245                 250                 255 gaa ata aat atc aag aga ggt gga atc atg act gta gat ggt gaa aaa       816
Glu Ile Asn Ile Lys Arg Gly Gly Ile Met Thr Val Asp Gly Glu Lys
            260                 265                 270 atg ggc gta aaa atc atg tta ttg gca ggc ggt gat ctt atc gaa tcc       864
Met Gly Val Lys Ile Met Leu Leu Ala Gly Gly Asp Leu Ile Glu Ser
        275                 280                 285 atg ggc gag cct cat gtg tgg gct gat tca gac ctg cac cat att ttg       912
Met Gly Glu Pro His Val Trp Ala Asp Ser Asp Leu His His Ile Leu
    290                 295                 300 ggt aat tat gga tgt ttg atc gtg gaa agg act ggt tct gat gtt agg       960
Gly Asn Tyr Gly Cys Leu Ile Val Glu Arg Thr Gly Ser Asp Val Arg
305                 310                 315                 320 tcc ttc ttg ctt tcc cat gat atc atg tat gaa cac aga aga aat atc      1008
Ser Phe Leu Leu Ser His Asp Ile Met Tyr Glu His Arg Arg Asn Ile
                325                 330                 335 ctt att atc aaa caa ctt att tac aat gat att tcc tct acg aaa gtg      1056
Leu Ile Ile Lys Gln Leu Ile Tyr Asn Asp Ile Ser Ser Thr Lys Val
            340                 345                 350 cgg ctt ttc atc aga cgt gga atg tca gtt caa tat ctt ctt cca aac      1104
Arg Leu Phe Ile Arg Arg Gly Met Ser Val Gln Tyr Leu Leu Pro Asn
        355                 360                 365 tct gtc atc cgt tac atc caa gag tat aat cta tac att aat caa agt      1152
Ser Val Ile Arg Tyr Ile Gln Glu Tyr Asn Leu Tyr Ile Asn Gln Ser
    370                 375                 380 gaa ccg gtc aag cag gtc ttg gat agc aaa gag tga                       1188
Glu Pro Val Lys Gln Val Leu Asp Ser Lys Glu
385                 390                 395

<210> SEQ ID NO 8
<211> LENGTH: 395
<212> TYPE: PRT
<213> ORGANISM: Saccharomyces cerevisiae

<400> SEQUENCE: 8

Met Asp Pro Thr Lys Ala Pro Asp Phe Lys Pro Pro Gln Pro Asn Glu
1               5                   10                  15

Glu Leu Gln Pro Pro Asp Pro Thr His Thr Ile Pro Lys Ser Gly
            20                  25                  30

Pro Ile Val Pro Tyr Val Leu Ala Asp Tyr Asn Ser Ser Ile Asp Ala
        35                  40                  45

Pro Phe Asn Leu Asp Ile Tyr Lys Thr Leu Ser Ser Arg Lys Lys Asn
    50                  55                  60

Ala Asn Ser Ser Asn Arg Met Asp His Ile Pro Leu Asn Thr Ser Asp
65                  70                  75                  80

Phe Gln Pro Leu Ser Arg Asp Val Ser Ser Glu Glu Ser Glu Gly
                85                  90                  95

Gln Ser Asn Gly Ile Asp Ala Thr Leu Gln Asp Val Thr Met Thr Gly
            100                 105                 110

Asn Leu Gly Val Leu Lys Ser Gln Ile Ala Asp Leu Glu Glu Val Pro
        115                 120                 125

His Thr Ile Val Arg Gln Ala Arg Thr Ile Glu Asp Tyr Glu Phe Pro
    130                 135                 140

Val His Arg Leu Thr Lys Lys Leu Gln Asp Pro Glu Lys Leu Pro Leu
145                 150                 155                 160
```

```
Ile Ile Val Ala Cys Gly Ser Phe Ser Pro Ile Thr Tyr Leu His Leu
                165                 170                 175
Arg Met Phe Glu Met Ala Leu Asp Asp Ile Asn Glu Gln Thr Arg Phe
            180                 185                 190
Glu Val Gly Gly Tyr Phe Ser Pro Val Ser Asp Asn Tyr Gln Lys
            195                 200                 205
Arg Gly Leu Ala Pro Ala Tyr His Arg Val Arg Met Cys Glu Leu Ala
        210                 215                 220
Cys Glu Arg Thr Ser Ser Trp Leu Met Val Asp Ala Trp Glu Ser Leu
225                 230                 235                 240
Gln Ser Ser Tyr Thr Arg Thr Ala Lys Val Leu Asp His Phe Asn His
                245                 250                 255
Glu Ile Asn Ile Lys Arg Gly Gly Ile Met Thr Val Asp Gly Glu Lys
            260                 265                 270
Met Gly Val Lys Ile Met Leu Leu Ala Gly Gly Asp Leu Ile Glu Ser
        275                 280                 285
Met Gly Glu Pro His Val Trp Ala Asp Ser Asp Leu His His Ile Leu
    290                 295                 300
Gly Asn Tyr Gly Cys Leu Ile Val Glu Arg Thr Gly Ser Asp Val Arg
305                 310                 315                 320
Ser Phe Leu Leu Ser His Asp Ile Met Tyr Glu His Arg Arg Asn Ile
                325                 330                 335
Leu Ile Ile Lys Gln Leu Ile Tyr Asn Asp Ile Ser Ser Thr Lys Val
            340                 345                 350
Arg Leu Phe Ile Arg Arg Gly Met Ser Val Gln Tyr Leu Leu Pro Asn
        355                 360                 365
Ser Val Ile Arg Tyr Ile Gln Glu Tyr Asn Leu Tyr Ile Asn Gln Ser
    370                 375                 380
Glu Pro Val Lys Gln Val Leu Asp Ser Lys Glu
385                 390                 395

<210> SEQ ID NO 9
<211> LENGTH: 952
<212> TYPE: DNA
<213> ORGANISM: Homo sapiens
<220> FEATURE:
<221> NAME/KEY: CDS
<222> LOCATION: (118)..(912)

<400> SEQUENCE: 9
tgaactctgg atgctgttag cctgagactc aggaagacaa cttctgcagg gtcactccct     60
ggcttctgga ggaaagagaa ggagggcagt gctccagtgg tacagaagtg agacata      117 atg gaa tca ggc ttc acc tcc aag gac acc tat cta agc cat ttt aac     165
Met Glu Ser Gly Phe Thr Ser Lys Asp Thr Tyr Leu Ser His Phe Asn
  1               5                  10                  15 cct cgg gat tac cta gaa aaa tat tac aag ttt ggt tct agg cac tct     213
Pro Arg Asp Tyr Leu Glu Lys Tyr Tyr Lys Phe Gly Ser Arg His Ser
                 20                  25                  30 gca gaa agc cag att ctt aag cac ctt ctg aaa aat ctt ttc aag ata     261
Ala Glu Ser Gln Ile Leu Lys His Leu Leu Lys Asn Leu Phe Lys Ile
             35                  40                  45 ttc tgc cta gac ggt gtg aag gga gac ctg ctg att gac atc ggc tct     309
Phe Cys Leu Asp Gly Val Lys Gly Asp Leu Leu Ile Asp Ile Gly Ser
         50                  55                  60 ggc ccc act atc tat cag ctc ctc tct gct tgt gaa tcc ttt aag gag     357
Gly Pro Thr Ile Tyr Gln Leu Leu Ser Ala Cys Glu Ser Phe Lys Glu
 65                  70                  75                  80
```

-continued

| | | |
|---|---|---|
| atc gtc gtc act gac tac tca gac cag aac ctg cag gag ctg gag aag<br>Ile Val Val Thr Asp Tyr Ser Asp Gln Asn Leu Gln Glu Leu Glu Lys<br>                      85                      90                      95 | 405 |
| tgg ctg aag aaa gag cca gag gcc ttt gac tgg tcc cca gtg gtg acc<br>Trp Leu Lys Lys Glu Pro Glu Ala Phe Asp Trp Ser Pro Val Val Thr<br>                100                      105                      110 | 453 |
| tat gtg tgt gat ctt gaa ggg aac aga gtc aag ggt cca gag aag gag<br>Tyr Val Cys Asp Leu Glu Gly Asn Arg Val Lys Gly Pro Glu Lys Glu<br>        115                      120                      125 | 501 |
| gag aag ttg aga cag gcg gtc aag cag gtg ctg aag tgt gat gtg act<br>Glu Lys Leu Arg Gln Ala Val Lys Gln Val Leu Lys Cys Asp Val Thr<br>130                      135                      140 | 549 |
| cag agc cag cca ctg ggg gcc gtc ccc tta ccc ccg gct gac tgc gtg<br>Gln Ser Gln Pro Leu Gly Ala Val Pro Leu Pro Pro Ala Asp Cys Val<br>145                      150                      155                      160 | 597 |
| ctc agc aca ctg tgt ctg gat gcc gcc tgc cca gac ctc ccc acc tac<br>Leu Ser Thr Leu Cys Leu Asp Ala Ala Cys Pro Asp Leu Pro Thr Tyr<br>                165                      170                      175 | 645 |
| tgc agg gcg ctc agg aac ctc ggc agc cta ctg aag cca ggg ggc ttc<br>Cys Arg Ala Leu Arg Asn Leu Gly Ser Leu Leu Lys Pro Gly Gly Phe<br>        180                      185                      190 | 693 |
| ctg gtg atc atg gat gcg ctc aag agc agc tac tac atg att ggt gag<br>Leu Val Ile Met Asp Ala Leu Lys Ser Ser Tyr Tyr Met Ile Gly Glu<br>                195                      200                      205 | 741 |
| cag aag ttc tcc agc ctc ccc ctg ggc cgg gag gca gta gag gct gct<br>Gln Lys Phe Ser Ser Leu Pro Leu Gly Arg Glu Ala Val Glu Ala Ala<br>        210                      215                      220 | 789 |
| gtg aaa gag gct ggc tac aca atc gaa tgg ttt gag gtg atc tcg caa<br>Val Lys Glu Ala Gly Tyr Thr Ile Glu Trp Phe Glu Val Ile Ser Gln<br>225                      230                      235                      240 | 837 |
| agt tat tct tcc acc atg gcc aac aac gaa gga ctt ttc tcc ctg gtg<br>Ser Tyr Ser Ser Thr Met Ala Asn Asn Glu Gly Leu Phe Ser Leu Val<br>                245                      250                      255 | 885 |
| gcg agg aag ctg agc aga ccc ctg tga tgcctgtgac ctcaattaaa<br>Ala Arg Lys Leu Ser Arg Pro Leu<br>        260 | 932 |
| gcaattcctt tgacctgtca | 952 |

<210> SEQ ID NO 10
<211> LENGTH: 264
<212> TYPE: PRT
<213> ORGANISM: Homo sapiens

<400> SEQUENCE: 10

Met Glu Ser Gly Phe Thr Ser Lys Asp Thr Tyr Leu Ser His Phe Asn
1               5                   10                  15

Pro Arg Asp Tyr Leu Glu Lys Tyr Tyr Lys Phe Gly Ser Arg His Ser
            20                  25                  30

Ala Glu Ser Gln Ile Leu Lys His Leu Leu Lys Asn Leu Phe Lys Ile
        35                  40                  45

Phe Cys Leu Asp Gly Val Lys Gly Asp Leu Leu Ile Asp Ile Gly Ser
    50                  55                  60

Gly Pro Thr Ile Tyr Gln Leu Leu Ser Ala Cys Glu Ser Phe Lys Glu
65                  70                  75                  80

Ile Val Val Thr Asp Tyr Ser Asp Gln Asn Leu Gln Glu Leu Glu Lys
                85                  90                  95

Trp Leu Lys Lys Glu Pro Glu Ala Phe Asp Trp Ser Pro Val Val Thr
            100                 105                 110

```
Tyr Val Cys Asp Leu Glu Gly Asn Arg Val Lys Gly Pro Glu Lys Glu
        115                 120                 125

Glu Lys Leu Arg Gln Ala Val Lys Gln Val Leu Lys Cys Asp Val Thr
    130                 135                 140

Gln Ser Gln Pro Leu Gly Ala Val Pro Leu Pro Pro Ala Asp Cys Val
145                 150                 155                 160

Leu Ser Thr Leu Cys Leu Asp Ala Ala Cys Pro Asp Leu Pro Thr Tyr
                165                 170                 175

Cys Arg Ala Leu Arg Asn Leu Gly Ser Leu Leu Lys Pro Gly Gly Phe
            180                 185                 190

Leu Val Ile Met Asp Ala Leu Lys Ser Ser Tyr Tyr Met Ile Gly Glu
        195                 200                 205

Gln Lys Phe Ser Ser Leu Pro Leu Gly Arg Glu Ala Val Glu Ala Ala
    210                 215                 220

Val Lys Glu Ala Gly Tyr Thr Ile Glu Trp Phe Glu Val Ile Ser Gln
225                 230                 235                 240

Ser Tyr Ser Ser Thr Met Ala Asn Asn Glu Gly Leu Phe Ser Leu Val
                245                 250                 255

Ala Arg Lys Leu Ser Arg Pro Leu
            260

<210> SEQ ID NO 11
<211> LENGTH: 1240
<212> TYPE: DNA
<213> ORGANISM: Homo sapiens
<220> FEATURE:
<221> NAME/KEY: CDS
<222> LOCATION: (38)..(1144)

<400> SEQUENCE: 11
gagctcgcag cgcgcggccc ctgtcctccg gcccgag atg aat cct gcg gca gaa        55
                                        Met Asn Pro Ala Ala Glu
                                          1               5 gcc gag ttc aac atc ctc ctg gcc acc gac tcc tac aag gtt act cac       103
Ala Glu Phe Asn Ile Leu Leu Ala Thr Asp Ser Tyr Lys Val Thr His
            10                  15                  20 tat aaa caa tat cca ccc aac aca agc aaa gtt tat tcc tac ttt gaa       151
Tyr Lys Gln Tyr Pro Pro Asn Thr Ser Lys Val Tyr Ser Tyr Phe Glu
        25                  30                  35 tgc cgt gaa aag aag aca gaa aac tcc aaa tta agg aag gtg aaa tat       199
Cys Arg Glu Lys Lys Thr Glu Asn Ser Lys Leu Arg Lys Val Lys Tyr
    40                  45                  50 gag gaa aca gta ttt tat ggg ttg cag tac att ctt aat aag tac tta       247
Glu Glu Thr Val Phe Tyr Gly Leu Gln Tyr Ile Leu Asn Lys Tyr Leu
55                  60                  65                  70 aaa ggt aaa gta gta acc aaa gag aaa atc cag gaa gcc aaa gat gtc       295
Lys Gly Lys Val Val Thr Lys Glu Lys Ile Gln Glu Ala Lys Asp Val
                75                  80                  85 tac aaa gaa cat ttc caa gat gat gtc ttt aat gaa aag gga tgg aac       343
Tyr Lys Glu His Phe Gln Asp Asp Val Phe Asn Glu Lys Gly Trp Asn
            90                  95                 100 tac att ctt gag aag tat gat ggg cat ctt cca ata gaa ata aaa gct       391
Tyr Ile Leu Glu Lys Tyr Asp Gly His Leu Pro Ile Glu Ile Lys Ala
        105                 110                 115 gtt cct gag ggc ttt gtc att ccc aga gga aat gtt ctc ttc acg gtg       439
Val Pro Glu Gly Phe Val Ile Pro Arg Gly Asn Val Leu Phe Thr Val
    120                 125                 130 gaa aac aca gat cca gag tgt tac tgg ctt aca aat tgg att gag act       487
Glu Asn Thr Asp Pro Glu Cys Tyr Trp Leu Thr Asn Trp Ile Glu Thr
135                 140                 145                 150
```

```
att ctt gtt cag tcc tgg tat cca atc aca gtg gcc aca aat tct aga      535
Ile Leu Val Gln Ser Trp Tyr Pro Ile Thr Val Ala Thr Asn Ser Arg
            155                 160                 165 gag cag aag aaa ata ttg gcc aaa tat ttg tta gaa act tct ggt aac      583
Glu Gln Lys Lys Ile Leu Ala Lys Tyr Leu Leu Glu Thr Ser Gly Asn
        170                 175                 180 tta gat ggt ctg gaa tac aag tta cat gat ttt ggc tac aga gga gtc      631
Leu Asp Gly Leu Glu Tyr Lys Leu His Asp Phe Gly Tyr Arg Gly Val
    185                 190                 195 tct tcc caa gag act gct ggc ata gga gca tct gct cac ttg gtt aac      679
Ser Ser Gln Glu Thr Ala Gly Ile Gly Ala Ser Ala His Leu Val Asn
200                 205                 210 ttc aaa gga aca gat aca gta gca ggt ctt gct cta att aaa aaa tat      727
Phe Lys Gly Thr Asp Thr Val Ala Gly Leu Ala Leu Ile Lys Lys Tyr
215                 220                 225                 230 tat gga acg aaa gat cct gtt cca ggc tat tct gtt cca gca gca gaa      775
Tyr Gly Thr Lys Asp Pro Val Pro Gly Tyr Ser Val Pro Ala Ala Glu
            235                 240                 245 cac agt acc ata aca gct tgg ggg aaa gac cat gaa aaa gat gct ttt      823
His Ser Thr Ile Thr Ala Trp Gly Lys Asp His Glu Lys Asp Ala Phe
        250                 255                 260 gaa cat att gta aca cag ttt tca tca gtg cct gta tct gtg gtc agc      871
Glu His Ile Val Thr Gln Phe Ser Ser Val Pro Val Ser Val Val Ser
    265                 270                 275 gat agc tat gac att tat aat gcg tgt gag aaa ata tgg ggt gaa gat      919
Asp Ser Tyr Asp Ile Tyr Asn Ala Cys Glu Lys Ile Trp Gly Glu Asp
280                 285                 290 cta aga cat tta ata gta tcg aga agt aca cag gca cca cta ata atc      967
Leu Arg His Leu Ile Val Ser Arg Ser Thr Gln Ala Pro Leu Ile Ile
295                 300                 305                 310 aga cct gat tct gga aac cct ctt gac act gtg tta aag gtt ttg gag     1015
Arg Pro Asp Ser Gly Asn Pro Leu Asp Thr Val Leu Lys Val Leu Glu
            315                 320                 325 att tta ggt aag aag ttt cct gtt act gag aac tca aag ggt tac aag     1063
Ile Leu Gly Lys Lys Phe Pro Val Thr Glu Asn Ser Lys Gly Tyr Lys
        330                 335                 340 ttg ctg cca cct tat ctt aga gtt att caa ggg gat gga gta gat att     1111
Leu Leu Pro Pro Tyr Leu Arg Val Ile Gln Gly Asp Gly Val Asp Ile
    345                 350                 355 aat acc tta caa gag gta tgt gtt tta tat taa aagtttcaat aaggcatttc   1164
Asn Thr Leu Gln Glu Val Cys Val Leu Tyr
360                 365 ttataattaa gtttgtttat gtttgataaa gaacacaata taaatacaaa aaaaaaaaa    1224 aaaaaaaaaa aaaaaa                                                   1240

<210> SEQ ID NO 12
<211> LENGTH: 368
<212> TYPE: PRT
<213> ORGANISM: Homo sapiens

<400> SEQUENCE: 12

Met Asn Pro Ala Ala Glu Ala Glu Phe Asn Ile Leu Leu Ala Thr Asp
 1               5                  10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Glu Thr Val Phe Tyr Gly Leu Gln Tyr
    50                  55                  60
```

```
Ile Leu Asn Lys Tyr Leu Lys Gly Lys Val Val Thr Lys Glu Lys Ile
 65                  70                  75                  80

Gln Glu Ala Lys Asp Val Tyr Lys Glu His Phe Gln Asp Asp Val Phe
                 85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125

Asn Val Leu Phe Thr Val Glu Asn Thr Asp Pro Glu Cys Tyr Trp Leu
    130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Leu
    210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
            260                 265                 270

Pro Val Ser Val Val Ser Asp Ser Tyr Asp Ile Tyr Asn Ala Cys Glu
        275                 280                 285

Lys Ile Trp Gly Glu Asp Leu Arg His Leu Ile Val Ser Arg Ser Thr
    290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
                325                 330                 335

Asn Ser Lys Gly Tyr Lys Leu Leu Pro Pro Tyr Leu Arg Val Ile Gln
            340                 345                 350

Gly Asp Gly Val Asp Ile Asn Thr Leu Gln Glu Val Cys Val Leu Tyr
        355                 360                 365

<210> SEQ ID NO 13
<211> LENGTH: 1011
<212> TYPE: DNA
<213> ORGANISM: Homo sapiens
<220> FEATURE:
<221> NAME/KEY: CDS
<222> LOCATION: (4)..(936)

<400> SEQUENCE: 13 ccg atg ttg gcg cca gca gct ggt gag ggc cct ggg gtg gac ctg gcg     48
    Met Leu Ala Pro Ala Ala Gly Glu Gly Pro Gly Val Asp Leu Ala
     1               5                  10                  15 gcc aaa gcc cag gtg tgg ctg gag cag gtg tgt gcc cac ctg ggg ctg     96
Ala Lys Ala Gln Val Trp Leu Glu Gln Val Cys Ala His Leu Gly Leu
                 20                  25                  30 ggg gtg cag gag cca cat cca ggc gag cgg gca gcc ttt gtg gcc tat    144
Gly Val Gln Glu Pro His Pro Gly Glu Arg Ala Ala Phe Val Ala Tyr
            35                  40                  45
```

```
gcc ttg gct ttt ccc cgg gcc ttc cag ggc ctc ctg gac acc tac agc      192
Ala Leu Ala Phe Pro Arg Ala Phe Gln Gly Leu Leu Asp Thr Tyr Ser
         50                  55                  60 gtg tgg agg agt ggt ctc ccc aac ttc cta gca gtc gcc ttg gcc ctg      240
Val Trp Arg Ser Gly Leu Pro Asn Phe Leu Ala Val Ala Leu Ala Leu
 65                  70                  75 gga gag ctg ggc tac cgg gca gtg ggc gtg agg ctg gac agt ggt gac      288
Gly Glu Leu Gly Tyr Arg Ala Val Gly Val Arg Leu Asp Ser Gly Asp
 80                  85                  90                  95 ctg cta cag cag gct cag gag atc cgc aag gtc ttc cga gct gct gca      336
Leu Leu Gln Gln Ala Gln Glu Ile Arg Lys Val Phe Arg Ala Ala Ala
                100                 105                 110 gcc cag ttc cag gtg ccc tgg ctg gag tca gtc ctc atc gta gtc agc      384
Ala Gln Phe Gln Val Pro Trp Leu Glu Ser Val Leu Ile Val Val Ser
             115                 120                 125 aac aac att gac gag gag gcg ctg gcc cga ctg gcc cag gag ggc agt      432
Asn Asn Ile Asp Glu Glu Ala Leu Ala Arg Leu Ala Gln Glu Gly Ser
         130                 135                 140 gag gtg aat gtc att ggc att ggc acc agt gtg gtc acc tgc ccc caa      480
Glu Val Asn Val Ile Gly Ile Gly Thr Ser Val Val Thr Cys Pro Gln
145                 150                 155 cag cct tcc ctg ggt ggc gtc tat aag ctg gtg gcc gtg ggg ggc cag      528
Gln Pro Ser Leu Gly Gly Val Tyr Lys Leu Val Ala Val Gly Gly Gln
160                 165                 170                 175 cca cga atg aag ctg acc gag gac ccc gag aag cag acg ttg cct ggg      576
Pro Arg Met Lys Leu Thr Glu Asp Pro Glu Lys Gln Thr Leu Pro Gly
                180                 185                 190 agc aag gct gct ttc cgg ctc ctg ggc tct gac ggg tct cca ctc atg      624
Ser Lys Ala Ala Phe Arg Leu Leu Gly Ser Asp Gly Ser Pro Leu Met
             195                 200                 205 gac atg ctg cag tta gca gaa gag cca gtg cca cag gct ggg cag gag      672
Asp Met Leu Gln Leu Ala Glu Glu Pro Val Pro Gln Ala Gly Gln Glu
         210                 215                 220 ctg agg gtg tgg cct cca ggg gcc cag gag ccc tgc acc gtg agg cca      720
Leu Arg Val Trp Pro Pro Gly Ala Gln Glu Pro Cys Thr Val Arg Pro
225                 230                 235 gcc cag gtg gag cca cta ctg cgg ctc tgc ctc cag cag gga cag ctg      768
Ala Gln Val Glu Pro Leu Leu Arg Leu Cys Leu Gln Gln Gly Gln Leu
240                 245                 250                 255 tgt gag ccg ctc cca tcc ctg gca gag tct aga gcc ttg gcc cag ctg      816
Cys Glu Pro Leu Pro Ser Leu Ala Glu Ser Arg Ala Leu Ala Gln Leu
                260                 265                 270 tcc ctg agc cga ctc agc cct gag cac agg cgg ctg cgg agc cct gca      864
Ser Leu Ser Arg Leu Ser Pro Glu His Arg Arg Leu Arg Ser Pro Ala
             275                 280                 285 cag tac cag gtg gtg ctg tcc gag agg ctg cag gcc ctg gtg aac agt      912
Gln Tyr Gln Val Val Leu Ser Glu Arg Leu Gln Ala Leu Val Asn Ser
         290                 295                 300 ctg tgt gcg ggg cag tcc ccc tga gactcggagc ggggctgact ggaaacaaca    966
Leu Cys Ala Gly Gln Ser Pro
305                 310 cgaatcactc actttccccc aaaaaaaaaa aaaaaaaaa aaaaa                    1011

<210> SEQ ID NO 14
<211> LENGTH: 310
<212> TYPE: PRT
<213> ORGANISM: Homo sapiens

<400> SEQUENCE: 14

Met Leu Ala Pro Ala Ala Gly Glu Gly Pro Gly Val Asp Leu Ala Ala
```

```
         1               5                  10                 15
Lys Ala Gln Val Trp Leu Glu Gln Val Cys Ala His Leu Gly Leu Gly
                    20                  25                  30

Val Gln Glu Pro His Pro Gly Glu Arg Ala Ala Phe Val Ala Tyr Ala
                35                  40                  45

Leu Ala Phe Pro Arg Ala Phe Gln Gly Leu Leu Asp Thr Tyr Ser Val
            50                  55                  60

Trp Arg Ser Gly Leu Pro Asn Phe Leu Ala Val Ala Leu Ala Leu Gly
65                  70                  75                  80

Glu Leu Gly Tyr Arg Ala Val Gly Val Arg Leu Asp Ser Gly Asp Leu
                85                  90                  95

Leu Gln Gln Ala Gln Glu Ile Arg Lys Val Phe Arg Ala Ala Ala Ala
            100                 105                 110

Gln Phe Gln Val Pro Trp Leu Glu Ser Val Leu Ile Val Val Ser Asn
        115                 120                 125

Asn Ile Asp Glu Glu Ala Leu Ala Arg Leu Ala Gln Glu Gly Ser Glu
    130                 135                 140

Val Asn Val Ile Gly Ile Gly Thr Ser Val Val Thr Cys Pro Gln Gln
145                 150                 155                 160

Pro Ser Leu Gly Gly Val Tyr Lys Leu Val Ala Val Gly Gly Gln Pro
                165                 170                 175

Arg Met Lys Leu Thr Glu Asp Pro Glu Lys Gln Thr Leu Pro Gly Ser
            180                 185                 190

Lys Ala Ala Phe Arg Leu Leu Gly Ser Asp Gly Ser Pro Leu Met Asp
        195                 200                 205

Met Leu Gln Leu Ala Glu Glu Pro Val Pro Gln Ala Gly Gln Glu Leu
    210                 215                 220

Arg Val Trp Pro Pro Gly Ala Gln Glu Pro Cys Thr Val Arg Pro Ala
225                 230                 235                 240

Gln Val Glu Pro Leu Leu Arg Leu Cys Leu Gln Gly Gln Leu Cys
                245                 250                 255

Glu Pro Leu Pro Ser Leu Ala Glu Ser Arg Ala Leu Ala Gln Leu Ser
            260                 265                 270

Leu Ser Arg Leu Ser Pro Glu His Arg Arg Leu Arg Ser Pro Ala Gln
        275                 280                 285

Tyr Gln Val Val Leu Ser Glu Arg Leu Gln Ala Leu Val Asn Ser Leu
    290                 295                 300

Cys Ala Gly Gln Ser Pro
305                 310

<210> SEQ ID NO 15
<211> LENGTH: 1073
<212> TYPE: DNA
<213> ORGANISM: Homo sapiens
<220> FEATURE:
<221> NAME/KEY: CDS
<222> LOCATION: (71)..(688)

<400> SEQUENCE: 15
ggcacgaggg gtgccccgc ctcacctgca gagggccgt tccgggctcg aacccggcac      60
cttccggaaa atg gcg gct gcc agg ccc agc ctg ggc cga gtc ctc cca     109
            Met Ala Ala Ala Arg Pro Ser Leu Gly Arg Val Leu Pro
              1               5                  10 gga tcc tct gtc ctg ttc ctg tgt gac atg cag gag aag ttc cgc cac   157
Gly Ser Ser Val Leu Phe Leu Cys Asp Met Gln Glu Lys Phe Arg His
       15                  20                  25
```

```
aac atc gcc tac ttc cca cag atc gtc tca gtg gct gcc cgc atg ctc    205
Asn Ile Ala Tyr Phe Pro Gln Ile Val Ser Val Ala Ala Arg Met Leu
 30              35                  40                  45 aag gtg gcc cgg ctg ctt gag gtg cca gtc atg ctg acg gag cag tac    253
Lys Val Ala Arg Leu Leu Glu Val Pro Val Met Leu Thr Glu Gln Tyr
             50                  55                  60 cca caa ggc ctg ggc ccc acg gtg ccc gag ctg ggg act gag ggc ctt    301
Pro Gln Gly Leu Gly Pro Thr Val Pro Glu Leu Gly Thr Glu Gly Leu
                 65                  70                  75 cgg ccg ctg gcc aag acc tgc ttc agc atg gtg cct gcc ctg cag cag    349
Arg Pro Leu Ala Lys Thr Cys Phe Ser Met Val Pro Ala Leu Gln Gln
         80                  85                  90 gag ctg gac agt cgg ccc cag ctg cgc tct gtg ctg ctc tgt ggc att    397
Glu Leu Asp Ser Arg Pro Gln Leu Arg Ser Val Leu Leu Cys Gly Ile
     95                 100                 105 gag gca cag gcc tgc atc ttg aac acg acc ctg gac ctc cta gac cgg    445
Glu Ala Gln Ala Cys Ile Leu Asn Thr Thr Leu Asp Leu Leu Asp Arg
110             115                 120                 125 ggg ctg cag gtc cat gtg gtg gtg gac gcc tgc tcc tca cgc agc cag    493
Gly Leu Gln Val His Val Val Val Asp Ala Cys Ser Ser Arg Ser Gln
                130                 135                 140 gtg gac cgg ctg gtg gct ctg gcc cgc atg aga cag agt ggt gcc ttc    541
Val Asp Arg Leu Val Ala Leu Ala Arg Met Arg Gln Ser Gly Ala Phe
            145                 150                 155 ctc tcc acc agc gaa ggg ctc att ctg cag ctt gtg ggc gat gcc gtc    589
Leu Ser Thr Ser Glu Gly Leu Ile Leu Gln Leu Val Gly Asp Ala Val
        160                 165                 170 cac ccc cag ttc aag gag atc cag aaa ctc atc aag gag ccc gcc cca    637
His Pro Gln Phe Lys Glu Ile Gln Lys Leu Ile Lys Glu Pro Ala Pro
    175                 180                 185 gac agc gga ctg ctg ggc ctc ttc caa ggc cag aac tcc ctc ctc cac    685
Asp Ser Gly Leu Leu Gly Leu Phe Gln Gly Gln Asn Ser Leu Leu His
190                 195                 200                 205 tga actccaaccc tgccttgagg gaagaccacc ctcctgtcac ccggacctca          738
gtggaagccc gttcccccca tccctggatc ccaagagtgg tgcgatccac caggagtgcc   798
gcccccttgt gggggggggc agggtgctgc cttcccattg acagctgct cccggaaatg    858 caaatgagac tcctggaaac tgggtgggaa ttggctgagc caagatggag gcggggctcg   918 gcccccgggcc acttcacggg gcgggaaggg gaggggaaga agagtctcag actgtgggac  978
acggactcgc agaataaaca tatatgtggc aaaaaaaaaa aaaaaaaaaa aaaaaaaaaa  1038
aaaaaaaaaa aaaaaaaaaa aaaaaaaaaa aaaaa                             1073

<210> SEQ ID NO 16
<211> LENGTH: 205
<212> TYPE: PRT
<213> ORGANISM: Homo sapiens

<400> SEQUENCE: 16

Met Ala Ala Ala Arg Pro Ser Leu Gly Arg Val Leu Pro Gly Ser Ser
 1               5                  10                  15

Val Leu Phe Leu Cys Asp Met Gln Glu Lys Phe Arg His Asn Ile Ala
             20                  25                  30

Tyr Phe Pro Gln Ile Val Ser Val Ala Ala Arg Met Leu Lys Val Ala
         35                  40                  45

Arg Leu Leu Glu Val Pro Val Met Leu Thr Glu Gln Tyr Pro Gln Gly
     50                  55                  60

Leu Gly Pro Thr Val Pro Glu Leu Gly Thr Glu Gly Leu Arg Pro Leu
 65                  70                  75                  80
```

```
Ala Lys Thr Cys Phe Ser Met Val Pro Ala Leu Gln Gln Glu Leu Asp
            85                  90                  95

Ser Arg Pro Gln Leu Arg Ser Val Leu Leu Cys Gly Ile Glu Ala Gln
        100                 105                 110

Ala Cys Ile Leu Asn Thr Thr Leu Asp Leu Leu Asp Arg Gly Leu Gln
            115                 120                 125

Val His Val Val Val Asp Ala Cys Ser Ser Arg Ser Gln Val Asp Arg
    130                 135                 140

Leu Val Ala Leu Ala Arg Met Arg Gln Ser Gly Ala Phe Leu Ser Thr
145                 150                 155                 160

Ser Glu Gly Leu Ile Leu Gln Leu Val Gly Asp Ala Val His Pro Gln
                165                 170                 175

Phe Lys Glu Ile Gln Lys Leu Ile Lys Glu Pro Ala Pro Asp Ser Gly
            180                 185                 190

Leu Leu Gly Leu Phe Gln Gly Gln Asn Ser Leu Leu His
        195                 200                 205

<210> SEQ ID NO 17
<211> LENGTH: 1825
<212> TYPE: DNA
<213> ORGANISM: Homo sapiens
<220> FEATURE:
<221> NAME/KEY: CDS
<222> LOCATION: (144)..(983)

<400> SEQUENCE: 17
agagtgcgac cgagatgttc cactcgctgg cgtccgggcc gctggtgatc tccggtagca      60
ctcgggccgg cggacagtga gggcgcgaca acaagggagg tgtcacagtt ttccatttag     120
atcaacaact tcaagttctt acc atg gaa aat tcc gag aag act gaa gtg gtt     173
                         Met Glu Asn Ser Glu Lys Thr Glu Val Val
                           1               5                  10 ctc ctt gct tgt ggt tca ttc aat ccc atc acc aac atg cac ctc agg       221
Leu Leu Ala Cys Gly Ser Phe Asn Pro Ile Thr Asn Met His Leu Arg
                15                  20                  25 ttg ttt gag ctg gcc aag gac tac atg aat gga aca gga agg tac aca       269
Leu Phe Glu Leu Ala Lys Asp Tyr Met Asn Gly Thr Gly Arg Tyr Thr
            30                  35                  40 gtt gtc aaa ggc atc atc tct cct gtt ggt gat gcc tac aag aag aaa       317
Val Val Lys Gly Ile Ile Ser Pro Val Gly Asp Ala Tyr Lys Lys Lys
        45                  50                  55 gga ctc att cct gcc tat cac cgg gtc atc atg gca gaa ctt gct acc       365
Gly Leu Ile Pro Ala Tyr His Arg Val Ile Met Ala Glu Leu Ala Thr
    60                  65                  70 aag aat tct aaa tgg gtg gaa gtt gat aca tgg gaa agt ctt cag aag       413
Lys Asn Ser Lys Trp Val Glu Val Asp Thr Trp Glu Ser Leu Gln Lys
75                  80                  85                  90 gag tgg aaa gag act ctg aag gtg cta aga cac cat caa gag aaa ttg       461
Glu Trp Lys Glu Thr Leu Lys Val Leu Arg His His Gln Glu Lys Leu
                95                 100                 105 gag gct agt gac tgt gat cac cag cag aac tca cct act cta gaa agg       509
Glu Ala Ser Asp Cys Asp His Gln Gln Asn Ser Pro Thr Leu Glu Arg
            110                 115                 120 cct gga agg aag agg aag tgg act gaa aca caa gat tct agt caa aag       557
Pro Gly Arg Lys Arg Lys Trp Thr Glu Thr Gln Asp Ser Ser Gln Lys
        125                 130                 135 aaa tcc cta gag cca aaa aca aaa gct gtg cca aag gtc aag ctg ctg       605
Lys Ser Leu Glu Pro Lys Thr Lys Ala Val Pro Lys Val Lys Leu Leu
    140                 145                 150
```

-continued

```
tgt ggg gca gat tta ttg gag tcc ttt gct gtt ccc aat ttg tgg aag    653
Cys Gly Ala Asp Leu Leu Glu Ser Phe Ala Val Pro Asn Leu Trp Lys
155                 160                 165                 170 agt gaa gac atc acc caa atc gtg gcc aac tat ggg ctc ata tgt gtt    701
Ser Glu Asp Ile Thr Gln Ile Val Ala Asn Tyr Gly Leu Ile Cys Val
            175                 180                 185 act cgg gct gga aat gat gct cag aag ttt atc tat gaa tcg gat gtg    749
Thr Arg Ala Gly Asn Asp Ala Gln Lys Phe Ile Tyr Glu Ser Asp Val
        190                 195                 200 ctg tgg aaa cac cgg agc aac att cac gtg gtg aat gaa tgg atc gct    797
Leu Trp Lys His Arg Ser Asn Ile His Val Val Asn Glu Trp Ile Ala
    205                 210                 215 aat gac atc tca tcc aca aaa atc cgg aga gcc ctc aga agg ggc cag    845
Asn Asp Ile Ser Ser Thr Lys Ile Arg Arg Ala Leu Arg Arg Gly Gln
220                 225                 230 agc att cgc tac ttg gta cca gat ctt gtc caa gaa tac att gaa aag    893
Ser Ile Arg Tyr Leu Val Pro Asp Leu Val Gln Glu Tyr Ile Glu Lys
235                 240                 245                 250 cat aat ttg tac agc tct gag agt gaa gac agg aat gct ggg gtc atc    941
His Asn Leu Tyr Ser Ser Glu Ser Glu Asp Arg Asn Ala Gly Val Ile
            255                 260                 265 ctg gcc cct ttg cag aga aac act gca gaa gct aag aca tag           983
Leu Ala Pro Leu Gln Arg Asn Thr Ala Glu Ala Lys Thr
        270                 275 gaattctaca gcatgatatt tcagacttcc catttgggga tctgaaacaa tctgggagtt    1043
aataactggg gaaagaagtt gtgatctgtt gcctaaacta agcttaaaa gtttagtaaa    1103 aatcgtctgg gcacagtggc tcacgcctgt agtcccagct acttgggagg ctgaggcagg    1163
agaatcactt gaccccaggt ggtggaggtt gcagtgagcc aagattgcac cattgcactc    1223
cagcctggcg acagagcaag actctgtctc aaaaaaaaaa aaaaaattta gtaaaaatca    1283
atggtaagct aaaataagtt tttgtttgtt tatttgtttt tgagatggag tctctactaa    1343
aaatacaaaa aattagccag gcatggtgcc gcataactat aatcccagct acttgggagg    1403
ctgaggcagg agaatcgctt gaacccggga ggcacaggtt ccagtgggcc aaggttgtgc    1463
cactgcactc cagcctgggc aaaaaagcaa aactccatct caaagagaaa aaaaaaaag    1523 accgggtgtg gtggctcaca cctgtaatcc cagcactttg ggaggcctaa gtgggtggat    1583
cacgtgaggt caagagttca agaccagcct ggccaatatg gtgaaacccc atctctacta    1643
agaatacaaa aaattagctg agcatggtgg tgggctcctg tagtcccagc tacttgggag    1703
gctgaggcag gagaatcgct tgaacctggg aggcagaggt tgcagtaagc caagatcgtg    1763
ccattgcact ccagcctggg tgacagagcg agactccatc tcaaaaaaaa aaaaaaaaaa    1823
aa                                                                   1825
```

<210> SEQ ID NO 18
<211> LENGTH: 279
<212> TYPE: PRT
<213> ORGANISM: Homo sapiens

<400> SEQUENCE: 18

```
Met Glu Asn Ser Glu Lys Thr Glu Val Val Leu Leu Ala Cys Gly Ser
1               5                   10                  15

Phe Asn Pro Ile Thr Asn Met His Leu Arg Leu Phe Glu Leu Ala Lys
            20                  25                  30

Asp Tyr Met Asn Gly Thr Gly Arg Tyr Thr Val Val Lys Gly Ile Ile
        35                  40                  45

Ser Pro Val Gly Asp Ala Tyr Lys Lys Lys Gly Leu Ile Pro Ala Tyr
```

```
                50                      55                      60
His Arg Val Ile Met Ala Glu Leu Ala Thr Lys Asn Ser Lys Trp Val
 65                      70                      75                      80

Glu Val Asp Thr Trp Glu Ser Leu Gln Lys Glu Trp Lys Glu Thr Leu
                        85                      90                      95

Lys Val Leu Arg His His Gln Glu Lys Leu Glu Ala Ser Asp Cys Asp
                100                     105                     110

His Gln Gln Asn Ser Pro Thr Leu Glu Arg Pro Gly Arg Lys Arg Lys
            115                     120                     125

Trp Thr Glu Thr Gln Asp Ser Ser Gln Lys Lys Ser Leu Glu Pro Lys
130                     135                     140

Thr Lys Ala Val Pro Lys Val Lys Leu Leu Cys Gly Ala Asp Leu Leu
145                     150                     155                     160

Glu Ser Phe Ala Val Pro Asn Leu Trp Lys Ser Glu Asp Ile Thr Gln
                165                     170                     175

Ile Val Ala Asn Tyr Gly Leu Ile Cys Val Thr Arg Ala Gly Asn Asp
                180                     185                     190

Ala Gln Lys Phe Ile Tyr Glu Ser Asp Val Leu Trp Lys His Arg Ser
            195                     200                     205

Asn Ile His Val Val Asn Glu Trp Ile Ala Asn Asp Ile Ser Ser Thr
210                     215                     220

Lys Ile Arg Arg Ala Leu Arg Arg Gly Gln Ser Ile Arg Tyr Leu Val
225                     230                     235                     240

Pro Asp Leu Val Gln Glu Tyr Ile Glu Lys His Asn Leu Tyr Ser Ser
                245                     250                     255

Glu Ser Glu Asp Arg Asn Ala Gly Val Ile Leu Ala Pro Leu Gln Arg
            260                     265                     270

Asn Thr Ala Glu Ala Lys Thr
            275

<210> SEQ ID NO 19
<211> LENGTH: 5690
<212> TYPE: DNA
<213> ORGANISM: Homo sapiens
<220> FEATURE:
<221> NAME/KEY: CDS
<222> LOCATION: (338)..(1261)

<400> SEQUENCE: 19
atataaactc taaggaagac agtgatggag tgaagtgggc tgggggcgat agagaggatg    60
gggtggggca ccaggcgaga gatgcgaagg aagccagaac gaaaagagag cgaccgagga   120
gagaagagag cagagcaata caaaagcagc ctcggatcta gccggagctg caagcgttaa   180
ggggaggcgg agagtgacgc ggtttgcgtc tggagcggct ccttggagtc cacagcatcc   240
accgccggag cctcgccttc ctttctccct ctgcagacac aacgagacac aaaaagagag   300
gcaaccccta gaccaccgcg aaggacccat ctgcacc atg acc gag acc acc aag   355
                                          Met Thr Glu Thr Thr Lys
                                            1               5 acc cac gtt atc ttg ctc gcc tgc ggc agc ttc aat ccc atc acc aaa   403
Thr His Val Ile Leu Leu Ala Cys Gly Ser Phe Asn Pro Ile Thr Lys
                10                  15                  20 ggg cac att cag atg ttt gaa aga gcc agg gat tat ctg cac aaa act   451
Gly His Ile Gln Met Phe Glu Arg Ala Arg Asp Tyr Leu His Lys Thr
            25                  30                  35 gga agg ttt att gtg att ggc ggg att gtc tcc cct gtc cac gac tcc   499
Gly Arg Phe Ile Val Ile Gly Gly Ile Val Ser Pro Val His Asp Ser
        40                  45                  50
```

| | | | | | | | | | | | | | | | | |
|---|---|---|---|---|---|---|---|---|---|---|---|---|---|---|---|---|
| tat | gga | aaa | cag | ggc | ctc | gtg | tca | agc | cgg | cac | cgt | ctc | atc | atg | tgt | 547 |
| Tyr | Gly | Lys | Gln | Gly | Leu | Val | Ser | Ser | Arg | His | Arg | Leu | Ile | Met | Cys | |
| 55 | | | | 60 | | | | | 65 | | | | | 70 | | |
| cag | ctg | gcc | gtc | cag | aat | tct | gat | tgg | atc | agg | gtg | gac | cct | tgg | gag | 595 |
| Gln | Leu | Ala | Val | Gln | Asn | Ser | Asp | Trp | Ile | Arg | Val | Asp | Pro | Trp | Glu | |
| | | | 75 | | | | | 80 | | | | | 85 | | | |
| tgc | tac | cag | gac | acc | tgg | cag | acg | acc | tgc | agc | gtg | ttg | gaa | cac | cac | 643 |
| Cys | Tyr | Gln | Asp | Thr | Trp | Gln | Thr | Thr | Cys | Ser | Val | Leu | Glu | His | His | |
| | | 90 | | | | | 95 | | | | | 100 | | | | |
| cgg | gac | ctc | atg | aag | agg | gtg | act | ggc | tgc | atc | ctc | tcc | aat | gtc | aac | 691 |
| Arg | Asp | Leu | Met | Lys | Arg | Val | Thr | Gly | Cys | Ile | Leu | Ser | Asn | Val | Asn | |
| | 105 | | | | | 110 | | | | | 115 | | | | | |
| aca | cct | tcc | atg | aca | cct | gtg | atc | gga | cag | cca | caa | aac | gag | acc | ccc | 739 |
| Thr | Pro | Ser | Met | Thr | Pro | Val | Ile | Gly | Gln | Pro | Gln | Asn | Glu | Thr | Pro | |
| 120 | | | | | 125 | | | | | 130 | | | | | | |
| cag | ccc | att | tac | cag | aac | agc | aac | gtg | gcc | acc | aag | ccc | act | gca | gcc | 787 |
| Gln | Pro | Ile | Tyr | Gln | Asn | Ser | Asn | Val | Ala | Thr | Lys | Pro | Thr | Ala | Ala | |
| 135 | | | | 140 | | | | | 145 | | | | | 150 | | |
| aag | atc | ttg | ggg | aag | gtg | gga | gaa | agc | ctc | agc | cgg | atc | tgc | tgt | gtc | 835 |
| Lys | Ile | Leu | Gly | Lys | Val | Gly | Glu | Ser | Leu | Ser | Arg | Ile | Cys | Cys | Val | |
| | | | | 155 | | | | | 160 | | | | | 165 | | |
| cgc | ccg | ccg | gtg | gag | cgt | ttc | acc | ttt | gta | gat | gag | aat | gcc | aat | ctg | 883 |
| Arg | Pro | Pro | Val | Glu | Arg | Phe | Thr | Phe | Val | Asp | Glu | Asn | Ala | Asn | Leu | |
| | | 170 | | | | | 175 | | | | | 180 | | | | |
| ggc | acg | gtg | atg | cgg | tat | gaa | gag | att | gag | cta | cgg | atc | ctg | ctg | ctg | 931 |
| Gly | Thr | Val | Met | Arg | Tyr | Glu | Glu | Ile | Glu | Leu | Arg | Ile | Leu | Leu | Leu | |
| | 185 | | | | | 190 | | | | | 195 | | | | | |
| tgt | ggt | agt | gac | ctg | ctg | gag | tcc | ttc | tgc | atc | cca | ggg | ctc | tgg | aac | 979 |
| Cys | Gly | Ser | Asp | Leu | Leu | Glu | Ser | Phe | Cys | Ile | Pro | Gly | Leu | Trp | Asn | |
| 200 | | | | | 205 | | | | | 210 | | | | | | |
| gag | gca | gat | atg | gag | gtg | att | gtt | ggt | gac | ttt | ggg | att | gtg | gtg | gtg | 1027 |
| Glu | Ala | Asp | Met | Glu | Val | Ile | Val | Gly | Asp | Phe | Gly | Ile | Val | Val | Val | |
| 215 | | | | 220 | | | | | 225 | | | | | 230 | | |
| ccc | cgg | gat | gca | gcc | gac | aca | gac | cga | atc | atg | aat | cac | tcc | tca | ata | 1075 |
| Pro | Arg | Asp | Ala | Ala | Asp | Thr | Asp | Arg | Ile | Met | Asn | His | Ser | Ser | Ile | |
| | | | 235 | | | | | 240 | | | | | 245 | | | |
| ctc | cgc | aaa | tac | aaa | aac | aac | atc | atg | gtg | gtg | aag | gat | gac | atc | aac | 1123 |
| Leu | Arg | Lys | Tyr | Lys | Asn | Asn | Ile | Met | Val | Val | Lys | Asp | Asp | Ile | Asn | |
| | | 250 | | | | | 255 | | | | | 260 | | | | |
| cat | ccc | atg | tct | gtt | gtc | agc | tca | acc | aag | agc | agg | ctg | gcc | ctg | cag | 1171 |
| His | Pro | Met | Ser | Val | Val | Ser | Ser | Thr | Lys | Ser | Arg | Leu | Ala | Leu | Gln | |
| | 265 | | | | | 270 | | | | | 275 | | | | | |
| cat | ggg | gac | ggc | cat | gtt | gtg | gat | tac | ctg | tcc | cag | ccg | gtc | atc | gac | 1219 |
| His | Gly | Asp | Gly | His | Val | Val | Asp | Tyr | Leu | Ser | Gln | Pro | Val | Ile | Asp | |
| 280 | | | | | 285 | | | | | 290 | | | | | | |
| tac | atc | ctc | aaa | agc | cag | ctg | tac | atc | aat | gcc | tcc | ggc | tag | | | 1261 |
| Tyr | Ile | Leu | Lys | Ser | Gln | Leu | Tyr | Ile | Asn | Ala | Ser | Gly | | | | |
| 295 | | | | 300 | | | | | 305 | | | | | | | |

| | | | | |
|---|---|---|---|---|
| cagcccctcg | tcctccggca | acacaatggc | ccctccatct | tgtcagccc | cctgtttctc | 1321 |
| tcctgcctct | ctgtttctcc | atctcctcgt | cttgactgtt | ttccctactt | gctgacttaa | 1381 |
| ccccccatag | tgtgggggac | ctgcagagaa | ccatggcatt | ccctattcca | cagtcatctt | 1441 |
| tggacagact | ttcctctagt | ctccgggttg | ggggtgggtg | agggaatggg | gtgggagtcg | 1501 |
| ggggaagtgc | agtccttgga | gatgtactgg | tgtccgtctc | ccagcatgct | ctagagaggc | 1561 |
| ggctctggtg | cccatcctcc | cagcacgctc | tggggaggcg | gctctggtgc | ccatcctccc | 1621 |
| agcatgctct | agagaggcgg | ctctggtgcc | cctcctccca | gcatgctctg | ggaggcggc | 1681 |
| tctggctctt | gccttcccag | catgcccttt | actacaaagg | gctatttttc | ttttctttct | 1741 |

```
tttgtttatt tattttttctt tgttcactcc ctgtagaact tggatgaaat cagtgtccat    1801
ggttctttat gtttgtagtc ttgatgtgct cctgtggtat tacttcccct ctgataggac    1861
attgtagcca gcctcagcac tcagtgagtt catcagggcc acacccagta gagaaggcca    1921
agcaacctcc acttcttcag caccacacac acgcacacac acacacacgc acacatgcgt    1981
gtgcacccgc gcacgcacat acacacacac atatagcagt agcagcagca gcagcagcag    2041
cagcaacctt tgatcaggag tgagattttc gggttctgaa acctgggaca cgagtctgtg    2101
aatagtcggt tttctcagaa taatttgaat ctgttttctt agtttcaaat gaccatttcc    2161
ctgatgctct gagcttatga tcacacagag ccagtccatc ctcatttcct ggtggcatct    2221
gttcatttac ctttgtggac tgtagctgat ggcacagtgc gggttcccta ccagccaggg    2281
gtttccaagg gacctttgga ggccatgctt agacacattc ctgtacctga aacaaccac     2341 ataggcagga ccagatccac atcgtgcagt cgtgtcataa aaaaacaaaa caaaacaaaa    2401
aaacactagg agtccactca accctggagg tctttgctaa ttggaattat gtattgtctg    2461
ttgggctggg aaatgtctct ttcatattgt aagtccagga tgaactagga gaaagcaatt    2521
tgttgccctg atgataactg atgattttca ccctctctag ctgaggtaac tcagacagtg    2581
catgaggtca gtttcttctt gagaagcagt gccttggtct tgtttctgtg gttggttcta    2641
gcccctgcag agcctgggag ctgcaggaac tgtctgagaa atctcccta ataggggagt     2701 gggttcccag aagggagatc tgggaggggt caggagccac taagttgctt cactccttt     2761 ttctctaatt ttctaccttc ctctctgttc ctgcagacag ttttgccagc tttgcttctg    2821
gttactaggg tctcatgcgt gtcctgcttg gagagccata aggaaattgc tgtcttgtgc    2881
tttgtgtctc tcatccagtc tctggctctt gggattctgg tctttgagaa atagtccctg    2941
agtattagga tacttttatc aaaatctagt accagctacg gccagaaagg gccaggtggg    3001
acctgaaagc aaagacaatg ttcttttacca cacgtttcac atctgcaaca tccttcaatt    3061
gcgggaaaag gaacttgatt taacagaaga acatggtaga gcagcatcca gaaagtctgt    3121
tattcctctt ggatttttg aaataatctt cagaggaagg aaggaaaatc ctattttggg     3181
gtatcagtgt ttgactaggg atcatgaaat aataaactga aaaaaacttt agagttcagt    3241
tgatccaaca ctttccttta aaagttgagg gagcagaggc ccatgggatt aaatggctgg    3301
tccaggtcag ccagcaggtg tagggcctga caagaacata ttgtttccct gaccctagg     3361 ccgtcacacc acaccctcca tttcctcatg ttgctgacca ggtgcccata tgatttctac    3421
acttcccaag ccttaccctg gcatcttct tttaaattat atctgtccca ggtgctctcc     3481
acacatagga tggtaatgcc agtcccaggg gagggtgtga tagtaaggaa ggccactgtt    3541
aggtttcctt tagaaataaa gagatctcag cagcttggaa gaaatcccag aagcggaact    3601
ccatcaatcc aagaaagagt tgcttttgtgg aaggtgaagg aagacccaca gagtgctcag   3661
gatgatgcta ttgctggaga gcgaaagatg gaacagcctt gtccaggcag aacagtcata    3721
agccaggaaa tgaaacaaag gaaaacaggt gcctgaattt cctggggaaa catggcttgt    3781
ttaaggactt ggagttatgg atggaattta tgggacccac gtgagcagac ctgaggaagg    3841
ctcgatttct tttgtttctt ggtccactct gtcactctgc tctggtcaag ccccatttgg    3901
tctacagccc atgagaagga atgaggctgg ttctgcactc tcagcatgca gtccgaaagc    3961
atgtgggagt ggggagggaa agtgagatga attaagacaa agaacaggtg ccatagaagt    4021
agatttctag gaatgaagtg gggcagatct tatctttgtg gattacaggc actgtactaa    4081
aaacaggttt cctatttaat ataaaaagaa agtgaatctt cttttggata gaatcatcca    4141
```

-continued

```
ttcccatcgc cgcacccct acccccaaa cacacacaca cacacacaca cacacacaca    4201
cacacacaca cacacacaca cgccctactc ttcatttgct aggggaaggt cacagcacaa   4261
ctaaatccag dacaggacat tgtgaccatg acccagccac agtcaatacc agaaagatga   4321
ttcagagtct gaagtggtgc cccaggtgcc aacaggataa cctctacccc ccgactttgt   4381
ctctggggtc ctgttccttc ctgcaaagcc aatccaaga ctggcatggc tcagaggttg    4441
tgagaaaggc atggactgga acaatcatgt ccagaggggt ctggagcttt gtttcctgtt   4501
caccagcaaa aaatgtctct cccatttttc tgaaagtggc tgatgtaaga caggcagaa    4561
ggaaaaccct ttttgtcaat aactctgtcc ttaaggaatg gtcctctggg agggctgtgc   4621
tgctagtggg tacctcagtc acacaccccc aaccccaggc agcctctaga gccttcttgc   4681
tttcattttc cttgaatgta cataggaaca agggggaaag tctcttactg aagtgcctga   4741
aacccaaagc tagagcttct agagacgccg ttcttcctgt ctcagcttgg ccagcctttc   4801
aacaatgttc tctagtttca agctccagct tctcagaaag aattaaagaa cttgctgttc   4861
aaattaagta gaaagtgaga ctcaataata actgaactac agcaaaggc agagaattac    4921
agggagaaaa aacttgtact taccagccca attctactct cctcaaactg acacacacac   4981
acacacacac acacacacac acacacacac acacacactc ttttagggga ctaagagaga   5041
gaagcatgtt attacatttt actcatccaa acagtaatgc aaaaataaaa cggtagaata   5101
tgaaaagctc aggatctctc ccaaggctac ctactgcagg agggccaaca ggtgagatgg   5161
gaagaatgga aacagggacc gatttttgtag ctcatacaat taggacacct taggaatagc  5221
attgtagtaa tggtgatgaa tatgctctgc caaattcatc cagtctgcac catcttatag   5281
ctgcccagca cactcgactg ttcatgtggt ctctttgtag tgtgagtttg gagtgtccta   5341
ttagcctgtt ctggttagga atgagttaac ggctcttttcc ctcaaccttta gtctagtccc  5401
agggctgagg attcagctgg atccacatgg tcttgagggt tggcatgagg aggggggaagc  5461
tttttttgaat cgcttttttga tcacataatc tgccatttta agagtaagat ttgctttatg  5521
gaaatcaatt cattaataaa aaatgatatt caagttgcaa taccatttca cagtgaaata   5581
ttttgagtac aattttgttg ctagaatagt catgggcaag agtttatgc aaaatgtttc    5641
aattatgtta ataaataaga caatgcwaaa aaaaaaaaaa aaaaaaaa                5690
```

<210> SEQ ID NO 20
<211> LENGTH: 307
<212> TYPE: PRT
<213> ORGANISM: Homo sapiens

<400> SEQUENCE: 20

```
Met Thr Glu Thr Thr Lys Thr His Val Ile Leu Leu Ala Cys Gly Ser
  1               5                  10                  15

Phe Asn Pro Ile Thr Lys Gly His Ile Gln Met Phe Glu Arg Ala Arg
             20                  25                  30

Asp Tyr Leu His Lys Thr Gly Arg Phe Ile Val Ile Gly Gly Ile Val
         35                  40                  45

Ser Pro Val His Asp Ser Tyr Gly Lys Gln Gly Leu Val Ser Ser Arg
     50                  55                  60

His Arg Leu Ile Met Cys Gln Leu Ala Val Gln Asn Ser Asp Trp Ile
 65                  70                  75                  80

Arg Val Asp Pro Trp Glu Cys Tyr Gln Asp Thr Trp Gln Thr Thr Cys
                 85                  90                  95

Ser Val Leu Glu His His Arg Asp Leu Met Lys Arg Val Thr Gly Cys
```

```
                        100                 105                 110
Ile Leu Ser Asn Val Asn Thr Pro Ser Met Thr Pro Val Ile Gly Gln
            115                 120                 125

Pro Gln Asn Glu Thr Pro Gln Pro Ile Tyr Gln Asn Ser Asn Val Ala
        130                 135                 140

Thr Lys Pro Thr Ala Ala Lys Ile Leu Gly Lys Val Gly Glu Ser Leu
145                 150                 155                 160

Ser Arg Ile Cys Cys Val Arg Pro Val Glu Arg Phe Thr Phe Val
            165                 170                 175

Asp Glu Asn Ala Asn Leu Gly Thr Val Met Arg Tyr Glu Glu Ile Glu
            180                 185                 190

Leu Arg Ile Leu Leu Leu Cys Gly Ser Asp Leu Leu Glu Ser Phe Cys
            195                 200                 205

Ile Pro Gly Leu Trp Asn Glu Ala Asp Met Glu Val Ile Val Gly Asp
            210                 215                 220

Phe Gly Ile Val Val Pro Arg Asp Ala Ala Asp Thr Asp Arg Ile
225                 230                 235                 240

Met Asn His Ser Ser Ile Leu Arg Lys Tyr Lys Asn Asn Ile Met Val
                245                 250                 255

Val Lys Asp Asp Ile Asn His Pro Met Ser Val Val Ser Ser Thr Lys
            260                 265                 270

Ser Arg Leu Ala Leu Gln His Gly Asp Gly His Val Val Asp Tyr Leu
            275                 280                 285

Ser Gln Pro Val Ile Asp Tyr Ile Leu Lys Ser Gln Leu Tyr Ile Asn
            290                 295                 300

Ala Ser Gly
305

<210> SEQ ID NO 21
<211> LENGTH: 2376
<212> TYPE: DNA
<213> ORGANISM: Homo sapiens
<220> FEATURE:
<221> NAME/KEY: CDS
<222> LOCATION: (28)..(1503)

<400> SEQUENCE: 21
cgcgcggccc ctgtcctccg gcccgag atg aat cct gcg gca gaa gcc gag ttc      54
                             Met Asn Pro Ala Ala Glu Ala Glu Phe
                              1               5 aac atc ctc ctg gcc acc gac tcc tac aag gtt act cac tat aaa caa      102
Asn Ile Leu Leu Ala Thr Asp Ser Tyr Lys Val Thr His Tyr Lys Gln
 10                  15                  20                  25 tat cca ccc aac aca agc aaa gtt tat tcc tac ttt gaa tgc cgt gaa      150
Tyr Pro Pro Asn Thr Ser Lys Val Tyr Ser Tyr Phe Glu Cys Arg Glu
                 30                  35                  40 aag aag aca gaa aac tcc aaa tta agg aag gtg aaa tat gag gaa aca      198
Lys Lys Thr Glu Asn Ser Lys Leu Arg Lys Val Lys Tyr Glu Glu Thr
             45                  50                  55 gta ttt tat ggg ttg cag tac att ctt aat aag tac tta aaa ggt aaa      246
Val Phe Tyr Gly Leu Gln Tyr Ile Leu Asn Lys Tyr Leu Lys Gly Lys
         60                  65                  70 gta gta acc aaa gag aaa atc cag gaa gcc aaa gat gtc tac aaa gaa      294
Val Val Thr Lys Glu Lys Ile Gln Glu Ala Lys Asp Val Tyr Lys Glu
 75                  80                  85 cat ttc caa gat gat gtc ttt aat gaa aag gga tgg aac tac att ctt      342
His Phe Gln Asp Asp Val Phe Asn Glu Lys Gly Trp Asn Tyr Ile Leu
 90                  95                 100                 105
```

```
gag aag tat gat ggg cat ctt cca ata gaa ata aaa gct gtt cct gag    390
Glu Lys Tyr Asp Gly His Leu Pro Ile Glu Ile Lys Ala Val Pro Glu
            110                 115                 120 ggc ttt gtc att ccc aga gga aat gtt ctc ttc acg gtg gaa aac aca    438
Gly Phe Val Ile Pro Arg Gly Asn Val Leu Phe Thr Val Glu Asn Thr
        125                 130                 135 gat cca gag tgt tac tgg ctt aca aat tgg att gag act att ctt gtt    486
Asp Pro Glu Cys Tyr Trp Leu Thr Asn Trp Ile Glu Thr Ile Leu Val
        140                 145                 150 cag tcc tgg tat cca atc aca gtg gcc aca aat tct aga gag cag aag    534
Gln Ser Trp Tyr Pro Ile Thr Val Ala Thr Asn Ser Arg Glu Gln Lys
        155                 160                 165 aaa ata ttg gcc aaa tat ttg tta gaa act tct ggt aac tta gat ggt    582
Lys Ile Leu Ala Lys Tyr Leu Leu Glu Thr Ser Gly Asn Leu Asp Gly
170                 175                 180                 185 ctg gaa tac aag tta cat gat ttt ggc tac aga gga gtc tct tcc caa    630
Leu Glu Tyr Lys Leu His Asp Phe Gly Tyr Arg Gly Val Ser Ser Gln
            190                 195                 200 gag act gct ggc ata gga gca tct gct cac ttg gtt aac ttc aaa gga    678
Glu Thr Ala Gly Ile Gly Ala Ser Ala His Leu Val Asn Phe Lys Gly
            205                 210                 215 aca gat aca gta gca gga ctt gct cta att aaa aaa tat tat gga acg    726
Thr Asp Thr Val Ala Gly Leu Ala Leu Ile Lys Lys Tyr Tyr Gly Thr
        220                 225                 230 aaa gat cct gtt cca ggc tat tct gtt cca gca gca gaa cac agt acc    774
Lys Asp Pro Val Pro Gly Tyr Ser Val Pro Ala Ala Glu His Ser Thr
        235                 240                 245 ata aca gct tgg ggg aaa gac cat gaa aaa gat gct ttt gaa cat att    822
Ile Thr Ala Trp Gly Lys Asp His Glu Lys Asp Ala Phe Glu His Ile
250                 255                 260                 265 gta aca cag ttt tca tca gtg cct gta tct gtg gtc agc gat agc tat    870
Val Thr Gln Phe Ser Ser Val Pro Val Ser Val Val Ser Asp Ser Tyr
            270                 275                 280 gac att tat aat gcg tgt gag aaa ata tgg ggt gaa gat cta aga cat    918
Asp Ile Tyr Asn Ala Cys Glu Lys Ile Trp Gly Glu Asp Leu Arg His
            285                 290                 295 tta ata gta tcg aga agt aca cag gca cca cta ata atc aga cct gat    966
Leu Ile Val Ser Arg Ser Thr Gln Ala Pro Leu Ile Ile Arg Pro Asp
            300                 305                 310 tct gga aac cct ctt gac act gtg tta aag gtt ttg gag att tta ggt   1014
Ser Gly Asn Pro Leu Asp Thr Val Leu Lys Val Leu Glu Ile Leu Gly
            315                 320                 325 aag aag ttt cct gtt act gag aac tca aag ggt tac aag ttg ctg cca   1062
Lys Lys Phe Pro Val Thr Glu Asn Ser Lys Gly Tyr Lys Leu Leu Pro
330                 335                 340                 345 cct tat ctt aga gtt att caa ggg gat gga gta gat att aat acc tta   1110
Pro Tyr Leu Arg Val Ile Gln Gly Asp Gly Val Asp Ile Asn Thr Leu
            350                 355                 360 caa gag att gta gaa ggc atg aaa caa aaa atg tgg agt att gaa aat   1158
Gln Glu Ile Val Glu Gly Met Lys Gln Lys Met Trp Ser Ile Glu Asn
            365                 370                 375 att gcc ttc ggt tct ggt gga ggt ttg cta cag aag ttg aca aga gat   1206
Ile Ala Phe Gly Ser Gly Gly Gly Leu Leu Gln Lys Leu Thr Arg Asp
            380                 385                 390 ctc ttg aat tgt tcc ttc aag tgt agc tat gtt gta act aat ggc ctt   1254
Leu Leu Asn Cys Ser Phe Lys Cys Ser Tyr Val Val Thr Asn Gly Leu
            395                 400                 405 ggg att aac gtc ttc aag gac cca gtt gct gat ccc aac aaa agg tcc   1302
Gly Ile Asn Val Phe Lys Asp Pro Val Ala Asp Pro Asn Lys Arg Ser
410                 415                 420                 425
```

```
aaa aag ggc cga tta tct tta cat agg acg cca gca ggg aat ttt gtt     1350
Lys Lys Gly Arg Leu Ser Leu His Arg Thr Pro Ala Gly Asn Phe Val
            430                 435                 440 aca ctg gag gaa gga aaa gga gac ctt gag gaa tat ggt cag gat ctt     1398
Thr Leu Glu Glu Gly Lys Gly Asp Leu Glu Glu Tyr Gly Gln Asp Leu
        445                 450                 455 ctc cat act gtc ttc aag aat ggc aag gtg aca aaa agc tat tca ttt     1446
Leu His Thr Val Phe Lys Asn Gly Lys Val Thr Lys Ser Tyr Ser Phe
    460                 465                 470 gat gaa ata aga aaa aat gca cag ctg aat att gaa ctg gaa gca gca     1494
Asp Glu Ile Arg Lys Asn Ala Gln Leu Asn Ile Glu Leu Glu Ala Ala
    475                 480                 485 cat cat tag gctttatgac tgggtgtgtg ttgtgtgtat gtaatacata             1543
His His
490 atgtttattg tacagatgtg tggggtttgt gttttatgat acattacagc caaattattt   1603
gttggtttat ggacatactg ccctttcatt ttttttcttt tccagtgttt aggtgatctc   1663
aaattaggaa atgcatttaa ccatgtaaaa gatgagtgct aaagtaagct ttttagggcc   1723
ctttgccaat aggtagtcat tcaatctggt attgatcttt tcacaaataa cagaactgag   1783
aaactttat atataactga tgatcacata aaacagattt gcataaaatt accatgattg   1843
ctttatgttt atatttaact tgtattttg tacaaacaag attgtgtaag atatatttga   1903
agtttcagtg atttaacagt ctttccaact tttcatgatt tttatgagca cagactttca   1963
agaaaatact tgaaaataaa ttacattgcc ttttgtccat taatcagcaa ataaaacatg   2023
gccttaacaa agttgtttgt gttattgtac aatttgaaaa ttatgtcggg acataccca    2083
tagaattact aaccttactg cccccttgtag aatatgtatt aatcattcta cattaaagaa  2143
aataatggtt cttactggaa tgtctaggca ctgtacagtt attatatatc ttggttgttg   2203
tattgtacca gtgaaatgcc aaatttgaaa ggcctgtact gcaattttat atgtcagaga   2263
ttgcctgtgg ctctaatatg cacctcaaga ttttaaggag ataatgtttt tagagagaat   2323
ttctgcttcc actatagaat atatacataa atgtaaaata cttacaaaag tgg          2376
```

<210> SEQ ID NO 22
<211> LENGTH: 491
<212> TYPE: PRT
<213> ORGANISM: Homo sapiens

<400> SEQUENCE: 22

```
Met Asn Pro Ala Ala Glu Ala Glu Phe Asn Ile Leu Leu Ala Thr Asp
 1               5                  10                  15

Ser Tyr Lys Val Thr His Tyr Lys Gln Tyr Pro Pro Asn Thr Ser Lys
            20                  25                  30

Val Tyr Ser Tyr Phe Glu Cys Arg Glu Lys Lys Thr Glu Asn Ser Lys
        35                  40                  45

Leu Arg Lys Val Lys Tyr Glu Thr Val Phe Tyr Gly Leu Gln Tyr
    50                  55                  60

Ile Leu Asn Lys Tyr Leu Lys Gly Lys Val Val Thr Lys Glu Lys Ile
65                  70                  75                  80

Gln Glu Ala Lys Asp Val Tyr Lys Glu His Phe Gln Asp Asp Val Phe
                85                  90                  95

Asn Glu Lys Gly Trp Asn Tyr Ile Leu Glu Lys Tyr Asp Gly His Leu
            100                 105                 110

Pro Ile Glu Ile Lys Ala Val Pro Glu Gly Phe Val Ile Pro Arg Gly
        115                 120                 125
```

Asn Val Leu Phe Thr Val Glu Asn Thr Asp Pro Glu Cys Tyr Trp Leu
130                 135                 140

Thr Asn Trp Ile Glu Thr Ile Leu Val Gln Ser Trp Tyr Pro Ile Thr
145                 150                 155                 160

Val Ala Thr Asn Ser Arg Glu Gln Lys Lys Ile Leu Ala Lys Tyr Leu
                165                 170                 175

Leu Glu Thr Ser Gly Asn Leu Asp Gly Leu Glu Tyr Lys Leu His Asp
            180                 185                 190

Phe Gly Tyr Arg Gly Val Ser Ser Gln Glu Thr Ala Gly Ile Gly Ala
        195                 200                 205

Ser Ala His Leu Val Asn Phe Lys Gly Thr Asp Thr Val Ala Gly Leu
210                 215                 220

Ala Leu Ile Lys Lys Tyr Tyr Gly Thr Lys Asp Pro Val Pro Gly Tyr
225                 230                 235                 240

Ser Val Pro Ala Ala Glu His Ser Thr Ile Thr Ala Trp Gly Lys Asp
                245                 250                 255

His Glu Lys Asp Ala Phe Glu His Ile Val Thr Gln Phe Ser Ser Val
            260                 265                 270

Pro Val Ser Val Ser Asp Ser Tyr Asp Ile Tyr Asn Ala Cys Glu
        275                 280                 285

Lys Ile Trp Gly Glu Asp Leu Arg His Leu Ile Val Ser Arg Ser Thr
290                 295                 300

Gln Ala Pro Leu Ile Ile Arg Pro Asp Ser Gly Asn Pro Leu Asp Thr
305                 310                 315                 320

Val Leu Lys Val Leu Glu Ile Leu Gly Lys Lys Phe Pro Val Thr Glu
                325                 330                 335

Asn Ser Lys Gly Tyr Lys Leu Leu Pro Pro Tyr Leu Arg Val Ile Gln
            340                 345                 350

Gly Asp Gly Val Asp Ile Asn Thr Leu Gln Glu Ile Val Glu Gly Met
        355                 360                 365

Lys Gln Lys Met Trp Ser Ile Glu Asn Ile Ala Phe Gly Ser Gly Gly
370                 375                 380

Gly Leu Leu Gln Lys Leu Thr Arg Asp Leu Leu Asn Cys Ser Phe Lys
385                 390                 395                 400

Cys Ser Tyr Val Val Thr Asn Gly Leu Gly Ile Asn Val Phe Lys Asp
                405                 410                 415

Pro Val Ala Asp Pro Asn Lys Arg Ser Lys Lys Gly Arg Leu Ser Leu
            420                 425                 430

His Arg Thr Pro Ala Gly Asn Phe Val Thr Leu Glu Glu Gly Lys Gly
        435                 440                 445

Asp Leu Glu Glu Tyr Gly Gln Asp Leu Leu His Thr Val Phe Lys Asn
450                 455                 460

Gly Lys Val Thr Lys Ser Tyr Ser Phe Asp Glu Ile Arg Lys Asn Ala
465                 470                 475                 480

Gln Leu Asn Ile Glu Leu Glu Ala Ala His His
                485                 490

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
aaatccgctc gacactgtcc tgaa                                              24
```

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24

```
ttgggatcag caactgggtc ctta                                              24
```

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25

```
ttcctccctg gagaagagct atga                                              24
```

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
tactcctgct tgctgatcca catc                                              24
```

<210> SEQ ID NO 27
<211> LENGTH: 1172
<212> TYPE: DNA
<213> ORGANISM: Homo sapiens
<220> FEATURE:
<221> NAME/KEY: CDS
<222> LOCATION: (211)..(810)

<400> SEQUENCE: 27

```
aaagggcct ctggtgaccg cccctacctg gcatccctct aacccaggag gagcgtgggg        60 aaagggctg tgggcctctc ggggagcgag ctgcgggtag cggcgcactg ggtacaggcg       120
cgcgcttggc tgtcgcctct tccgctgtgt ttgggaggac tcgaactggc gccaggaaat     180
attaggaagc tgtgattttc aaagctaatt atg aaa aca ttt atc att gga atc     234
                                  Met Lys Thr Phe Ile Ile Gly Ile
                                    1               5 agt ggt gtg aca aac agt ggc aaa aca aca ctg gct aag aat ttg cag       282
Ser Gly Val Thr Asn Ser Gly Lys Thr Thr Leu Ala Lys Asn Leu Gln
       10                  15                  20 aaa cac ctc cca aat tgc agt gtc ata tct cag gat gat ttc ttc aag       330
Lys His Leu Pro Asn Cys Ser Val Ile Ser Gln Asp Asp Phe Phe Lys
 25                  30                  35                  40 cca gag tct gag ata gag aca gat aaa aat gga ttt ttg cag tac gat       378
Pro Glu Ser Glu Ile Glu Thr Asp Lys Asn Gly Phe Leu Gln Tyr Asp
                 45                  50                  55 gtg ctt gaa gca ctt aac atg gaa aaa atg atg tca gcc att tcc tgc       426
Val Leu Glu Ala Leu Asn Met Glu Lys Met Met Ser Ala Ile Ser Cys
             60                  65                  70 tgg atg gaa agc gca aga cac tct gtg gta tca aca gac cag gaa agt       474
Trp Met Glu Ser Ala Arg His Ser Val Val Ser Thr Asp Gln Glu Ser
```

```
                75                  80                  85
gct gag gaa att ccc att tta atc atc gaa ggt ttt ctt ctt ttt aat      522
Ala Glu Glu Ile Pro Ile Leu Ile Ile Glu Gly Phe Leu Leu Phe Asn
         90                  95                 100 tat aag ccc ctt gac act ata tgg aat aga agc tat ttc ctg act att      570
Tyr Lys Pro Leu Asp Thr Ile Trp Asn Arg Ser Tyr Phe Leu Thr Ile
105                 110                 115                 120 cca tat gaa gaa tgt aaa agg agg agg agt aca agg gtc tat cag cct      618
Pro Tyr Glu Glu Cys Lys Arg Arg Arg Ser Thr Arg Val Tyr Gln Pro
                125                 130                 135 cca gac tct ccg gga tac ttt gat ggc cat gtg tgg ccc atg tat cta      666
Pro Asp Ser Pro Gly Tyr Phe Asp Gly His Val Trp Pro Met Tyr Leu
        140                 145                 150 aag tac aga caa gaa atg cag gac atc aca tgg gaa gtt gtg tac ctg      714
Lys Tyr Arg Gln Glu Met Gln Asp Ile Thr Trp Glu Val Val Tyr Leu
                155                 160                 165 gat gga aca aaa tct gaa gag gac ctc ttt ttg caa gta tat gaa gat      762
Asp Gly Thr Lys Ser Glu Glu Asp Leu Phe Leu Gln Val Tyr Glu Asp
170                 175                 180 cta ata caa gaa cta gca aag caa aag tgt ttg caa gtg aca gca taa      810
Leu Ile Gln Glu Leu Ala Lys Gln Lys Cys Leu Gln Val Thr Ala
185                 190                 195 agacggaaca caacaaatcc ttcctgaagt gaattaggaa actccaagga gtaatttaag     870
aaccttcacc aagatacaat gtatactgtg gtacaatgac agccattgtt tcatatgttt     930
gatttttatt gcatggtt ttcccaacat gtggaacaat aaatatccat gccaatggac       990
aggactgtac cttagcaagt tgctccctct ccagggagcg catagataca gcagagctca    1050
cagtgagtca gaaagtctcc actttctgaa catagctcta taacaatgat tgtcaaactt    1110
ttctaactgg agctcagagt aagaaataaa gattacatca caatccaaaa aaaaaaaaaa    1170
aa                                                                   1172

<210> SEQ ID NO 28
<211> LENGTH: 199
<212> TYPE: PRT
<213> ORGANISM: Homo sapiens

<400> SEQUENCE: 28

Met Lys Thr Phe Ile Ile Gly Ile Ser Gly Val Thr Asn Ser Gly Lys
 1               5                  10                  15

Thr Thr Leu Ala Lys Asn Leu Gln Lys His Leu Pro Asn Cys Ser Val
                20                  25                  30

Ile Ser Gln Asp Asp Phe Phe Lys Pro Glu Ser Glu Ile Glu Thr Asp
            35                  40                  45

Lys Asn Gly Phe Leu Gln Tyr Asp Val Leu Glu Ala Leu Asn Met Glu
        50                  55                  60

Lys Met Met Ser Ala Ile Ser Cys Trp Met Glu Ser Ala Arg His Ser
65                  70                  75                  80

Val Val Ser Thr Asp Gln Glu Ser Ala Glu Glu Ile Pro Ile Leu Ile
                85                  90                  95

Ile Glu Gly Phe Leu Leu Phe Asn Tyr Lys Pro Leu Asp Thr Ile Trp
            100                 105                 110

Asn Arg Ser Tyr Phe Leu Thr Ile Pro Tyr Glu Glu Cys Lys Arg Arg
        115                 120                 125

Arg Ser Thr Arg Val Tyr Gln Pro Pro Asp Ser Pro Gly Tyr Phe Asp
    130                 135                 140

Gly His Val Trp Pro Met Tyr Leu Lys Tyr Arg Gln Glu Met Gln Asp
```

```
                       145                 150                 155                 160
Ile Thr Trp Glu Val Val Tyr Leu Asp Gly Thr Lys Ser Glu Asp
                165                 170                 175

Leu Phe Leu Gln Val Tyr Glu Asp Leu Ile Gln Glu Leu Ala Lys Gln
            180                 185                 190

Lys Cys Leu Gln Val Thr Ala
        195

<210> SEQ ID NO 29
<211> LENGTH: 1134
<212> TYPE: DNA
<213> ORGANISM: Homo sapiens
<220> FEATURE:
<221> NAME/KEY: CDS
<222> LOCATION: (301)..(993)

<400> SEQUENCE: 29
aatcatcttg ttggccctga cctcgttgga aaacgaagct ccccgcaggg tcccggcctc    60
tagggctgct gtgcgggcgg gggtggcctg gagctatttc cattcggcgg cgggaacagg   120
tgccggcgcc tccgcccat ccccaggggc cgcctccccc ggggcggcct ccaggctgcc    180
gagacctata aaggcgccag gttttctcaa tgaagccggg acgcactccg gagcgcactg   240
cgtggtcgca ccctacccgg gctgccttgg aagtcgtccc cgccgcccct ccgcaccggc   300 atg aag ctc atc gtg ggc atc gga ggc atg acc aac ggc ggc aag acc    348
Met Lys Leu Ile Val Gly Ile Gly Gly Met Thr Asn Gly Gly Lys Thr
  1               5                  10                  15 acg ctg acc aac agc ctg ctc aga gcc ctg ccc aac tgc tgc gtg atc    396
Thr Leu Thr Asn Ser Leu Leu Arg Ala Leu Pro Asn Cys Cys Val Ile
                 20                  25                  30 cat cag gat gac ttc ttc aag ccc caa gac caa ata gca gtt ggg gaa    444
His Gln Asp Asp Phe Phe Lys Pro Gln Asp Gln Ile Ala Val Gly Glu
             35                  40                  45 gac ggc ttc aaa cag tgg gac gtg ctg gag tct ctg gac atg gag gcc    492
Asp Gly Phe Lys Gln Trp Asp Val Leu Glu Ser Leu Asp Met Glu Ala
         50                  55                  60 atg ctg gac acc gtg cag gcc tgg ctg agc agc ccg cag aag ttt gcc    540
Met Leu Asp Thr Val Gln Ala Trp Leu Ser Ser Pro Gln Lys Phe Ala
 65                  70                  75                  80 cgt gcc cac ggg gtc agc gtc cag cca gag gcc tcg gac acc cac atc    588
Arg Ala His Gly Val Ser Val Gln Pro Glu Ala Ser Asp Thr His Ile
                 85                  90                  95 ctc ctc ctg gaa ggc ttc ctg ctc tac agc tac aag ccc ctg gtg gac    636
Leu Leu Leu Glu Gly Phe Leu Leu Tyr Ser Tyr Lys Pro Leu Val Asp
            100                 105                 110 ttg tac agc cgc cgg tac ttc ctg acc gtc ccg tat gaa gag tgc aag    684
Leu Tyr Ser Arg Arg Tyr Phe Leu Thr Val Pro Tyr Glu Glu Cys Lys
        115                 120                 125 tgg agg aga agt acc cgc aac tac aca gtc cct gat ccc ccc ggc ctc    732
Trp Arg Arg Ser Thr Arg Asn Tyr Thr Val Pro Asp Pro Pro Gly Leu
    130                 135                 140 ttc gat ggc cac gtg tgg ccc atg tac cag aag tat agg cag gag atg    780
Phe Asp Gly His Val Trp Pro Met Tyr Gln Lys Tyr Arg Gln Glu Met
145                 150                 155                 160 gag gcc aac ggt gtg gaa gtg gtc tac ctg gac ggc atg aag tcc cga    828
Glu Ala Asn Gly Val Glu Val Val Tyr Leu Asp Gly Met Lys Ser Arg
                165                 170                 175 gag gag ctc ttc cgt gaa gtc ctg gaa gac att cag aac tcg ctg ctg    876
Glu Glu Leu Phe Arg Glu Val Leu Glu Asp Ile Gln Asn Ser Leu Leu
            180                 185                 190
```

```
aac cgc tcc cag gaa tca gcc ccc tcc ccg gct cgc cca gcc agg aca    924
Asn Arg Ser Gln Glu Ser Ala Pro Ser Pro Ala Arg Pro Ala Arg Thr
        195                 200                 205 cag gga ccc gga cgc gga tgc ggc cac aga acg gcc agg cct gca gcg    972
Gln Gly Pro Gly Arg Gly Cys Gly His Arg Thr Ala Arg Pro Ala Ala
    210                 215                 220 tcc cag cag gac agc atg tga gcgtttccct atggggtgt ctgtacgtag        1023
Ser Gln Gln Asp Ser Met
225             230 gagagtggag gccccactcc cagttgggcg tcccggagct cagggactga gccccaagac  1083
gcctctgtaa cctcgctgca gcttcagtag taaactgggt cctgtttttt t           1134

<210> SEQ ID NO 30
<211> LENGTH: 230
<212> TYPE: PRT
<213> ORGANISM: Homo sapiens

<400> SEQUENCE: 30

Met Lys Leu Ile Val Gly Ile Gly Gly Met Thr Asn Gly Gly Lys Thr
  1               5                  10                  15

Thr Leu Thr Asn Ser Leu Leu Arg Ala Leu Pro Asn Cys Cys Val Ile
                 20                  25                  30

His Gln Asp Asp Phe Phe Lys Pro Gln Asp Gln Ile Ala Val Gly Glu
             35                  40                  45

Asp Gly Phe Lys Gln Trp Asp Val Leu Glu Ser Leu Asp Met Glu Ala
         50                  55                  60

Met Leu Asp Thr Val Gln Ala Trp Leu Ser Ser Pro Gln Lys Phe Ala
 65                  70                  75                  80

Arg Ala His Gly Val Ser Val Gln Pro Glu Ala Ser Asp Thr His Ile
                 85                  90                  95

Leu Leu Leu Glu Gly Phe Leu Leu Tyr Ser Tyr Lys Pro Leu Val Asp
            100                 105                 110

Leu Tyr Ser Arg Arg Tyr Phe Leu Thr Val Pro Tyr Glu Glu Cys Lys
        115                 120                 125

Trp Arg Arg Ser Thr Arg Asn Tyr Thr Val Pro Asp Pro Pro Gly Leu
    130                 135                 140

Phe Asp Gly His Val Trp Pro Met Tyr Gln Lys Tyr Arg Gln Glu Met
145                 150                 155                 160

Glu Ala Asn Gly Val Glu Val Val Tyr Leu Asp Gly Met Lys Ser Arg
                165                 170                 175

Glu Glu Leu Phe Arg Glu Val Leu Glu Asp Ile Gln Asn Ser Leu Leu
            180                 185                 190

Asn Arg Ser Gln Glu Ser Ala Pro Ser Pro Ala Arg Pro Ala Arg Thr
        195                 200                 205

Gln Gly Pro Gly Arg Gly Cys Gly His Arg Thr Ala Arg Pro Ala Ala
    210                 215                 220

Ser Gln Gln Asp Ser Met
225             230

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
```
caggcagtcc tttctatttc                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcttgttaac tctccgacag                                              20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
aatgtcttat caagaccgac                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tacagtccag aaatcgctcc                                              20

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gaaaggattt gcccggacag tttg                                         24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cttcttccca gtagcctgtt cctt                                         24

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gtggcattac tccacttcaa gtaag                                        25

-continued

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
caagagcaag acgatgggg                                                  19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttttccgctg aaccgttcca                                                 20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cattggcact catgaccttc                                                 20

<210> SEQ ID NO 41
<211> LENGTH: 40
<212> TYPE: PRT
<213> ORGANISM: Drosophila melanogaster

<400> SEQUENCE: 41

Phe Asp Gly Thr Ser Asn Val Leu Ala Gly Lys Leu Phe Asn Ile Pro
  1               5                  10                  15

Val Lys Gly Thr His Ala His Ala Tyr Ile Thr Ser Phe Ser Ser Ile
             20                  25                  30

Gly Glu Leu Lys Thr Arg Leu Ile
         35                  40

<210> SEQ ID NO 42
<211> LENGTH: 40
<212> TYPE: PRT
<213> ORGANISM: Caenorhabditis elegans

<400> SEQUENCE: 42

Phe Asp Ala Thr Ser Asn Val Leu Ala Gly Lys Leu Tyr Gly Ile Pro
  1               5                  10                  15

Val Lys Gly Thr Gln Ala His Ser Phe Ile Cys Ser Phe Ser Ser Pro
             20                  25                  30

Ala Glu Leu Lys Val Arg Leu Leu
         35                  40

<210> SEQ ID NO 43
<211> LENGTH: 40
<212> TYPE: PRT
<213> ORGANISM: Homo sapiens

<400> SEQUENCE: 43

Phe Asp Ser Ser Ser Asn Val Leu Ala Gly Gln Leu Arg Gly Val Pro
1               5                   10                  15

Val Ala Gly Thr Leu Ala His Ser Phe Val Thr Ser Phe Ser Gly Ser
            20                  25                  30

Glu Val Pro Pro Asp Pro Met Leu
        35                  40

<210> SEQ ID NO 44
<211> LENGTH: 37
<212> TYPE: PRT
<213> ORGANISM: Saccharomyces cerevisiae

<400> SEQUENCE: 44

Leu Leu Leu Gly Thr Ser Asn Ile Leu Phe Ala Lys Lys Tyr Gly Val
1               5                   10                  15

Lys Pro Ile Gly Thr Val Ala His Glu Trp Val Met Gly Val Ala Ser
            20                  25                  30

Ile Ser Glu Asp Tyr
        35

<210> SEQ ID NO 45
<211> LENGTH: 221
<212> TYPE: PRT
<213> ORGANISM: Homo sapiens

<400> SEQUENCE: 45

Met Ala Ala Ala Arg Pro Ser Leu Gly Arg Val Leu Pro Gly Ser Ser
1               5                   10                  15

Val Leu Phe Leu Cys Asp Met Gln Glu Lys Phe Arg His Asn Ile Ala
            20                  25                  30

Tyr Phe Pro Gln Ile Val Ser Val Ala Ala Arg Met Leu Lys Val Ala
        35                  40                  45

Arg Leu Leu Glu Val Pro Val Met Leu Thr Glu Gln Tyr Pro Gln Gly
    50                  55                  60

Leu Gly Pro Thr Val Pro Glu Leu Gly Thr Glu Gly Leu Arg Pro Leu
65                  70                  75                  80

Ala Lys Thr Cys Phe Ser Met Val Pro Ala Leu Gln Gln Glu Leu Asp
                85                  90                  95

Ser Arg Pro Gln Leu Arg Ser Val Leu Leu Cys Gly Ile Glu Ala Gln
            100                 105                 110

Ala Cys Ile Leu Asp Pro Arg Ser Tyr Pro Gly Leu Ala Leu Thr Ser
        115                 120                 125

Leu Tyr Pro Gln Asn Thr Thr Leu Asp Leu Leu Asp Arg Gly Leu Gln
    130                 135                 140

Val His Val Val Asp Ala Cys Ser Ser Arg Ser Gln Val Asp Arg
145                 150                 155                 160

Leu Val Ala Leu Ala Arg Met Arg Gln Ser Gly Ala Phe Leu Ser Thr
                165                 170                 175

Ser Glu Gly Leu Ile Leu Gln Leu Val Gly Asp Ala Val His Pro Gln
            180                 185                 190

Phe Lys Glu Ile Gln Lys Leu Ile Lys Glu Pro Ala Pro Asp Ser Gly
        195                 200                 205

Leu Leu Gly Leu Phe Gln Gly Gln Asn Ser Leu Leu His
    210                 215                 220

<210> SEQ ID NO 46
<211> LENGTH: 241

```
<212> TYPE: PRT
<213> ORGANISM: Homo sapiens

<400> SEQUENCE: 46

Tyr Gly Asp Gln Ile Asp Met His Arg Lys Phe Val Val Gln Leu Phe
 1               5                  10                  15

Ala Glu Glu Trp Gly Gln Tyr Val Asp Leu Pro Lys Gly Phe Ala Val
             20                  25                  30

Ser Glu Arg Cys Lys Val Arg Leu Val Pro Leu Gln Ile Gln Leu Thr
         35                  40                  45

Thr Leu Gly Asn Leu Thr Pro Ser Ser Thr Val Phe Phe Cys Cys Asp
     50                  55                  60

Met Gln Glu Arg Phe Arg Pro Ala Ile Lys Tyr Phe Gly Asp Ile Ile
 65                  70                  75                  80

Ser Val Gly Gln Arg Leu Leu Gln Gly Ala Arg Ile Leu Gly Ile Pro
                 85                  90                  95

Val Ile Val Thr Glu Gln Tyr Pro Lys Gly Leu Gly Ser Thr Val Gln
             100                 105                 110

Glu Ile Asp Leu Thr Gly Val Lys Leu Val Leu Pro Lys Thr Lys Phe
         115                 120                 125

Ser Met Val Leu Pro Glu Val Glu Ala Ala Leu Ala Glu Ile Pro Gly
     130                 135                 140

Val Arg Ser Val Val Leu Phe Gly Val Glu Thr His Val Cys Ile Gln
145                 150                 155                 160

Gln Thr Ala Leu Glu Leu Val Gly Arg Gly Val Glu Val His Ile Val
                 165                 170                 175

Ala Asp Ala Thr Ser Ser Arg Ser Met Met Asp Arg Met Phe Ala Leu
             180                 185                 190

Glu Arg Leu Ala Arg Thr Gly Ile Ile Val Thr Thr Ser Glu Ala Val
         195                 200                 205

Leu Leu Gln Leu Val Ala Asp Lys Asp His Pro Lys Phe Lys Glu Ile
     210                 215                 220

Gln Asn Leu Ile Lys Ala Ser Ala Pro Glu Ser Gly Leu Leu Ser Lys
225                 230                 235                 240

Val

<210> SEQ ID NO 47
<211> LENGTH: 199
<212> TYPE: PRT
<213> ORGANISM: Homo sapiens

<400> SEQUENCE: 47

Met His Arg Lys Phe Val Val Gln Leu Phe Ala Glu Glu Trp Gly Gln
 1               5                  10                  15

Tyr Val Asp Leu Pro Lys Gly Phe Ala Val Ser Glu Arg Cys Lys Val
             20                  25                  30

Arg Leu Val Pro Leu Gln Ile Gln Leu Thr Thr Leu Gly Asn Leu Thr
         35                  40                  45

Pro Ser Ser Thr Val Phe Phe Cys Cys Asp Met Gln Glu Arg Phe Arg
     50                  55                  60

Pro Ala Ile Lys Tyr Phe Gly Asp Ile Ile Ser Val Gly Gln Arg Leu
 65                  70                  75                  80

Leu Gln Gly Ala Arg Ile Leu Gly Ile Pro Val Ile Val Thr Glu Gln
                 85                  90                  95

Tyr Pro Lys Gly Leu Gly Ser Thr Val Gln Glu Ile Asp Leu Thr Gly
             100                 105                 110
```

Val Lys Leu Val Leu Pro Lys Thr Lys Phe Ser Met Val Leu Pro Glu
            115                 120                 125

Val Glu Ala Ala Leu Ala Glu Ile Pro Gly Val Arg Ser Val Val Leu
        130                 135                 140

Phe Gly Val Glu Thr His Val Cys Ile Gln Gln Thr Ala Leu Glu Leu
145                 150                 155                 160

Val Gly Arg Gly Val Glu Val His Ile Val Ala Asp Ala Thr Ser Ser
                165                 170                 175

Arg Ser Met Met Asp Arg Met Phe Ala Arg Leu Thr Ser Arg Ser Asn
            180                 185                 190

Gly Asp His Ser Asp His Glu
            195

<210> SEQ ID NO 48
<211> LENGTH: 288
<212> TYPE: PRT
<213> ORGANISM: Drosophila melanogaster

<400> SEQUENCE: 48

Ser Gln Asp Ser Asn Asp Asn Leu Thr Ser Cys Ser Leu Cys Val Cys
1               5                   10                  15

Val Cys Gln Ser Leu Arg Ile Val Arg Pro Val Asn Ala Phe Leu Ile
            20                  25                  30

Val Asp Val Gln Asn Asp Phe Ile Ser Gly Ser Leu Asp Ile Ser Asn
        35                  40                  45

Cys Ser Ala Gln Gln Gln Gly His Glu Ile Leu Glu Pro Ile Asn Lys
    50                  55                  60

Leu Leu Asp Thr Val Asp Phe Asp Ala Val Phe Tyr Ser Leu Asp Trp
65                  70                  75                  80

His Pro Ser Asp His Val Ser Phe Ile Asp Asn Val Lys Met Arg Pro
                85                  90                  95

Met Asp Glu Ser Ser Ala Leu Asp Ser Asp Ser Ala Lys Val Phe Asp
            100                 105                 110

Thr Val Ile Phe Ala Gly Pro Pro Met Lys Gln Arg Leu Trp Pro
        115                 120                 125

Arg His Cys Val Gln Asp Ser Trp Gly Ala Glu Leu His Lys Asp Leu
    130                 135                 140

Lys Val Val Asp His Gly Ile Lys Val Tyr Lys Gly Thr Asn Pro Glu
145                 150                 155                 160

Val Asp Ser Tyr Ser Val Phe Trp Asp Asn Lys Lys Leu Ser Asp Thr
                165                 170                 175

Thr Leu Asn Ala Gln Leu Lys Met Lys Gly Ala Thr Asp Ile Tyr Val
            180                 185                 190

Cys Gly Leu Ala Tyr Asp Val Cys Val Gly Thr Ala Val Asp Ala
    195                 200                 205

Leu Ser Ala Gly Tyr Arg Thr Ile Leu Ile Asp Asp Cys Cys Arg Gly
    210                 215                 220

Thr Asp Val His Asp Ile Glu His Thr Lys Glu Lys Val Asn Thr Ser
225                 230                 235                 240

Asp Gly Val Ile Val His Thr Asn Gln Val Lys Ala Met Ala Glu Gly
                245                 250                 255

Arg Asp Arg Arg Pro Glu Leu Gly Tyr Lys Leu Ala Met Glu Leu Lys
            260                 265                 270

Ser Pro Asp Ser Val Leu Ser Gln Arg Asn Gly Phe Arg Pro Ser Tyr
        275                 280                 285

```
<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      3xHA tag

<400> SEQUENCE: 49

His Ala His Ala His Ala
 1               5
```